US009755164B2

(12) United States Patent
Lin et al.

(10) Patent No.: US 9,755,164 B2
(45) Date of Patent: Sep. 5, 2017

(54) ORGANIC ELECTROLUMINESCENT MATERIALS AND DEVICES

(75) Inventors: Chun Lin, Ewing, NJ (US); Chuanjun Xia, Ewing, NJ (US); Jui-Yi Tsai, Ewing, NJ (US); Bin Ma, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 764 days.

(21) Appl. No.: 14/113,537

(22) PCT Filed: Jun. 6, 2012

(86) PCT No.: PCT/US2012/040990
§ 371 (c)(1),
(2), (4) Date: Jan. 13, 2014

(87) PCT Pub. No.: WO2012/170461
PCT Pub. Date: Dec. 13, 2012

(65) Prior Publication Data
US 2014/0175408 A1 Jun. 26, 2014

Related U.S. Application Data

(60) Provisional application No. 61/494,667, filed on Jun. 8, 2011.

(51) Int. Cl.
*H01L 51/00* (2006.01)
*C07F 15/00* (2006.01)
*H01L 51/50* (2006.01)

(52) U.S. Cl.
CPC ...... *H01L 51/0085* (2013.01); *C07F 15/0033* (2013.01); *H01L 51/50* (2013.01); *H01L 51/5012* (2013.01); *H01L 51/0072* (2013.01); *H01L 51/5016* (2013.01)

(58) Field of Classification Search
CPC .................................................. H01L 51/0085
See application file for complete search history.

(56) References Cited

U.S. PATENT DOCUMENTS

| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Robert Vetere
(74) *Attorney, Agent, or Firm* — Duane Morris LLP

(57) ABSTRACT

Novel heteroleptic iridium carbene complexes are provided, which contain at least two different carbene ligands. Selective substitution of the carbene ligands provides for phosphorescent compounds hat are suitable for use in a variety of OLED devices.

17 Claims, 3 Drawing Sheets

Formula I

(56) References Cited

U.S. PATENT DOCUMENTS

| | | |
|---|---|---|
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1* | 1/2008 | Egen .............. C09K 11/06 313/483 |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0205645 A1* | 8/2012 | Fuchs .............. C07F 15/0033 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008016827 A * | 1/2008 |
| JP | 2008074939 | 4/2008 |
| JP | 2008-521946 A | 6/2008 |
| JP | 2010135467 | 6/2010 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005113704 A2 | 12/2005 |
| WO | 2005123873 | 12/2005 |
| WO | 2006009024 | 1/2006 |
| WO | 2006056418 | 6/2006 |
| WO | 2006056418 A2 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011/051404 | 5/2011 |
| WO | 2011073149 A1 | 6/2011 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett, vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett, 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lel, 77(15)2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSLYKE, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Japanese Patent Office, Notice of Reasons for Rejection—English Version of Japanese Office Action regarding corresponding Japanese Application No. JP2014-514571 issued Aug. 26, 2015, pp. 1-9.

Office Action issued May 19, 2015 for corresponding Taiwanese Patent Application No. 101120813.

International Search Report issued Aug. 30, 2012 for corresponding PCT Application No. PCT/US2012/040990.

* cited by examiner

Formula I

ORGANIC ELECTROLUMINESCENT MATERIALS AND DEVICES

This application claims priority to U.S. Application Ser. No. 61/494,667, filed Jun. 8, 2011, which is herein incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel heteroleptic iridium carbene complexes. In particular, these iridium complexes are phosphorescent and are useful as emitters in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

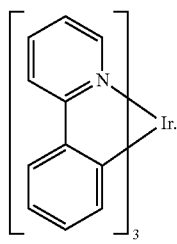

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound comprising a heteroleptic iridium complex having the formula, Formula I Formula I

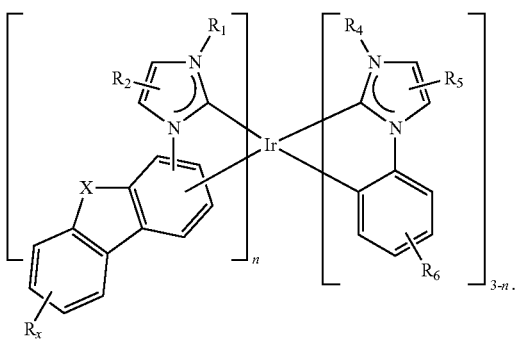

In the compound of Formula I, X is selected from the group consisting of CRR', SiRR', C=O, N—R, B—R, O, S, SO, SO$_2$, and Se. $R_2$, $R_x$, $R_5$, and $R_6$ represent mono, di, tri, tetra substitutions or no substitution, and R, R', $R_1$, $R_2$, $R_x$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two adjacent substituents are optionally joined together to form a ring, which may be further substituted; and wherein n is 1 or 2.

In one aspect, n is 2. In one aspect, n is 1. In one aspect, X is O. In one aspect, X is S.

In one aspect, compound has the formula:

Formula II

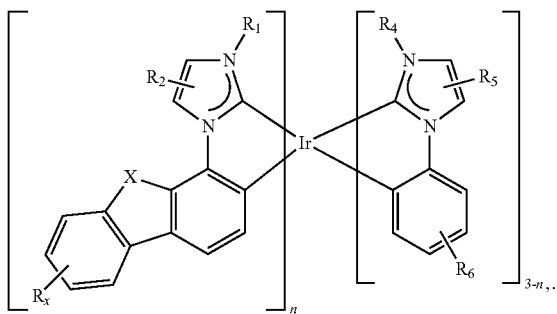

In one aspect, the compound has the formula:

Formula III

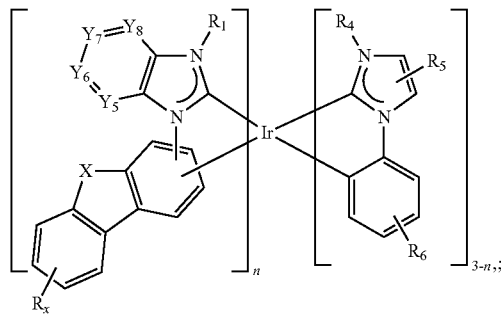

where $Y_5$ to $Y_8$ is $CR_3$ or N and each $R_3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_3$ are optionally joined to form into ring and may be further substituted.

In one aspect, the compound has the formula:

Formula IV

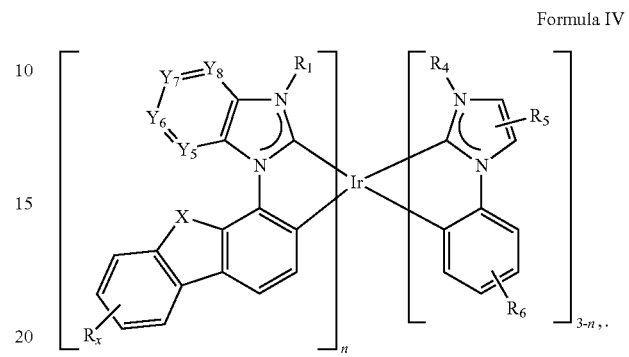

In one aspect, $R_1$ is alkyl or cycloalkyl. In one aspect, $R_1$ is aryl or substituted aryl: In one aspect, $R_1$ is a 2,6-disubstituted aryl.

In one aspect, the compound has the formula:

Formula V

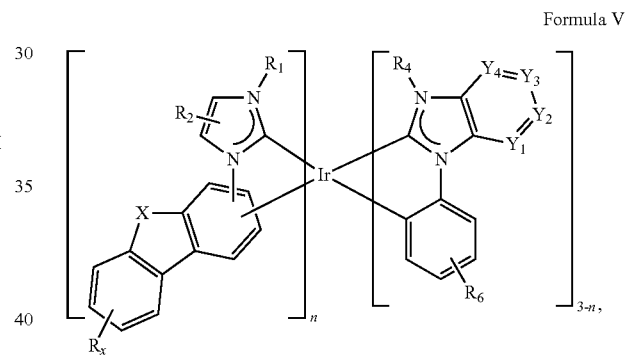

where $Y_1$ to $Y_4$ is $CR_7$ or N, and each $R_7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, at least one of $Y_1$ to $Y_4$ is N. In one aspect, the compound has the formula:

Formula VI

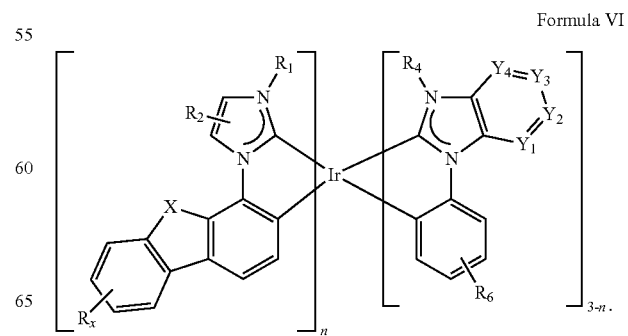

In one aspect, the compound has the formula:

Formula VII

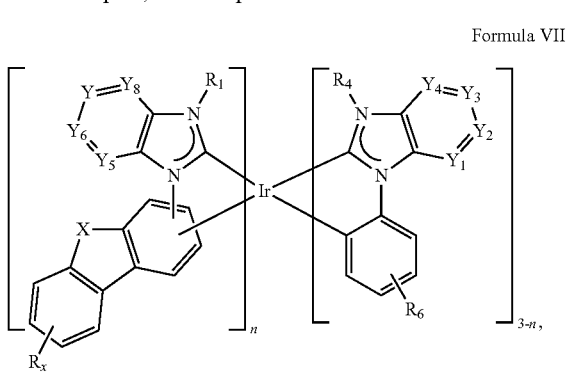

where $Y_5$ to $Y_8$ is $CR_3$ or N, and each $R_3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent substituents of $R_3$ are optionally joined together to form a ring, which may be further substituted.

In one aspect, at least one of $Y_1$ to $Y_4$ is N.

In one aspect, the compound has the formula:

Formula VIII

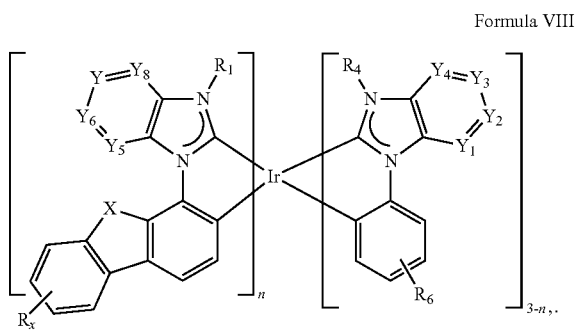

In one aspect, the compound is selected from the group consisting of:

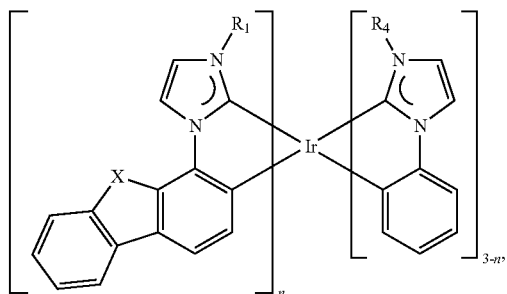

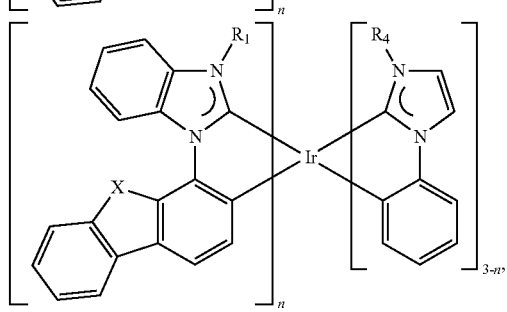

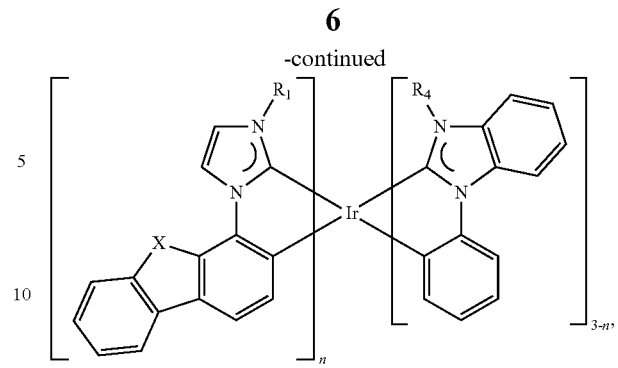

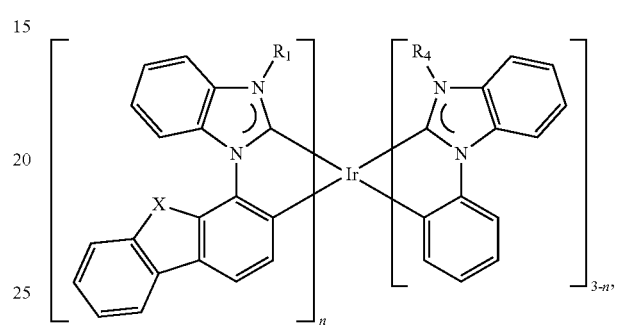

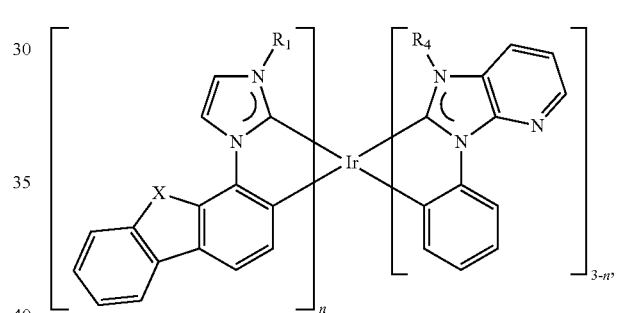

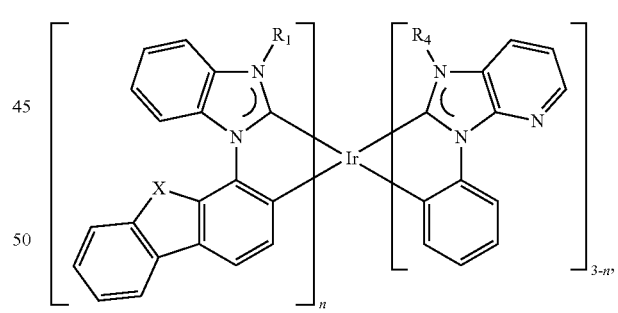

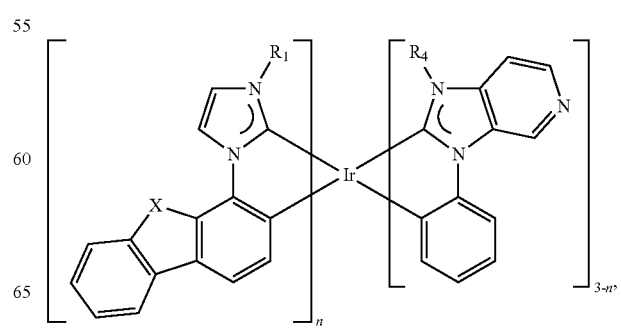

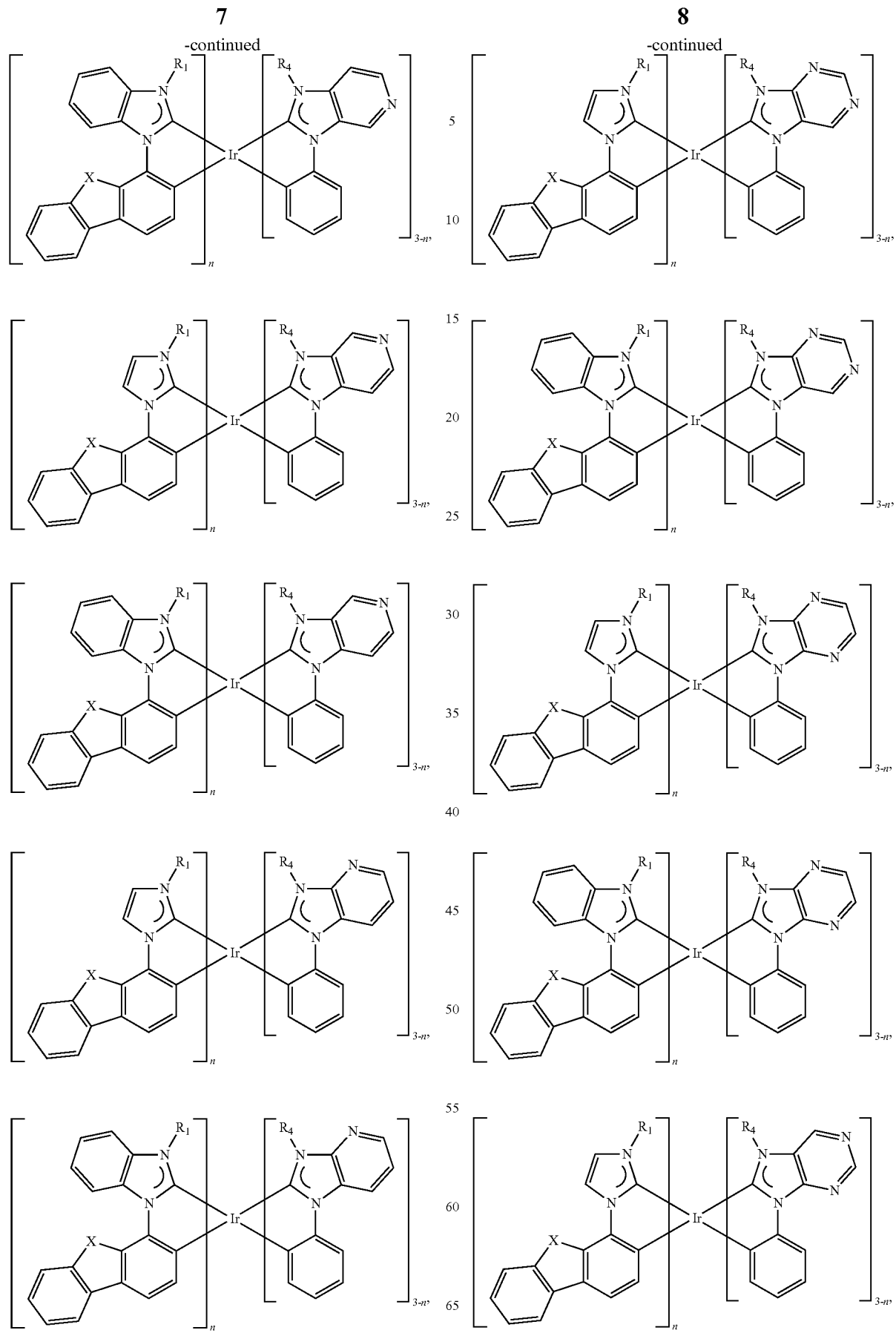

-continued

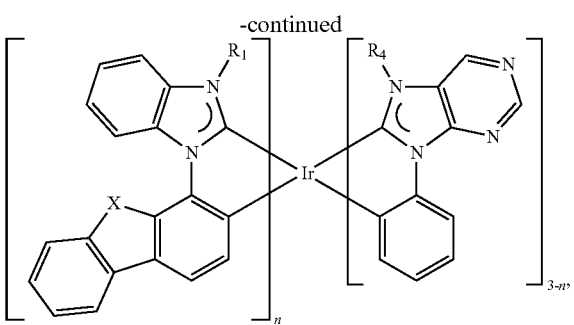

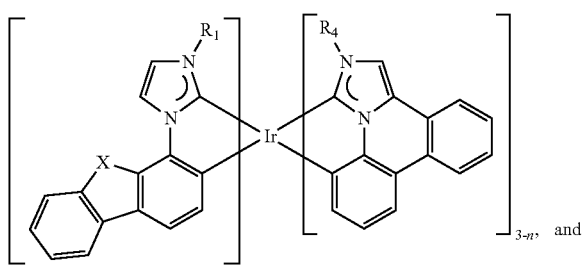

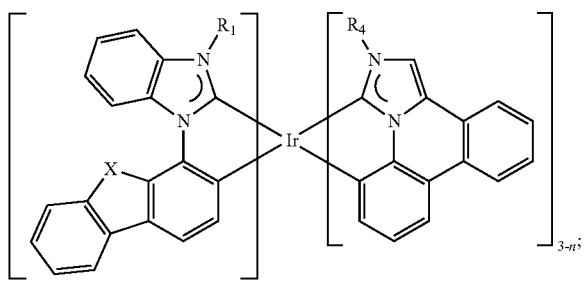

where X is O or S, and where $R_1$ and $R_4$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof, wherein any of the groups are optionally partially or fully deuterated.

In one aspect, the compound has the formula:

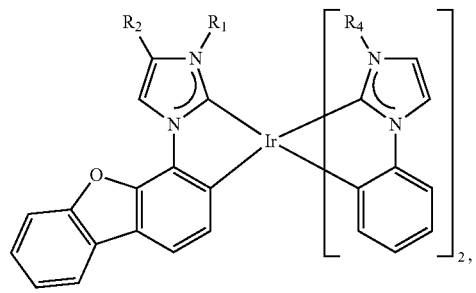

wherein $R_1$, $R_2$, and $R_4$ are alkyl. In one aspect, $R_1$, $R_2$, and $R_4$ are methyl.

In one aspect, a first device is provided. The first device comprises an organic light emitting device, further comprising: an anode, a cathode, and an organic layer, disposed between the anode and the cathode, comprising a compound having the formula:

Formula I

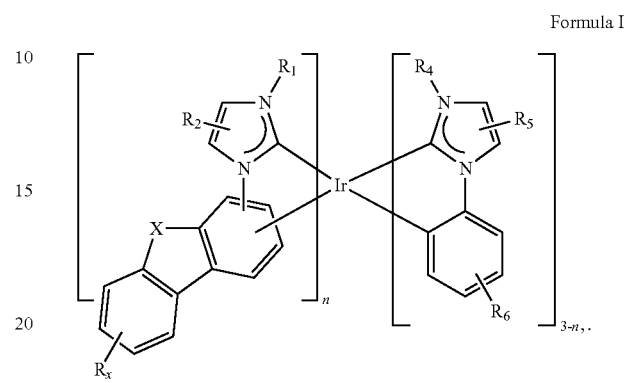

In the compound of Formula I, X is selected from the group consisting of CRR', SiRR', C=O, N—R, B—R, O, S, SO, $SO_2$, and Se. $R_2$, $R_x$, $R_5$, and $R_6$ represent mono, di, tri, tetra substitutions or no substitution, and R, R', $R_1$, $R_2$, $R_x$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two adjacent substituents are optionally joined together to form a ring, which may be further substituted; and wherein n is 1 or 2.

In one aspect, the organic layer is an emissive layer and the compound is an emissive dopant. In one aspect, the organic layer further comprises a host.

In one aspect, the host comprises at least one of the chemical groups selected from the group consisting of carbazole, dibenzothiphene, dibenzofuran, dibenzoselenophene, azacarbazole, aza-dibenzothiophene, aza-dibenzofuran, and aza-dibenzoselenophene.

In one aspect, the host is a metal complex. In one aspect, the host is a metal carbene complex. In one aspect, the metal carbene complex is selected from the group consisting of:

Compd H1

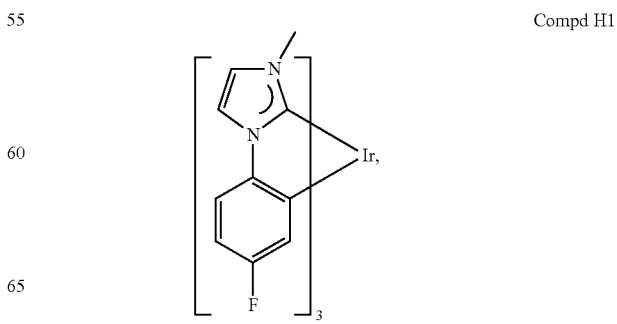

Compd H2
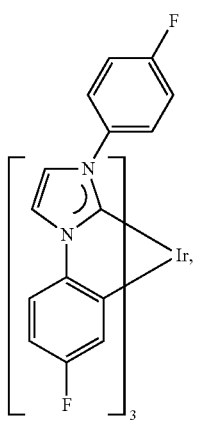
Compd H3
Compd H4
Compd H5
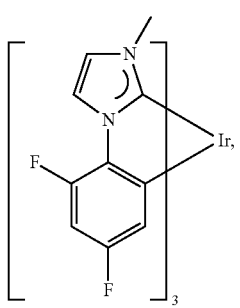
Compd H6
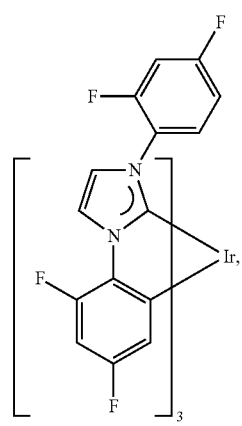
Compd H7
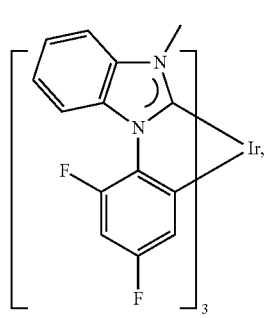
Compd H8
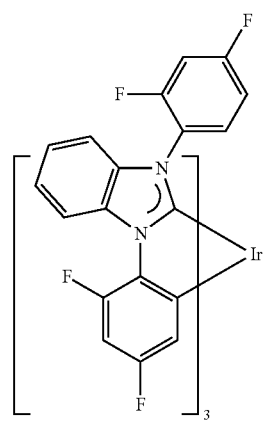
Compnd H9
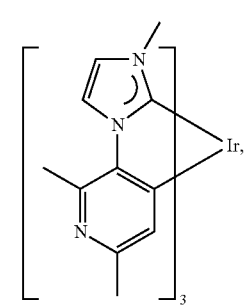

-continued
Compd H10
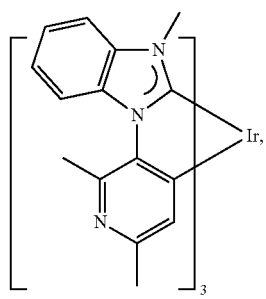
Compd H11
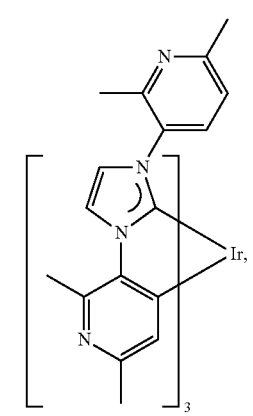
Compd H12
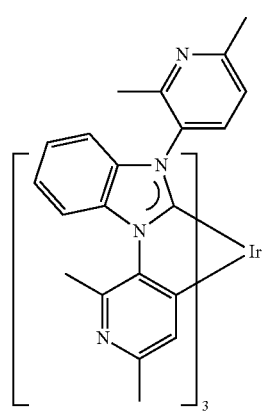
Compd H13
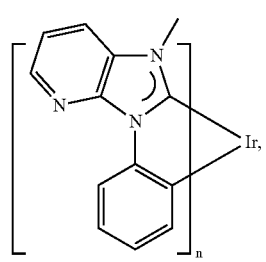
Compd H14
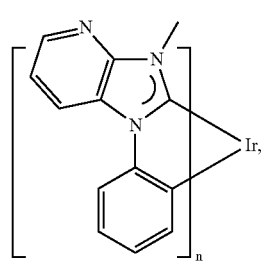
-continued
Compd H15
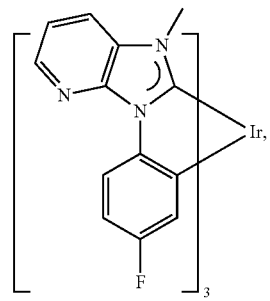
Compd H16
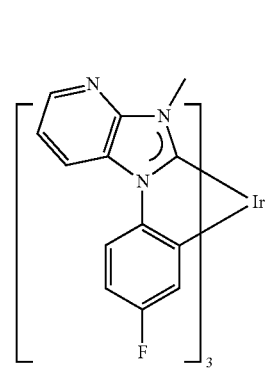
Compd H17
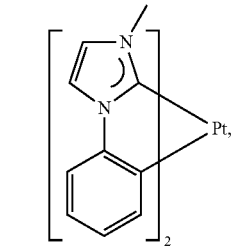
Compd H18
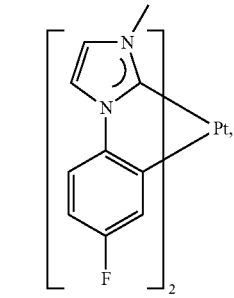
Compd H19
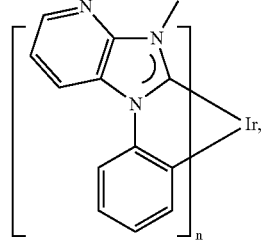

-continued

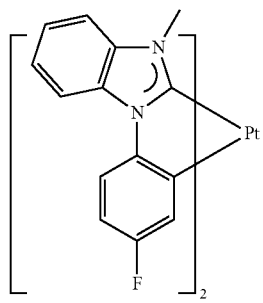

Compd H20

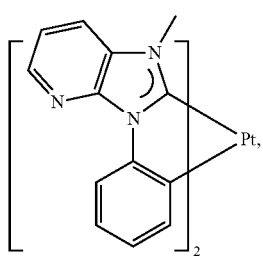

Compd H21

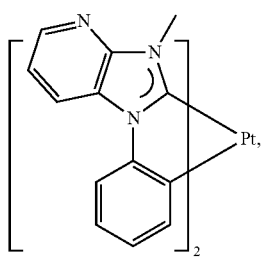

Compd H22

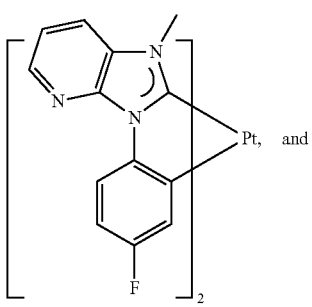

Compd H23

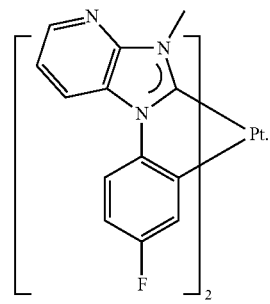

Compd H24

In one aspect, the device further comprises a second organic layer that is a non-emissive layer between anode and the emissive layer; and wherein the material in the second organic layer is a metal carbene complex.

In one aspect, the device further comprises a third organic layer that is a non-emissive layer between cathode and the emissive layer; and wherein the material in the third organic layer is a metal carbene complex.

In one aspect, the device further comprises a second organic layer that is a non-emissive layer and the compound of Formula I is a material in the second organic layer. In one aspect, the second organic layer is a hole transporting layer and the compound of Formula I is a transporting material in the second organic layer. In one aspect, the second organic layer is a blocking layer and the compound having Formula I is a blocking material in the second organic layer.

In one aspect, the first device is an organic light-emitting device. In one aspect, the first device is a consumer product. In one aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
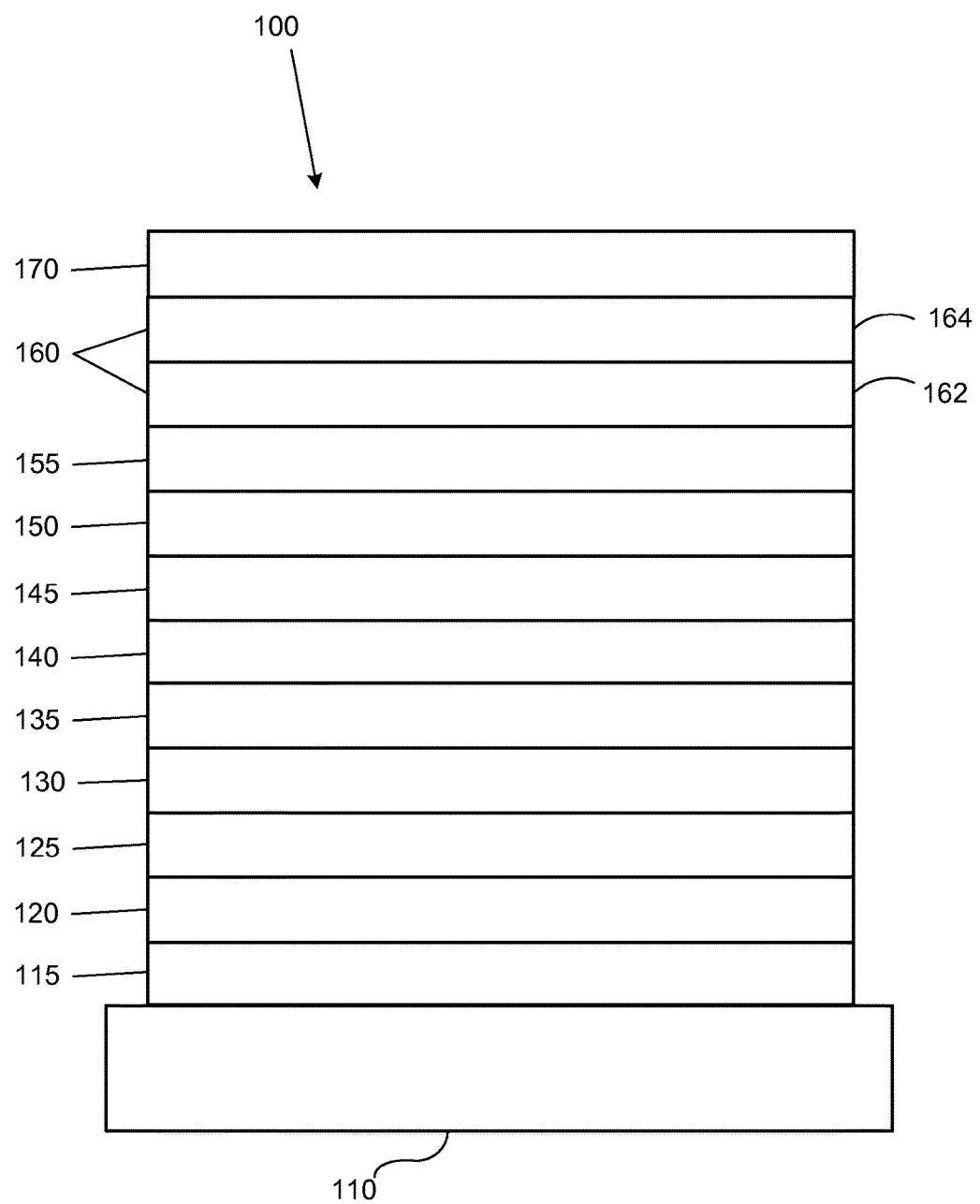
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
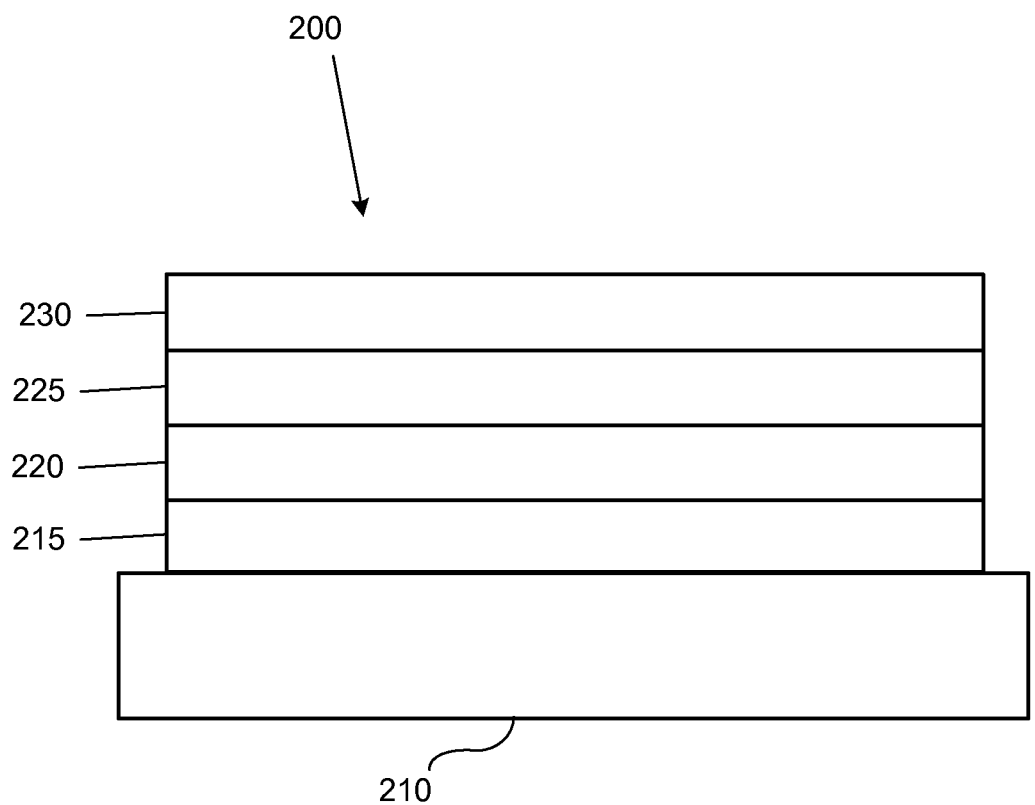
FIG. 2 shows an inverted organic light emitting device that does not have a separate electron transport layer.
Figure 3:
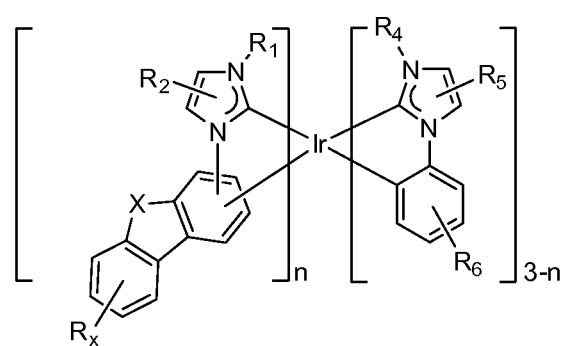
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound comprising a heteroleptic iridium complex having the formula, Formula I

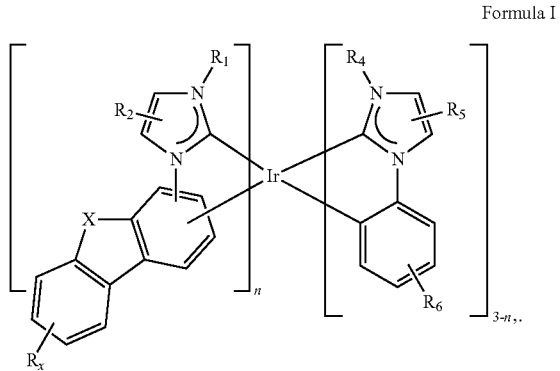

Formula I

In the compound of Formula I, X is selected from the group consisting of CRR', SiRR', C=O, N—R, B—R, O, S, SO, $SO_2$, and Se. $R_2$, $R_x$, $R_5$, and $R_6$ represent mono, di, tri, tetra substitutions or no substitution, and R, R', $R_1$, $R_2$, $R_x$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof. Any two adjacent substituents are optionally joined together to form a ring, which may be further substituted; and wherein n is 1 or 2.

In one embodiment, n is 2. In one embodiment, n is 1. In one embodiment, X is O. In one embodiment, X is S.

In one embodiment, compound has the formula:

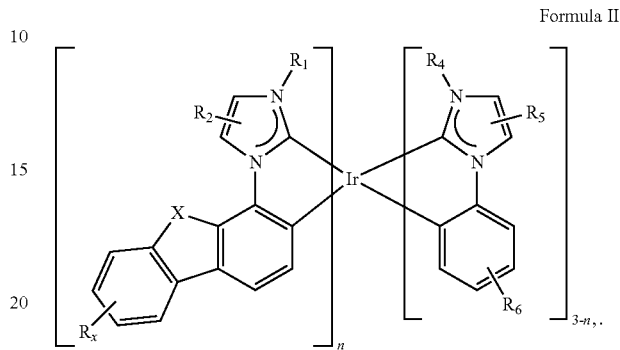

Formula II

In one embodiment, the compound has the formula:

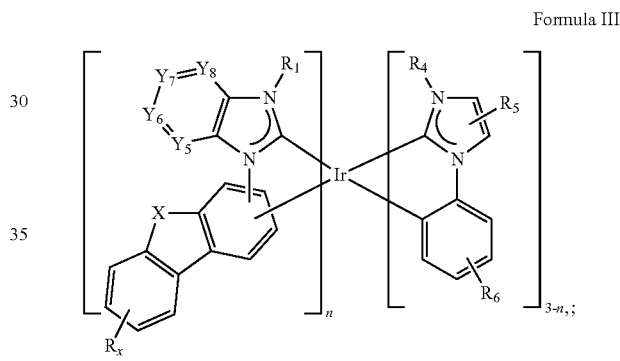

Formula III where $Y_5$ to $Y_8$ is $CR_3$ or N and each $R_3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_3$ are optionally joined to form into ring and may be further substituted.

In one embodiment, the compound has the formula:

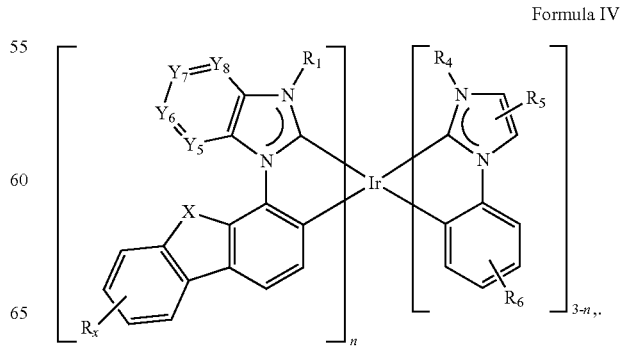

Formula IV

In one embodiment, $R_1$ is alkyl or cycloalkyl. In one embodiment, $R_1$ is aryl or substituted aryl. In one embodiment, $R_1$ is a 2,6-disubstituted aryl.

In one embodiment, the compound has the formula:

Formula V

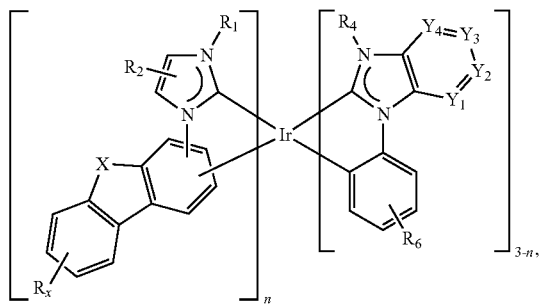

where $Y_1$ to $Y_4$ is $CR_7$ or N, and each $R_7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, at least one of $Y_1$ to $Y_4$ is N. In one embodiment, the compound has the formula:

Formula VI

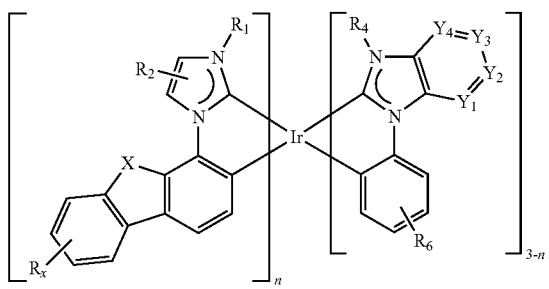

In one embodiment, the compound has the formula:

Formula VII

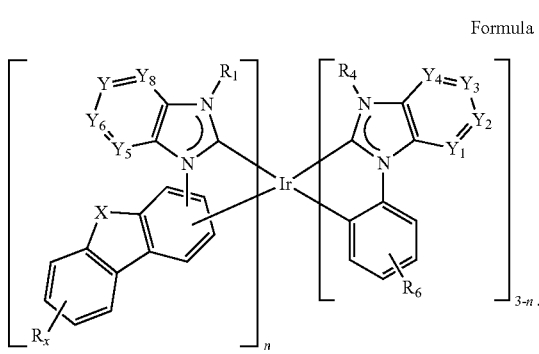

where $Y_5$ to $Y_8$ is $CR_3$ or N, and each $R_3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein any two adjacent substituents of $R_3$ are optionally joined together to form a ring, which may be further substituted.

In one embodiment, at least one of $Y_1$ to $Y_4$ is N.

In one embodiment, the compound has the formula:

Formula VIII

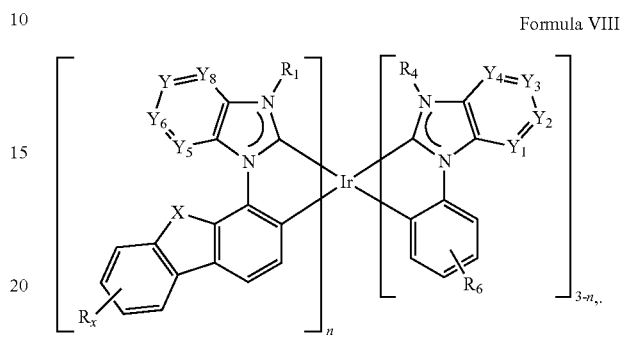

In one embodiment, the compound is selected from the group consisting of:

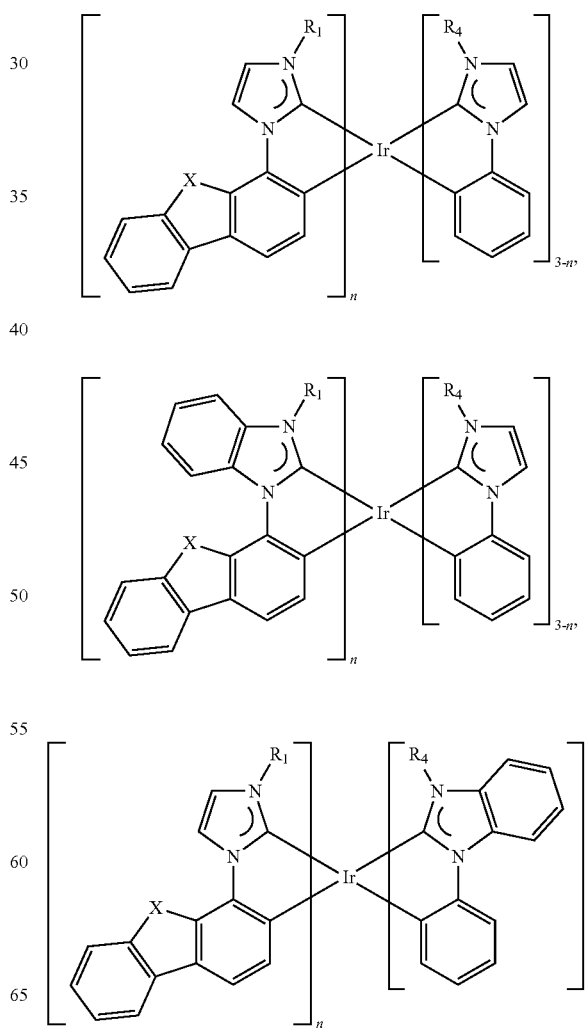

-continued
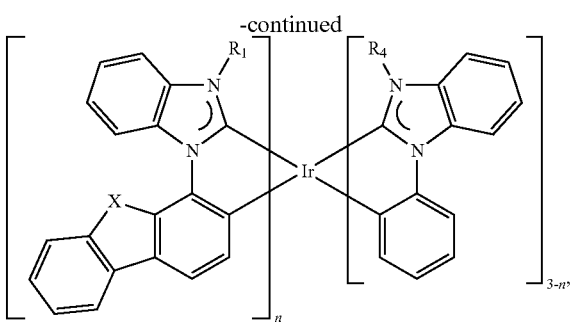
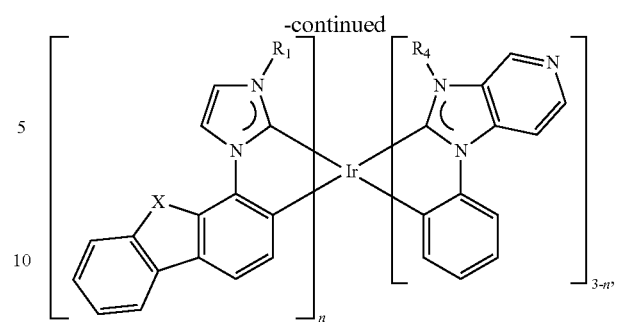
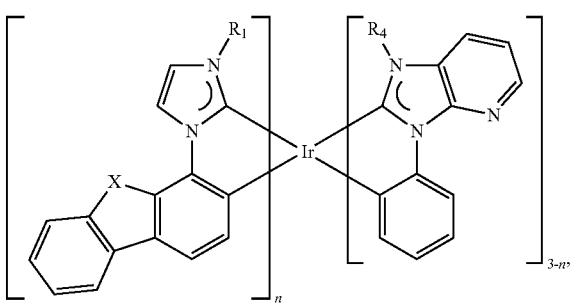
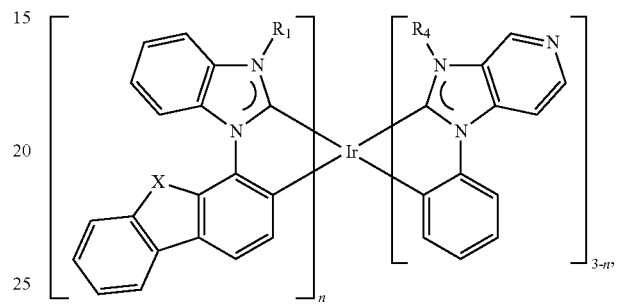
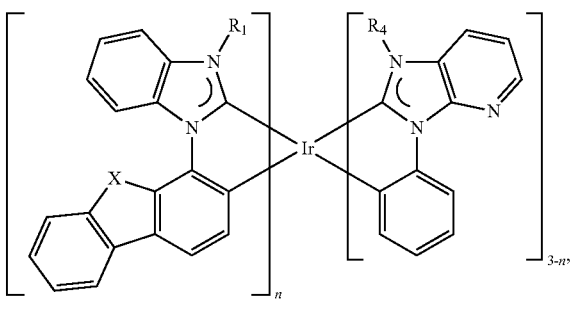
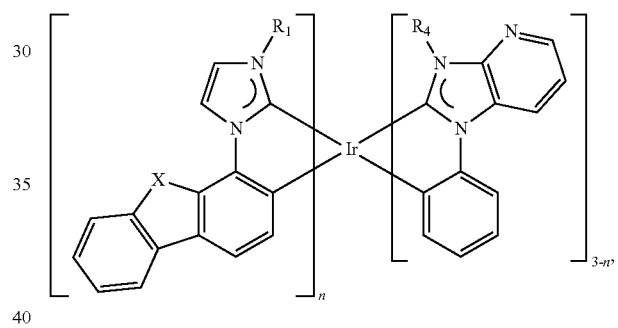
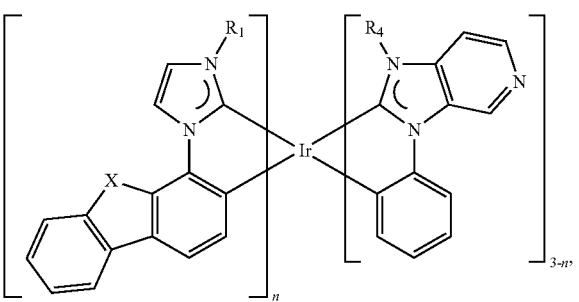
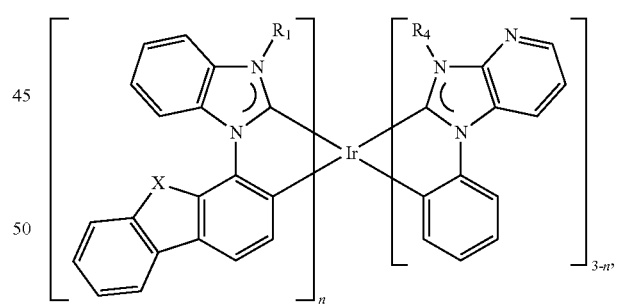
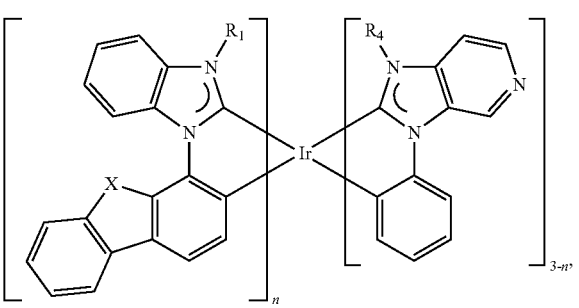
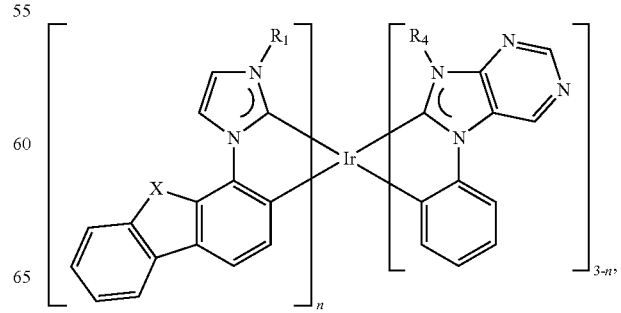

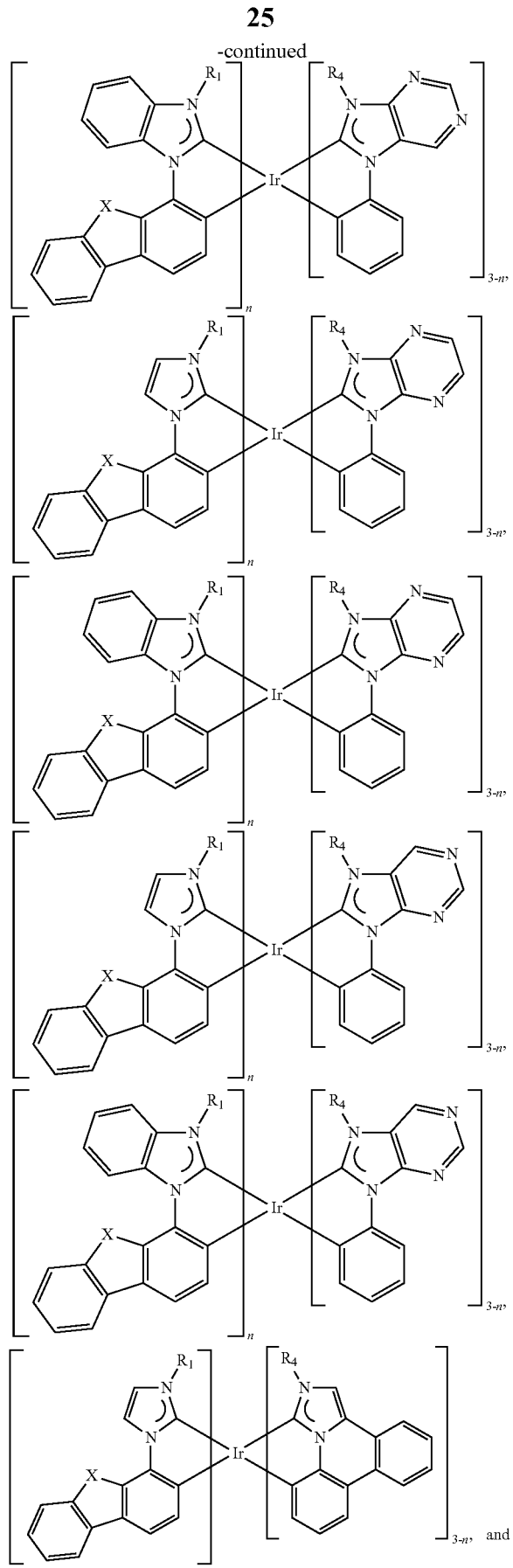

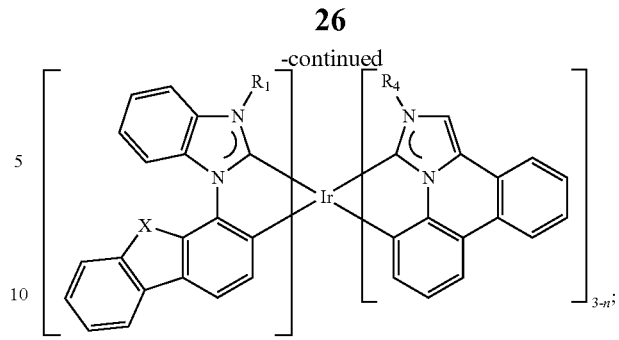

where X is O or S, and where $R_1$ and $R_4$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof, wherein any of the groups are optionally partially or fully deuterated.

In one embodiment, the compound has the formula:

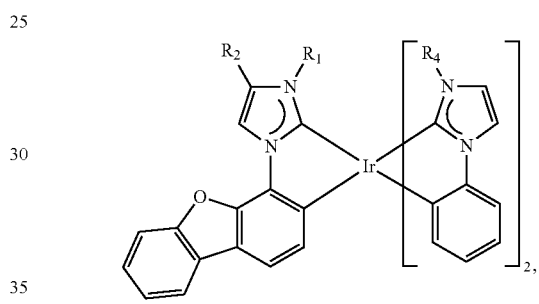

wherein $R_1$, $R_2$, and $R_4$ are alkyl. In one embodiment, $R_1$, $R_2$, and $R_4$ are methyl.

In one embodiment, a first device is provided. The first device comprises an organic light emitting device, further comprising: an anode, a cathode, and an organic layer, disposed between the anode and the cathode, comprising a compound having the formula:

Formula I

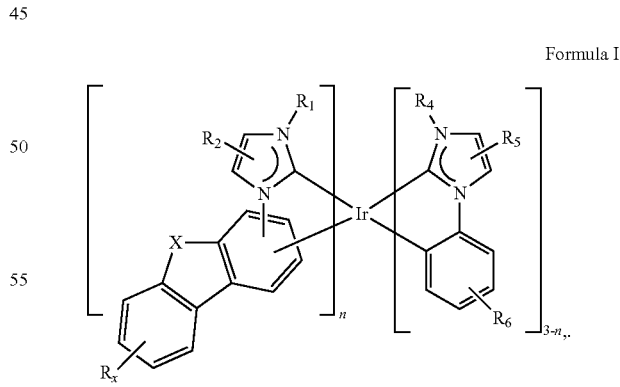

In the compound of Formula I, X is selected from the group consisting of CRR', SiRR', C=O, N—R, B—R, O, S, SO, $SO_2$, and Se. $R_2$, $R_x$, $R_5$, and $R_6$ represent mono, di, tri, tetra substitutions or no substitution, and R, R', $R_1$, $R_2$, $R_x$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two adjacent substituents are optionally joined together to form a ring, which may be further substituted; and wherein n is 1 or 2.

In one embodiment, the organic layer is an emissive layer and the compound is an emissive dopant. In one embodiment, the organic layer further comprises a host.

In one embodiment, the host comprises at least one of the chemical groups selected from the group consisting of carbazole, dibenzothiphene, dibenzofuran, dibenzoselenophene, azacarbazole, aza-dibenzothiophene, aza-dibenzofuran, and aza-dibenzoselenophene.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

In one embodiment, the host is a metal complex. In one embodiment, the host is a metal carbene complex. The term "metal carbene complex," as used herein to refer to a metal coordination complex comprising at least one carbene ligand. In one embodiment, the metal carbene complex is selected from the group consisting of:

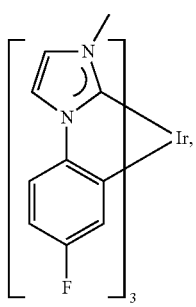

Compd H1

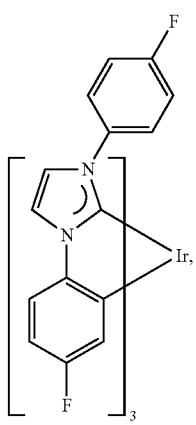

Compd H2

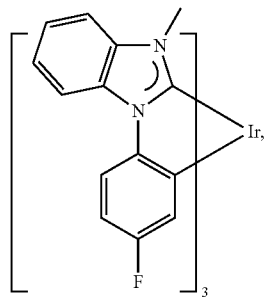

Compd H3

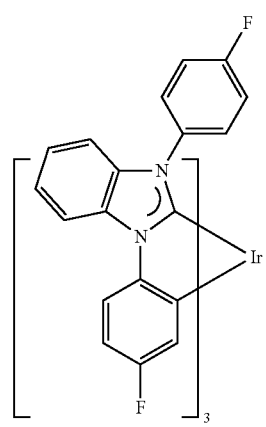

Compd H4

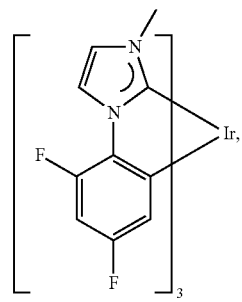

Compd H5

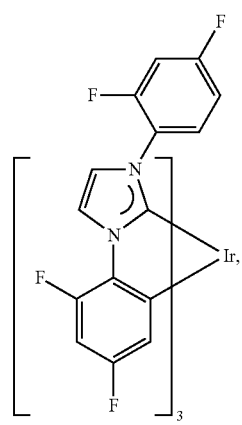

Compd H6

-continued
Compd H7
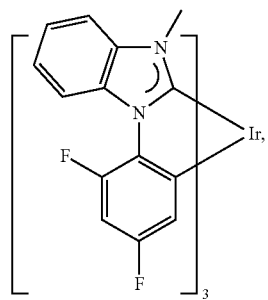
Compd H8
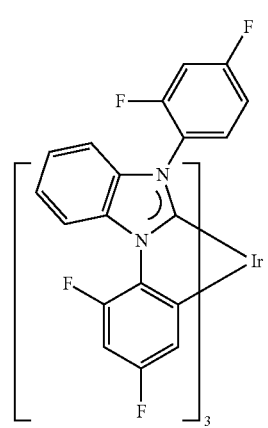
Compd H9
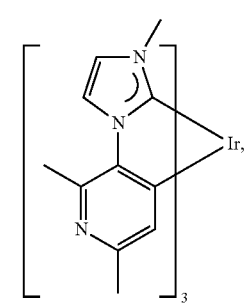
Compd H10
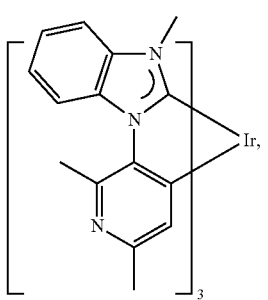
-continued
Compd H11
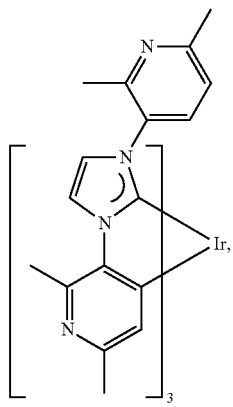
Compd H12
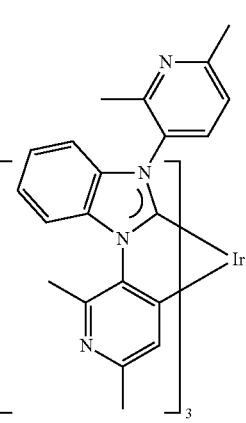
Compd H13
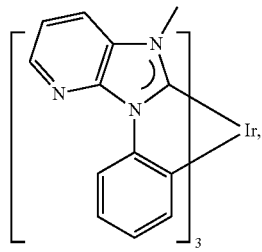
Compd H14
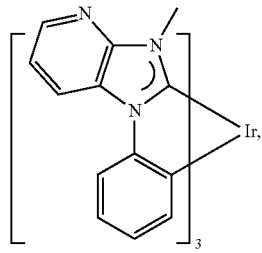
Compd H15
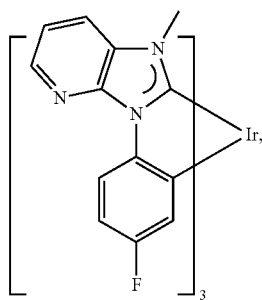

Compd H16
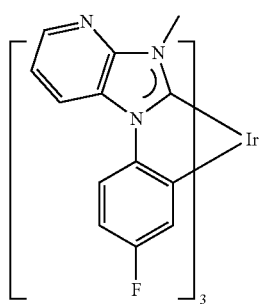

Compd H17
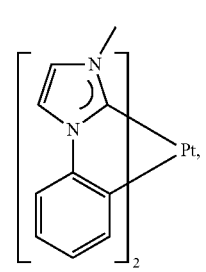

Compd H18
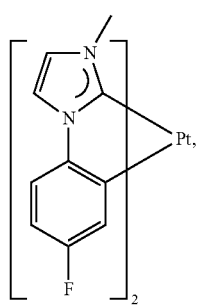

Compd H19
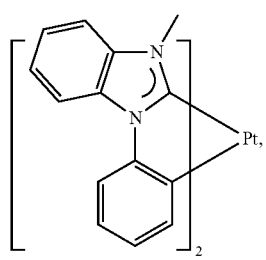

Compd H20
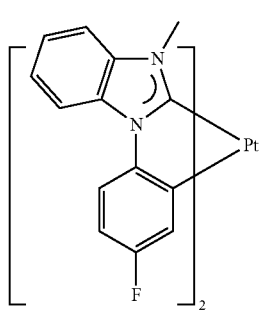

Compd H21
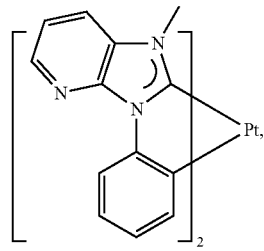

Compd H22
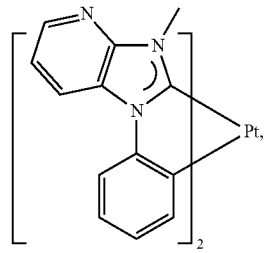

Compd H23
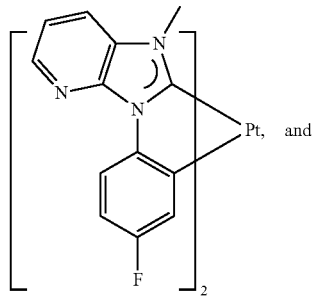

and

Compd H24
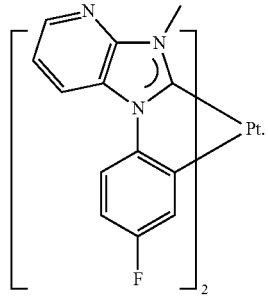

In one embodiment, the device further comprises a second organic layer that is a non-emissive layer between anode and the emissive layer; and wherein the material in the second organic layer is a metal carbene complex.

In one embodiment, the device further comprises a third organic layer that is a non-emissive layer between cathode and the emissive layer; and wherein the material in the third organic layer is a metal carbene complex.

In one embodiment, the device further comprises a second organic layer that is a non-emissive layer and the compound of Formula I is a material in the second organic layer. In one embodiment, the second organic layer is a hole transporting layer and the compound of Formula I is a transporting material in the second organic layer. In one embodiment, the second organic layer is a blocking layer and the compound having Formula I is a blocking material in the second organic layer.

In one embodiment, the first device is an organic light-emitting device. In one embodiment, the first device is a consumer product. In one embodiment, the first device comprises a lighting panel.

In one embodiment, the compounds of Formula II have the following compositions:

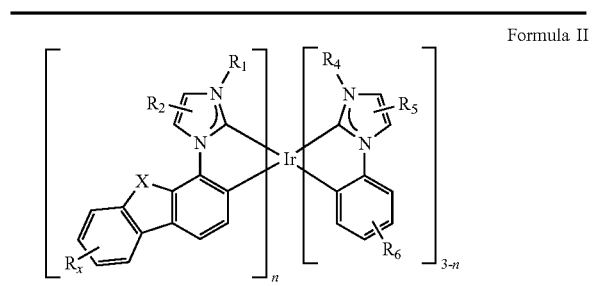

Formula II

| Compd. | n | X | $R_x$ | $R_1$ | $R_2$ | $R_4$ | $R_5$ | $R_6$ |
|---|---|---|---|---|---|---|---|---|
| 1. | 1 | O | H | $CH_3$ | H | $CH_3$ | H | H |
| 2. | 1 | O | H | $CH_3$ | H | $CH(CH_3)_2$ | H | H |
| 3. | 1 | O | H | $CH_3$ | H | $CH_2CH(CH_3)_2$ | H | H |
| 4. | 1 | O | H | $CH_3$ | H | $C_6H_{11}$ | H | H |
| 5. | 1 | O | H | $CH_3$ | H | Ph | H | H |
| 6. | 1 | O | H | $CH_3$ | H | 2,6-dimethylphenyl | H | H |
| 7. | 1 | O | H | $CH_3$ | H | 2,6-diisopropylphenyl | H | H |
| 8. | 1 | O | H | $CH(CH_3)_2$ | H | $CH_3$ | H | H |
| 9. | 1 | O | H | $CH(CH_3)_2$ | H | $CH(CH_3)_2$ | H | H |
| 10. | 1 | O | H | $CH(CH_3)_2$ | H | $CH_2CH(CH_3)_2$ | H | H |
| 11. | 1 | O | H | $CH(CH_3)_2$ | H | $C_6H_{11}$ | H | H |
| 12. | 1 | O | H | $CH(CH_3)_2$ | H | Ph | H | H |
| 13. | 1 | O | H | $CH(CH_3)_2$ | H | 2,6-dimethylphenyl | H | H |
| 14. | 1 | O | H | $CH(CH_3)_2$ | H | 2,6-diisopropylphenyl | H | H |
| 15. | 1 | O | H | $CH_2CH(CH_3)_2$ | H | $CH_3$ | H | H |
| 16. | 1 | O | H | $CH_2CH(CH_3)_2$ | H | $CH(CH_3)_2$ | H | H |
| 17. | 1 | O | H | $CH_2CH(CH_3)_2$ | H | $CH_2CH(CH_3)_2$ | H | H |
| 18. | 1 | O | H | $CH_2CH(CH_3)_2$ | H | $C_6H_{11}$ | H | H |
| 19. | 1 | O | H | $CH_2CH(CH_3)_2$ | H | Ph | H | H |
| 20. | 1 | O | H | $CH_2CH(CH_3)_2$ | H | 2,6-dimethylphenyl | H | H |
| 21. | 1 | O | H | $CH_2CH(CH_3)_2$ | H | 2,6-diisopropylphenyl | H | H |
| 22. | 1 | O | H | $C_6H_{11}$ | H | $CH_3$ | H | H |
| 23. | 1 | O | H | $C_6H_{11}$ | H | $CH(CH_3)_2$ | H | H |
| 24. | 1 | O | H | $C_6H_{11}$ | H | $CH_2CH(CH_3)_2$ | H | H |
| 25. | 1 | O | H | $C_6H_{11}$ | H | $C_6H_{11}$ | H | H |
| 26. | 1 | O | H | $C_6H_{11}$ | H | Ph | H | H |
| 27. | 1 | O | H | $C_6H_{11}$ | H | 2,6-dimethylphenyl | H | H |
| 28. | 1 | O | H | $C_6H_{11}$ | H | 2,6-diisopropylphenyl | H | H |
| 29. | 1 | O | H | Ph | H | $CH_3$ | H | H |
| 30. | 1 | O | H | Ph | H | $CH(CH_3)_2$ | H | H |
| 31. | 1 | O | H | Ph | H | $CH_2CH(CH_3)_2$ | H | H |
| 32. | 1 | O | H | Ph | H | $C_6H_{11}$ | H | H |
| 33. | 1 | O | H | Ph | H | Ph | H | H |
| 34. | 1 | O | H | Ph | H | 2,6-dimethylphenyl | H | H |
| 35. | 1 | O | H | Ph | H | 2,6-diisopropylphenyl | H | H |
| 36. | 1 | O | H | 2,6-dimethylphenyl | H | $CH_3$ | H | H |
| 37. | 1 | O | H | 2,6-dimethylphenyl | H | $CH(CH_3)_2$ | H | H |
| 38. | 1 | O | H | 2,6-dimethylphenyl | H | $CH_2CH(CH_3)_2$ | H | H |
| 39. | 1 | O | H | 2,6-dimethylphenyl | H | $C_6H_{11}$ | H | H |
| 40. | 1 | O | H | 2,6-dimethylphenyl | H | Ph | H | H |
| 41. | 1 | O | H | 2,6-dimethylphenyl | H | 2,6-dimethylphenyl | H | H |
| 42. | 1 | O | H | 2,6-dimethylphenyl | H | 2,6-diisopropylphenyl | H | H |

-continued

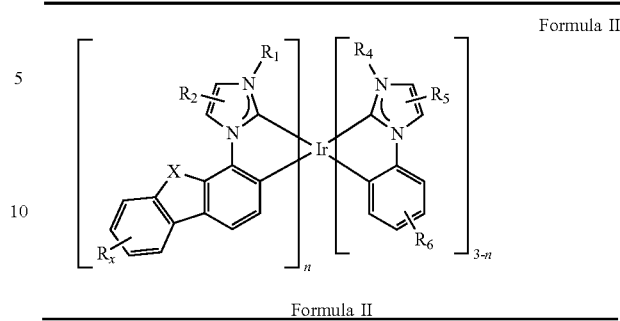

Formula II

| Compd. | n | X | $R_x$ | $R_1$ | $R_2$ | $R_4$ | $R_5$ | $R_6$ |
|---|---|---|---|---|---|---|---|---|
| 43. | 1 | O | H | 2,6-diisopropylphenyl | H | $CH_3$ | H | H |
| 44. | 1 | O | H | 2,6-diisopropylphenyl | H | $CH(CH_3)_2$ | H | H |
| 45. | 1 | O | H | 2,6-diisopropylphenyl | H | $CH_2CH(CH_3)_2$ | H | H |
| 46. | 1 | O | H | 2,6-diisopropylphenyl | H | $C_6H_{11}$ | H | H |
| 47. | 1 | O | H | 2,6-diisopropylphenyl | H | Ph | H | H |
| 48. | 1 | O | H | 2,6-diisopropylphenyl | H | 2,6-dimethylphenyl | H | H |
| 49. | 1 | O | H | 2,6-diisopropylphenyl | H | 2,6-diisopropylphenyl | H | H |
| 50. | 1 | S | H | $CH_3$ | H | $CH_3$ | H | H |
| 51. | 1 | S | H | $CH_3$ | H | $CH(CH_3)_2$ | H | H |
| 52. | 1 | S | H | $CH_3$ | H | $CH_2CH(CH_3)_2$ | H | H |
| 53. | 1 | S | H | $CH_3$ | H | $C_6H_{11}$ | H | H |
| 54. | 1 | S | H | $CH_3$ | H | Ph | H | H |
| 55. | 1 | S | H | $CH_3$ | H | 2,6-dimethylphenyl | H | H |
| 56. | 1 | S | H | $CH_3$ | H | 2,6-diisopropylphenyl | H | H |
| 57. | 1 | S | H | $CH(CH_3)_2$ | H | $CH_3$ | H | H |
| 58. | 1 | S | H | $CH(CH_3)_2$ | H | $CH(CH_3)_2$ | H | H |
| 59. | 1 | S | H | $CH(CH_3)_2$ | H | $CH_2CH(CH_3)_2$ | H | H |
| 60. | 1 | S | H | $CH(CH_3)_2$ | H | $C_6H_{11}$ | H | H |
| 61. | 1 | S | H | $CH(CH_3)_2$ | H | Ph | H | H |
| 62. | 1 | S | H | $CH(CH_3)_2$ | H | 2,6-dimethylphenyl | H | H |
| 63. | 1 | S | H | $CH(CH_3)_2$ | H | 2,6-diisopropylphenyl | H | H |
| 64. | 1 | S | H | $CH_2CH(CH_3)_2$ | H | $CH_3$ | H | H |
| 65. | 1 | S | H | $CH_2CH(CH_3)_2$ | H | $CH(CH_3)_2$ | H | H |
| 66. | 1 | S | H | $CH_2CH(CH_3)_2$ | H | $CH_2CH(CH_3)_2$ | H | H |
| 67. | 1 | S | H | $CH_2CH(CH_3)_2$ | H | $C_6H_{11}$ | H | H |
| 68. | 1 | S | H | $CH_2CH(CH_3)_2$ | H | Ph | H | H |
| 69. | 1 | S | H | $CH_2CH(CH_3)_2$ | H | 2,6-dimethylphenyl | H | H |
| 70. | 1 | S | H | $CH_2CH(CH_3)_2$ | H | 2,6-diisopropylphenyl | H | H |
| 71. | 1 | S | H | $C_6H_{11}$ | H | $CH_3$ | H | H |
| 72. | 1 | S | H | $C_6H_{11}$ | H | $CH(CH_3)_2$ | H | H |
| 73. | 1 | S | H | $C_6H_{11}$ | H | $CH_2CH(CH_3)_2$ | H | H |
| 74. | 1 | S | H | $C_6H_{11}$ | H | $C_6H_{11}$ | H | H |
| 75. | 1 | S | H | $C_6H_{11}$ | H | Ph | H | H |
| 76. | 1 | S | H | $C_6H_{11}$ | H | 2,6-dimethylphenyl | H | H |
| 77. | 1 | S | H | $C_6H_{11}$ | H | 2,6-diisopropylphenyl | H | H |
| 78. | 1 | S | H | Ph | H | $CH_3$ | H | H |
| 79. | 1 | S | H | Ph | H | $CH(CH_3)_2$ | H | H |
| 80. | 1 | S | H | Ph | H | $CH_2CH(CH_3)_2$ | H | H |
| 81. | 1 | S | H | Ph | H | $C_6H_{11}$ | H | H |
| 82. | 1 | S | H | Ph | H | Ph | H | H |
| 83. | 1 | S | H | Ph | H | 2,6-dimethylphenyl | H | H |
| 84. | 1 | S | H | Ph | H | 2,6-diisopropylphenyl | H | H |
| 85. | 1 | S | H | 2,6-dimethylphenyl | H | $CH_3$ | H | H |

-continued

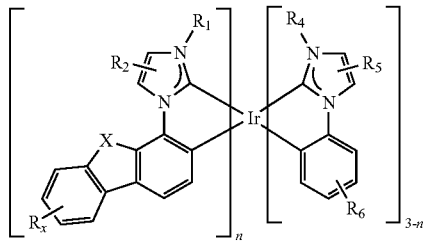

Formula II

| Compd. | n | X | $R_x$ | $R_1$ | $R_2$ | $R_4$ | $R_5$ | $R_6$ |
|---|---|---|---|---|---|---|---|---|
| 86. | 1 | S | H | 2,6-dimethylphenyl | H | $CH(CH_3)_2$ | H | H |
| 87. | 1 | S | H | 2,6-dimethylphenyl | H | $CH_2CH(CH_3)_2$ | H | H |
| 88 | 1 | S | H | 2,6-dimethylphenyl | H | $C_6H_{11}$ | H | H |
| 89. | 1 | S | H | 2,6-dimethylphenyl | H | Ph | H | H |
| 90. | 1 | S | H | 2,6-dimethylphenyl | H | 2,6-dimethylphenyl | H | H |
| 91. | 1 | S | H | 2,6-dimethylphenyl | H | 2,6-diisopropylphenyl | H | H |
| 92. | 1 | S | H | 2,6-diisopropylphenyl | H | $CH_3$ | H | H |
| 93. | 1 | S | H | 2,6-diisopropylphenyl | H | $CH(CH_3)_2$ | H | H |
| 94. | 1 | S | H | 2,6-diisopropylphenyl | H | $CH_2CH(CH_3)_2$ | H | H |
| 95. | 1 | S | H | 2,6-diisopropylphenyl | H | $C_6H_{11}$ | H | H |
| 96. | 1 | S | H | 2,6-diisopropylphenyl | H | Ph | H | H |
| 97. | 1 | S | H | 2,6-diisopropylphenyl | H | 2,6-dimethylphenyl | H | H |
| 98. | 1 | S | H | 2,6-diisopropylphenyl | H | 2,6-diisopropylphenyl | H | H |
| 99. | 2 | O | H | $CH_3$ | H | $CH_3$ | H | H |
| 100. | 2 | O | H | $CH_3$ | H | $CH(CH_3)_2$ | H | H |
| 101. | 2 | O | H | $CH_3$ | H | $CH_2CH(CH_3)_2$ | H | H |
| 102. | 2 | O | H | $CH_3$ | H | $C_6H_{11}$ | H | H |
| 103. | 2 | O | H | $CH_3$ | H | Ph | H | H |
| 104. | 2 | O | H | $CH_3$ | H | 2,6-dimethylphenyl | H | H |
| 105. | 2 | O | H | $CH_3$ | H | 2,6-diisopropylphenyl | H | H |
| 106. | 2 | O | H | $CH(CH_3)_2$ | H | $CH_3$ | H | H |
| 107. | 2 | O | H | $CH(CH_3)_2$ | H | $CH(CH_3)_2$ | H | H |
| 108. | 2 | O | H | $CH(CH_3)_2$ | H | $CH_2CH(CH_3)_2$ | H | H |
| 109. | 2 | O | H | $CH(CH_3)_2$ | H | $C_6H_{11}$ | H | H |
| 110. | 2 | O | H | $CH(CH_3)_2$ | H | Ph | H | H |
| 111. | 2 | O | H | $CH(CH_3)_2$ | H | 2,6-dimethylphenyl | H | H |
| 112. | 2 | O | H | $CH(CH_3)_2$ | H | 2,6-diisopropylphenyl | H | H |
| 113. | 2 | O | H | $CH_2CH(CH_3)_2$ | H | $CH_3$ | H | H |
| 114. | 2 | O | H | $CH_2CH(CH_3)_2$ | H | $CH(CH_3)_2$ | H | H |
| 115. | 2 | O | H | $CH_2CH(CH_3)_2$ | H | $CH_2CH(CH_3)_2$ | H | H |
| 116. | 2 | O | H | $CH_2CH(CH_3)_2$ | H | $C_6H_{11}$ | H | H |
| 117. | 2 | O | H | $CH_2CH(CH_3)_2$ | H | Ph | H | H |
| 118. | 2 | O | H | $CH_2CH(CH_3)_2$ | H | 2,6-dimethylphenyl | H | H |
| 119. | 2 | O | H | $CH_2CH(CH_3)_2$ | H | 2,6-diisopropylphenyl | H | H |
| 120. | 2 | O | H | $C_6H_{11}$ | H | $CH_3$ | H | H |
| 121. | 2 | O | H | $C_6H_{11}$ | H | $CH(CH_3)_2$ | H | H |
| 122. | 2 | O | H | $C_6H_{11}$ | H | $CH_2CH(CH_3)_2$ | H | H |
| 123. | 2 | O | H | $C_6H_{11}$ | H | $C_6H_{11}$ | H | H |
| 124. | 2 | O | H | $C_6H_{11}$ | H | Ph | H | H |
| 125. | 2 | O | H | $C_6H_{11}$ | H | 2,6-dimethylphenyl | H | H |
| 126. | 2 | O | H | $C_6H_{11}$ | H | 2,6-diisopropylphenyl | H | H |

-continued

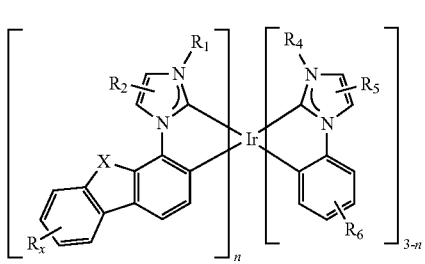

Formula II

| Compd. | n | X | $R_x$ | $R_1$ | $R_2$ | $R_4$ | $R_5$ | $R_6$ |
|---|---|---|---|---|---|---|---|---|
| 127. | 2 | O | H | Ph | H | $CH_3$ | H | H |
| 128. | 2 | O | H | Ph | H | $CH(CH_3)_2$ | H | H |
| 129. | 2 | O | H | Ph | H | $CH_2CH(CH_3)_2$ | H | H |
| 130. | 2 | O | H | Ph | H | $C_6H_{11}$ | H | H |
| 131. | 2 | O | H | Ph | H | Ph | H | H |
| 132. | 2 | O | H | Ph | H | 2,6-dimethylphenyl | H | H |
| 133. | 2 | O | H | Ph | H | 2,6-diisopropylphenyl | H | H |
| 134. | 2 | O | H | 2,6-dimethylphenyl | H | $CH_3$ | H | H |
| 135. | 2 | O | H | 2,6-dimethylphenyl | H | $CH(CH_3)_2$ | H | H |
| 136. | 2 | O | H | 2,6-dimethylphenyl | H | $CH_2CH(CH_3)_2$ | H | H |
| 137. | 2 | O | H | 2,6-dimethylphenyl | H | $C_6H_{11}$ | H | H |
| 138. | 2 | O | H | 2,6-dimethylphenyl | H | Ph | H | H |
| 139. | 2 | O | H | 2,6-dimethylphenyl | H | 2,6-dimethylphenyl | H | H |
| 140. | 2 | O | H | 2,6-dimethylphenyl | H | 2,6-diisopropylphenyl | H | H |
| 141. | 2 | O | H | 2,6-diisopropylphenyl | H | $CH_3$ | H | H |
| 142. | 2 | O | H | 2,6-diisopropylphenyl | H | $CH(CH_3)_2$ | H | H |
| 143. | 2 | O | H | 2,6-diisopropylphenyl | H | $CH_2CH(CH_3)_2$ | H | H |
| 144. | 2 | O | H | 2,6-diisopropylphenyl | H | $C_6H_{11}$ | H | H |
| 145. | 2 | O | H | 2,6-diisopropylphenyl | H | Ph | H | H |
| 146. | 2 | O | H | 2,6-diisopropylphenyl | H | 2,6-dimethylphenyl | H | H |
| 147. | 2 | O | H | 2,6-diisopropylphenyl | H | 2,6-diisopropylphenyl | H | H |
| 148. | 2 | S | H | $CH_3$ | H | $CH_3$ | H | H |
| 149. | 2 | S | H | $CH_3$ | H | $CH(CH_3)_2$ | H | H |
| 150. | 2 | S | H | $CH_3$ | H | $CH_2CH(CH_3)_2$ | H | H |
| 151. | 2 | S | H | $CH_3$ | H | $C_6H_{11}$ | H | H |
| 152. | 2 | S | H | $CH_3$ | H | Ph | H | H |
| 153. | 2 | S | H | $CH_3$ | H | 2,6-dimethylphenyl | H | H |
| 154. | 2 | S | H | $CH_3$ | H | 2,6-diisopropylphenyl | H | H |
| 155. | 2 | S | H | $CH(CH_3)_2$ | H | $CH_3$ | H | H |
| 156. | 2 | S | H | $CH(CH_3)_2$ | H | $CH(CH_3)_2$ | H | H |
| 157. | 2 | S | H | $CH(CH_3)_2$ | H | $CH_2CH(CH_3)_2$ | H | H |
| 158. | 2 | S | H | $CH(CH_3)_2$ | H | $C_6H_{11}$ | H | H |
| 159. | 2 | S | H | $CH(CH_3)_2$ | H | Ph | H | H |
| 160. | 2 | S | H | $CH(CH_3)_2$ | H | 2,6-dimethylphenyl | H | H |
| 161. | 2 | S | H | $CH(CH_3)_2$ | H | 2,6-diisopropylphenyl | H | H |
| 162. | 2 | S | H | $CH_2CH(CH_3)_2$ | H | $CH_3$ | H | H |
| 163. | 2 | S | H | $CH_2CH(CH_3)_2$ | H | $CH(CH_3)_2$ | H | H |
| 164. | 2 | S | H | $CH_2CH(CH_3)_2$ | H | $CH_2CH(CH_3)_2$ | H | H |
| 165. | 2 | S | H | $CH_2CH(CH_3)_2$ | H | $C_6H_{11}$ | H | H |
| 166. | 2 | S | H | $CH_2CH(CH_3)_2$ | H | Ph | H | H |
| 167. | 2 | S | H | $CH_2CH(CH_3)_2$ | H | 2,6-dimethylphenyl | H | H |

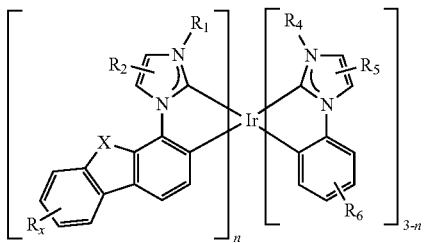

Formula II

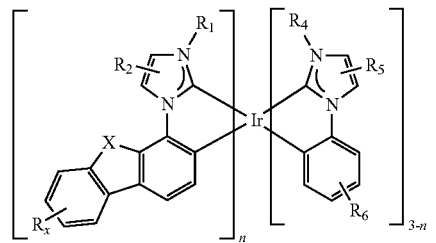

Formula II

Formula II

| Compd. | n | X | $R_x$ | $R_1$ | $R_2$ | $R_4$ | $R_5$ | $R_6$ |
|---|---|---|---|---|---|---|---|---|
| 168. | 2 | S | H | $CH_2CH(CH_3)_2$ | H | 2,6-diisopropylphenyl | H | H |
| 169. | 2 | S | H | $C_6H_{11}$ | H | $CH_3$ | H | H |
| 170. | 2 | S | H | $C_6H_{11}$ | H | $CH(CH_3)_2$ | H | H |
| 171. | 2 | S | H | $C_6H_{11}$ | H | $CH_2CH(CH_3)_2$ | H | H |
| 172. | 2 | S | H | $C_6H_{11}$ | H | $C_6H_{11}$ | H | H |
| 173. | 2 | S | H | $C_6H_{11}$ | H | Ph | H | H |
| 174. | 2 | S | H | $C_6H_{11}$ | H | 2,6-dimethylphenyl | H | H |
| 175. | 2 | S | H | $C_6H_{11}$ | H | 2,6-diisopropylphenyl | H | H |
| 176. | 2 | S | H | Ph | H | $CH_3$ | H | H |
| 177. | 2 | S | H | Ph | H | $CH(CH_3)_2$ | H | H |
| 178. | 2 | S | H | Ph | H | $CH_2CH(CH_3)_2$ | H | H |
| 179. | 2 | S | H | Ph | H | $C_6H_{11}$ | H | H |
| 180. | 2 | S | H | Ph | H | Ph | H | H |
| 181. | 2 | S | H | Ph | H | 2,6-dimethylphenyl | H | H |
| 182. | 2 | S | H | Ph | H | 2,6-diisopropylphenyl | H | H |
| 183. | 2 | S | H | 2,6-dimethylphenyl | H | $CH_3$ | H | H |
| 184. | 2 | S | H | 2,6-dimethylphenyl | H | $CH(CH_3)_2$ | H | H |
| 185. | 2 | S | H | 2,6-dimethylphenyl | H | $CH_2CH(CH_3)_2$ | H | H |
| 186. | 2 | S | H | 2,6-dimethylphenyl | H | $C_6H_{11}$ | H | H |
| 187. | 2 | S | H | 2,6-dimethylphenyl | H | Ph | H | H |
| 188. | 2 | S | H | 2,6-dimethylphenyl | H | 2,6-dimethylphenyl | H | H |
| 189. | 2 | S | H | 2,6-dimethylphenyl | H | 2,6-diisopropylphenyl | H | H |
| 190. | 2 | S | H | 2,6-diisopropylphenyl | H | $CH_3$ | H | H |
| 191. | 2 | S | H | 2,6-diisopropylphenyl | H | $CH(CH_3)_2$ | H | H |
| 192. | 2 | S | H | 2,6-diisopropylphenyl | H | $CH_2CH(CH_3)_2$ | H | H |
| 193. | 2 | S | H | 2,6-diisopropylphenyl | H | $C_6H_{11}$ | H | H |
| 194. | 2 | S | H | 2,6-diisopropylphenyl | H | Ph | H | H |
| 195. | 2 | S | H | 2,6-diisopropylphenyl | H | 2,6-dimethylphenyl | H | H |
| 196. | 2 | S | H | 2,6-diisopropylphenyl | H | 2,6-diisopropylphenyl | H | H |

In one embodiment, the compounds of Formula IX have the following compositions:

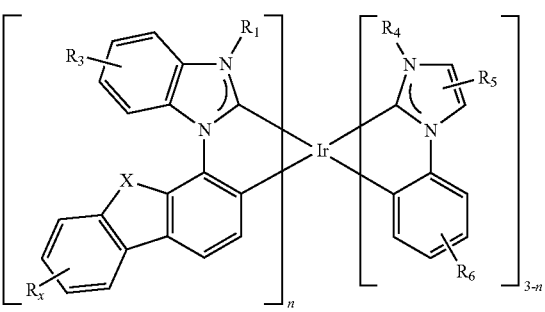

Formula IX

| Compd. | n | X | $R_x$ | $R_1$ | $R_3$ | $R_4$ | $R_5$ | $R_6$ |
|---|---|---|---|---|---|---|---|---|
| 197. | 1 | O | H | $CH_3$ | H | $CH_3$ | H | H |
| 198. | 1 | O | H | $CH_3$ | H | $CH(CH_3)_2$ | H | H |
| 199. | 1 | O | H | $CH_3$ | H | $CH_2CH(CH_3)_2$ | H | H |
| 200. | 1 | O | H | $CH_3$ | H | $C_6H_{11}$ | H | H |
| 201. | 1 | O | H | $CH_3$ | H | Ph | H | H |
| 202. | 1 | O | H | $CH_3$ | H | 2,6-dimethylphenyl | H | H |
| 203. | 1 | O | H | $CH_3$ | H | 2,6-diisopropylphenyl | H | H |
| 204. | 1 | O | H | $CH(CH_3)_2$ | H | $CH_3$ | H | H |
| 205. | 1 | O | H | $CH(CH_3)_2$ | H | $CH(CH_3)_2$ | H | H |
| 206. | 1 | O | H | $CH(CH_3)_2$ | H | $CH_2CH(CH_3)_2$ | H | H |
| 207. | 1 | O | H | $CH(CH_3)_2$ | H | $C_6H_{11}$ | H | H |

-continued

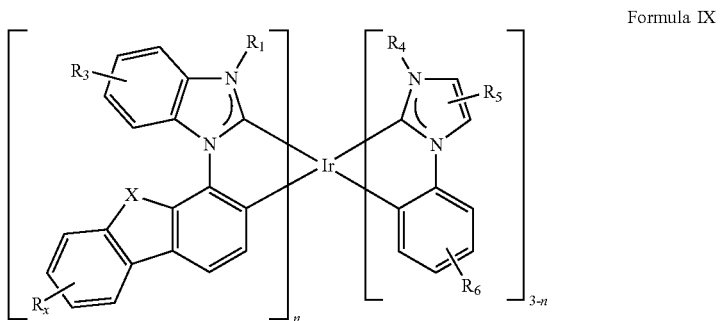

Formula IX

| Compd. | n | X | $R_x$ | $R_1$ | $R_3$ | $R_4$ | $R_5$ | $R_6$ |
|---|---|---|---|---|---|---|---|---|
| 208. | 1 | O | H | CH(CH$_3$)$_2$ | H | Ph | H | H |
| 209. | 1 | O | H | CH(CH$_3$)$_2$ | H | 2,6-dimethylphenyl | H | H |
| 210. | 1 | O | H | CH(CH$_3$)$_2$ | H | 2,6-diisopropylphenyl | H | H |
| 211. | 1 | O | H | CH$_2$CH(CH$_3$)$_2$ | H | CH$_3$ | H | H |
| 212. | 1 | O | H | CH$_2$CH(CH$_3$)$_2$ | H | CH(CH$_3$)$_2$ | H | H |
| 213. | 1 | O | H | CH$_2$CH(CH$_3$)$_2$ | H | CH$_2$CH(CH$_3$)$_2$ | H | H |
| 214. | 1 | O | H | CH$_2$CH(CH$_3$)$_2$ | H | C$_6$H$_{11}$ | H | H |
| 215. | 1 | O | H | CH$_2$CH(CH$_3$)$_2$ | H | Ph | H | H |
| 216. | 1 | O | H | CH$_2$CH(CH$_3$)$_2$ | H | 2,6-dimethylphenyl | H | H |
| 217. | 1 | O | H | CH$_2$CH(CH$_3$)$_2$ | H | 2,6-diisopropylphenyl | H | H |
| 218. | 1 | O | H | C$_6$H$_{11}$ | H | CH$_3$ | H | H |
| 219. | 1 | O | H | C$_6$H$_{11}$ | H | CH(CH$_3$)$_2$ | H | H |
| 220. | 1 | O | H | C$_6$H$_{11}$ | H | CH$_2$CH(CH$_3$)$_2$ | H | H |
| 221. | 1 | O | H | C$_6$H$_{11}$ | H | C$_6$H$_{11}$ | H | H |
| 222. | 1 | O | H | C$_6$H$_{11}$ | H | Ph | H | H |
| 223. | 1 | O | H | C$_6$H$_{11}$ | H | 2,6-dimethylphenyl | H | H |
| 224. | 1 | O | H | C$_6$H$_{11}$ | H | 2,6-diisopropylphenyl | H | H |
| 225. | 1 | O | H | Ph | H | CH$_3$ | H | H |
| 226. | 1 | O | H | Ph | H | CH(CH$_3$)$_2$ | H | H |
| 227. | 1 | O | H | Ph | H | CH$_2$CH(CH$_3$)$_2$ | H | H |
| 228. | 1 | O | H | Ph | H | C$_6$H$_{11}$ | H | H |
| 229. | 1 | O | H | Ph | H | Ph | H | H |
| 230. | 1 | O | H | Ph | H | 2,6-dimethylphenyl | H | H |
| 231. | 1 | O | H | Ph | H | 2,6-diisopropylphenyl | H | H |
| 232. | 1 | O | H | 2,6-dimethylphenyl | H | CH$_3$ | H | H |
| 233. | 1 | O | H | 2,6-dimethylphenyl | H | CH(CH$_3$)$_2$ | H | H |
| 234. | 1 | O | H | 2,6-dimethylphenyl | H | CH$_2$CH(CH$_3$)$_2$ | H | H |
| 235. | 1 | O | H | 2,6-dimethylphenyl | H | C$_6$H$_{11}$ | H | H |
| 236. | 1 | O | H | 2,6-dimethylphenyl | H | Ph | H | H |
| 237. | 1 | O | H | 2,6-dimethylphenyl | H | 2,6-dimethylphenyl | H | H |
| 238. | 1 | O | H | 2,6-dimethylphenyl | H | 2,6-diisopropylphenyl | H | H |
| 239. | 1 | O | H | 2,6-diisopropylphenyl | H | CH$_3$ | H | H |
| 240. | 1 | O | H | 2,6-diisopropylphenyl | H | CH(CH$_3$)$_2$ | H | H |
| 241. | 1 | O | H | 2,6-diisopropylphenyl | H | CH$_2$CH(CH$_3$)$_2$ | H | H |
| 242. | 1 | O | H | 2,6-diisopropylphenyl | H | C$_6$H$_{11}$ | H | H |
| 243. | 1 | O | H | 2,6-diisopropylphenyl | H | Ph | H | H |
| 244. | 1 | O | H | 2,6-diisopropylphenyl | H | 2,6-dimethylphenyl | H | H |

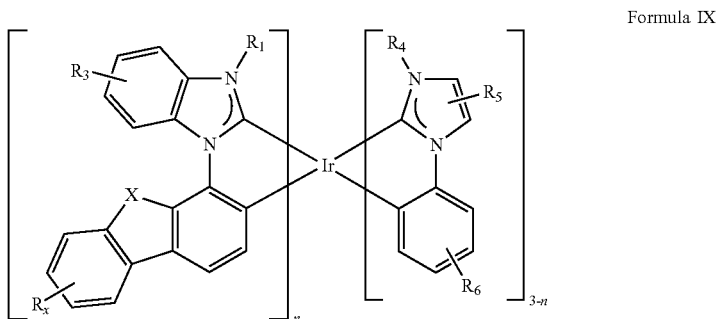

Formula IX

| Compd. | n | X | $R_x$ | $R_1$ | $R_3$ | $R_4$ | $R_5$ | $R_6$ |
|---|---|---|---|---|---|---|---|---|
| 245. | 1 | O | H | 2,6-diisopropylphenyl | H | 2,6-diisopropylphenyl | H | H |
| 246. | 1 | S | H | $CH_3$ | H | $CH_3$ | H | H |
| 247. | 1 | S | H | $CH_3$ | H | $CH(CH_3)_2$ | H | H |
| 248. | 1 | S | H | $CH_3$ | H | $CH_2CH(CH_3)_2$ | H | H |
| 249. | 1 | S | H | $CH_3$ | H | $C_6H_{11}$ | H | H |
| 250. | 1 | S | H | $CH_3$ | H | Ph | H | H |
| 251. | 1 | S | H | $CH_3$ | H | 2,6-dimethylphenyl | H | H |
| 252. | 1 | S | H | $CH_3$ | H | 2,6-diisopropylphenyl | H | H |
| 253. | 1 | S | H | $CH(CH_3)_2$ | H | $CH_3$ | H | H |
| 254. | 1 | S | H | $CH(CH_3)_2$ | H | $CH(CH_3)_2$ | H | H |
| 255. | 1 | S | H | $CH(CH_3)_2$ | H | $CH_2CH(CH_3)_2$ | H | H |
| 256. | 1 | S | H | $CH(CH_3)_2$ | H | $C_6H_{11}$ | H | H |
| 257. | 1 | S | H | $CH(CH_3)_2$ | H | Ph | H | H |
| 258. | 1 | S | H | $CH(CH_3)_2$ | H | 2,6-dimethylphenyl | H | H |
| 259. | 1 | S | H | $CH(CH_3)_2$ | H | 2,6-diisopropylphenyl | H | H |
| 260. | 1 | S | H | $CH_2CH(CH_3)_2$ | H | $CH_3$ | H | H |
| 261. | 1 | S | H | $CH_2CH(CH_3)_2$ | H | $CH(CH_3)_2$ | H | H |
| 262. | 1 | S | H | $CH_2CH(CH_3)_2$ | H | $CH_2CH(CH_3)_2$ | H | H |
| 263. | 1 | S | H | $CH_2CH(CH_3)_2$ | H | $C_6H_{11}$ | H | H |
| 264. | 1 | S | H | $CH_2CH(CH_3)_2$ | H | Ph | H | H |
| 265. | 1 | S | H | $CH_2CH(CH_3)_2$ | H | 2,6-dimethylphenyl | H | H |
| 266. | 1 | S | H | $CH_2CH(CH_3)_2$ | H | 2,6-diisopropylphenyl | H | H |
| 267. | 1 | S | H | $C_6H_{11}$ | H | $CH_3$ | H | H |
| 268. | 1 | S | H | $C_6H_{11}$ | H | $CH(CH_3)_2$ | H | H |
| 269. | 1 | S | H | $C_6H_{11}$ | H | $CH_2CH(CH_3)_2$ | H | H |
| 270. | 1 | S | H | $C_6H_{11}$ | H | $C_6H_{11}$ | H | H |
| 271. | 1 | S | H | $C_6H_{11}$ | H | Ph | H | H |
| 272. | 1 | S | H | $C_6H_{11}$ | H | 2,6-dimethylphenyl | H | H |
| 273. | 1 | S | H | $C_6H_{11}$ | H | 2,6-diisopropylphenyl | H | H |
| 274. | 1 | S | H | Ph | H | $CH_3$ | H | H |
| 275. | 1 | S | H | Ph | H | $CH(CH_3)_2$ | H | H |
| 276. | 1 | S | H | Ph | H | $CH_2CH(CH_3)_2$ | H | H |
| 277. | 1 | S | H | Ph | H | $C_6H_{11}$ | H | H |
| 278. | 1 | S | H | Ph | H | Ph | H | H |
| 279. | 1 | S | H | Ph | H | 2,6-dimethylphenyl | H | H |
| 280. | 1 | S | H | Ph | H | 2,6-diisopropylphenyl | H | H |
| 281. | 1 | S | H | 2,6-dimethylphenyl | H | $CH_3$ | H | H |
| 282. | 1 | S | H | 2,6-dimethylphenyl | H | $CH(CH_3)_2$ | H | H |
| 283. | 1 | S | H | 2,6-dimethylphenyl | H | $CH_2CH(CH_3)_2$ | H | H |
| 284. | 1 | S | H | 2,6-dimethylphenyl | H | $C_6H_{11}$ | H | H |
| 285. | 1 | S | H | 2,6-dimethylphenyl | H | Ph | H | H |
| 286. | 1 | S | H | 2,6-dimethylphenyl | H | 2,6-dimethylphenyl | H | H |

-continued

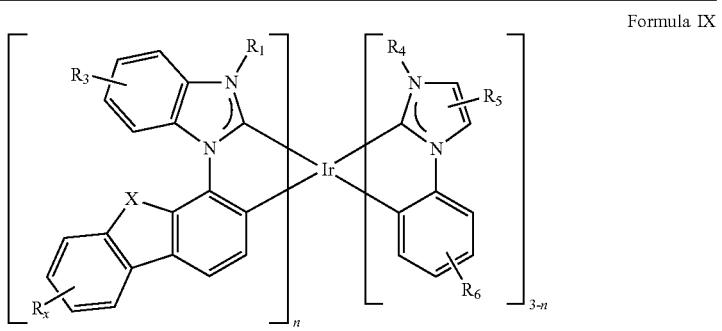

Formula IX

| Compd. | n | X | $R_x$ | $R_1$ | $R_3$ | $R_4$ | $R_5$ | $R_6$ |
|---|---|---|---|---|---|---|---|---|
| 287. | 1 | S | H | 2,6-dimethylphenyl | H | 2,6-diisopropylphenyl | H | H |
| 288. | 1 | S | H | 2,6-diisopropylphenyl | H | $CH_3$ | H | H |
| 289. | 1 | S | H | 2,6-diisopropylphenyl | H | $CH(CH_3)_2$ | H | H |
| 290. | 1 | S | H | 2,6-diisopropylphenyl | H | $CH_2CH(CH_3)_2$ | H | H |
| 291. | 1 | S | H | 2,6-diisopropylphenyl | H | $C_6H_{11}$ | H | H |
| 292. | 1 | S | H | 2,6-diisopropylphenyl | H | Ph | H | H |
| 293. | 1 | S | H | 2,6-diisopropylphenyl | H | 2,6-dimethylphenyl | H | H |
| 294. | 1 | S | H | 2,6-diisopropylphenyl | H | 2,6-diisopropylphenyl | H | H |
| 295. | 2 | O | H | $CH_3$ | H | $CH_3$ | H | H |
| 296. | 2 | O | H | $CH_3$ | H | $CH(CH_3)_2$ | H | H |
| 297. | 2 | O | H | $CH_3$ | H | $CH_2CH(CH_3)_2$ | H | H |
| 298. | 2 | O | H | $CH_3$ | H | $C_6H_{11}$ | H | H |
| 299. | 2 | O | H | $CH_3$ | H | Ph | H | H |
| 300. | 2 | O | H | $CH_3$ | H | 2,6-dimethylphenyl | H | H |
| 301. | 2 | O | H | $CH_3$ | H | 2,6-diisopropylphenyl | H | H |
| 302. | 2 | O | H | $CH(CH_3)_2$ | H | $CH_3$ | H | H |
| 303. | 2 | O | H | $CH(CH_3)_2$ | H | $CH(CH_3)_2$ | H | H |
| 304. | 2 | O | H | $CH(CH_3)_2$ | H | $CH_2CH(CH_3)_2$ | H | H |
| 305. | 2 | O | H | $CH(CH_3)_2$ | H | $C_6H_{11}$ | H | H |
| 306. | 2 | O | H | $CH(CH_3)_2$ | H | Ph | H | H |
| 307. | 2 | O | H | $CH(CH_3)_2$ | H | 2,6-dimethylphenyl | H | H |
| 308. | 2 | O | H | $CH(CH_3)_2$ | H | 2,6-diisopropylphenyl | H | H |
| 309. | 2 | O | H | $CH_2CH(CH_3)_2$ | H | $CH_3$ | H | H |
| 310. | 2 | O | H | $CH_2CH(CH_3)_2$ | H | $CH(CH_3)_2$ | H | H |
| 311. | 2 | O | H | $CH_2CH(CH_3)_2$ | H | $CH_2CH(CH_3)_2$ | H | H |
| 312. | 2 | O | H | $CH_2CH(CH_3)_2$ | H | $C_6H_{11}$ | H | H |
| 313. | 2 | O | H | $CH_2CH(CH_3)_2$ | H | Ph | H | H |
| 314. | 2 | O | H | $CH_2CH(CH_3)_2$ | H | 2,6-dimethylphenyl | H | H |
| 315. | 2 | O | H | $CH_2CH(CH_3)_2$ | H | 2,6-diisopropylphenyl | H | H |
| 316. | 2 | O | H | $C_6H_{11}$ | H | $CH_3$ | H | H |
| 317. | 2 | O | H | $C_6H_{11}$ | H | $CH(CH_3)_2$ | H | H |
| 318. | 2 | O | H | $C_6H_{11}$ | H | $CH_2CH(CH_3)_2$ | H | H |
| 319. | 2 | O | H | $C_6H_{11}$ | H | $C_6H_{11}$ | H | H |
| 320. | 2 | O | H | $C_6H_{11}$ | H | Ph | H | H |
| 321. | 2 | O | H | $C_6H_{11}$ | H | 2,6-dimethylphenyl | H | H |
| 322. | 2 | O | H | $C_6H_{11}$ | H | 2,6-diisopropylphenyl | H | H |
| 323. | 2 | O | H | Ph | H | $CH_3$ | H | H |
| 324. | 2 | O | H | Ph | H | $CH(CH_3)_2$ | H | H |
| 325. | 2 | O | H | Ph | H | $CH_2CH(CH_3)_2$ | H | H |
| 326. | 2 | O | H | Ph | H | $C_6H_{11}$ | H | H |
| 327. | 2 | O | H | Ph | H | Ph | H | H |
| 328. | 2 | O | H | Ph | H | 2,6-dimethylphenyl | H | H |

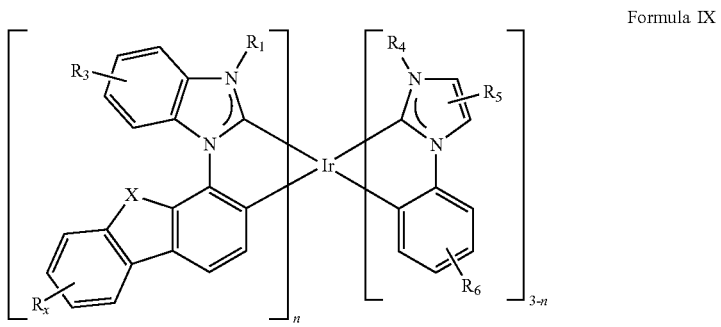

Formula IX

| Compd. | n | X | $R_x$ | $R_1$ | $R_3$ | $R_4$ | $R_5$ | $R_6$ |
|---|---|---|---|---|---|---|---|---|
| 329. | 2 | O | H | Ph | H | 2,6-diisopropylphenyl | H | H |
| 330. | 2 | O | H | 2,6-dimethylphenyl | H | $CH_3$ | H | H |
| 331. | 2 | O | H | 2,6-dimethylphenyl | H | $CH(CH_3)_2$ | H | H |
| 332. | 2 | O | H | 2,6-dimethylphenyl | H | $CH_2CH(CH_3)_2$ | H | H |
| 333. | 2 | O | H | 2,6-dimethylphenyl | H | $C_6H_{11}$ | H | H |
| 334. | 2 | O | H | 2,6-dimethylphenyl | H | Ph | H | H |
| 335. | 2 | O | H | 2,6-dimethylphenyl | H | 2,6-dimethylphenyl | H | H |
| 336. | 2 | O | H | 2,6-dimethylphenyl | H | 2,6-diisopropylphenyl | H | H |
| 337. | 2 | O | H | 2,6-diisopropylphenyl | H | $CH_3$ | H | H |
| 338. | 2 | O | H | 2,6-diisopropylphenyl | H | $CH(CH_3)_2$ | H | H |
| 339. | 2 | O | H | 2,6-diisopropylphenyl | H | $CH_2CH(CH_3)_2$ | H | H |
| 340. | 2 | O | H | 2,6-diisopropylphenyl | H | $C_6H_{11}$ | H | H |
| 341. | 2 | O | H | 2,6-diisopropylphenyl | H | Ph | H | H |
| 342. | 2 | O | H | 2,6-diisopropylphenyl | H | 2,6-dimethylphenyl | H | H |
| 343. | 2 | O | H | 2,6-diisopropylphenyl | H | 2,6-diisopropylphenyl | H | H |
| 344. | 2 | S | H | $CH_3$ | H | $CH_3$ | H | H |
| 345. | 2 | S | H | $CH_3$ | H | $CH(CH_3)_2$ | H | H |
| 346. | 2 | S | H | $CH_3$ | H | $CH_2CH(CH_3)_2$ | H | H |
| 347. | 2 | S | H | $CH_3$ | H | $C_6H_{11}$ | H | H |
| 348. | 2 | S | H | $CH_3$ | H | Ph | H | H |
| 349. | 2 | S | H | $CH_3$ | H | 2,6-dimethylphenyl | H | H |
| 350. | 2 | S | H | $CH_3$ | H | 2,6-diisopropylphenyl | H | H |
| 351. | 2 | S | H | $CH(CH_3)_2$ | H | $CH_3$ | H | H |
| 352. | 2 | S | H | $CH(CH_3)_2$ | H | $CH(CH_3)_2$ | H | H |
| 353. | 2 | S | H | $CH(CH_3)_2$ | H | $CH_2CH(CH_3)_2$ | H | H |
| 354. | 2 | S | H | $CH(CH_3)_2$ | H | $C_6H_{11}$ | H | H |
| 355. | 2 | S | H | $CH(CH_3)_2$ | H | Ph | H | H |
| 356. | 2 | S | H | $CH(CH_3)_2$ | H | 2,6-dimethylphenyl | H | H |
| 357. | 2 | S | H | $CH(CH_3)_2$ | H | 2,6-diisopropylphenyl | H | H |
| 358. | 2 | S | H | $CH_2CH(CH_3)_2$ | H | $CH_3$ | H | H |
| 359. | 2 | S | H | $CH_2CH(CH_3)_2$ | H | $CH(CH_3)_2$ | H | H |
| 360. | 2 | S | H | $CH_2CH(CH_3)_2$ | H | $CH_2CH(CH_3)_2$ | H | H |
| 361. | 2 | S | H | $CH_2CH(CH_3)_2$ | H | $C_6H_{11}$ | H | H |
| 362. | 2 | S | H | $CH_2CH(CH_3)_2$ | H | Ph | H | H |
| 363. | 2 | S | H | $CH_2CH(CH_3)_2$ | H | 2,6-dimethylphenyl | H | H |
| 364. | 2 | S | H | $CH_2CH(CH_3)_2$ | H | 2,6-diisopropylphenyl | H | H |

-continued

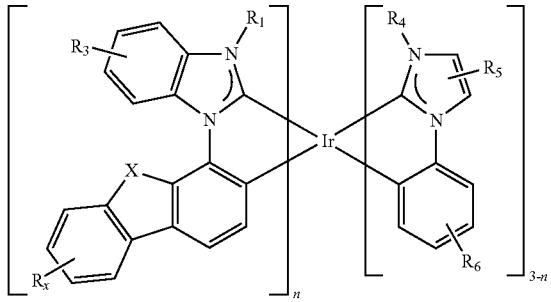

Formula IX

Formula IX

| Compd. | n | X | Rₓ | R₁ | R₃ | R₄ | R₅ | R₆ |
|---|---|---|---|---|---|---|---|---|
| 365. | 2 | S | H | $C_6H_{11}$ | H | $CH_3$ | H | H |
| 366. | 2 | S | H | $C_6H_{11}$ | H | $CH(CH_3)_2$ | H | H |
| 367. | 2 | S | H | $C_6H_{11}$ | H | $CH_2CH(CH_3)_2$ | H | H |
| 368. | 2 | S | H | $C_6H_{11}$ | H | $C_6H_{11}$ | H | H |
| 369. | 2 | S | H | $C_6H_{11}$ | H | Ph | H | H |
| 370. | 2 | S | H | $C_6H_{11}$ | H | 2,6-dimethylphenyl | H | H |
| 371. | 2 | S | H | $C_6H_{11}$ | H | 2,6-diisopropylphenyl | H | H |
| 372. | 2 | S | H | Ph | H | $CH_3$ | H | H |
| 373. | 2 | S | H | Ph | H | $CH(CH_3)_2$ | H | H |
| 374. | 2 | S | H | Ph | H | $CH_2CH(CH_3)_2$ | H | H |
| 375. | 2 | S | H | Ph | H | $C_6H_{11}$ | H | H |
| 376. | 2 | S | H | Ph | H | Ph | H | H |
| 377. | 2 | S | H | Ph | H | 2,6-dimethylphenyl | H | H |
| 378. | 2 | S | H | Ph | H | 2,6-diisopropylphenyl | H | H |
| 389. | 2 | S | H | 2,6-dimethylphenyl | H | $CH_3$ | H | H |
| 380. | 2 | S | H | 2,6-dimethylphenyl | H | $CH(CH_3)_2$ | H | H |
| 381. | 2 | S | H | 2,6-dimethylphenyl | H | $CH_2CH(CH_3)_2$ | H | H |
| 382. | 2 | S | H | 2,6-dimethylphenyl | H | $C_6H_{11}$ | H | H |
| 383. | 2 | S | H | 2,6-dimethylphenyl | H | Ph | H | H |
| 384. | 2 | S | H | 2,6-dimethylphenyl | H | 2,6-dimethylphenyl | H | H |
| 385. | 2 | S | H | 2,6-dimethylphenyl | H | 2,6-diisopropylphenyl | H | H |
| 386. | 2 | S | H | 2,6-diisopropylphenyl | H | $CH_3$ | H | H |
| 387. | 2 | S | H | 2,6-diisopropylphenyl | H | $CH(CH_3)_2$ | H | H |
| 388. | 2 | S | H | 2,6-diisopropylphenyl | H | $CH_2CH(CH_3)_2$ | H | H |
| 389. | 2 | S | H | 2,6-diisopropylphenyl | H | $C_6H_{11}$ | H | H |
| 390. | 2 | S | H | 2,6-diisopropylphenyl | H | Ph | H | H |

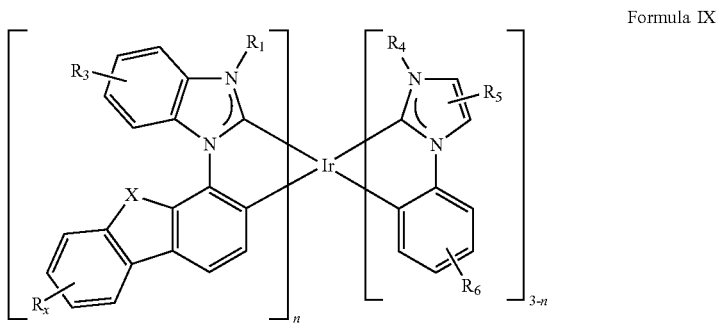

Formula IX

| Compd. | n | X | $R_x$ | $R_1$ | $R_3$ | $R_4$ | $R_5$ | $R_6$ |
|---|---|---|---|---|---|---|---|---|
| 391. | 2 | S | H | 2,6-diisopropylphenyl | H | 2,6-dimethylphenyl | H | H |
| 392. | 2 | S | H | 2,6-diisopropylphenyl | H | 2,6-diisopropylphenyl | H | H |

In one embodiment, the compound of Formula VI has the following composition:

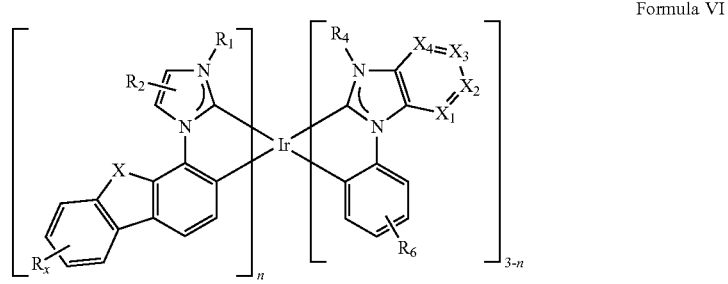

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 393. | 1 | O | H | $CH_3$ | H | $CH_3$ | H | H | CH | CH | CH | CH |
| 394. | 1 | O | H | $CH_3$ | H | $CH(CH_3)_2$ | H | H | CH | CH | CH | CH |
| 395. | 1 | O | H | $CH_3$ | H | $CH_2CH(CH_3)_2$ | H | H | CH | CH | CH | CH |
| 396. | 1 | O | H | $CH_3$ | H | $C_6H_{11}$ | H | H | CH | CH | CH | CH |
| 397. | 1 | O | H | $CH_3$ | H | Ph | H | H | CH | CH | CH | CH |
| 398. | 1 | O | H | $CH_3$ | H | 2,6-dimethylphenyl | H | H | CH | CH | CH | CH |
| 399. | 1 | O | H | $CH_3$ | H | 2,6-diisopropylphenyl | H | H | CH | CH | CH | CH |
| 400. | 1 | O | H | $CH(CH_3)_2$ | H | $CH_3$ | H | H | CH | CH | CH | CH |
| 401. | 1 | O | H | $CH(CH_3)_2$ | H | $CH(CH_3)_2$ | H | H | CH | CH | CH | CH |
| 402. | 1 | O | H | $CH(CH_3)_2$ | H | $CH_2CH(CH_3)_2$ | H | H | CH | CH | CH | CH |
| 403. | 1 | O | H | $CH(CH_3)_2$ | H | $C_6H_{11}$ | H | H | CH | CH | CH | CH |
| 404. | 1 | O | H | $CH(CH_3)_2$ | H | Ph | H | H | CH | CH | CH | CH |
| 405. | 1 | O | H | $CH(CH_3)_2$ | H | 2,6-dimethylphenyl | H | H | CH | CH | CH | CH |
| 406. | 1 | O | H | $CH(CH_3)_2$ | H | 2,6-diisopropylphenyl | H | H | CH | CH | CH | CH |
| 407. | 1 | O | H | $CH_2CH(CH_3)_2$ | H | $CH_3$ | H | H | CH | CH | CH | CH |
| 408. | 1 | O | H | $CH_2CH(CH_3)_2$ | H | $CH(CH_3)_2$ | H | H | CH | CH | CH | CH |
| 409. | 1 | O | H | $CH_2CH(CH_3)_2$ | H | $CH_2CH(CH_3)_2$ | H | H | CH | CH | CH | CH |
| 410. | 1 | O | H | $CH_2CH(CH_3)_2$ | H | $C_6H_{11}$ | H | H | CH | CH | CH | CH |
| 411. | 1 | O | H | $CH_2CH(CH_3)_2$ | H | Ph | H | H | CH | CH | CH | CH |
| 412. | 1 | O | H | $CH_2CH(CH_3)_2$ | H | 2,6-dimethylphenyl | H | H | CH | CH | CH | CH |
| 413. | 1 | O | H | $CH_2CH(CH_3)_2$ | H | 2,6-diisopropylphenyl | H | H | CH | CH | CH | CH |
| 414. | 1 | O | H | $C_6H_{11}$ | H | $CH_3$ | H | H | CH | CH | CH | CH |
| 415. | 1 | O | H | $C_6H_{11}$ | H | $CH(CH_3)_2$ | H | H | CH | CH | CH | CH |

-continued

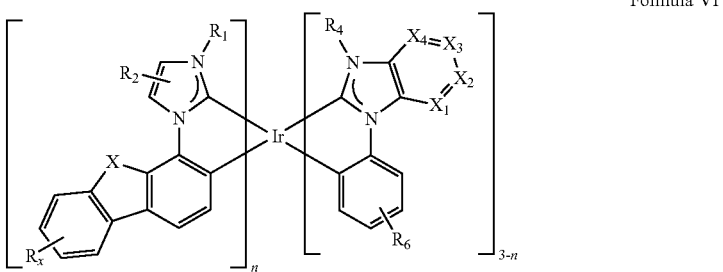

Formula VI

| Compd. | n | X | R$_x$ | R$_1$ | R$_2$ | R$_4$ | R$_5$ | R$_6$ | X$_1$ | X$_2$ | X$_3$ | X$_4$ |
|---|---|---|---|---|---|---|---|---|---|---|---|---|
| 416. | 1 | O | H | C$_6$H$_{11}$ | H | CH$_2$CH(CH$_3$)$_2$ | H | H | CH | CH | CH | CH |
| 417. | 1 | O | H | C$_6$H$_{11}$ | H | C$_6$H$_{11}$ | H | H | CH | CH | CH | CH |
| 418. | 1 | O | H | C$_6$H$_{11}$ | H | Ph | H | H | CH | CH | CH | CH |
| 419. | 1 | O | H | C$_6$H$_{11}$ | H | 2,6-dimethylphenyl | H | H | CH | CH | CH | CH |
| 420. | 1 | O | H | C$_6$H$_{11}$ | H | 2,6-diisopropylphenyl | H | H | CH | CH | CH | CH |
| 421. | 1 | O | H | Ph | H | CH$_3$ | H | H | CH | CH | CH | CH |
| 422. | 1 | O | H | Ph | H | CH(CH$_3$)$_2$ | H | H | CH | CH | CH | CH |
| 423. | 1 | O | H | Ph | H | CH$_2$CH(CH$_3$)$_2$ | H | H | CH | CH | CH | CH |
| 424. | 1 | O | H | Ph | H | C$_6$H$_{11}$ | H | H | CH | CH | CH | CH |
| 425. | 1 | O | H | Ph | H | Ph | H | H | CH | CH | CH | CH |
| 426. | 1 | O | H | Ph | H | 2,6-dimethylphenyl | H | H | CH | CH | CH | CH |
| 427. | 1 | O | H | Ph | H | 2,6-diisopropylphenyl | H | H | CH | CH | CH | CH |
| 428. | 1 | O | H | 2,6-dimethylphenyl | H | CH$_3$ | H | H | CH | CH | CH | CH |
| 429. | 1 | O | H | 2,6-dimethylphenyl | H | CH(CH$_3$)$_2$ | H | H | CH | CH | CH | CH |
| 430. | 1 | O | H | 2,6-dimethylphenyl | H | CH$_2$CH(CH$_3$)$_2$ | H | H | CH | CH | CH | CH |
| 431. | 1 | O | H | 2,6-dimethylphenyl | H | C$_6$H$_{11}$ | H | H | CH | CH | CH | CH |
| 432. | 1 | O | H | 2,6-dimethylphenyl | H | Ph | H | H | CH | CH | CH | CH |
| 433. | 1 | O | H | 2,6-dimethylphenyl | H | 2,6-dimethylphenyl | H | H | CH | CH | CH | CH |
| 434. | 1 | O | H | 2,6-dimethylphenyl | H | 2,6-diisopropylphenyl | H | H | CH | CH | CH | CH |
| 435. | 1 | O | H | 2,6-diisopropylphenyl | H | CH$_3$ | H | H | CH | CH | CH | CH |
| 436. | 1 | O | H | 2,6-diisopropylphenyl | H | CH(CH$_3$)$_2$ | H | H | CH | CH | CH | CH |
| 437. | 1 | O | H | 2,6-diisopropylphenyl | H | CH$_2$CH(CH$_3$)$_2$ | H | H | CH | CH | CH | CH |
| 438. | 1 | O | H | 2,6-diisopropylphenyl | H | C$_6$H$_{11}$ | H | H | CH | CH | CH | CH |
| 439. | 1 | O | H | 2,6-diisopropylphenyl | H | Ph | H | H | CH | CH | CH | CH |
| 440. | 1 | O | H | 2,6-diisopropylphenyl | H | 2,6-dimethylphenyl | H | H | CH | CH | CH | CH |
| 441. | 1 | O | H | 2,6-diisopropylphenyl | H | 2,6-diisopropylphenyl | H | H | CH | CH | CH | CH |
| 442. | 1 | S | H | CH$_3$ | H | CH$_3$ | H | H | CH | CH | CH | CH |
| 443. | 1 | S | H | CH$_3$ | H | CH(CH$_3$)$_2$ | H | H | CH | CH | CH | CH |
| 444. | 1 | S | H | CH$_3$ | H | CH$_2$CH(CH$_3$)$_2$ | H | H | CH | CH | CH | CH |
| 445. | 1 | S | H | CH$_3$ | H | C$_6$H$_{11}$ | H | H | CH | CH | CH | CH |
| 446. | 1 | S | H | CH$_3$ | H | Ph | H | H | CH | CH | CH | CH |
| 447. | 1 | S | H | CH$_3$ | H | 2,6-dimethylphenyl | H | H | CH | CH | CH | CH |
| 448. | 1 | S | H | CH$_3$ | H | 2,6-diisopropylphenyl | H | H | CH | CH | CH | CH |
| 449. | 1 | S | H | CH(CH$_3$)$_2$ | H | CH$_3$ | H | H | CH | CH | CH | CH |
| 450. | 1 | S | H | CH(CH$_3$)$_2$ | H | CH(CH$_3$)$_2$ | H | H | CH | CH | CH | CH |
| 451. | 1 | S | H | CH(CH$_3$)$_2$ | H | CH$_2$CH(CH$_3$)$_2$ | H | H | CH | CH | CH | CH |
| 452. | 1 | S | H | CH(CH$_3$)$_2$ | H | C$_6$H$_{11}$ | H | H | CH | CH | CH | CH |
| 453. | 1 | S | H | CH(CH$_3$)$_2$ | H | Ph | H | H | CH | CH | CH | CH |
| 454. | 1 | S | H | CH(CH$_3$)$_2$ | H | 2,6-dimethylphenyl | H | H | CH | CH | CH | CH |

-continued

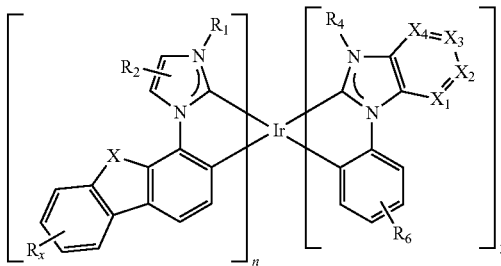

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 455. | 1 | S | H | $CH(CH_3)_2$ | H | 2,6-diisopropylphenyl | H | H | CH | CH | CH | CH |
| 456. | 1 | S | H | $CH_2CH(CH_3)_2$ | H | $CH_3$ | H | H | CH | CH | CH | CH |
| 457. | 1 | S | H | $CH_2CH(CH_3)_2$ | H | $CH(CH_3)_2$ | H | H | CH | CH | CH | CH |
| 458. | 1 | S | H | $CH_2CH(CH_3)_2$ | H | $CH_2CH(CH_3)_2$ | H | H | CH | CH | CH | CH |
| 459. | 1 | S | H | $CH_2CH(CH_3)_2$ | H | $C_6H_{11}$ | H | H | CH | CH | CH | CH |
| 460. | 1 | S | H | $CH_2CH(CH_3)_2$ | H | Ph | H | H | CH | CH | CH | CH |
| 461. | 1 | S | H | $CH_2CH(CH_3)_2$ | H | 2,6-dimethylphenyl | H | H | CH | CH | CH | CH |
| 462. | 1 | S | H | $CH_2CH(CH_3)_2$ | H | 2,6-diisopropylphenyl | H | H | CH | CH | CH | CH |
| 463. | 1 | S | H | $C_6H_{11}$ | H | $CH_3$ | H | H | CH | CH | CH | CH |
| 464. | 1 | S | H | $C_6H_{11}$ | H | $CH(CH_3)_2$ | H | H | CH | CH | CH | CH |
| 465. | 1 | S | H | $C_6H_{11}$ | H | $CH_2CH(CH_3)_2$ | H | H | CH | CH | CH | CH |
| 466. | 1 | S | H | $C_6H_{11}$ | H | $C_6H_{11}$ | H | H | CH | CH | CH | CH |
| 467. | 1 | S | H | $C_6H_{11}$ | H | Ph | H | H | CH | CH | CH | CH |
| 468. | 1 | S | H | $C_6H_{11}$ | H | 2,6-dimethylphenyl | H | H | CH | CH | CH | CH |
| 469. | 1 | S | H | $C_6H_{11}$ | H | 2,6-diisopropylphenyl | H | H | CH | CH | CH | CH |
| 470. | 1 | S | H | Ph | H | $CH_3$ | H | H | CH | CH | CH | CH |
| 471. | 1 | S | H | Ph | H | $CH(CH_3)_2$ | H | H | CH | CH | CH | CH |
| 472. | 1 | S | H | Ph | H | $CH_2CH(CH_3)_2$ | H | H | CH | CH | CH | CH |
| 473. | 1 | S | H | Ph | H | $C_6H_{11}$ | H | H | CH | CH | CH | CH |
| 474. | 1 | S | H | Ph | H | Ph | H | H | CH | CH | CH | CH |
| 475. | 1 | S | H | Ph | H | 2,6-dimethylphenyl | H | H | CH | CH | CH | CH |
| 476. | 1 | S | H | Ph | H | 2,6-diisopropylphenyl | H | H | CH | CH | CH | CH |
| 477. | 1 | S | H | 2,6-dimethylphenyl | H | $CH_3$ | H | H | CH | CH | CH | CH |
| 478. | 1 | S | H | 2,6-dimethylphenyl | H | $CH(CH_3)_2$ | H | H | CH | CH | CH | CH |
| 479. | 1 | S | H | 2,6-dimethylphenyl | H | $CH_2CH(CH_3)_2$ | H | H | CH | CH | CH | CH |
| 480. | 1 | S | H | 2,6-dimethylphenyl | H | $C_6H_{11}$ | H | H | CH | CH | CH | CH |
| 481. | 1 | S | H | 2,6-dimethylphenyl | H | Ph | H | H | CH | CH | CH | CH |
| 482. | 1 | S | H | 2,6-dimethylphenyl | H | 2,6-dimethylphenyl | H | H | CH | CH | CH | CH |
| 483. | 1 | S | H | 2,6-dimethylphenyl | H | 2,6-diisopropylphenyl | H | H | CH | CH | CH | CH |
| 484. | 1 | S | H | 2,6-diisopropylphenyl | H | $CH_3$ | H | H | CH | CH | CH | CH |
| 485. | 1 | S | H | 2,6-diisopropylphenyl | H | $CH(CH_3)_2$ | H | H | CH | CH | CH | CH |
| 486. | 1 | S | H | 2,6-diisopropylphenyl | H | $CH_2CH(CH_3)_2$ | H | H | CH | CH | CH | CH |
| 487. | 1 | S | H | 2,6-diisopropylphenyl | H | $C_6H_{11}$ | H | H | CH | CH | CH | CH |
| 488. | 1 | S | H | 2,6-diisopropylphenyl | H | Ph | H | H | CH | CH | CH | CH |
| 489. | 1 | S | H | 2,6-diisopropylphenyl | H | 2,6-dimethylphenyl | H | H | CH | CH | CH | CH |
| 490. | 1 | S | H | 2,6-diisopropylphenyl | H | 2,6-diisopropylphenyl | H | H | CH | CH | CH | CH |
| 491. | 2 | O | H | $CH_3$ | H | $CH_3$ | H | H | CH | CH | CH | CH |
| 492. | 2 | O | H | $CH_3$ | H | $CH(CH_3)_2$ | H | H | CH | CH | CH | CH |
| 493. | 2 | O | H | $CH_3$ | H | $CH_2CH(CH_3)_2$ | H | H | CH | CH | CH | CH |
| 494. | 2 | O | H | $CH_3$ | H | $C_6H_{11}$ | H | H | CH | CH | CH | CH |

-continued

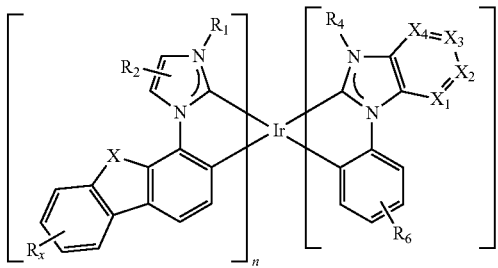

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 495. | 2 | O | H | $CH_3$ | H | Ph | H | H | CH | CH | CH | CH |
| 496. | 2 | O | H | $CH_3$ | H | 2,6-dimethylphenyl | H | H | CH | CH | CH | CH |
| 497. | 2 | O | H | $CH_3$ | H | 2,6-diisopropylphenyl | H | H | CH | CH | CH | CH |
| 498. | 2 | O | H | $CH(CH_3)_2$ | H | $CH_3$ | H | H | CH | CH | CH | CH |
| 499. | 2 | O | H | $CH(CH_3)_2$ | H | $CH(CH_3)_2$ | H | H | CH | CH | CH | CH |
| 500. | 2 | O | H | $CH(CH_3)_2$ | H | $CH_2CH(CH_3)_2$ | H | H | CH | CH | CH | CH |
| 501. | 2 | O | H | $CH(CH_3)_2$ | H | $C_6H_{11}$ | H | H | CH | CH | CH | CH |
| 502. | 2 | O | H | $CH(CH_3)_2$ | H | Ph | H | H | CH | CH | CH | CH |
| 503. | 2 | O | H | $CH(CH_3)_2$ | H | 2,6-dimethylphenyl | H | H | CH | CH | CH | CH |
| 504. | 2 | O | H | $CH(CH_3)_2$ | H | 2,6-diisopropylphenyl | H | H | CH | CH | CH | CH |
| 505. | | | | | | | | | CH | CH | CH | CH |
| 506. | 2 | O | H | $CH_2CH(CH_3)_2$ | H | $CH_3$ | H | H | CH | CH | CH | CH |
| 507. | 2 | O | H | $CH_2CH(CH_3)_2$ | H | $CH(CH_3)_2$ | H | H | CH | CH | CH | CH |
| 508. | 2 | O | H | $CH_2CH(CH_3)_2$ | H | $CH_2CH(CH_3)_2$ | H | H | CH | CH | CH | CH |
| 509. | 2 | O | H | $CH_2CH(CH_3)_2$ | H | $C_6H_{11}$ | H | H | CH | CH | CH | CH |
| 510. | 2 | O | H | $CH_2CH(CH_3)_2$ | H | Ph | H | H | CH | CH | CH | CH |
| 511. | 2 | O | H | $CH_2CH(CH_3)_2$ | H | 2,6-dimethylphenyl | H | H | CH | CH | CH | CH |
| 512. | 2 | O | H | $CH_2CH(CH_3)_2$ | H | 2,6-diisopropylphenyl | H | H | CH | CH | CH | CH |
| 513. | 2 | O | H | $C_6H_{11}$ | H | $CH_3$ | H | H | CH | CH | CH | CH |
| 514. | 2 | O | H | $C_6H_{11}$ | H | $CH(CH_3)_2$ | H | H | CH | CH | CH | CH |
| 515. | 2 | O | H | $C_6H_{11}$ | H | $CH_2CH(CH_3)_2$ | H | H | CH | CH | CH | CH |
| 516. | 2 | O | H | $C_6H_{11}$ | H | $C_6H_{11}$ | H | H | CH | CH | CH | CH |
| 517. | 2 | O | H | $C_6H_{11}$ | H | Ph | H | H | CH | CH | CH | CH |
| 518. | 2 | O | H | $C_6H_{11}$ | H | 2,6-dimethylphenyl | H | H | CH | CH | CH | CH |
| 519. | 2 | O | H | $C_6H_{11}$ | H | 2,6-diisopropylphenyl | H | H | CH | CH | CH | CH |
| 520. | 2 | O | H | Ph | H | $CH_3$ | H | H | CH | CH | CH | CH |
| 521. | 2 | O | H | Ph | H | $CH(CH_3)_2$ | H | H | CH | CH | CH | CH |
| 522. | 2 | O | H | Ph | H | $CH_2CH(CH_3)_2$ | H | H | CH | CH | CH | CH |
| 523. | 2 | O | H | Ph | H | $C_6H_{11}$ | H | H | CH | CH | CH | CH |
| 524. | 2 | O | H | Ph | H | Ph | H | H | CH | CH | CH | CH |
| 525. | 2 | O | H | Ph | H | 2,6-dimethylphenyl | H | H | CH | CH | CH | CH |
| 526. | 2 | O | H | Ph | H | 2,6-diisopropylphenyl | H | H | CH | CH | CH | CH |
| 527. | 2 | O | H | 2,6-dimethylphenyl | H | $CH_3$ | H | H | CH | CH | CH | CH |
| 528. | 2 | O | H | 2,6-dimethylphenyl | H | $CH(CH_3)_2$ | H | H | CH | CH | CH | CH |
| 529. | 2 | O | H | 2,6-dimethylphenyl | H | $CH_2CH(CH_3)_2$ | H | H | CH | CH | CH | CH |
| 530. | 2 | O | H | 2,6-dimethylphenyl | H | $C_6H_{11}$ | H | H | CH | CH | CH | CH |
| 531. | 2 | O | H | 2,6-dimethylphenyl | H | Ph | H | H | CH | CH | CH | CH |
| 532. | 2 | O | H | 2,6-dimethylphenyl | H | 2,6-dimethylphenyl | H | H | CH | CH | CH | CH |
| 533. | 2 | O | H | 2,6-dimethylphenyl | H | 2,6-diisopropylphenyl | H | H | CH | CH | CH | CH |
| 534. | 2 | O | H | 2,6-diisopropylphenyl | H | $CH_3$ | H | H | CH | CH | CH | CH |
| 535. | 2 | O | H | 2,6-diisopropylphenyl | H | $CH(CH_3)_2$ | H | H | CH | CH | CH | CH |

-continued

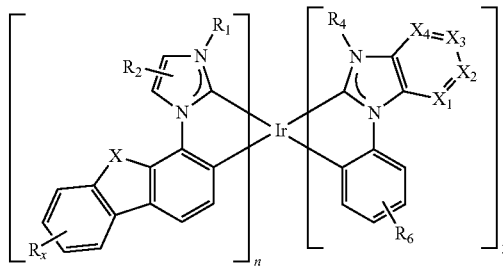

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 536. | 2 | O | H | 2,6-diisopropylphenyl | H | $CH_2CH(CH_3)_2$ | H | H | CH | CH | CH | CH |
| 537. | 2 | O | H | 2,6-diisopropylphenyl | H | $C_6H_{11}$ | H | H | CH | CH | CH | CH |
| 538. | 2 | O | H | 2,6-diisopropylphenyl | H | Ph | H | H | CH | CH | CH | CH |
| 539. | 2 | O | H | 2,6-diisopropylphenyl | H | 2,6-dimethylphenyl | H | H | CH | CH | CH | CH |
| 540. | 2 | O | H | 2,6-diisopropylphenyl | H | 2,6-diisopropylphenyl | H | H | CH | CH | CH | CH |
| 541. | 2 | S | H | $CH_3$ | H | $CH_3$ | H | H | CH | CH | CH | CH |
| 542. | 2 | S | H | $CH_3$ | H | $CH(CH_3)_2$ | H | H | CH | CH | CH | CH |
| 543. | 2 | S | H | $CH_3$ | H | $CH_2CH(CH_3)_2$ | H | H | CH | CH | CH | CH |
| 544. | 2 | S | H | $CH_3$ | H | $C_6H_{11}$ | H | H | CH | CH | CH | CH |
| 545. | 2 | S | H | $CH_3$ | H | Ph | H | H | CH | CH | CH | CH |
| 546. | 2 | S | H | $CH_3$ | H | 2,6-dimethylphenyl | H | H | CH | CH | CH | CH |
| 547. | 2 | S | H | $CH_3$ | H | 2,6-diisopropylphenyl | H | H | CH | CH | CH | CH |
| 548. | 2 | S | H | $CH(CH_3)_2$ | H | $CH_3$ | H | H | CH | CH | CH | CH |
| 549. | 2 | S | H | $CH(CH_3)_2$ | H | $CH(CH_3)_2$ | H | H | CH | CH | CH | CH |
| 550. | 2 | S | H | $CH(CH_3)_2$ | H | $CH_2CH(CH_3)_2$ | H | H | CH | CH | CH | CH |
| 551. | 2 | S | H | $CH(CH_3)_2$ | H | $C_6H_{11}$ | H | H | CH | CH | CH | CH |
| 552. | 2 | S | H | $CH(CH_3)_2$ | H | Ph | H | H | CH | CH | CH | CH |
| 553. | 2 | S | H | $CH(CH_3)_2$ | H | 2,6-dimethylphenyl | H | H | CH | CH | CH | CH |
| 554. | 2 | S | H | $CH(CH_3)_2$ | H | 2,6-diisopropylphenyl | H | H | CH | CH | CH | CH |
| 555. | 2 | S | H | $CH_2CH(CH_3)_2$ | H | $CH_3$ | H | H | CH | CH | CH | CH |
| 556. | 2 | S | H | $CH_2CH(CH_3)_2$ | H | $CH(CH_3)_2$ | H | H | CH | CH | CH | CH |
| 557. | 2 | S | H | $CH_2CH(CH_3)_2$ | H | $CH_2CH(CH_3)_2$ | H | H | CH | CH | CH | CH |
| 558. | 2 | S | H | $CH_2CH(CH_3)_2$ | H | $C_6H_{11}$ | H | H | CH | CH | CH | CH |
| 559. | 2 | S | H | $CH_2CH(CH_3)_2$ | H | Ph | H | H | CH | CH | CH | CH |
| 560. | 2 | S | H | $CH_2CH(CH_3)_2$ | H | 2,6-dimethylphenyl | H | H | CH | CH | CH | CH |
| 561. | 2 | S | H | $CH_2CH(CH_3)_2$ | H | 2,6-diisopropylphenyl | H | H | CH | CH | CH | CH |
| 562. | 2 | S | H | $C_6H_{11}$ | H | $CH_3$ | H | H | CH | CH | CH | CH |
| 563. | 2 | S | H | $C_6H_{11}$ | H | $CH(CH_3)_2$ | H | H | CH | CH | CH | CH |
| 564. | 2 | S | H | $C_6H_{11}$ | H | $CH_2CH(CH_3)_2$ | H | H | CH | CH | CH | CH |
| 565. | 2 | S | H | $C_6H_{11}$ | H | $C_6H_{11}$ | H | H | CH | CH | CH | CH |
| 566. | 2 | S | H | $C_6H_{11}$ | H | Ph | H | H | CH | CH | CH | CH |
| 567. | 2 | S | H | $C_6H_{11}$ | H | 2,6-dimethylphenyl | H | H | CH | CH | CH | CH |
| 568. | 2 | S | H | $C_6H_{11}$ | H | 2,6-diisopropylphenyl | H | H | CH | CH | CH | CH |
| 569. | 2 | S | H | Ph | H | $CH_3$ | H | H | CH | CH | CH | CH |
| 570. | 2 | S | H | Ph | H | $CH(CH_3)_2$ | H | H | CH | CH | CH | CH |
| 571. | 2 | S | H | Ph | H | $CH_2CH(CH_3)_2$ | H | H | CH | CH | CH | CH |
| 572. | 2 | S | H | Ph | H | $C_6H_{11}$ | H | H | CH | CH | CH | CH |
| 573. | 2 | S | H | Ph | H | Ph | H | H | CH | CH | CH | CH |
| 574. | 2 | S | H | Ph | H | 2,6-dimethylphenyl | H | H | CH | CH | CH | CH |
| 575. | 2 | S | H | Ph | H | 2,6-diisopropylphenyl | H | H | CH | CH | CH | CH |
| 576. | 2 | S | H | 2,6-dimethylphenyl | H | $CH_3$ | H | H | CH | CH | CH | CH |
| 577. | 2 | S | H | 2,6-dimethylphenyl | H | $CH(CH_3)_2$ | H | H | CH | CH | CH | CH |
| 578. | 2 | S | H | 2,6-dimethylphenyl | H | $CH_2CH(CH_3)_2$ | H | H | CH | CH | CH | CH |

-continued

Formula VI

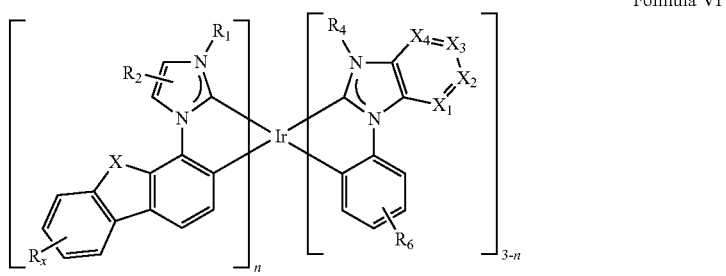

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 579. | 2 | S | H | 2,6-dimethylphenyl | H | $C_6H_{11}$ | H | H | CH | CH | CH | CH |
| 580. | 2 | S | H | 2,6-dimethylphenyl | H | Ph | H | H | CH | CH | CH | CH |
| 581. | 2 | S | H | 2,6-dimethylphenyl | H | 2,6-dimethylphenyl | H | H | CH | CH | CH | CH |
| 582. | 2 | S | H | 2,6-dimethylphenyl | H | 2,6-diisopropylphenyl | H | H | CH | CH | CH | CH |
| 583. | 2 | S | H | 2,6-diisopropylphenyl | H | $CH_3$ | H | H | CH | CH | CH | CH |
| 584. | 2 | S | H | 2,6-diisopropylphenyl | H | $CH(CH_3)_2$ | H | H | CH | CH | CH | CH |
| 585. | 2 | S | H | 2,6-diisopropylphenyl | H | $CH_2CH(CH_3)_2$ | H | H | CH | CH | CH | CH |
| 586. | 2 | S | H | 2,6-diisopropylphenyl | H | $C_6H_{11}$ | H | H | CH | CH | CH | CH |
| 587. | 2 | S | H | 2,6-diisopropylphenyl | H | Ph | H | H | CH | CH | CH | CH |
| 588. | 2 | S | H | 2,6-diisopropylphenyl | H | 2,6-dimethylphenyl | H | H | CH | CH | CH | CH |
| 589. | 2 | S | H | 2,6-diisopropylphenyl | H | 2,6-diisopropylphenyl | H | H | CH | CH | CH | CH |
| 590. | 1 | O | H | $CH_3$ | H | $CH_3$ | H | H | N | CH | CH | CH |
| 591. | 1 | O | H | $CH_3$ | H | $CH(CH_3)_2$ | H | H | N | CH | CH | CH |
| 592. | 1 | O | H | $CH_3$ | H | $CH_2CH(CH_3)_2$ | H | H | N | CH | CH | CH |
| 593. | 1 | O | H | $CH_3$ | H | $C_6H_{11}$ | H | H | N | CH | CH | CH |
| 594. | 1 | O | H | $CH_3$ | H | Ph | H | H | N | CH | CH | CH |
| 595. | 1 | O | H | $CH_3$ | H | 2,6-dimethylphenyl | H | H | N | CH | CH | CH |
| 596. | 1 | O | H | $CH_3$ | H | 2,6-diisopropylphenyl | H | H | N | CH | CH | CH |
| 597. | 1 | O | H | $CH(CH_3)_2$ | H | $CH_3$ | H | H | N | CH | CH | CH |
| 598. | 1 | O | H | $CH(CH_3)_2$ | H | $CH(CH_3)_2$ | H | H | N | CH | CH | CH |
| 599. | 1 | O | H | $CH(CH_3)_2$ | H | $CH_2CH(CH_3)_2$ | H | H | N | CH | CH | CH |
| 600. | 1 | O | H | $CH(CH_3)_2$ | H | $C_6H_{11}$ | H | H | N | CH | CH | CH |
| 601. | 1 | O | H | $CH(CH_3)_2$ | H | Ph | H | H | N | CH | CH | CH |
| 602. | 1 | O | H | $CH(CH_3)_2$ | H | 2,6-dimethylphenyl | H | H | N | CH | CH | CH |
| 603. | 1 | O | H | $CH(CH_3)_2$ | H | 2,6-diisopropylphenyl | H | H | N | CH | CH | CH |
| 604. | 1 | O | H | $CH_2CH(CH_3)_2$ | H | $CH_3$ | H | H | N | CH | CH | CH |
| 605. | 1 | O | H | $CH_2CH(CH_3)_2$ | H | $CH(CH_3)_2$ | H | H | N | CH | CH | CH |
| 606. | 1 | O | H | $CH_2CH(CH_3)_2$ | H | $CH_2CH(CH_3)_2$ | H | H | N | CH | CH | CH |
| 607. | 1 | O | H | $CH_2CH(CH_3)_2$ | H | $C_6H_{11}$ | H | H | N | CH | CH | CH |
| 608. | 1 | O | H | $CH_2CH(CH_3)_2$ | H | Ph | H | H | N | CH | CH | CH |
| 609. | 1 | O | H | $CH_2CH(CH_3)_2$ | H | 2,6-dimethylphenyl | H | H | N | CH | CH | CH |
| 610. | 1 | O | H | $CH_2CH(CH_3)_2$ | H | 2,6-diisopropylphenyl | H | H | N | CH | CH | CH |
| 611. | 1 | O | H | $C_6H_{11}$ | H | $CH_3$ | H | H | N | CH | CH | CH |
| 612. | 1 | O | H | $C_6H_{11}$ | H | $CH(CH_3)_2$ | H | H | N | CH | CH | CH |
| 613. | 1 | O | H | $C_6H_{11}$ | H | $CH_2CH(CH_3)_2$ | H | H | N | CH | CH | CH |
| 614. | 1 | O | H | $C_6H_{11}$ | H | $C_6H_{11}$ | H | H | N | CH | CH | CH |
| 615. | 1 | O | H | $C_6H_{11}$ | H | Ph | H | H | N | CH | CH | CH |
| 616. | 1 | O | H | $C_6H_{11}$ | H | 2,6-dimethylphenyl | H | H | N | CH | CH | CH |
| 617. | 1 | O | H | $C_6H_{11}$ | H | 2,6-diisopropylphenyl | H | H | N | CH | CH | CH |
| 618. | 1 | O | H | Ph | H | $CH_3$ | H | H | N | CH | CH | CH |
| 619. | 1 | O | H | Ph | H | $CH(CH_3)_2$ | H | H | N | CH | CH | CH |
| 620. | 1 | O | H | Ph | H | $CH_2CH(CH_3)_2$ | H | H | N | CH | CH | CH |

-continued

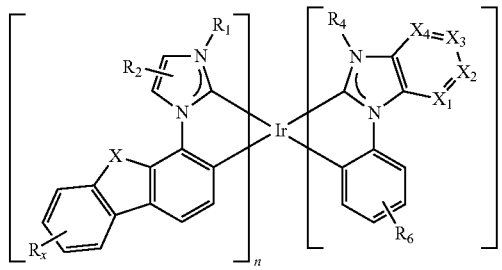

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 621. | 1 | O | H | Ph | H | $C_6H_{11}$ | H | H | N | CH | CH | CH |
| 622. | 1 | O | H | Ph | H | Ph | H | H | N | CH | CH | CH |
| 623. | 1 | O | H | Ph | H | 2,6-dimethylphenyl | H | H | N | CH | CH | CH |
| 624. | 1 | O | H | Ph | H | 2,6-diisopropylphenyl | H | H | N | CH | CH | CH |
| 625. | 1 | O | H | 2,6-dimethylphenyl | H | $CH_3$ | H | H | N | CH | CH | CH |
| 626. | 1 | O | H | 2,6-dimethylphenyl | H | $CH(CH_3)_2$ | H | H | N | CH | CH | CH |
| 627. | 1 | O | H | 2,6-dimethylphenyl | H | $CH_2CH(CH_3)_2$ | H | H | N | CH | CH | CH |
| 628. | 1 | O | H | 2,6-dimethylphenyl | H | $C_6H_{11}$ | H | H | N | CH | CH | CH |
| 629. | 1 | O | H | 2,6-dimethylphenyl | H | Ph | H | H | N | CH | CH | CH |
| 630. | 1 | O | H | 2,6-dimethylphenyl | H | 2,6-dimethylphenyl | H | H | N | CH | CH | CH |
| 631. | 1 | O | H | 2,6-dimethylphenyl | H | 2,6-diisopropylphenyl | H | H | N | CH | CH | CH |
| 632. | 1 | O | H | 2,6-diisopropylphenyl | H | $CH_3$ | H | H | N | CH | CH | CH |
| 633. | 1 | O | H | 2,6-diisopropylphenyl | H | $CH(CH_3)_2$ | H | H | N | CH | CH | CH |
| 634. | 1 | O | H | 2,6-diisopropylphenyl | H | $CH_2CH(CH_3)_2$ | H | H | N | CH | CH | CH |
| 635. | 1 | O | H | 2,6-diisopropylphenyl | H | $C_6H_{11}$ | H | H | N | CH | CH | CH |
| 636. | 1 | O | H | 2,6-diisopropylphenyl | H | Ph | H | H | N | CH | CH | CH |
| 637. | 1 | O | H | 2,6-diisopropylphenyl | H | 2,6-dimethylphenyl | H | H | N | CH | CH | CH |
| 638. | 1 | O | H | 2,6-diisopropylphenyl | H | 2,6-diisopropylphenyl | H | H | N | CH | CH | CH |
| 639. | 1 | S | H | $CH_3$ | H | $CH_3$ | H | H | N | CH | CH | CH |
| 640. | 1 | S | H | $CH_3$ | H | $CH(CH_3)_2$ | H | H | N | CH | CH | CH |
| 641. | 1 | S | H | $CH_3$ | H | $CH_2CH(CH_3)_2$ | H | H | N | CH | CH | CH |
| 642. | 1 | S | H | $CH_3$ | H | $C_6H_{11}$ | H | H | N | CH | CH | CH |
| 643. | 1 | S | H | $CH_3$ | H | Ph | H | H | N | CH | CH | CH |
| 644. | 1 | S | H | $CH_3$ | H | 2,6-dimethylphenyl | H | H | N | CH | CH | CH |
| 645. | 1 | S | H | $CH_3$ | H | 2,6-diisopropylphenyl | H | H | N | CH | CH | CH |
| 646. | 1 | S | H | $CH(CH_3)_2$ | H | $CH_3$ | H | H | N | CH | CH | CH |
| 647. | 1 | S | H | $CH(CH_3)_2$ | H | $CH(CH_3)_2$ | H | H | N | CH | CH | CH |
| 648. | 1 | S | H | $CH(CH_3)_2$ | H | $CH_2CH(CH_3)_2$ | H | H | N | CH | CH | CH |
| 649. | 1 | S | H | $CH(CH_3)_2$ | H | $C_6H_{11}$ | H | H | N | CH | CH | CH |
| 650. | 1 | S | H | $CH(CH_3)_2$ | H | Ph | H | H | N | CH | CH | CH |
| 651. | 1 | S | H | $CH(CH_3)_2$ | H | 2,6-dimethylphenyl | H | H | N | CH | CH | CH |
| 652. | 1 | S | H | $CH(CH_3)_2$ | H | 2,6-diisopropylphenyl | H | H | N | CH | CH | CH |
| 653. | 1 | S | H | $CH_2CH(CH_3)_2$ | H | $CH_3$ | H | H | N | CH | CH | CH |
| 654. | 1 | S | H | $CH_2CH(CH_3)_2$ | H | $CH(CH_3)_2$ | H | H | N | CH | CH | CH |
| 655. | 1 | S | H | $CH_2CH(CH_3)_2$ | H | $CH_2CH(CH_3)_2$ | H | H | N | CH | CH | CH |
| 656. | 1 | S | H | $CH_2CH(CH_3)_2$ | H | $C_6H_{11}$ | H | H | N | CH | CH | CH |
| 657. | 1 | S | H | $CH_2CH(CH_3)_2$ | H | Ph | H | H | N | CH | CH | CH |
| 658. | 1 | S | H | $CH_2CH(CH_3)_2$ | H | 2,6-dimethylphenyl | H | H | N | CH | CH | CH |
| 659. | 1 | S | H | $CH_2CH(CH_3)_2$ | H | 2,6-diisopropylphenyl | H | H | N | CH | CH | CH |

-continued

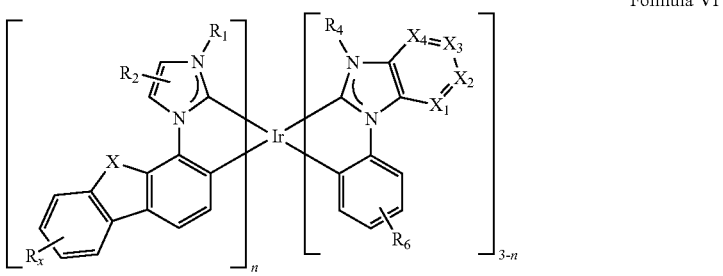

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 660. | 1 | S | H | $C_6H_{11}$ | H | $CH_3$ | H | H | N | CH | CH | CH |
| 661. | 1 | S | H | $C_6H_{11}$ | H | $CH(CH_3)_2$ | H | H | N | CH | CH | CH |
| 662. | 1 | S | H | $C_6H_{11}$ | H | $CH_2CH(CH_3)_2$ | H | H | N | CH | CH | CH |
| 663. | 1 | S | H | $C_6H_{11}$ | H | $C_6H_{11}$ | H | H | N | CH | CH | CH |
| 664. | 1 | S | H | $C_6H_{11}$ | H | Ph | H | H | N | CH | CH | CH |
| 665. | 1 | S | H | $C_6H_{11}$ | H | 2,6-dimethylphenyl | H | H | N | CH | CH | CH |
| 666. | 1 | S | H | $C_6H_{11}$ | H | 2,6-diisopropylphenyl | H | H | N | CH | CH | CH |
| 667. | 1 | S | H | Ph | H | $CH_3$ | H | H | N | CH | CH | CH |
| 668. | 1 | S | H | Ph | H | $CH(CH_3)_2$ | H | H | N | CH | CH | CH |
| 669. | 1 | S | H | Ph | H | $CH_2CH(CH_3)_2$ | H | H | N | CH | CH | CH |
| 670. | 1 | S | H | Ph | H | $C_6H_{11}$ | H | H | N | CH | CH | CH |
| 671. | 1 | S | H | Ph | H | Ph | H | H | N | CH | CH | CH |
| 672. | 1 | S | H | Ph | H | 2,6-dimethylphenyl | H | H | N | CH | CH | CH |
| 673. | 1 | S | H | Ph | H | 2,6-diisopropylphenyl | H | H | N | CH | CH | CH |
| 674. | 1 | S | H | 2,6-dimethylphenyl | H | $CH_3$ | H | H | N | CH | CH | CH |
| 675. | 1 | S | H | 2,6-dimethylphenyl | H | $CH(CH_3)_2$ | H | H | N | CH | CH | CH |
| 676. | 1 | S | H | 2,6-dimethylphenyl | H | $CH_2CH(CH_3)_2$ | H | H | N | CH | CH | CH |
| 677. | 1 | S | H | 2,6-dimethylphenyl | H | $C_6H_{11}$ | H | H | N | CH | CH | CH |
| 678. | 1 | S | H | 2,6-dimethylphenyl | H | Ph | H | H | N | CH | CH | CH |
| 679. | 1 | S | H | 2,6-dimethylphenyl | H | 2,6-dimethylphenyl | H | H | N | CH | CH | CH |
| 680. | 1 | S | H | 2,6-dimethylphenyl | H | 2,6-diisopropylphenyl | H | H | N | CH | CH | CH |
| 681. | 1 | S | H | 2,6-diisopropylphenyl | H | $CH_3$ | H | H | N | CH | CH | CH |
| 682. | 1 | S | H | 2,6-diisopropylphenyl | H | $CH(CH_3)_2$ | H | H | N | CH | CH | CH |
| 683. | 1 | S | H | 2,6-diisopropylphenyl | H | $CH_2CH(CH_3)_2$ | H | H | N | CH | CH | CH |
| 684. | 1 | S | H | 2,6-diisopropylphenyl | H | $C_6H_{11}$ | H | H | N | CH | CH | CH |
| 685. | 1 | S | H | 2,6-diisopropylphenyl | H | Ph | H | H | N | CH | CH | CH |
| 686. | 1 | S | H | 2,6-diisopropylphenyl | H | 2,6-dimethylphenyl | H | H | N | CH | CH | CH |
| 687. | 1 | S | H | 2,6-diisopropylphenyl | H | 2,6-diisopropylphenyl | H | H | N | CH | CH | CH |
| 688. | 2 | O | H | $CH_3$ | H | $CH_3$ | H | H | N | CH | CH | CH |
| 689. | 2 | O | H | $CH_3$ | H | $CH(CH_3)_2$ | H | H | N | CH | CH | CH |
| 690. | 2 | O | H | $CH_3$ | H | $CH_2CH(CH_3)_2$ | H | H | N | CH | CH | CH |
| 691. | 2 | O | H | $CH_3$ | H | $C_6H_{11}$ | H | H | N | CH | CH | CH |
| 692. | 2 | O | H | $CH_3$ | H | Ph | H | H | N | CH | CH | CH |
| 693. | 2 | O | H | $CH_3$ | H | 2,6-dimethylphenyl | H | H | N | CH | CH | CH |
| 694. | 2 | O | H | $CH_3$ | H | 2,6-diisopropylphenyl | H | H | N | CH | CH | CH |
| 695. | 2 | O | H | $CH(CH_3)_2$ | H | $CH_3$ | H | H | N | CH | CH | CH |
| 696. | 2 | O | H | $CH(CH_3)_2$ | H | $CH(CH_3)_2$ | H | H | N | CH | CH | CH |
| 697. | 2 | O | H | $CH(CH_3)_2$ | H | $CH_2CH(CH_3)_2$ | H | H | N | CH | CH | CH |
| 698. | 2 | O | H | $CH(CH_3)_2$ | H | $C_6H_{11}$ | H | H | N | CH | CH | CH |
| 699. | 2 | O | H | $CH(CH_3)_2$ | H | Ph | H | H | N | CH | CH | CH |

-continued

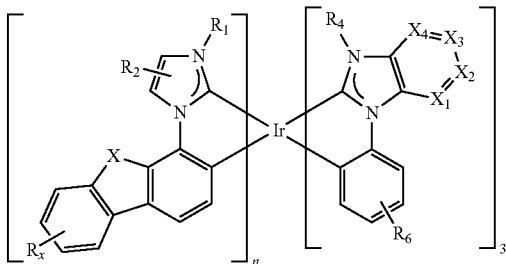

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 700. | 2 | O | H | $CH(CH_3)_2$ | H | 2,6-dimethylphenyl | H | H | N | CH | CH | CH |
| 701. | 2 | O | H | $CH(CH_3)_2$ | H | 2,6-diisopropylphenyl | H | H | N | CH | CH | CH |
| 702. | | | | | | | | | N | CH | CH | CH |
| 703. | 2 | O | H | $CH_2CH(CH_3)_2$ | H | $CH_3$ | H | H | N | CH | CH | CH |
| 704. | 2 | O | H | $CH_2CH(CH_3)_2$ | H | $CH(CH_3)_2$ | H | H | N | CH | CH | CH |
| 705. | 2 | O | H | $CH_2CH(CH_3)_2$ | H | $CH_2CH(CH_3)_2$ | H | H | N | CH | CH | CH |
| 706. | 2 | O | H | $CH_2CH(CH_3)_2$ | H | $C_6H_{11}$ | H | H | N | CH | CH | CH |
| 707. | 2 | O | H | $CH_2CH(CH_3)_2$ | H | Ph | H | H | N | CH | CH | CH |
| 708. | 2 | O | H | $CH_2CH(CH_3)_2$ | H | 2,6-dimethylphenyl | H | H | N | CH | CH | CH |
| 709. | 2 | O | H | $CH_2CH(CH_3)_2$ | H | 2,6-diisopropylphenyl | H | H | N | CH | CH | CH |
| 710. | 2 | O | H | $C_6H_{11}$ | H | $CH_3$ | H | H | N | CH | CH | CH |
| 711. | 2 | O | H | $C_6H_{11}$ | H | $CH(CH_3)_2$ | H | H | N | CH | CH | CH |
| 712. | 2 | O | H | $C_6H_{11}$ | H | $CH_2CH(CH_3)_2$ | H | H | N | CH | CH | CH |
| 713. | 2 | O | H | $C_6H_{11}$ | H | $C_6H_{11}$ | H | H | N | CH | CH | CH |
| 714. | 2 | O | H | $C_6H_{11}$ | H | Ph | H | H | N | CH | CH | CH |
| 715. | 2 | O | H | $C_6H_{11}$ | H | 2,6-dimethylphenyl | H | H | N | CH | CH | CH |
| 716. | 2 | O | H | $C_6H_{11}$ | H | 2,6-diisopropylphenyl | H | H | N | CH | CH | CH |
| 717. | 2 | O | H | Ph | H | $CH_3$ | H | H | N | CH | CH | CH |
| 718. | 2 | O | H | Ph | H | $CH(CH_3)_2$ | H | H | N | CH | CH | CH |
| 719. | 2 | O | H | Ph | H | $CH_2CH(CH_3)_2$ | H | H | N | CH | CH | CH |
| 720. | 2 | O | H | Ph | H | $C_6H_{11}$ | H | H | N | CH | CH | CH |
| 721. | 2 | O | H | Ph | H | Ph | H | H | N | CH | CH | CH |
| 722. | 2 | O | H | Ph | H | 2,6-dimethylphenyl | H | H | N | CH | CH | CH |
| 723. | 2 | O | H | Ph | H | 2,6-diisopropylphenyl | H | H | N | CH | CH | CH |
| 724. | 2 | O | H | 2,6-dimethylphenyl | H | $CH_3$ | H | H | N | CH | CH | CH |
| 725. | 2 | O | H | 2,6-dimethylphenyl | H | $CH(CH_3)_2$ | H | H | N | CH | CH | CH |
| 726. | 2 | O | H | 2,6-dimethylphenyl | H | $CH_2CH(CH_3)_2$ | H | H | N | CH | CH | CH |
| 727. | 2 | O | H | 2,6-dimethylphenyl | H | $C_6H_{11}$ | H | H | N | CH | CH | CH |
| 728. | 2 | O | H | 2,6-dimethylphenyl | H | Ph | H | H | N | CH | CH | CH |
| 729. | 2 | O | H | 2,6-dimethylphenyl | H | 2,6-dimethylphenyl | H | H | N | CH | CH | CH |
| 730. | 2 | O | H | 2,6-dimethylphenyl | H | 2,6-diisopropylphenyl | H | H | N | CH | CH | CH |
| 731. | 2 | O | H | 2,6-diisopropylphenyl | H | $CH_3$ | H | H | N | CH | CH | CH |
| 732. | 2 | O | H | 2,6-diisopropylphenyl | H | $CH(CH_3)_2$ | H | H | N | CH | CH | CH |
| 733. | 2 | O | H | 2,6-diisopropylphenyl | H | $CH_2CH(CH_3)_2$ | H | H | N | CH | CH | CH |
| 734. | 2 | O | H | 2,6-diisopropylphenyl | H | $C_6H_{11}$ | H | H | N | CH | CH | CH |
| 735. | 2 | O | H | 2,6-diisopropylphenyl | H | Ph | H | H | N | CH | CH | CH |
| 736. | 2 | O | H | 2,6-diisopropylphenyl | H | 2,6-dimethylphenyl | H | H | N | CH | CH | CH |
| 737. | 2 | O | H | 2,6-diisopropylphenyl | H | 2,6-diisopropylphenyl | H | H | N | CH | CH | CH |
| 738. | 2 | S | H | $CH_3$ | H | $CH_3$ | H | H | N | CH | CH | CH |

-continued

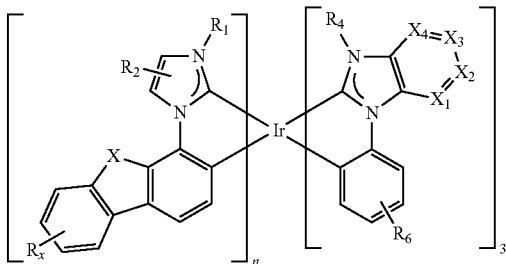

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 739. | 2 | S | H | $CH_3$ | H | $CH(CH_3)_2$ | H | H | N | CH | CH | CH |
| 740. | 2 | S | H | $CH_3$ | H | $CH_2CH(CH_3)_2$ | H | H | N | CH | CH | CH |
| 741. | 2 | S | H | $CH_3$ | H | $C_6H_{11}$ | H | H | N | CH | CH | CH |
| 742. | 2 | S | H | $CH_3$ | H | Ph | H | H | N | CH | CH | CH |
| 743. | 2 | S | H | $CH_3$ | H | 2,6-dimethylphenyl | H | H | N | CH | CH | CH |
| 744. | 2 | S | H | $CH_3$ | H | 2,6-diisopropylphenyl | H | H | N | CH | CH | CH |
| 745. | 2 | S | H | $CH(CH_3)_2$ | H | $CH_3$ | H | H | N | CH | CH | CH |
| 746. | 2 | S | H | $CH(CH_3)_2$ | H | $CH(CH_3)_2$ | H | H | N | CH | CH | CH |
| 747. | 2 | S | H | $CH(CH_3)_2$ | H | $CH_2CH(CH_3)_2$ | H | H | N | CH | CH | CH |
| 748. | 2 | S | H | $CH(CH_3)_2$ | H | $C_6H_{11}$ | H | H | N | CH | CH | CH |
| 749. | 2 | S | H | $CH(CH_3)_2$ | H | Ph | H | H | N | CH | CH | CH |
| 750. | 2 | S | H | $CH(CH_3)_2$ | H | 2,6-dimethylphenyl | H | H | N | CH | CH | CH |
| 751. | 2 | S | H | $CH(CH_3)_2$ | H | 2,6-diisopropylphenyl | H | H | N | CH | CH | CH |
| 752. | 2 | S | H | $CH_2CH(CH_3)_2$ | H | $CH_3$ | H | H | N | CH | CH | CH |
| 753. | 2 | S | H | $CH_2CH(CH_3)_2$ | H | $CH(CH_3)_2$ | H | H | N | CH | CH | CH |
| 754. | 2 | S | H | $CH_2CH(CH_3)_2$ | H | $CH_2CH(CH_3)_2$ | H | H | N | CH | CH | CH |
| 755. | 2 | S | H | $CH_2CH(CH_3)_2$ | H | $C_6H_{11}$ | H | H | N | CH | CH | CH |
| 756. | 2 | S | H | $CH_2CH(CH_3)_2$ | H | Ph | H | H | N | CH | CH | CH |
| 757. | 2 | S | H | $CH_2CH(CH_3)_2$ | H | 2,6-dimethylphenyl | H | H | N | CH | CH | CH |
| 758. | 2 | S | H | $CH_2CH(CH_3)_2$ | H | 2,6-diisopropylphenyl | H | H | N | CH | CH | CH |
| 759. | 2 | S | H | $C_6H_{11}$ | H | $CH_3$ | H | H | N | CH | CH | CH |
| 760. | 2 | S | H | $C_6H_{11}$ | H | $CH(CH_3)_2$ | H | H | N | CH | CH | CH |
| 761. | 2 | S | H | $C_6H_{11}$ | H | $CH_2CH(CH_3)_2$ | H | H | N | CH | CH | CH |
| 762. | 2 | S | H | $C_6H_{11}$ | H | $C_6H_{11}$ | H | H | N | CH | CH | CH |
| 763. | 2 | S | H | $C_6H_{11}$ | H | Ph | H | H | N | CH | CH | CH |
| 764. | 2 | S | H | $C_6H_{11}$ | H | 2,6-dimethylphenyl | H | H | N | CH | CH | CH |
| 765. | 2 | S | H | $C_6H_{11}$ | H | 2,6-diisopropylphenyl | H | H | N | CH | CH | CH |
| 766. | 2 | S | H | Ph | H | $CH_3$ | H | H | N | CH | CH | CH |
| 767. | 2 | S | H | Ph | H | $CH(CH_3)_2$ | H | H | N | CH | CH | CH |
| 768. | 2 | S | H | Ph | H | $CH_2CH(CH_3)_2$ | H | H | N | CH | CH | CH |
| 769. | 2 | S | H | Ph | H | $C_6H_{11}$ | H | H | N | CH | CH | CH |
| 770. | 2 | S | H | Ph | H | Ph | H | H | N | CH | CH | CH |
| 771. | 2 | S | H | Ph | H | 2,6-dimethylphenyl | H | H | N | CH | CH | CH |
| 772. | 2 | S | H | Ph | H | 2,6-diisopropylphenyl | H | H | N | CH | CH | CH |
| 773. | 2 | S | H | 2,6-dimethylphenyl | H | $CH_3$ | H | H | N | CH | CH | CH |
| 774. | 2 | S | H | 2,6-dimethylphenyl | H | $CH(CH_3)_2$ | H | H | N | CH | CH | CH |
| 775. | 2 | S | H | 2,6-dimethylphenyl | H | $CH_2CH(CH_3)_2$ | H | H | N | CH | CH | CH |
| 776. | 2 | S | H | 2,6-dimethylphenyl | H | $C_6H_{11}$ | H | H | N | CH | CH | CH |
| 777. | 2 | S | H | 2,6-dimethylphenyl | H | Ph | H | H | N | CH | CH | CH |
| 778. | 2 | S | H | 2,6-dimethylphenyl | H | 2,6-dimethylphenyl | H | H | N | CH | CH | CH |
| 779. | 2 | S | H | 2,6-dimethylphenyl | H | 2,6-diisopropylphenyl | H | H | N | CH | CH | CH |
| 780. | 2 | S | H | 2,6-diisopropylphenyl | H | $CH_3$ | H | H | N | CH | CH | CH |

-continued

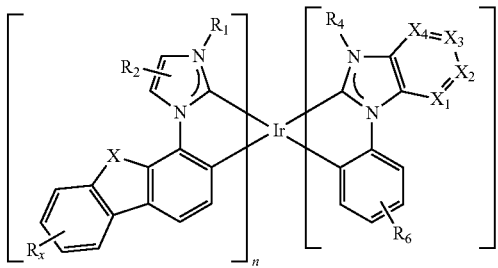

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 781. | 2 | S | H | 2,6-diisopropylphenyl | H | $CH(CH_3)_2$ | H | H | N | CH | CH | CH |
| 782. | 2 | S | H | 2,6-diisopropylphenyl | H | $CH_2CH(CH_3)_2$ | H | H | N | CH | CH | CH |
| 783. | 2 | S | H | 2,6-diisopropylphenyl | H | $C_6H_{11}$ | H | H | N | CH | CH | CH |
| 784. | 2 | S | H | 2,6-diisopropylphenyl | H | Ph | H | H | N | CH | CH | CH |
| 785. | 2 | S | H | 2,6-diisopropylphenyl | H | 2,6-dimethylphenyl | H | H | N | CH | CH | CH |
| 786. | 2 | S | H | 2,6-diisopropylphenyl | H | 2,6-diisopropylphenyl | H | H | N | CH | CH | CH |
| 787. | 1 | O | H | $CH_3$ | H | $CH_3$ | H | H | CH | N | CH | CH |
| 788. | 1 | O | H | $CH_3$ | H | $CH(CH_3)_2$ | H | H | CH | N | CH | CH |
| 789. | 1 | O | H | $CH_3$ | H | $CH_2CH(CH_3)_2$ | H | H | CH | N | CH | CH |
| 790. | 1 | O | H | $CH_3$ | H | $C_6H_{11}$ | H | H | CH | N | CH | CH |
| 791. | 1 | O | H | $CH_3$ | H | Ph | H | H | CH | N | CH | CH |
| 792. | 1 | O | H | $CH_3$ | H | 2,6-dimethylphenyl | H | H | CH | N | CH | CH |
| 793. | 1 | O | H | $CH_3$ | H | 2,6-diisopropylphenyl | H | H | CH | N | CH | CH |
| 794. | 1 | O | H | $CH(CH_3)_2$ | H | $CH_3$ | H | H | CH | N | CH | CH |
| 795. | 1 | O | H | $CH(CH_3)_2$ | H | $CH(CH_3)_2$ | H | H | CH | N | CH | CH |
| 796. | 1 | O | H | $CH(CH_3)_2$ | H | $CH_2CH(CH_3)_2$ | H | H | CH | N | CH | CH |
| 797. | 1 | O | H | $CH(CH_3)_2$ | H | $C_6H_{11}$ | H | H | CH | N | CH | CH |
| 798. | 1 | O | H | $CH(CH_3)_2$ | H | Ph | H | H | CH | N | CH | CH |
| 799. | 1 | O | H | $CH(CH_3)_2$ | H | 2,6-dimethylphenyl | H | H | CH | N | CH | CH |
| 800. | 1 | O | H | $CH(CH_3)_2$ | H | 2,6-diisopropylphenyl | H | H | CH | N | CH | CH |
| 801. | 1 | O | H | $CH_2CH(CH_3)_2$ | H | $CH_3$ | H | H | CH | N | CH | CH |
| 802. | 1 | O | H | $CH_2CH(CH_3)_2$ | H | $CH(CH_3)_2$ | H | H | CH | N | CH | CH |
| 803. | 1 | O | H | $CH_2CH(CH_3)_2$ | H | $CH_2CH(CH_3)_2$ | H | H | CH | N | CH | CH |
| 804. | 1 | O | H | $CH_2CH(CH_3)_2$ | H | $C_6H_{11}$ | H | H | CH | N | CH | CH |
| 805. | 1 | O | H | $CH_2CH(CH_3)_2$ | H | Ph | H | H | CH | N | CH | CH |
| 806. | 1 | O | H | $CH_2CH(CH_3)_2$ | H | 2,6-dimethylphenyl | H | H | CH | N | CH | CH |
| 807. | 1 | O | H | $CH_2CH(CH_3)_2$ | H | 2,6-diisopropylphenyl | H | H | CH | N | CH | CH |
| 808. | 1 | O | H | $C_6H_{11}$ | H | $CH_3$ | H | H | CH | N | CH | CH |
| 809. | 1 | O | H | $C_6H_{11}$ | H | $CH(CH_3)_2$ | H | H | CH | N | CH | CH |
| 810. | 1 | O | H | $C_6H_{11}$ | H | $CH_2CH(CH_3)_2$ | H | H | CH | N | CH | CH |
| 811. | 1 | O | H | $C_6H_{11}$ | H | $C_6H_{11}$ | H | H | CH | N | CH | CH |
| 812. | 1 | O | H | $C_6H_{11}$ | H | Ph | H | H | CH | N | CH | CH |
| 813. | 1 | O | H | $C_6H_{11}$ | H | 2,6-dimethylphenyl | H | H | CH | N | CH | CH |
| 814. | 1 | O | H | $C_6H_{11}$ | H | 2,6-diisopropylphenyl | H | H | CH | N | CH | CH |
| 815. | 1 | O | H | Ph | H | $CH_3$ | H | H | CH | N | CH | CH |
| 816. | 1 | O | H | Ph | H | $CH(CH_3)_2$ | H | H | CH | N | CH | CH |
| 817. | 1 | O | H | Ph | H | $CH_2CH(CH_3)_2$ | H | H | CH | N | CH | CH |
| 818. | 1 | O | H | Ph | H | $C_6H_{11}$ | H | H | CH | N | CH | CH |
| 819. | 1 | O | H | Ph | H | Ph | H | H | CH | N | CH | CH |
| 820. | 1 | O | H | Ph | H | 2,6-dimethylphenyl | H | H | CH | N | CH | CH |
| 821. | 1 | O | H | Ph | H | 2,6-diisopropylphenyl | H | H | CH | N | CH | CH |
| 822. | 1 | O | H | 2,6-dimethylphenyl | H | $CH_3$ | H | H | CH | N | CH | CH |
| 823. | 1 | O | H | 2,6-dimethylphenyl | H | $CH(CH_3)_2$ | H | H | CH | N | CH | CH |

-continued

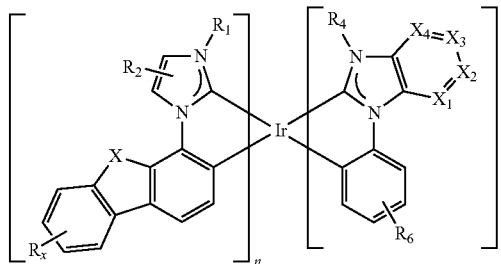

Formula VI

| Compd. | n | X | R$_x$ | R$_1$ | R$_2$ | R$_4$ | R$_5$ | R$_6$ | X$_1$ | X$_2$ | X$_3$ | X$_4$ |
|---|---|---|---|---|---|---|---|---|---|---|---|---|
| 824. | 1 | O | H | 2,6-dimethylphenyl | H | CH$_2$CH(CH$_3$)$_2$ | H | H | CH | N | CH | CH |
| 825. | 1 | O | H | 2,6-dimethylphenyl | H | C$_6$H$_{11}$ | H | H | CH | N | CH | CH |
| 826. | 1 | O | H | 2,6-dimethylphenyl | H | Ph | H | H | CH | N | CH | CH |
| 827. | 1 | O | H | 2,6-dimethylphenyl | H | 2,6-dimethylphenyl | H | H | CH | N | CH | CH |
| 828. | 1 | O | H | 2,6-dimethylphenyl | H | 2,6-diisopropylphenyl | H | H | CH | N | CH | CH |
| 829. | 1 | O | H | 2,6-diisopropylphenyl | H | CH$_3$ | H | H | CH | N | CH | CH |
| 830. | 1 | O | H | 2,6-diisopropylphenyl | H | CH(CH$_3$)$_2$ | H | H | CH | N | CH | CH |
| 831. | 1 | O | H | 2,6-diisopropylphenyl | H | CH$_2$CH(CH$_3$)$_2$ | H | H | CH | N | CH | CH |
| 832. | 1 | O | H | 2,6-diisopropylphenyl | H | C$_6$H$_{11}$ | H | H | CH | N | CH | CH |
| 833. | 1 | O | H | 2,6-diisopropylphenyl | H | Ph | H | H | CH | N | CH | CH |
| 834. | 1 | O | H | 2,6-diisopropylphenyl | H | 2,6-dimethylphenyl | H | H | CH | N | CH | CH |
| 835. | 1 | O | H | 2,6-diisopropylphenyl | H | 2,6-diisopropylphenyl | H | H | CH | N | CH | CH |
| 836. | 1 | S | H | CH$_3$ | H | CH$_3$ | H | H | CH | N | CH | CH |
| 837. | 1 | S | H | CH$_3$ | H | CH(CH$_3$)$_2$ | H | H | CH | N | CH | CH |
| 838. | 1 | S | H | CH$_3$ | H | CH$_2$CH(CH$_3$)$_2$ | H | H | CH | N | CH | CH |
| 839. | 1 | S | H | CH$_3$ | H | C$_6$H$_{11}$ | H | H | CH | N | CH | CH |
| 840. | 1 | S | H | CH$_3$ | H | Ph | H | H | CH | N | CH | CH |
| 841. | 1 | S | H | CH$_3$ | H | 2,6-dimethylphenyl | H | H | CH | N | CH | CH |
| 842. | 1 | S | H | CH$_3$ | H | 2,6-diisopropylphenyl | H | H | CH | N | CH | CH |
| 843. | 1 | S | H | CH(CH$_3$)$_2$ | H | CH$_3$ | H | H | CH | N | CH | CH |
| 844. | 1 | S | H | CH(CH$_3$)$_2$ | H | CH(CH$_3$)$_2$ | H | H | CH | N | CH | CH |
| 845. | 1 | S | H | CH(CH$_3$)$_2$ | H | CH$_2$CH(CH$_3$)$_2$ | H | H | CH | N | CH | CH |
| 846. | 1 | S | H | CH(CH$_3$)$_2$ | H | C$_6$H$_{11}$ | H | H | CH | N | CH | CH |
| 847. | 1 | S | H | CH(CH$_3$)$_2$ | H | Ph | H | H | CH | N | CH | CH |
| 848. | 1 | S | H | CH(CH$_3$)$_2$ | H | 2,6-dimethylphenyl | H | H | CH | N | CH | CH |
| 849. | 1 | S | H | CH(CH$_3$)$_2$ | H | 2,6-diisopropylphenyl | H | H | CH | N | CH | CH |
| 850. | 1 | S | H | CH$_2$CH(CH$_3$)$_2$ | H | CH$_3$ | H | H | CH | N | CH | CH |
| 851. | 1 | S | H | CH$_2$CH(CH$_3$)$_2$ | H | CH(CH$_3$)$_2$ | H | H | CH | N | CH | CH |
| 852. | 1 | S | H | CH$_2$CH(CH$_3$)$_2$ | H | CH$_2$CH(CH$_3$)$_2$ | H | H | CH | N | CH | CH |
| 853. | 1 | S | H | CH$_2$CH(CH$_3$)$_2$ | H | C$_6$H$_{11}$ | H | H | CH | N | CH | CH |
| 854. | 1 | S | H | CH$_2$CH(CH$_3$)$_2$ | H | Ph | H | H | CH | N | CH | CH |
| 855. | 1 | S | H | CH$_2$CH(CH$_3$)$_2$ | H | 2,6-dimethylphenyl | H | H | CH | N | CH | CH |
| 856. | 1 | S | H | CH$_2$CH(CH$_3$)$_2$ | H | 2,6-diisopropylphenyl | H | H | CH | N | CH | CH |
| 857. | 1 | S | H | C$_6$H$_{11}$ | H | CH$_3$ | H | H | CH | N | CH | CH |
| 858. | 1 | S | H | C$_6$H$_{11}$ | H | CH(CH$_3$)$_2$ | H | H | CH | N | CH | CH |
| 859. | 1 | S | H | C$_6$H$_{11}$ | H | CH$_2$CH(CH$_3$)$_2$ | H | H | CH | N | CH | CH |
| 860. | 1 | S | H | C$_6$H$_{11}$ | H | C$_6$H$_{11}$ | H | H | CH | N | CH | CH |
| 861. | 1 | S | H | C$_6$H$_{11}$ | H | Ph | H | H | CH | N | CH | CH |
| 862. | 1 | S | H | C$_6$H$_{11}$ | H | 2,6-dimethylphenyl | H | H | CH | N | CH | CH |
| 863. | 1 | S | H | C$_6$H$_{11}$ | H | 2,6-diisopropylphenyl | H | H | CH | N | CH | CH |
| 864. | 1 | S | H | Ph | H | CH$_3$ | H | H | CH | N | CH | CH |

-continued

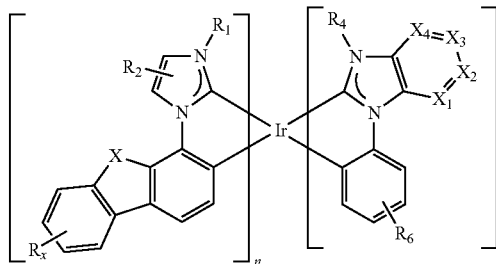

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 865. | 1 | S | H | Ph | H | $CH(CH_3)_2$ | H | H | CH | N | CH | CH |
| 866. | 1 | S | H | Ph | H | $CH_2CH(CH_3)_2$ | H | H | CH | N | CH | CH |
| 867. | 1 | S | H | Ph | H | $C_6H_{11}$ | H | H | CH | N | CH | CH |
| 868. | 1 | S | H | Ph | H | Ph | H | H | CH | N | CH | CH |
| 869. | 1 | S | H | Ph | H | 2,6-dimethylphenyl | H | H | CH | N | CH | CH |
| 870. | 1 | S | H | Ph | H | 2,6-diisopropylphenyl | H | H | CH | N | CH | CH |
| 871. | 1 | S | H | 2,6-dimethylphenyl | H | $CH_3$ | H | H | CH | N | CH | CH |
| 872. | 1 | S | H | 2,6-dimethylphenyl | H | $CH(CH_3)_2$ | H | H | CH | N | CH | CH |
| 873. | 1 | S | H | 2,6-dimethylphenyl | H | $CH_2CH(CH_3)_2$ | H | H | CH | N | CH | CH |
| 874. | 1 | S | H | 2,6-dimethylphenyl | H | $C_6H_{11}$ | H | H | CH | N | CH | CH |
| 875. | 1 | S | H | 2,6-dimethylphenyl | H | Ph | H | H | CH | N | CH | CH |
| 876. | 1 | S | H | 2,6-dimethylphenyl | H | 2,6-dimethylphenyl | H | H | CH | N | CH | CH |
| 877. | 1 | S | H | 2,6-dimethylphenyl | H | 2,6-diisopropylphenyl | H | H | CH | N | CH | CH |
| 878. | 1 | S | H | 2,6-diisopropylphenyl | H | $CH_3$ | H | H | CH | N | CH | CH |
| 879. | 1 | S | H | 2,6-diisopropylphenyl | H | $CH(CH_3)_2$ | H | H | CH | N | CH | CH |
| 880. | 1 | S | H | 2,6-diisopropylphenyl | H | $CH_2CH(CH_3)_2$ | H | H | CH | N | CH | CH |
| 881. | 1 | S | H | 2,6-diisopropylphenyl | H | $C_6H_{11}$ | H | H | CH | N | CH | CH |
| 882. | 1 | S | H | 2,6-diisopropylphenyl | H | Ph | H | H | CH | N | CH | CH |
| 883. | 1 | S | H | 2,6-diisopropylphenyl | H | 2,6-dimethylphenyl | H | H | CH | N | CH | CH |
| 884. | 1 | S | H | 2,6-diisopropylphenyl | H | 2,6-diisopropylphenyl | H | H | CH | N | CH | CH |
| 885. | 2 | O | H | $CH_3$ | H | $CH_3$ | H | H | CH | N | CH | CH |
| 886. | 2 | O | H | $CH_3$ | H | $CH(CH_3)_2$ | H | H | CH | N | CH | CH |
| 887. | 2 | O | H | $CH_3$ | H | $CH_2CH(CH_3)_2$ | H | H | CH | N | CH | CH |
| 888. | 2 | O | H | $CH_3$ | H | $C_6H_{11}$ | H | H | CH | N | CH | CH |
| 889. | 2 | O | H | $CH_3$ | H | Ph | H | H | CH | N | CH | CH |
| 890. | 2 | O | H | $CH_3$ | H | 2,6-dimethylphenyl | H | H | CH | N | CH | CH |
| 891. | 2 | O | H | $CH_3$ | H | 2,6-diisopropylphenyl | H | H | CH | N | CH | CH |
| 892. | 2 | O | H | $CH(CH_3)_2$ | H | $CH_3$ | H | H | CH | N | CH | CH |
| 893. | 2 | O | H | $CH(CH_3)_2$ | H | $CH(CH_3)_2$ | H | H | CH | N | CH | CH |
| 894. | 2 | O | H | $CH(CH_3)_2$ | H | $CH_2CH(CH_3)_2$ | H | H | CH | N | CH | CH |
| 895. | 2 | O | H | $CH(CH_3)_2$ | H | $C_6H_{11}$ | H | H | CH | N | CH | CH |
| 896. | 2 | O | H | $CH(CH_3)_2$ | H | Ph | H | H | CH | N | CH | CH |
| 897. | 2 | O | H | $CH(CH_3)_2$ | H | 2,6-dimethylphenyl | H | H | CH | N | CH | CH |
| 898. | 2 | O | H | $CH(CH_3)_2$ | H | 2,6-diisopropylphenyl | H | H | CH | N | CH | CH |
| 899. | 2 | O | H | $CH_2CH(CH_3)_2$ | H | $CH_3$ | H | H | CH | N | CH | CH |
| 900. | 2 | O | H | $CH_2CH(CH_3)_2$ | H | $CH(CH_3)_2$ | H | H | CH | N | CH | CH |
| 901. | 2 | O | H | $CH_2CH(CH_3)_2$ | H | $CH_2CH(CH_3)_2$ | H | H | CH | N | CH | CH |
| 902. | 2 | O | H | $CH_2CH(CH_3)_2$ | H | $C_6H_{11}$ | H | H | CH | N | CH | CH |
| 903. | 2 | O | H | $CH_2CH(CH_3)_2$ | H | Ph | H | H | CH | N | CH | CH |
| 904. | 2 | O | H | $CH_2CH(CH_3)_2$ | H | 2,6-dimethylphenyl | H | H | CH | N | CH | CH |

-continued

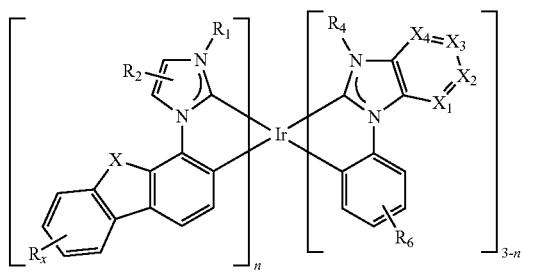

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 905. | 2 | O | H | $CH_2CH(CH_3)_2$ | H | 2,6-diisopropylphenyl | H | H | CH | N | CH | CH |
| 906. | 2 | O | H | $C_6H_{11}$ | H | $CH_3$ | H | H | CH | N | CH | CH |
| 907. | 2 | O | H | $C_6H_{11}$ | H | $CH(CH_3)_2$ | H | H | CH | N | CH | CH |
| 908. | 2 | O | H | $C_6H_{11}$ | H | $CH_2CH(CH_3)_2$ | H | H | CH | N | CH | CH |
| 909. | 2 | O | H | $C_6H_{11}$ | H | $C_6H_{11}$ | H | H | CH | N | CH | CH |
| 910. | 2 | O | H | $C_6H_{11}$ | H | Ph | H | H | CH | N | CH | CH |
| 911. | 2 | O | H | $C_6H_{11}$ | H | 2,6-dimethylphenyl | H | H | CH | N | CH | CH |
| 912. | 2 | O | H | $C_6H_{11}$ | H | 2,6-diisopropylphenyl | H | H | CH | N | CH | CH |
| 913. | 2 | O | H | Ph | H | $CH_3$ | H | H | CH | N | CH | CH |
| 914. | 2 | O | H | Ph | H | $CH(CH_3)_2$ | H | H | CH | N | CH | CH |
| 915. | 2 | O | H | Ph | H | $CH_2CH(CH_3)_2$ | H | H | CH | N | CH | CH |
| 916. | 2 | O | H | Ph | H | $C_6H_{11}$ | H | H | CH | N | CH | CH |
| 917. | 2 | O | H | Ph | H | Ph | H | H | CH | N | CH | CH |
| 918. | 2 | O | H | Ph | H | 2,6-dimethylphenyl | H | H | CH | N | CH | CH |
| 919. | 2 | O | H | Ph | H | 2,6-diisopropylphenyl | H | H | CH | N | CH | CH |
| 920. | 2 | O | H | 2,6-dimethylphenyl | H | $CH_3$ | H | H | CH | N | CH | CH |
| 921. | 2 | O | H | 2,6-dimethylphenyl | H | $CH(CH_3)_2$ | H | H | CH | N | CH | CH |
| 922. | 2 | O | H | 2,6-dimethylphenyl | H | $CH_2CH(CH_3)_2$ | H | H | CH | N | CH | CH |
| 923. | 2 | O | H | 2,6-dimethylphenyl | H | $C_6H_{11}$ | H | H | CH | N | CH | CH |
| 924. | 2 | O | H | 2,6-dimethylphenyl | H | Ph | H | H | CH | N | CH | CH |
| 925. | 2 | O | H | 2,6-dimethylphenyl | H | 2,6-dimethylphenyl | H | H | CH | N | CH | CH |
| 926. | 2 | O | H | 2,6-dimethylphenyl | H | 2,6-diisopropylphenyl | H | H | CH | N | CH | CH |
| 927. | 2 | O | H | 2,6-diisopropylphenyl | H | $CH_3$ | H | H | CH | N | CH | CH |
| 928. | 2 | O | H | 2,6-diisopropylphenyl | H | $CH(CH_3)_2$ | H | H | CH | N | CH | CH |
| 929. | 2 | O | H | 2,6-diisopropylphenyl | H | $CH_2CH(CH_3)_2$ | H | H | CH | N | CH | CH |
| 930. | 2 | O | H | 2,6-diisopropylphenyl | H | $C_6H_{11}$ | H | H | CH | N | CH | CH |
| 931. | 2 | O | H | 2,6-diisopropylphenyl | H | Ph | H | H | CH | N | CH | CH |
| 932. | 2 | O | H | 2,6-diisopropylphenyl | H | 2,6-dimethylphenyl | H | H | CH | N | CH | CH |
| 933. | 2 | O | H | 2,6-diisopropylphenyl | H | 2,6-diisopropylphenyl | H | H | CH | N | CH | CH |
| 934. | 2 | S | H | $CH_3$ | H | $CH_3$ | H | H | CH | N | CH | CH |
| 935. | 2 | S | H | $CH_3$ | H | $CH(CH_3)_2$ | H | H | CH | N | CH | CH |
| 936. | 2 | S | H | $CH_3$ | H | $CH_2CH(CH_3)_2$ | H | H | CH | N | CH | CH |
| 937. | 2 | S | H | $CH_3$ | H | $C_6H_{11}$ | H | H | CH | N | CH | CH |
| 938. | 2 | S | H | $CH_3$ | H | Ph | H | H | CH | N | CH | CH |
| 939. | 2 | S | H | $CH_3$ | H | 2,6-dimethylphenyl | H | H | CH | N | CH | CH |
| 940. | 2 | S | H | $CH_3$ | H | 2,6-diisopropylphenyl | H | H | CH | N | CH | CH |
| 941. | 2 | S | H | $CH(CH_3)_2$ | H | $CH_3$ | H | H | CH | N | CH | CH |
| 942. | 2 | S | H | $CH(CH_3)_2$ | H | $CH(CH_3)_2$ | H | H | CH | N | CH | CH |
| 943. | 2 | S | H | $CH(CH_3)_2$ | H | $CH_2CH(CH_3)_2$ | H | H | CH | N | CH | CH |
| 944. | 2 | S | H | $CH(CH_3)_2$ | H | $C_6H_{11}$ | H | H | CH | N | CH | CH |

-continued

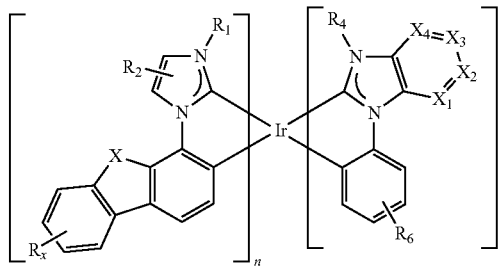

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 945. | 2 | S | H | $CH(CH_3)_2$ | H | Ph | H | H | CH | N | CH | CH |
| 946. | 2 | S | H | $CH(CH_3)_2$ | H | 2,6-dimethylphenyl | H | H | CH | N | CH | CH |
| 947. | 2 | S | H | $CH(CH_3)_2$ | H | 2,6-diisopropylphenyl | H | H | CH | N | CH | CH |
| 948. | 2 | S | H | $CH_2CH(CH_3)_2$ | H | $CH_3$ | H | H | CH | N | CH | CH |
| 949. | 2 | S | H | $CH_2CH(CH_3)_2$ | H | $CH(CH_3)_2$ | H | H | CH | N | CH | CH |
| 950. | 2 | S | H | $CH_2CH(CH_3)_2$ | H | $CH_2CH(CH_3)_2$ | H | H | CH | N | CH | CH |
| 951. | 2 | S | H | $CH_2CH(CH_3)_2$ | H | $C_6H_{11}$ | H | H | CH | N | CH | CH |
| 952. | 2 | S | H | $CH_2CH(CH_3)_2$ | H | Ph | H | H | CH | N | CH | CH |
| 953. | 2 | S | H | $CH_2CH(CH_3)_2$ | H | 2,6-dimethylphenyl | H | H | CH | N | CH | CH |
| 954. | 2 | S | H | $CH_2CH(CH_3)_2$ | H | 2,6-diisopropylphenyl | H | H | CH | N | CH | CH |
| 955. | 2 | S | H | $C_6H_{11}$ | H | $CH_3$ | H | H | CH | N | CH | CH |
| 956. | 2 | S | H | $C_6H_{11}$ | H | $CH(CH_3)_2$ | H | H | CH | N | CH | CH |
| 957. | 2 | S | H | $C_6H_{11}$ | H | $CH_2CH(CH_3)_2$ | H | H | CH | N | CH | CH |
| 958. | 2 | S | H | $C_6H_{11}$ | H | $C_6H_{11}$ | H | H | CH | N | CH | CH |
| 959. | 2 | S | H | $C_6H_{11}$ | H | Ph | H | H | CH | N | CH | CH |
| 960. | 2 | S | H | $C_6H_{11}$ | H | 2,6-dimethylphenyl | H | H | CH | N | CH | CH |
| 961. | 2 | S | H | $C_6H_{11}$ | H | 2,6-diisopropylphenyl | H | H | CH | N | CH | CH |
| 962. | 2 | S | H | Ph | H | $CH_3$ | H | H | CH | N | CH | CH |
| 963. | 2 | S | H | Ph | H | $CH(CH_3)_2$ | H | H | CH | N | CH | CH |
| 964. | 2 | S | H | Ph | H | $CH_2CH(CH_3)_2$ | H | H | CH | N | CH | CH |
| 965. | 2 | S | H | Ph | H | $C_6H_{11}$ | H | H | CH | N | CH | CH |
| 966. | 2 | S | H | Ph | H | Ph | H | H | CH | N | CH | CH |
| 967. | 2 | S | H | Ph | H | 2,6-dimethylphenyl | H | H | CH | N | CH | CH |
| 968. | 2 | S | H | Ph | H | 2,6-diisopropylphenyl | H | H | CH | N | CH | CH |
| 969. | 2 | S | H | 2,6-dimethylphenyl | H | $CH_3$ | H | H | CH | N | CH | CH |
| 970. | 2 | S | H | 2,6-dimethylphenyl | H | $CH(CH_3)_2$ | H | H | CH | N | CH | CH |
| 971. | 2 | S | H | 2,6-dimethylphenyl | H | $CH_2CH(CH_3)_2$ | H | H | CH | N | CH | CH |
| 972. | 2 | S | H | 2,6-dimethylphenyl | H | $C_6H_{11}$ | H | H | CH | N | CH | CH |
| 973. | 2 | S | H | 2,6-dimethylphenyl | H | Ph | H | H | CH | N | CH | CH |
| 974. | 2 | S | H | 2,6-dimethylphenyl | H | 2,6-dimethylphenyl | H | H | CH | N | CH | CH |
| 975. | 2 | S | H | 2,6-dimethylphenyl | H | 2,6-diisopropylphenyl | H | H | CH | N | CH | CH |
| 976. | 2 | S | H | 2,6-diisopropylphenyl | H | $CH_3$ | H | H | CH | N | CH | CH |
| 977. | 2 | S | H | 2,6-diisopropylphenyl | H | $CH(CH_3)_2$ | H | H | CH | N | CH | CH |
| 978. | 2 | S | H | 2,6-diisopropylphenyl | H | $CH_2CH(CH_3)_2$ | H | H | CH | N | CH | CH |
| 979. | 2 | S | H | 2,6-diisopropylphenyl | H | $C_6H_{11}$ | H | H | CH | N | CH | CH |
| 980. | 2 | S | H | 2,6-diisopropylphenyl | H | Ph | H | H | CH | N | CH | CH |
| 981. | 2 | S | H | 2,6-diisopropylphenyl | H | 2,6-dimethylphenyl | H | H | CH | N | CH | CH |
| 982. | 2 | S | H | 2,6-diisopropylphenyl | H | 2,6-diisopropylphenyl | H | H | CH | N | CH | CH |
| 983. | 1 | O | H | $CH_3$ | H | $CH_3$ | H | H | CH | CH | N | CH |

-continued

Formula VI

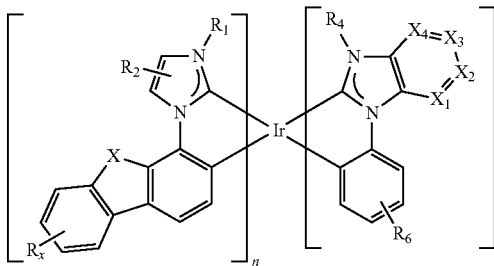

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 984. | 1 | O | H | CH$_3$ | H | CH(CH$_3$)$_2$ | H | H | CH | CH | N | CH |
| 985. | 1 | O | H | CH$_3$ | H | CH$_2$CH(CH$_3$)$_2$ | H | H | CH | CH | N | CH |
| 986. | 1 | O | H | CH$_3$ | H | C$_6$H$_{11}$ | H | H | CH | CH | N | CH |
| 987. | 1 | O | H | CH$_3$ | H | Ph | H | H | CH | CH | N | CH |
| 988. | 1 | O | H | CH$_3$ | H | 2,6-dimethylphenyl | H | H | CH | CH | N | CH |
| 989. | 1 | O | H | CH$_3$ | H | 2,6-diisopropylphenyl | H | H | CH | CH | N | CH |
| 990. | 1 | O | H | CH(CH$_3$)$_2$ | H | CH$_3$ | H | H | CH | CH | N | CH |
| 991. | 1 | O | H | CH(CH$_3$)$_2$ | H | CH(CH$_3$)$_2$ | H | H | CH | CH | N | CH |
| 992. | 1 | O | H | CH(CH$_3$)$_2$ | H | CH$_2$CH(CH$_3$)$_2$ | H | H | CH | CH | N | CH |
| 993. | 1 | O | H | CH(CH$_3$)$_2$ | H | C$_6$H$_{11}$ | H | H | CH | CH | N | CH |
| 994. | 1 | O | H | CH(CH$_3$)$_2$ | H | Ph | H | H | CH | CH | N | CH |
| 995. | 1 | O | H | CH(CH$_3$)$_2$ | H | 2,6-dimethylphenyl | H | H | CH | CH | N | CH |
| 996. | 1 | O | H | CH(CH$_3$)$_2$ | H | 2,6-diisopropylphenyl | H | H | CH | CH | N | CH |
| 997. | 1 | O | H | CH$_2$CH(CH$_3$)$_2$ | H | CH$_3$ | H | H | CH | CH | N | CH |
| 998. | 1 | O | H | CH$_2$CH(CH$_3$)$_2$ | H | CH(CH$_3$)$_2$ | H | H | CH | CH | N | CH |
| 999. | 1 | O | H | CH$_2$CH(CH$_3$)$_2$ | H | CH$_2$CH(CH$_3$)$_2$ | H | H | CH | CH | N | CH |
| 1000. | 1 | O | H | CH$_2$CH(CH$_3$)$_2$ | H | C$_6$H$_{11}$ | H | H | CH | CH | N | CH |
| 1001. | 1 | O | H | CH$_2$CH(CH$_3$)$_2$ | H | Ph | H | H | CH | CH | N | CH |
| 1002. | 1 | O | H | CH$_2$CH(CH$_3$)$_2$ | H | 2,6-dimethylphenyl | H | H | CH | CH | N | CH |
| 1003. | 1 | O | H | CH$_2$CH(CH$_3$)$_2$ | H | 2,6-diisopropylphenyl | H | H | CH | CH | N | CH |
| 1004. | 1 | O | H | C$_6$H$_{11}$ | H | CH$_3$ | H | H | CH | CH | N | CH |
| 1005. | 1 | O | H | C$_6$H$_{11}$ | H | CH(CH$_3$)$_2$ | H | H | CH | CH | N | CH |
| 1006. | 1 | O | H | C$_6$H$_{11}$ | H | CH$_2$CH(CH$_3$)$_2$ | H | H | CH | CH | N | CH |
| 1007. | 1 | O | H | C$_6$H$_{11}$ | H | C$_6$H$_{11}$ | H | H | CH | CH | N | CH |
| 1008. | 1 | O | H | C$_6$H$_{11}$ | H | Ph | H | H | CH | CH | N | CH |
| 1009. | 1 | O | H | C$_6$H$_{11}$ | H | 2,6-dimethylphenyl | H | H | CH | CH | N | CH |
| 1010. | 1 | O | H | C$_6$H$_{11}$ | H | 2,6-diisopropylphenyl | H | H | CH | CH | N | CH |
| 1011. | 1 | O | H | Ph | H | CH$_3$ | H | H | CH | CH | N | CH |
| 1012. | 1 | O | H | Ph | H | CH(CH$_3$)$_2$ | H | H | CH | CH | N | CH |
| 1013. | 1 | O | H | Ph | H | CH$_2$CH(CH$_3$)$_2$ | H | H | CH | CH | N | CH |
| 1014. | 1 | O | H | Ph | H | C$_6$H$_{11}$ | H | H | CH | CH | N | CH |
| 1015. | 1 | O | H | Ph | H | Ph | H | H | CH | CH | N | CH |
| 1016. | 1 | O | H | Ph | H | 2,6-dimethylphenyl | H | H | CH | CH | N | CH |
| 1017. | 1 | O | H | Ph | H | 2,6-diisopropylphenyl | H | H | CH | CH | N | CH |
| 1018. | 1 | O | H | 2,6-dimethylphenyl | H | CH$_3$ | H | H | CH | CH | N | CH |
| 1019. | 1 | O | H | 2,6-dimethylphenyl | H | CH(CH$_3$)$_2$ | H | H | CH | CH | N | CH |
| 1020. | 1 | O | H | 2,6-dimethylphenyl | H | CH$_2$CH(CH$_3$)$_2$ | H | H | CH | CH | N | CH |
| 1021. | 1 | O | H | 2,6-dimethylphenyl | H | C$_6$H$_{11}$ | H | H | CH | CH | N | CH |
| 1022. | 1 | O | H | 2,6-dimethylphenyl | H | Ph | H | H | CH | CH | N | CH |
| 1023. | 1 | O | H | 2,6-dimethylphenyl | H | 2,6-dimethylphenyl | H | H | CH | CH | N | CH |
| 1024. | 1 | O | H | 2,6-dimethylphenyl | H | 2,6-diisopropylphenyl | H | H | CH | CH | N | CH |
| 1025. | 1 | O | H | 2,6-diisopropylphenyl | H | CH$_3$ | H | H | CH | CH | N | CH |

-continued

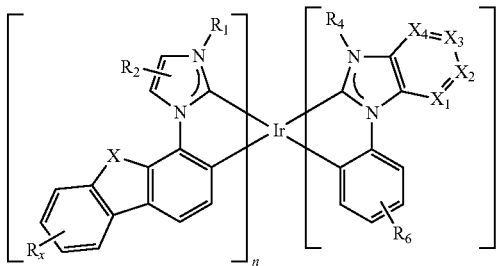

Formula VI

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1026. | 1 | O | H | 2,6-diisopropylphenyl | H | $CH(CH_3)_2$ | H | H | CH | CH | N | CH |
| 1027. | 1 | O | H | 2,6-diisopropylphenyl | H | $CH_2CH(CH_3)_2$ | H | H | CH | CH | N | CH |
| 1028. | 1 | O | H | 2,6-diisopropylphenyl | H | $C_6H_{11}$ | H | H | CH | CH | N | CH |
| 1029. | 1 | O | H | 2,6-diisopropylphenyl | H | Ph | H | H | CH | CH | N | CH |
| 1030. | 1 | O | H | 2,6-diisopropylphenyl | H | 2,6-dimethylphenyl | H | H | CH | CH | N | CH |
| 1031. | 1 | O | H | 2,6-diisopropylphenyl | H | 2,6-diisopropylphenyl | H | H | CH | CH | N | CH |
| 1032. | 1 | S | H | $CH_3$ | H | $CH_3$ | H | H | CH | CH | N | CH |
| 1033. | 1 | S | H | $CH_3$ | H | $CH(CH_3)_2$ | H | H | CH | CH | N | CH |
| 1034. | 1 | S | H | $CH_3$ | H | $CH_2CH(CH_3)_2$ | H | H | CH | CH | N | CH |
| 1035. | 1 | S | H | $CH_3$ | H | $C_6H_{11}$ | H | H | CH | CH | N | CH |
| 1036. | 1 | S | H | $CH_3$ | H | Ph | H | H | CH | CH | N | CH |
| 1037. | 1 | S | H | $CH_3$ | H | 2,6-dimethylphenyl | H | H | CH | CH | N | CH |
| 1038. | 1 | S | H | $CH_3$ | H | 2,6-diisopropylphenyl | H | H | CH | CH | N | CH |
| 1039. | 1 | S | H | $CH(CH_3)_2$ | H | $CH_3$ | H | H | CH | CH | N | CH |
| 1040. | 1 | S | H | $CH(CH_3)_2$ | H | $CH(CH_3)_2$ | H | H | CH | CH | N | CH |
| 1041. | 1 | S | H | $CH(CH_3)_2$ | H | $CH_2CH(CH_3)_2$ | H | H | CH | CH | N | CH |
| 1042. | 1 | S | H | $CH(CH_3)_2$ | H | $C_6H_{11}$ | H | H | CH | CH | N | CH |
| 1043. | 1 | S | H | $CH(CH_3)_2$ | H | Ph | H | H | CH | CH | N | CH |
| 1044. | 1 | S | H | $CH(CH_3)_2$ | H | 2,6-dimethylphenyl | H | H | CH | CH | N | CH |
| 1045. | 1 | S | H | $CH(CH_3)_2$ | H | 2,6-diisopropylphenyl | H | H | CH | CH | N | CH |
| 1046. | 1 | S | H | $CH_2CH(CH_3)_2$ | H | $CH_3$ | H | H | CH | CH | N | CH |
| 1047. | 1 | S | H | $CH_2CH(CH_3)_2$ | H | $CH(CH_3)_2$ | H | H | CH | CH | N | CH |
| 1048. | 1 | S | H | $CH_2CH(CH_3)_2$ | H | $CH_2CH(CH_3)_2$ | H | H | CH | CH | N | CH |
| 1049. | 1 | S | H | $CH_2CH(CH_3)_2$ | H | $C_6H_{11}$ | H | H | CH | CH | N | CH |
| 1050. | 1 | S | H | $CH_2CH(CH_3)_2$ | H | Ph | H | H | CH | CH | N | CH |
| 1051. | 1 | S | H | $CH_2CH(CH_3)_2$ | H | 2,6-dimethylphenyl | H | H | CH | CH | N | CH |
| 1052. | 1 | S | H | $CH_2CH(CH_3)_2$ | H | 2,6-diisopropylphenyl | H | H | CH | CH | N | CH |
| 1053. | 1 | S | H | $C_6H_{11}$ | H | $CH_3$ | H | H | CH | CH | N | CH |
| 1054. | 1 | S | H | $C_6H_{11}$ | H | $CH(CH_3)_2$ | H | H | CH | CH | N | CH |
| 1055. | 1 | S | H | $C_6H_{11}$ | H | $CH_2CH(CH_3)_2$ | H | H | CH | CH | N | CH |
| 1056. | 1 | S | H | $C_6H_{11}$ | H | $C_6H_{11}$ | H | H | CH | CH | N | CH |
| 1057. | 1 | S | H | $C_6H_{11}$ | H | Ph | H | H | CH | CH | N | CH |
| 1058. | 1 | S | H | $C_6H_{11}$ | H | 2,6-dimethylphenyl | H | H | CH | CH | N | CH |
| 1059. | 1 | S | H | $C_6H_{11}$ | H | 2,6-diisopropylphenyl | H | H | CH | CH | N | CH |
| 1060. | 1 | S | H | Ph | H | $CH_3$ | H | H | CH | CH | N | CH |
| 1061. | 1 | S | H | Ph | H | $CH(CH_3)_2$ | H | H | CH | CH | N | CH |
| 1062. | 1 | S | H | Ph | H | $CH_2CH(CH_3)_2$ | H | H | CH | CH | N | CH |
| 1063. | 1 | S | H | Ph | H | $C_6H_{11}$ | H | H | CH | CH | N | CH |
| 1064. | 1 | S | H | Ph | H | Ph | H | H | CH | CH | N | CH |
| 1065. | 1 | S | H | Ph | H | 2,6-dimethylphenyl | H | H | CH | CH | N | CH |
| 1066. | 1 | S | H | Ph | H | 2,6-diisopropylphenyl | H | H | CH | CH | N | CH |
| 1067. | 1 | S | H | 2,6-dimethylphenyl | H | $CH_3$ | H | H | CH | CH | N | CH |
| 1068. | 1 | S | H | 2,6-dimethylphenyl | H | $CH(CH_3)_2$ | H | H | CH | CH | N | CH |

-continued

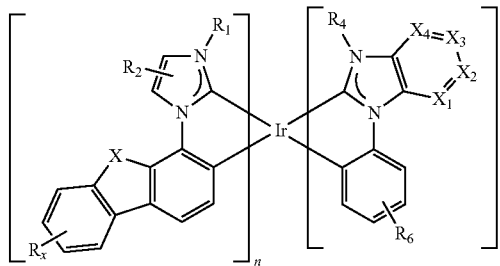

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1069. | 1 | S | H | 2,6-dimethylphenyl | H | $CH_2CH(CH_3)_2$ | H | H | CH | CH | N | CH |
| 1070. | 1 | S | H | 2,6-dimethylphenyl | H | $C_6H_{11}$ | H | H | CH | CH | N | CH |
| 1071. | 1 | S | H | 2,6-dimethylphenyl | H | Ph | H | H | CH | CH | N | CH |
| 1072. | 1 | S | H | 2,6-dimethylphenyl | H | 2,6-dimethylphenyl | H | H | CH | CH | N | CH |
| 1073. | 1 | S | H | 2,6-dimethylphenyl | H | 2,6-diisopropylphenyl | H | H | CH | CH | N | CH |
| 1074. | 1 | S | H | 2,6-diisopropylphenyl | H | $CH_3$ | H | H | CH | CH | N | CH |
| 1075. | 1 | S | H | 2,6-diisopropylphenyl | H | $CH(CH_3)_2$ | H | H | CH | CH | N | CH |
| 1076. | 1 | S | H | 2,6-diisopropylphenyl | H | $CH_2CH(CH_3)_2$ | H | H | CH | CH | N | CH |
| 1077. | 1 | S | H | 2,6-diisopropylphenyl | H | $C_6H_{11}$ | H | H | CH | CH | N | CH |
| 1078. | 1 | S | H | 2,6-diisopropylphenyl | H | Ph | H | H | CH | CH | N | CH |
| 1079. | 1 | S | H | 2,6-diisopropylphenyl | H | 2,6-dimethylphenyl | H | H | CH | CH | N | CH |
| 1080. | 1 | S | H | 2,6-diisopropylphenyl | H | 2,6-diisopropylphenyl | H | H | CH | CH | N | CH |
| 1081. | 2 | O | H | $CH_3$ | H | $CH_3$ | H | H | CH | CH | N | CH |
| 1082. | 2 | O | H | $CH_3$ | H | $CH(CH_3)_2$ | H | H | CH | CH | N | CH |
| 1083. | 2 | O | H | $CH_3$ | H | $CH_2CH(CH_3)_2$ | H | H | CH | CH | N | CH |
| 1084. | 2 | O | H | $CH_3$ | H | $C_6H_{11}$ | H | H | CH | CH | N | CH |
| 1085. | 2 | O | H | $CH_3$ | H | Ph | H | H | CH | CH | N | CH |
| 1086. | 2 | O | H | $CH_3$ | H | 2,6-dimethylphenyl | H | H | CH | CH | N | CH |
| 1087. | 2 | O | H | $CH_3$ | H | 2,6-diisopropylphenyl | H | H | CH | CH | N | CH |
| 1088. | 2 | O | H | $CH(CH_3)_2$ | H | $CH_3$ | H | H | CH | CH | N | CH |
| 1089. | 2 | O | H | $CH(CH_3)_2$ | H | $CH(CH_3)_2$ | H | H | CH | CH | N | CH |
| 1090. | 2 | O | H | $CH(CH_3)_2$ | H | $CH_2CH(CH_3)_2$ | H | H | CH | CH | N | CH |
| 1091. | 2 | O | H | $CH(CH_3)_2$ | H | $C_6H_{11}$ | H | H | CH | CH | N | CH |
| 1092. | 2 | O | H | $CH(CH_3)_2$ | H | Ph | H | H | CH | CH | N | CH |
| 1093. | 2 | O | H | $CH(CH_3)_2$ | H | 2,6-dimethylphenyl | H | H | CH | CH | N | CH |
| 1094. | 2 | O | H | $CH(CH_3)_2$ | H | 2,6-diisopropylphenyl | H | H | CH | CH | N | CH |
| 1095. | | | | | | | | | | | | |
| 1096. | 2 | O | H | $CH_2CH(CH_3)_2$ | H | $CH_3$ | H | H | CH | CH | N | CH |
| 1097. | 2 | O | H | $CH_2CH(CH_3)_2$ | H | $CH(CH_3)_2$ | H | H | CH | CH | N | CH |
| 1098. | 2 | O | H | $CH_2CH(CH_3)_2$ | H | $CH_2CH(CH_3)_2$ | H | H | CH | CH | N | CH |
| 1099. | 2 | O | H | $CH_2CH(CH_3)_2$ | H | $C_6H_{11}$ | H | H | CH | CH | N | CH |
| 1100. | 2 | O | H | $CH_2CH(CH_3)_2$ | H | Ph | H | H | CH | CH | N | CH |
| 1101. | 2 | O | H | $CH_2CH(CH_3)_2$ | H | 2,6-dimethylphenyl | H | H | CH | CH | N | CH |
| 1102. | 2 | O | H | $CH_2CH(CH_3)_2$ | H | 2,6-diisopropylphenyl | H | H | CH | CH | N | CH |
| 1103. | 2 | O | H | $C_6H_{11}$ | H | $CH_3$ | H | H | CH | CH | N | CH |
| 1104. | 2 | O | H | $C_6H_{11}$ | H | $CH(CH_3)_2$ | H | H | CH | CH | N | CH |
| 1105. | 2 | O | H | $C_6H_{11}$ | H | $CH_2CH(CH_3)_2$ | H | H | CH | CH | N | CH |
| 1106. | 2 | O | H | $C_6H_{11}$ | H | $C_6H_{11}$ | H | H | CH | CH | N | CH |
| 1107. | 2 | O | H | $C_6H_{11}$ | H | Ph | H | H | CH | CH | N | CH |
| 1108. | 2 | O | H | $C_6H_{11}$ | H | 2,6-dimethylphenyl | H | H | CH | CH | N | CH |
| 1109. | 2 | O | H | $C_6H_{11}$ | H | 2,6-diisopropylphenyl | H | H | CH | CH | N | CH |

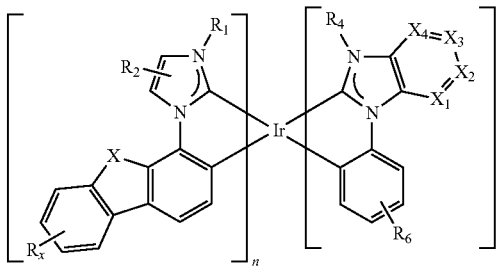

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1110. | 2 | O | H | Ph | H | $CH_3$ | H | H | CH | CH | N | CH |
| 1111. | 2 | O | H | Ph | H | $CH(CH_3)_2$ | H | H | CH | CH | N | CH |
| 1112. | 2 | O | H | Ph | H | $CH_2CH(CH_3)_2$ | H | H | CH | CH | N | CH |
| 1113. | 2 | O | H | Ph | H | $C_6H_{11}$ | H | H | CH | CH | N | CH |
| 1114. | 2 | O | H | Ph | H | Ph | H | H | CH | CH | N | CH |
| 1115. | 2 | O | H | Ph | H | 2,6-dimethylphenyl | H | H | CH | CH | N | CH |
| 1116. | 2 | O | H | Ph | H | 2,6-diisopropylphenyl | H | H | CH | CH | N | CH |
| 1117. | 2 | O | H | 2,6-dimethylphenyl | H | $CH_3$ | H | H | CH | CH | N | CH |
| 1118. | 2 | O | H | 2,6-dimethylphenyl | H | $CH(CH_3)_2$ | H | H | CH | CH | N | CH |
| 1119. | 2 | O | H | 2,6-dimethylphenyl | H | $CH_2CH(CH_3)_2$ | H | H | CH | CH | N | CH |
| 1120. | 2 | O | H | 2,6-dimethylphenyl | H | $C_6H_{11}$ | H | H | CH | CH | N | CH |
| 1121. | 2 | O | H | 2,6-dimethylphenyl | H | Ph | H | H | CH | CH | N | CH |
| 1122. | 2 | O | H | 2,6-dimethylphenyl | H | 2,6-dimethylphenyl | H | H | CH | CH | N | CH |
| 1123. | 2 | O | H | 2,6-dimethylphenyl | H | 2,6-diisopropylphenyl | H | H | CH | CH | N | CH |
| 1124. | 2 | O | H | 2,6-diisopropylphenyl | H | $CH_3$ | H | H | CH | CH | N | CH |
| 1125. | 2 | O | H | 2,6-diisopropylphenyl | H | $CH(CH_3)_2$ | H | H | CH | CH | N | CH |
| 1126. | 2 | O | H | 2,6-diisopropylphenyl | H | $CH_2CH(CH_3)_2$ | H | H | CH | CH | N | CH |
| 1127. | 2 | O | H | 2,6-diisopropylphenyl | H | $C_6H_{11}$ | H | H | CH | CH | N | CH |
| 1128. | 2 | O | H | 2,6-diisopropylphenyl | H | Ph | H | H | CH | CH | N | CH |
| 1129. | 2 | O | H | 2,6-diisopropylphenyl | H | 2,6-dimethylphenyl | H | H | CH | CH | N | CH |
| 1130. | 2 | O | H | 2,6-diisopropylphenyl | H | 2,6-diisopropylphenyl | H | H | CH | CH | N | CH |
| 1131. | 2 | S | H | $CH_3$ | H | $CH_3$ | H | H | CH | CH | N | CH |
| 1132. | 2 | S | H | $CH_3$ | H | $CH(CH_3)_2$ | H | H | CH | CH | N | CH |
| 1133. | 2 | S | H | $CH_3$ | H | $CH_2CH(CH_3)_2$ | H | H | CH | CH | N | CH |
| 1134. | 2 | S | H | $CH_3$ | H | $C_6H_{11}$ | H | H | CH | CH | N | CH |
| 1135. | 2 | S | H | $CH_3$ | H | Ph | H | H | CH | CH | N | CH |
| 1136. | 2 | S | H | $CH_3$ | H | 2,6-dimethylphenyl | H | H | CH | CH | N | CH |
| 1137. | 2 | S | H | $CH_3$ | H | 2,6-diisopropylphenyl | H | H | CH | CH | N | CH |
| 1138. | 2 | S | H | $CH(CH_3)_2$ | H | $CH_3$ | H | H | CH | CH | N | CH |
| 1139. | 2 | S | H | $CH(CH_3)_2$ | H | $CH(CH_3)_2$ | H | H | CH | CH | N | CH |
| 1140. | 2 | S | H | $CH(CH_3)_2$ | H | $CH_2CH(CH_3)_2$ | H | H | CH | CH | N | CH |
| 1141. | 2 | S | H | $CH(CH_3)_2$ | H | $C_6H_{11}$ | H | H | CH | CH | N | CH |
| 1142. | 2 | S | H | $CH(CH_3)_2$ | H | Ph | H | H | CH | CH | N | CH |
| 1143. | 2 | S | H | $CH(CH_3)_2$ | H | 2,6-dimethylphenyl | H | H | CH | CH | N | CH |
| 1144. | 2 | S | H | $CH(CH_3)_2$ | H | 2,6-diisopropylphenyl | H | H | CH | CH | N | CH |
| 1145. | 2 | S | H | $CH_2CH(CH_3)_2$ | H | $CH_3$ | H | H | CH | CH | N | CH |
| 1146. | 2 | S | H | $CH_2CH(CH_3)_2$ | H | $CH(CH_3)_2$ | H | H | CH | CH | N | CH |
| 1147. | 2 | S | H | $CH_2CH(CH_3)_2$ | H | $CH_2CH(CH_3)_2$ | H | H | CH | CH | N | CH |
| 1148. | 2 | S | H | $CH_2CH(CH_3)_2$ | H | $C_6H_{11}$ | H | H | CH | CH | N | CH |
| 1149. | 2 | S | H | $CH_2CH(CH_3)_2$ | H | Ph | H | H | CH | CH | N | CH |

-continued

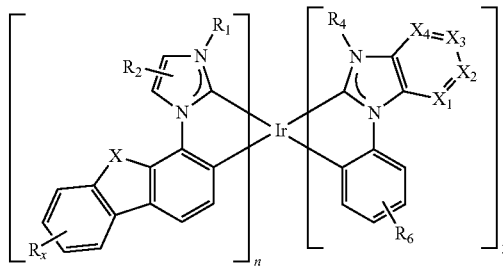

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1150. | 2 | S | H | $CH_2CH(CH_3)_2$ | H | 2,6-dimethylphenyl | H | H | CH | CH | N | CH |
| 1151. | 2 | S | H | $CH_2CH(CH_3)_2$ | H | 2,6-diisopropylphenyl | H | H | CH | CH | N | CH |
| 1152. | 2 | S | H | $C_6H_{11}$ | H | $CH_3$ | H | H | CH | CH | N | CH |
| 1153. | 2 | S | H | $C_6H_{11}$ | H | $CH(CH_3)_2$ | H | H | CH | CH | N | CH |
| 1154. | 2 | S | H | $C_6H_{11}$ | H | $CH_2CH(CH_3)_2$ | H | H | CH | CH | N | CH |
| 1155. | 2 | S | H | $C_6H_{11}$ | H | $C_6H_{11}$ | H | H | CH | CH | N | CH |
| 1156. | 2 | S | H | $C_6H_{11}$ | H | Ph | H | H | CH | CH | N | CH |
| 1157. | 2 | S | H | $C_6H_{11}$ | H | 2,6-dimethylphenyl | H | H | CH | CH | N | CH |
| 1158. | 2 | S | H | $C_6H_{11}$ | H | 2,6-diisopropylphenyl | H | H | CH | CH | N | CH |
| 1159. | 2 | S | H | Ph | H | $CH_3$ | H | H | CH | CH | N | CH |
| 1160. | 2 | S | H | Ph | H | $CH(CH_3)_2$ | H | H | CH | CH | N | CH |
| 1161. | 2 | S | H | Ph | H | $CH_2CH(CH_3)_2$ | H | H | CH | CH | N | CH |
| 1162. | 2 | S | H | Ph | H | $C_6H_{11}$ | H | H | CH | CH | N | CH |
| 1163. | 2 | S | H | Ph | H | Ph | H | H | CH | CH | N | CH |
| 1164. | 2 | S | H | Ph | H | 2,6-dimethylphenyl | H | H | CH | CH | N | CH |
| 1165. | 2 | S | H | Ph | H | 2,6-diisopropylphenyl | H | H | CH | CH | N | CH |
| 1166. | 2 | S | H | 2,6-dimethylphenyl | H | $CH_3$ | H | H | CH | CH | N | CH |
| 1167. | 2 | S | H | 2,6-dimethylphenyl | H | $CH(CH_3)_2$ | H | H | CH | CH | N | CH |
| 1168. | 2 | S | H | 2,6-dimethylphenyl | H | $CH_2CH(CH_3)_2$ | H | H | CH | CH | N | CH |
| 1169. | 2 | S | H | 2,6-dimethylphenyl | H | $C_6H_{11}$ | H | H | CH | CH | N | CH |
| 1170. | 2 | S | H | 2,6-dimethylphenyl | H | Ph | H | H | CH | CH | N | CH |
| 1171. | 2 | S | H | 2,6-dimethylphenyl | H | 2,6-dimethylphenyl | H | H | CH | CH | N | CH |
| 1172. | 2 | S | H | 2,6-dimethylphenyl | H | 2,6-diisopropylphenyl | H | H | CH | CH | N | CH |
| 1173. | 2 | S | H | 2,6-diisopropylphenyl | H | $CH_3$ | H | H | CH | CH | N | CH |
| 1174. | 2 | S | H | 2,6-diisopropylphenyl | H | $CH(CH_3)_2$ | H | H | CH | CH | N | CH |
| 1175. | 2 | S | H | 2,6-diisopropylphenyl | H | $CH_2CH(CH_3)_2$ | H | H | CH | CH | N | CH |
| 1176. | 2 | S | H | 2,6-diisopropylphenyl | H | $C_6H_{11}$ | H | H | CH | CH | N | CH |
| 1177. | 2 | S | H | 2,6-diisopropylphenyl | H | Ph | H | H | CH | CH | N | CH |
| 1178. | 2 | S | H | 2,6-diisopropylphenyl | H | 2,6-dimethylphenyl | H | H | CH | CH | N | CH |
| 1179. | 2 | S | H | 2,6-diisopropylphenyl | H | 2,6-diisopropylphenyl | H | H | CH | CH | N | CH |
| 1180. | 1 | O | H | $CH_3$ | H | $CH_3$ | H | H | CH | CH | CH | N |
| 1181. | 1 | O | H | $CH_3$ | H | $CH(CH_3)_2$ | H | H | CH | CH | CH | N |
| 1182. | 1 | O | H | $CH_3$ | H | $CH_2CH(CH_3)_2$ | H | H | CH | CH | CH | N |
| 1183. | 1 | O | H | $CH_3$ | H | $C_6H_{11}$ | H | H | CH | CH | CH | N |
| 1184. | 1 | O | H | $CH_3$ | H | Ph | H | H | CH | CH | CH | N |
| 1185. | 1 | O | H | $CH_3$ | H | 2,6-dimethylphenyl | H | H | CH | CH | CH | N |
| 1186. | 1 | O | H | $CH_3$ | H | 2,6-diisopropylphenyl | H | H | CH | CH | CH | N |
| 1187. | 1 | O | H | $CH(CH_3)_2$ | H | $CH_3$ | H | H | CH | CH | CH | N |
| 1188. | 1 | O | H | $CH(CH_3)_2$ | H | $CH(CH_3)_2$ | H | H | CH | CH | CH | N |

-continued

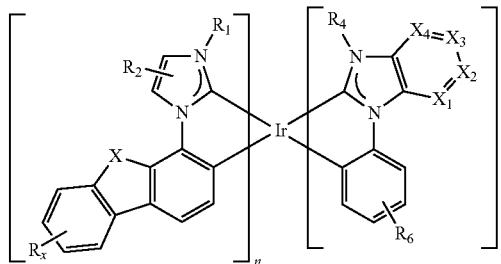

Formula VI

| Compd. | n | X | R$_x$ | R$_1$ | R$_2$ | R$_4$ | R$_5$ | R$_6$ | X$_1$ | X$_2$ | X$_3$ | X$_4$ |
|---|---|---|---|---|---|---|---|---|---|---|---|---|
| 1189. | 1 | O | H | CH(CH$_3$)$_2$ | H | CH$_2$CH(CH$_3$)$_2$ | H | H | CH | CH | CH | N |
| 1190. | 1 | O | H | CH(CH$_3$)$_2$ | H | C$_6$H$_{11}$ | H | H | CH | CH | CH | N |
| 1191. | 1 | O | H | CH(CH$_3$)$_2$ | H | Ph | H | H | CH | CH | CH | N |
| 1192. | 1 | O | H | CH(CH$_3$)$_2$ | H | 2,6-dimethylphenyl | H | H | CH | CH | CH | N |
| 1193. | 1 | O | H | CH(CH$_3$)$_2$ | H | 2,6-diisopropylphenyl | H | H | CH | CH | CH | N |
| 1194. | 1 | O | H | CH$_2$CH(CH$_3$)$_2$ | H | CH$_3$ | H | H | CH | CH | CH | N |
| 1195. | 1 | O | H | CH$_2$CH(CH$_3$)$_2$ | H | CH(CH$_3$)$_2$ | H | H | CH | CH | CH | N |
| 1196. | 1 | O | H | CH$_2$CH(CH$_3$)$_2$ | H | CH$_2$CH(CH$_3$)$_2$ | H | H | CH | CH | CH | N |
| 1197. | 1 | O | H | CH$_2$CH(CH$_3$)$_2$ | H | C$_6$H$_{11}$ | H | H | CH | CH | CH | N |
| 1198. | 1 | O | H | CH$_2$CH(CH$_3$)$_2$ | H | Ph | H | H | CH | CH | CH | N |
| 1199. | 1 | O | H | CH$_2$CH(CH$_3$)$_2$ | H | 2,6-dimethylphenyl | H | H | CH | CH | CH | N |
| 1200. | 1 | O | H | CH$_2$CH(CH$_3$)$_2$ | H | 2,6-diisopropylphenyl | H | H | CH | CH | CH | N |
| 1201. | 1 | O | H | C$_6$H$_{11}$ | H | CH$_3$ | H | H | CH | CH | CH | N |
| 1202. | 1 | O | H | C$_6$H$_{11}$ | H | CH(CH$_3$)$_2$ | H | H | CH | CH | CH | N |
| 1203. | 1 | O | H | C$_6$H$_{11}$ | H | CH$_2$CH(CH$_3$)$_2$ | H | H | CH | CH | CH | N |
| 1204. | 1 | O | H | C$_6$H$_{11}$ | H | C$_6$H$_{11}$ | H | H | CH | CH | CH | N |
| 1205. | 1 | O | H | C$_6$H$_{11}$ | H | Ph | H | H | CH | CH | CH | N |
| 1206. | 1 | O | H | C$_6$H$_{11}$ | H | 2,6-dimethylphenyl | H | H | CH | CH | CH | N |
| 1207. | 1 | O | H | C$_6$H$_{11}$ | H | 2,6-diisopropylphenyl | H | H | CH | CH | CH | N |
| 1208. | 1 | O | H | Ph | H | CH$_3$ | H | H | CH | CH | CH | N |
| 1209. | 1 | O | H | Ph | H | CH(CH$_3$)$_2$ | H | H | CH | CH | CH | N |
| 1210. | 1 | O | H | Ph | H | CH$_2$CH(CH$_3$)$_2$ | H | H | CH | CH | CH | N |
| 1211. | 1 | O | H | Ph | H | C$_6$H$_{11}$ | H | H | CH | CH | CH | N |
| 1212. | 1 | O | H | Ph | H | Ph | H | H | CH | CH | CH | N |
| 1213. | 1 | O | H | Ph | H | 2,6-dimethylphenyl | H | H | CH | CH | CH | N |
| 1214. | 1 | O | H | Ph | H | 2,6-diisopropylphenyl | H | H | CH | CH | CH | N |
| 1215. | 1 | O | H | 2,6-dimethylphenyl | H | CH$_3$ | H | H | CH | CH | CH | N |
| 1216. | 1 | O | H | 2,6-dimethylphenyl | H | CH(CH$_3$)$_2$ | H | H | CH | CH | CH | N |
| 1217. | 1 | O | H | 2,6-dimethylphenyl | H | CH$_2$CH(CH$_3$)$_2$ | H | H | CH | CH | CH | N |
| 1218. | 1 | O | H | 2,6-dimethylphenyl | H | C$_6$H$_{11}$ | H | H | CH | CH | CH | N |
| 1219. | 1 | O | H | 2,6-dimethylphenyl | H | Ph | H | H | CH | CH | CH | N |
| 1220. | 1 | O | H | 2,6-dimethylphenyl | H | 2,6-dimethylphenyl | H | H | CH | CH | CH | N |
| 1221. | 1 | O | H | 2,6-dimethylphenyl | H | 2,6-diisopropylphenyl | H | H | CH | CH | CH | N |
| 1222. | 1 | O | H | 2,6-diisopropylphenyl | H | CH$_3$ | H | H | CH | CH | CH | N |
| 1223. | 1 | O | H | 2,6-diisopropylphenyl | H | CH(CH$_3$)$_2$ | H | H | CH | CH | CH | N |
| 1224. | 1 | O | H | 2,6-diisopropylphenyl | H | CH$_2$CH(CH$_3$)$_2$ | H | H | CH | CH | CH | N |
| 1225. | 1 | O | H | 2,6-diisopropylphenyl | H | C$_6$H$_{11}$ | H | H | CH | CH | CH | N |
| 1226. | 1 | O | H | 2,6-diisopropylphenyl | H | Ph | H | H | CH | CH | CH | N |
| 1227. | 1 | O | H | 2,6-diisopropylphenyl | H | 2,6-dimethylphenyl | H | H | CH | CH | CH | N |

-continued

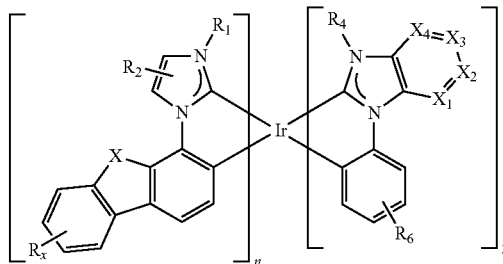

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1228. | 1 | O | H | 2,6-diisopropylphenyl | H | 2,6-diisopropylphenyl | H | H | CH | CH | CH | N |
| 1229. | 1 | S | H | CH₃ | H | CH₃ | H | H | CH | CH | CH | N |
| 1230. | 1 | S | H | CH₃ | H | CH(CH₃)₂ | H | H | CH | CH | CH | N |
| 1231. | 1 | S | H | CH₃ | H | CH₂CH(CH₃)₂ | H | H | CH | CH | CH | N |
| 1232. | 1 | S | H | CH₃ | H | C₆H₁₁ | H | H | CH | CH | CH | N |
| 1233. | 1 | S | H | CH₃ | H | Ph | H | H | CH | CH | CH | N |
| 1234. | 1 | S | H | CH₃ | H | 2,6-dimethylphenyl | H | H | CH | CH | CH | N |
| 1235. | 1 | S | H | CH₃ | H | 2,6-diisopropylphenyl | H | H | CH | CH | CH | N |
| 1236. | 1 | S | H | CH(CH₃)₂ | H | CH₃ | H | H | CH | CH | CH | N |
| 1237. | 1 | S | H | CH(CH₃)₂ | H | CH(CH₃)₂ | H | H | CH | CH | CH | N |
| 1238. | 1 | S | H | CH(CH₃)₂ | H | CH₂CH(CH₃)₂ | H | H | CH | CH | CH | N |
| 1239. | 1 | S | H | CH(CH₃)₂ | H | C₆H₁₁ | H | H | CH | CH | CH | N |
| 1240. | 1 | S | H | CH(CH₃)₂ | H | Ph | H | H | CH | CH | CH | N |
| 1241. | 1 | S | H | CH(CH₃)₂ | H | 2,6-dimethylphenyl | H | H | CH | CH | CH | N |
| 1242. | 1 | S | H | CH(CH₃)₂ | H | 2,6-diisopropylphenyl | H | H | CH | CH | CH | N |
| 1243. | 1 | S | H | CH₂CH(CH₃)₂ | H | CH₃ | H | H | CH | CH | CH | N |
| 1244. | 1 | S | H | CH₂CH(CH₃)₂ | H | CH(CH₃)₂ | H | H | CH | CH | CH | N |
| 1245. | 1 | S | H | CH₂CH(CH₃)₂ | H | CH₂CH(CH₃)₂ | H | H | CH | CH | CH | N |
| 1246. | 1 | S | H | CH₂CH(CH₃)₂ | H | C₆H₁₁ | H | H | CH | CH | CH | N |
| 1247. | 1 | S | H | CH₂CH(CH₃)₂ | H | Ph | H | H | CH | CH | CH | N |
| 1248. | 1 | S | H | CH₂CH(CH₃)₂ | H | 2,6-dimethylphenyl | H | H | CH | CH | CH | N |
| 1249. | 1 | S | H | CH₂CH(CH₃)₂ | H | 2,6-diisopropylphenyl | H | H | CH | CH | CH | N |
| 1250. | 1 | S | H | C₆H₁₁ | H | CH₃ | H | H | CH | CH | CH | N |
| 1251. | 1 | S | H | C₆H₁₁ | H | CH(CH₃)₂ | H | H | CH | CH | CH | N |
| 1252. | 1 | S | H | C₆H₁₁ | H | CH₂CH(CH₃)₂ | H | H | CH | CH | CH | N |
| 1253. | 1 | S | H | C₆H₁₁ | H | C₆H₁₁ | H | H | CH | CH | CH | N |
| 1254. | 1 | S | H | C₆H₁₁ | H | Ph | H | H | CH | CH | CH | N |
| 1255. | 1 | S | H | C₆H₁₁ | H | 2,6-dimethylphenyl | H | H | CH | CH | CH | N |
| 1256. | 1 | S | H | C₆H₁₁ | H | 2,6-diisopropylphenyl | H | H | CH | CH | CH | N |
| 1257. | 1 | S | H | Ph | H | CH₃ | H | H | CH | CH | CH | N |
| 1258. | 1 | S | H | Ph | H | CH(CH₃)₂ | H | H | CH | CH | CH | N |
| 1259. | 1 | S | H | Ph | H | CH₂CH(CH₃)₂ | H | H | CH | CH | CH | N |
| 1260. | 1 | S | H | Ph | H | C₆H₁₁ | H | H | CH | CH | CH | N |
| 1261. | 1 | S | H | Ph | H | Ph | H | H | CH | CH | CH | N |
| 1262. | 1 | S | H | Ph | H | 2,6-dimethylphenyl | H | H | CH | CH | CH | N |
| 1263. | 1 | S | H | Ph | H | 2,6-diisopropylphenyl | H | H | CH | CH | CH | N |
| 1264. | 1 | S | H | 2,6-dimethylphenyl | H | CH₃ | H | H | CH | CH | CH | N |
| 1265. | 1 | S | H | 2,6-dimethylphenyl | H | CH(CH₃)₂ | H | H | CH | CH | CH | N |
| 1266. | 1 | S | H | 2,6-dimethylphenyl | H | CH₂CH(CH₃)₂ | H | H | CH | CH | CH | N |
| 1267. | 1 | S | H | 2,6-dimethylphenyl | H | C₆H₁₁ | H | H | CH | CH | CH | N |
| 1268. | 1 | S | H | 2,6-dimethylphenyl | H | Ph | H | H | CH | CH | CH | N |
| 1269. | 1 | S | H | 2,6-dimethylphenyl | H | 2,6-dimethylphenyl | H | H | CH | CH | CH | N |
| 1270. | 1 | S | H | 2,6-dimethylphenyl | H | 2,6-diisopropylphenyl | H | H | CH | CH | CH | N |

-continued

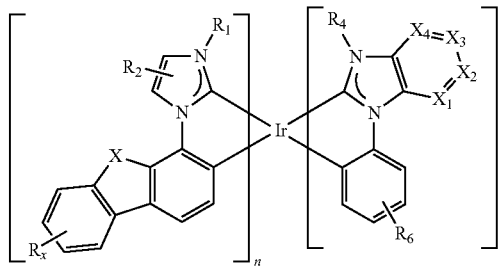

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1271. | 1 | S | H | 2,6-diisopropylphenyl | H | $CH_3$ | H | H | CH | CH | CH | N |
| 1272. | 1 | S | H | 2,6-diisopropylphenyl | H | $CH(CH_3)_2$ | H | H | CH | CH | CH | N |
| 1273. | 1 | S | H | 2,6-diisopropylphenyl | H | $CH_2CH(CH_3)_2$ | H | H | CH | CH | CH | N |
| 1274. | 1 | S | H | 2,6-diisopropylphenyl | H | $C_6H_{11}$ | H | H | CH | CH | CH | N |
| 1275. | 1 | S | H | 2,6-diisopropylphenyl | H | Ph | H | H | CH | CH | CH | N |
| 1276. | 1 | S | H | 2,6-diisopropylphenyl | H | 2,6-dimethylphenyl | H | H | CH | CH | CH | N |
| 1277. | 1 | S | H | 2,6-diisopropylphenyl | H | 2,6-diisopropylphenyl | H | H | CH | CH | CH | N |
| 1278. | 2 | O | H | $CH_3$ | H | $CH_3$ | H | H | CH | CH | CH | N |
| 1279. | 2 | O | H | $CH_3$ | H | $CH(CH_3)_2$ | H | H | CH | CH | CH | N |
| 1280. | 2 | O | H | $CH_3$ | H | $CH_2CH(CH_3)_2$ | H | H | CH | CH | CH | N |
| 1281. | 2 | O | H | $CH_3$ | H | $C_6H_{11}$ | H | H | CH | CH | CH | N |
| 1282. | 2 | O | H | $CH_3$ | H | Ph | H | H | CH | CH | CH | N |
| 1283. | 2 | O | H | $CH_3$ | H | 2,6-dimethylphenyl | H | H | CH | CH | CH | N |
| 1284. | 2 | O | H | $CH_3$ | H | 2,6-diisopropylphenyl | H | H | CH | CH | CH | N |
| 1285. | 2 | O | H | $CH(CH_3)_2$ | H | $CH_3$ | H | H | CH | CH | CH | N |
| 1286. | 2 | O | H | $CH(CH_3)_2$ | H | $CH(CH_3)_2$ | H | H | CH | CH | CH | N |
| 1287. | 2 | O | H | $CH(CH_3)_2$ | H | $CH_2CH(CH_3)_2$ | H | H | CH | CH | CH | N |
| 1288. | 2 | O | H | $CH(CH_3)_2$ | H | $C_6H_{11}$ | H | H | CH | CH | CH | N |
| 1289. | 2 | O | H | $CH(CH_3)_2$ | H | Ph | H | H | CH | CH | CH | N |
| 1290. | 2 | O | H | $CH(CH_3)_2$ | H | 2,6-dimethylphenyl | H | H | CH | CH | CH | N |
| 1291. | 2 | O | H | $CH(CH_3)_2$ | H | 2,6-diisopropylphenyl | H | H | CH | CH | CH | N |
| 1292. | 2 | O | H | $CH_2CH(CH_3)_2$ | H | $CH_3$ | H | H | CH | CH | CH | N |
| 1293. | 2 | O | H | $CH_2CH(CH_3)_2$ | H | $CH(CH_3)_2$ | H | H | CH | CH | CH | N |
| 1294. | 2 | O | H | $CH_2CH(CH_3)_2$ | H | $CH_2CH(CH_3)_2$ | H | H | CH | CH | CH | N |
| 1295. | 2 | O | H | $CH_2CH(CH_3)_2$ | H | $C_6H_{11}$ | H | H | CH | CH | CH | N |
| 1296. | 2 | O | H | $CH_2CH(CH_3)_2$ | H | Ph | H | H | CH | CH | CH | N |
| 1297. | 2 | O | H | $CH_2CH(CH_3)_2$ | H | 2,6-dimethylphenyl | H | H | CH | CH | CH | N |
| 1298. | 2 | O | H | $CH_2CH(CH_3)_2$ | H | 2,6-diisopropylphenyl | H | H | CH | CH | CH | N |
| 1299. | 2 | O | H | $C_6H_{11}$ | H | $CH_3$ | H | H | CH | CH | CH | N |
| 1300. | 2 | O | H | $C_6H_{11}$ | H | $CH(CH_3)_2$ | H | H | CH | CH | CH | N |
| 1301. | 2 | O | H | $C_6H_{11}$ | H | $CH_2CH(CH_3)_2$ | H | H | CH | CH | CH | N |
| 1302. | 2 | O | H | $C_6H_{11}$ | H | $C_6H_{11}$ | H | H | CH | CH | CH | N |
| 1303. | 2 | O | H | $C_6H_{11}$ | H | Ph | H | H | CH | CH | CH | N |
| 1304. | 2 | O | H | $C_6H_{11}$ | H | 2,6-dimethylphenyl | H | H | CH | CH | CH | N |
| 1305. | 2 | O | H | $C_6H_{11}$ | H | 2,6-diisopropylphenyl | H | H | CH | CH | CH | N |
| 1306. | 2 | O | H | Ph | H | $CH_3$ | H | H | CH | CH | CH | N |
| 1307. | 2 | O | H | Ph | H | $CH(CH_3)_2$ | H | H | CH | CH | CH | N |
| 1308. | 2 | O | H | Ph | H | $CH_2CH(CH_3)_2$ | H | H | CH | CH | CH | N |
| 1309. | 2 | O | H | Ph | H | $C_6H_{11}$ | H | H | CH | CH | CH | N |
| 1310. | 2 | O | H | Ph | H | Ph | H | H | CH | CH | CH | N |
| 1311. | 2 | O | H | Ph | H | 2,6-dimethylphenyl | H | H | CH | CH | CH | N |
| 1312. | 2 | O | H | Ph | H | 2,6-diisopropylphenyl | H | H | CH | CH | CH | N |
| 1313. | 2 | O | H | 2,6-dimethylphenyl | H | $CH_3$ | H | H | CH | CH | CH | N |

-continued

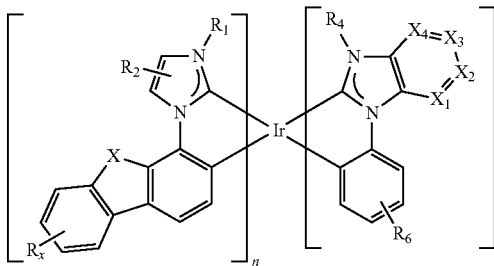

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1314. | 2 | O | H | 2,6-dimethylphenyl | H | $CH(CH_3)_2$ | H | H | CH | CH | CH | N |
| 1315. | 2 | O | H | 2,6-dimethylphenyl | H | $CH_2CH(CH_3)_2$ | H | H | CH | CH | CH | N |
| 1316. | 2 | O | H | 2,6-dimethylphenyl | H | $C_6H_{11}$ | H | H | CH | CH | CH | N |
| 1317. | 2 | O | H | 2,6-dimethylphenyl | H | Ph | H | H | CH | CH | CH | N |
| 1318. | 2 | O | H | 2,6-dimethylphenyl | H | 2,6-dimethylphenyl | H | H | CH | CH | CH | N |
| 1319. | 2 | O | H | 2,6-dimethylphenyl | H | 2,6-diisopropylphenyl | H | H | CH | CH | CH | N |
| 1320. | 2 | O | H | 2,6-diisopropylphenyl | H | $CH_3$ | H | H | CH | CH | CH | N |
| 1321. | 2 | O | H | 2,6-diisopropylphenyl | H | $CH(CH_3)_2$ | H | H | CH | CH | CH | N |
| 1322. | 2 | O | H | 2,6-diisopropylphenyl | H | $CH_2CH(CH_3)_2$ | H | H | CH | CH | CH | N |
| 1323. | 2 | O | H | 2,6-diisopropylphenyl | H | $C_6H_{11}$ | H | H | CH | CH | CH | N |
| 1324. | 2 | O | H | 2,6-diisopropylphenyl | H | Ph | H | H | CH | CH | CH | N |
| 1325. | 2 | O | H | 2,6-diisopropylphenyl | H | 2,6-dimethylphenyl | H | H | CH | CH | CH | N |
| 1326. | 2 | O | H | 2,6-diisopropylphenyl | H | 2,6-diisopropylphenyl | H | H | CH | CH | CH | N |
| 1327. | 2 | S | H | $CH_3$ | H | $CH_3$ | H | H | CH | CH | CH | N |
| 1328. | 2 | S | H | $CH_3$ | H | $CH(CH_3)_2$ | H | H | CH | CH | CH | N |
| 1329. | 2 | S | H | $CH_3$ | H | $CH_2CH(CH_3)_2$ | H | H | CH | CH | CH | N |
| 1330. | 2 | S | H | $CH_3$ | H | $C_6H_{11}$ | H | H | CH | CH | CH | N |
| 1331. | 2 | S | H | $CH_3$ | H | Ph | H | H | CH | CH | CH | N |
| 1332. | 2 | S | H | $CH_3$ | H | 2,6-dimethylphenyl | H | H | CH | CH | CH | N |
| 1333. | 2 | S | H | $CH_3$ | H | 2,6-diisopropylphenyl | H | H | CH | CH | CH | N |
| 1334. | 2 | S | H | $CH(CH_3)_2$ | H | $CH_3$ | H | H | CH | CH | CH | N |
| 1335. | 2 | S | H | $CH(CH_3)_2$ | H | $CH(CH_3)_2$ | H | H | CH | CH | CH | N |
| 1336. | 2 | S | H | $CH(CH_3)_2$ | H | $CH_2CH(CH_3)_2$ | H | H | CH | CH | CH | N |
| 1337. | 2 | S | H | $CH(CH_3)_2$ | H | $C_6H_{11}$ | H | H | CH | CH | CH | N |
| 1338. | 2 | S | H | $CH(CH_3)_2$ | H | Ph | H | H | CH | CH | CH | N |
| 1339. | 2 | S | H | $CH(CH_3)_2$ | H | 2,6-dimethylphenyl | H | H | CH | CH | CH | N |
| 1340. | 2 | S | H | $CH(CH_3)_2$ | H | 2,6-diisopropylphenyl | H | H | CH | CH | CH | N |
| 1341. | 2 | S | H | $CH_2CH(CH_3)_2$ | H | $CH_3$ | H | H | CH | CH | CH | N |
| 1342. | 2 | S | H | $CH_2CH(CH_3)_2$ | H | $CH(CH_3)_2$ | H | H | CH | CH | CH | N |
| 1343. | 2 | S | H | $CH_2CH(CH_3)_2$ | H | $CH_2CH(CH_3)_2$ | H | H | CH | CH | CH | N |
| 1344. | 2 | S | H | $CH_2CH(CH_3)_2$ | H | $C_6H_{11}$ | H | H | CH | CH | CH | N |
| 1345. | 2 | S | H | $CH_2CH(CH_3)_2$ | H | Ph | H | H | CH | CH | CH | N |
| 1346. | 2 | S | H | $CH_2CH(CH_3)_2$ | H | 2,6-dimethylphenyl | H | H | CH | CH | CH | N |
| 1347. | 2 | S | H | $CH_2CH(CH_3)_2$ | H | 2,6-diisopropylphenyl | H | H | CH | CH | CH | N |
| 1348. | 2 | S | H | $C_6H_{11}$ | H | $CH_3$ | H | H | CH | CH | CH | N |
| 1349. | 2 | S | H | $C_6H_{11}$ | H | $CH(CH_3)_2$ | H | H | CH | CH | CH | N |
| 1350. | 2 | S | H | $C_6H_{11}$ | H | $CH_2CH(CH_3)_2$ | H | H | CH | CH | CH | N |
| 1351. | 2 | S | H | $C_6H_{11}$ | H | $C_6H_{11}$ | H | H | CH | CH | CH | N |
| 1352. | 2 | S | H | $C_6H_{11}$ | H | Ph | H | H | CH | CH | CH | N |
| 1353. | 2 | S | H | $C_6H_{11}$ | H | 2,6-dimethylphenyl | H | H | CH | CH | CH | N |

-continued

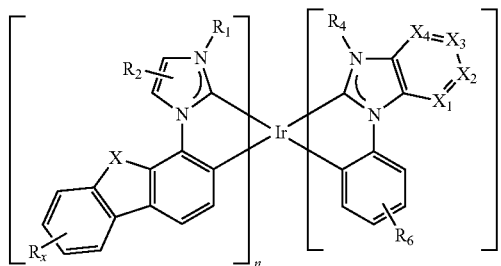

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1354. | 2 | S | H | $C_6H_{11}$ | H | 2,6-diisopropylphenyl | H | H | CH | CH | CH | N |
| 1355. | 2 | S | H | Ph | H | $CH_3$ | H | H | CH | CH | CH | N |
| 1356. | 2 | S | H | Ph | H | $CH(CH_3)_2$ | H | H | CH | CH | CH | N |
| 1357. | 2 | S | H | Ph | H | $CH_2CH(CH_3)_2$ | H | H | CH | CH | CH | N |
| 1358. | 2 | S | H | Ph | H | $C_6H_{11}$ | H | H | CH | CH | CH | N |
| 1359. | 2 | S | H | Ph | H | Ph | H | H | CH | CH | CH | N |
| 1360. | 2 | S | H | Ph | H | 2,6-dimethylphenyl | H | H | CH | CH | CH | N |
| 1361. | 2 | S | H | Ph | H | 2,6-diisopropylphenyl | H | H | CH | CH | CH | N |
| 1362. | 2 | S | H | 2,6-dimethylphenyl | H | $CH_3$ | H | H | CH | CH | CH | N |
| 1363. | 2 | S | H | 2,6-dimethylphenyl | H | $CH(CH_3)_2$ | H | H | CH | CH | CH | N |
| 1364. | 2 | S | H | 2,6-dimethylphenyl | H | $CH_2CH(CH_3)_2$ | H | H | CH | CH | CH | N |
| 1365. | 2 | S | H | 2,6-dimethylphenyl | H | $C_6H_{11}$ | H | H | CH | CH | CH | N |
| 1366. | 2 | S | H | 2,6-dimethylphenyl | H | Ph | H | H | CH | CH | CH | N |
| 1367. | 2 | S | H | 2,6-dimethylphenyl | H | 2,6-dimethylphenyl | H | H | CH | CH | CH | N |
| 1368. | 2 | S | H | 2,6-dimethylphenyl | H | 2,6-diisopropylphenyl | H | H | CH | CH | CH | N |
| 1369. | 2 | S | H | 2,6-diisopropylphenyl | H | $CH_3$ | H | H | CH | CH | CH | N |
| 1370. | 2 | S | H | 2,6-diisopropylphenyl | H | $CH(CH_3)_2$ | H | H | CH | CH | CH | N |
| 1371. | 2 | S | H | 2,6-diisopropylphenyl | H | $CH_2CH(CH_3)_2$ | H | H | CH | CH | CH | N |
| 1372. | 2 | S | H | 2,6-diisopropylphenyl | H | $C_6H_{11}$ | H | H | CH | CH | CH | N |
| 1373. | 2 | S | H | 2,6-diisopropylphenyl | H | Ph | H | H | CH | CH | CH | N |
| 1374. | 2 | S | H | 2,6-diisopropylphenyl | H | 2,6-dimethylphenyl | H | H | CH | CH | CH | N |
| 1375. | 2 | S | H | 2,6-diisopropylphenyl | H | 2,6-diisopropylphenyl | H | H | CH | CH | CH | N |
| 1376. | 1 | O | H | $CH_3$ | H | $CH_3$ | H | H | N | CH | N | CH |
| 1377. | 1 | O | H | $CH_3$ | H | $CH(CH_3)_2$ | H | H | N | CH | N | CH |
| 1378. | 1 | O | H | $CH_3$ | H | $CH_2CH(CH_3)_2$ | H | H | N | CH | N | CH |
| 1379. | 1 | O | H | $CH_3$ | H | $C_6H_{11}$ | H | H | N | CH | N | CH |
| 1380. | 1 | O | H | $CH_3$ | H | Ph | H | H | N | CH | N | CH |
| 1381. | 1 | O | H | $CH_3$ | H | 2,6-dimethylphenyl | H | H | N | CH | N | CH |
| 1382. | 1 | O | H | $CH_3$ | H | 2,6-diisopropylphenyl | H | H | N | CH | N | CH |
| 1383. | 1 | O | H | $CH(CH_3)_2$ | H | $CH_3$ | H | H | N | CH | N | CH |
| 1384. | 1 | O | H | $CH(CH_3)_2$ | H | $CH(CH_3)_2$ | H | H | N | CH | N | CH |
| 1385. | 1 | O | H | $CH(CH_3)_2$ | H | $CH_2CH(CH_3)_2$ | H | H | N | CH | N | CH |
| 1386. | 1 | O | H | $CH(CH_3)_2$ | H | $C_6H_{11}$ | H | H | N | CH | N | CH |
| 1387. | 1 | O | H | $CH(CH_3)_2$ | H | Ph | H | H | N | CH | N | CH |
| 1388. | 1 | O | H | $CH(CH_3)_2$ | H | 2,6-dimethylphenyl | H | H | N | CH | N | CH |
| 1389. | 1 | O | H | $CH(CH_3)_2$ | H | 2,6-diisopropylphenyl | H | H | N | CH | N | CH |
| 1390. | 1 | O | H | $CH_2CH(CH_3)_2$ | H | $CH_3$ | H | H | N | CH | N | CH |
| 1391. | 1 | O | H | $CH_2CH(CH_3)_2$ | H | $CH(CH_3)_2$ | H | H | N | CH | N | CH |
| 1392. | 1 | O | H | $CH_2CH(CH_3)_2$ | H | $CH_2CH(CH_3)_2$ | H | H | N | CH | N | CH |
| 1393. | 1 | O | H | $CH_2CH(CH_3)_2$ | H | $C_6H_{11}$ | H | H | N | CH | N | CH |

-continued

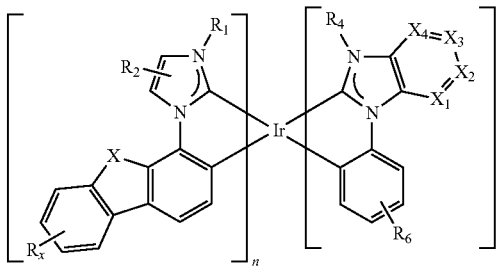

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1394. | 1 | O | H | $CH_2CH(CH_3)_2$ | H | Ph | H | H | N | CH | N | CH |
| 1395. | 1 | O | H | $CH_2CH(CH_3)_2$ | H | 2,6-dimethylphenyl | H | H | N | CH | N | CH |
| 1396. | 1 | O | H | $CH_2CH(CH_3)_2$ | H | 2,6-diisopropylphenyl | H | H | N | CH | N | CH |
| 1397. | 1 | O | H | $C_6H_{11}$ | H | $CH_3$ | H | H | N | CH | N | CH |
| 1398. | 1 | O | H | $C_6H_{11}$ | H | $CH(CH_3)_2$ | H | H | N | CH | N | CH |
| 1399. | 1 | O | H | $C_6H_{11}$ | H | $CH_2CH(CH_3)_2$ | H | H | N | CH | N | CH |
| 1400. | 1 | O | H | $C_6H_{11}$ | H | $C_6H_{11}$ | H | H | N | CH | N | CH |
| 1401. | 1 | O | H | $C_6H_{11}$ | H | Ph | H | H | N | CH | N | CH |
| 1402. | 1 | O | H | $C_6H_{11}$ | H | 2,6-dimethylphenyl | H | H | N | CH | N | CH |
| 1403. | 1 | O | H | $C_6H_{11}$ | H | 2,6-diisopropylphenyl | H | H | N | CH | N | CH |
| 1404. | 1 | O | H | Ph | H | $CH_3$ | H | H | N | CH | N | CH |
| 1405. | 1 | O | H | Ph | H | $CH(CH_3)_2$ | H | H | N | CH | N | CH |
| 1406. | 1 | O | H | Ph | H | $CH_2CH(CH_3)_2$ | H | H | N | CH | N | CH |
| 1407. | 1 | O | H | Ph | H | $C_6H_{11}$ | H | H | N | CH | N | CH |
| 1408. | 1 | O | H | Ph | H | Ph | H | H | N | CH | N | CH |
| 1409. | 1 | O | H | Ph | H | 2,6-dimethylphenyl | H | H | N | CH | N | CH |
| 1410. | 1 | O | H | Ph | H | 2,6-diisopropylphenyl | H | H | N | CH | N | CH |
| 1411. | 1 | O | H | 2,6-dimethylphenyl | H | $CH_3$ | H | H | N | CH | N | CH |
| 1412. | 1 | O | H | 2,6-dimethylphenyl | H | $CH(CH_3)_2$ | H | H | N | CH | N | CH |
| 1413. | 1 | O | H | 2,6-dimethylphenyl | H | $CH_2CH(CH_3)_2$ | H | H | N | CH | N | CH |
| 1414. | 1 | O | H | 2,6-dimethylphenyl | H | $C_6H_{11}$ | H | H | N | CH | N | CH |
| 1415. | 1 | O | H | 2,6-dimethylphenyl | H | Ph | H | H | N | CH | N | CH |
| 1416. | 1 | O | H | 2,6-dimethylphenyl | H | 2,6-dimethylphenyl | H | H | N | CH | N | CH |
| 1417. | 1 | O | H | 2,6-dimethylphenyl | H | 2,6-diisopropylphenyl | H | H | N | CH | N | CH |
| 1418. | 1 | O | H | 2,6-diisopropylphenyl | H | $CH_3$ | H | H | N | CH | N | CH |
| 1419. | 1 | O | H | 2,6-diisopropylphenyl | H | $CH(CH_3)_2$ | H | H | N | CH | N | CH |
| 1420. | 1 | O | H | 2,6-diisopropylphenyl | H | $CH_2CH(CH_3)_2$ | H | H | N | CH | N | CH |
| 1421. | 1 | O | H | 2,6-diisopropylphenyl | H | $C_6H_{11}$ | H | H | N | CH | N | CH |
| 1422. | 1 | O | H | 2,6-diisopropylphenyl | H | Ph | H | H | N | CH | N | CH |
| 1423. | 1 | O | H | 2,6-diisopropylphenyl | H | 2,6-dimethylphenyl | H | H | N | CH | N | CH |
| 1424. | 1 | O | H | 2,6-diisopropylphenyl | H | 2,6-diisopropylphenyl | H | H | N | CH | N | CH |
| 1425. | 1 | S | H | $CH_3$ | H | $CH_3$ | H | H | N | CH | N | CH |
| 1426. | 1 | S | H | $CH_3$ | H | $CH(CH_3)_2$ | H | H | N | CH | N | CH |
| 1427. | 1 | S | H | $CH_3$ | H | $CH_2CH(CH_3)_2$ | H | H | N | CH | N | CH |
| 1428. | 1 | S | H | $CH_3$ | H | $C_6H_{11}$ | H | H | N | CH | N | CH |
| 1429. | 1 | S | H | $CH_3$ | H | Ph | H | H | N | CH | N | CH |
| 1430. | 1 | S | H | $CH_3$ | H | 2,6-dimethylphenyl | H | H | N | CH | N | CH |
| 1431. | 1 | S | H | $CH_3$ | H | 2,6-diisopropylphenyl | H | H | N | CH | N | CH |
| 1432. | 1 | S | H | $CH(CH_3)_2$ | H | $CH_3$ | H | H | N | CH | N | CH |

-continued

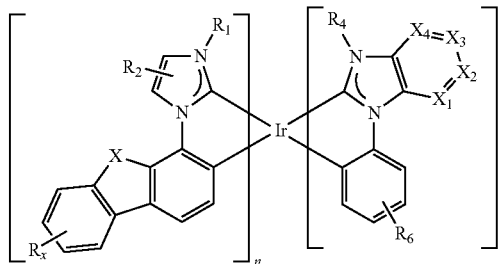

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1433. | 1 | S | H | $CH(CH_3)_2$ | H | $CH(CH_3)_2$ | H | H | N | CH | N | CH |
| 1434. | 1 | S | H | $CH(CH_3)_2$ | H | $CH_2CH(CH_3)_2$ | H | H | N | CH | N | CH |
| 1435. | 1 | S | H | $CH(CH_3)_2$ | H | $C_6H_{11}$ | H | H | N | CH | N | CH |
| 1436. | 1 | S | H | $CH(CH_3)_2$ | H | Ph | H | H | N | CH | N | CH |
| 1437. | 1 | S | H | $CH(CH_3)_2$ | H | 2,6-dimethylphenyl | H | H | N | CH | N | CH |
| 1438. | 1 | S | H | $CH(CH_3)_2$ | H | 2,6-diisopropylphenyl | H | H | N | CH | N | CH |
| 1439. | 1 | S | H | $CH_2CH(CH_3)_2$ | H | $CH_3$ | H | H | N | CH | N | CH |
| 1440. | 1 | S | H | $CH_2CH(CH_3)_2$ | H | $CH(CH_3)_2$ | H | H | N | CH | N | CH |
| 1441. | 1 | S | H | $CH_2CH(CH_3)_2$ | H | $CH_2CH(CH_3)_2$ | H | H | N | CH | N | CH |
| 1442. | 1 | S | H | $CH_2CH(CH_3)_2$ | H | $C_6H_{11}$ | H | H | N | CH | N | CH |
| 1443. | 1 | S | H | $CH_2CH(CH_3)_2$ | H | Ph | H | H | N | CH | N | CH |
| 1444. | 1 | S | H | $CH_2CH(CH_3)_2$ | H | 2,6-dimethylphenyl | H | H | N | CH | N | CH |
| 1445. | 1 | S | H | $CH_2CH(CH_3)_2$ | H | 2,6-diisopropylphenyl | H | H | N | CH | N | CH |
| 1446. | 1 | S | H | $C_6H_{11}$ | H | $CH_3$ | H | H | N | CH | N | CH |
| 1447. | 1 | S | H | $C_6H_{11}$ | H | $CH(CH_3)_2$ | H | H | N | CH | N | CH |
| 1448. | 1 | S | H | $C_6H_{11}$ | H | $CH_2CH(CH_3)_2$ | H | H | N | CH | N | CH |
| 1449. | 1 | S | H | $C_6H_{11}$ | H | $C_6H_{11}$ | H | H | N | CH | N | CH |
| 1450. | 1 | S | H | $C_6H_{11}$ | H | Ph | H | H | N | CH | N | CH |
| 1451. | 1 | S | H | $C_6H_{11}$ | H | 2,6-dimethylphenyl | H | H | N | CH | N | CH |
| 1452. | 1 | S | H | $C_6H_{11}$ | H | 2,6-diisopropylphenyl | H | H | N | CH | N | CH |
| 1453. | 1 | S | H | Ph | H | $CH_3$ | H | H | N | CH | N | CH |
| 1454. | 1 | S | H | Ph | H | $CH(CH_3)_2$ | H | H | N | CH | N | CH |
| 1455. | 1 | S | H | Ph | H | $CH_2CH(CH_3)_2$ | H | H | N | CH | N | CH |
| 1456. | 1 | S | H | Ph | H | $C_6H_{11}$ | H | H | N | CH | N | CH |
| 1457. | 1 | S | H | Ph | H | Ph | H | H | N | CH | N | CH |
| 1458. | 1 | S | H | Ph | H | 2,6-dimethylphenyl | H | H | N | CH | N | CH |
| 1459. | 1 | S | H | Ph | H | 2,6-diisopropylphenyl | H | H | N | CH | N | CH |
| 1460. | 1 | S | H | 2,6-dimethylphenyl | H | $CH_3$ | H | H | N | CH | N | CH |
| 1461. | 1 | S | H | 2,6-dimethylphenyl | H | $CH(CH_3)_2$ | H | H | N | CH | N | CH |
| 1462. | 1 | S | H | 2,6-dimethylphenyl | H | $CH_2CH(CH_3)_2$ | H | H | N | CH | N | CH |
| 1463. | 1 | S | H | 2,6-dimethylphenyl | H | $C_6H_{11}$ | H | H | N | CH | N | CH |
| 1464. | 1 | S | H | 2,6-dimethylphenyl | H | Ph | H | H | N | CH | N | CH |
| 1465. | 1 | S | H | 2,6-dimethylphenyl | H | 2,6-dimethylphenyl | H | H | N | CH | N | CH |
| 1466. | 1 | S | H | 2,6-dimethylphenyl | H | 2,6-diisopropylphenyl | H | H | N | CH | N | CH |
| 1467. | 1 | S | H | 2,6-diisopropylphenyl | H | $CH_3$ | H | H | N | CH | N | CH |
| 1468. | 1 | S | H | 2,6-diisopropylphenyl | H | $CH(CH_3)_2$ | H | H | N | CH | N | CH |
| 1469. | 1 | S | H | 2,6-diisopropylphenyl | H | $CH_2CH(CH_3)_2$ | H | H | N | CH | N | CH |
| 1470. | 1 | S | H | 2,6-diisopropylphenyl | H | $C_6H_{11}$ | H | H | N | CH | N | CH |
| 1471. | 1 | S | H | 2,6-diisopropylphenyl | H | Ph | H | H | N | CH | N | CH |
| 1472. | 1 | S | H | 2,6-diisopropylphenyl | H | 2,6-dimethylphenyl | H | H | N | CH | N | CH |

-continued

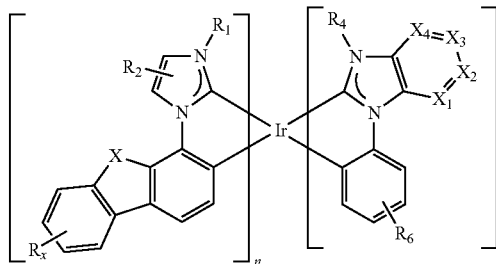

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1473. | 1 | S | H | 2,6-diisopropylphenyl | H | 2,6-diisopropylphenyl | H | H | N | CH | N | CH |
| 1474. | 2 | O | H | $CH_3$ | H | $CH_3$ | H | H | N | CH | N | CH |
| 1475. | 2 | O | H | $CH_3$ | H | $CH(CH_3)_2$ | H | H | N | CH | N | CH |
| 1476. | 2 | O | H | $CH_3$ | H | $CH_2CH(CH_3)_2$ | H | H | N | CH | N | CH |
| 1477. | 2 | O | H | $CH_3$ | H | $C_6H_{11}$ | H | H | N | CH | N | CH |
| 1478. | 2 | O | H | $CH_3$ | H | Ph | H | H | N | CH | N | CH |
| 1479. | 2 | O | H | $CH_3$ | H | 2,6-dimethylphenyl | H | H | N | CH | N | CH |
| 1480. | 2 | O | H | $CH_3$ | H | 2,6-diisopropylphenyl | H | H | N | CH | N | CH |
| 1481. | 2 | O | H | $CH(CH_3)_2$ | H | $CH_3$ | H | H | N | CH | N | CH |
| 1482. | 2 | O | H | $CH(CH_3)_2$ | H | $CH(CH_3)_2$ | H | H | N | CH | N | CH |
| 1483. | 2 | O | H | $CH(CH_3)_2$ | H | $CH_2CH(CH_3)_2$ | H | H | N | CH | N | CH |
| 1484. | 2 | O | H | $CH(CH_3)_2$ | H | $C_6H_{11}$ | H | H | N | CH | N | CH |
| 1485. | 2 | O | H | $CH(CH_3)_2$ | H | Ph | H | H | N | CH | N | CH |
| 1486. | 2 | O | H | $CH(CH_3)_2$ | H | 2,6-dimethylphenyl | H | H | N | CH | N | CH |
| 1487. | 2 | O | H | $CH(CH_3)_2$ | H | 2,6-diisopropylphenyl | H | H | N | CH | N | CH |
| 1488. | | | | | | | | | N | CH | N | CH |
| 1489. | 2 | O | H | $CH_2CH(CH_3)_2$ | H | $CH_3$ | H | H | N | CH | N | CH |
| 1490. | 2 | O | H | $CH_2CH(CH_3)_2$ | H | $CH(CH_3)_2$ | H | H | N | CH | N | CH |
| 1491. | 2 | O | H | $CH_2CH(CH_3)_2$ | H | $CH_2CH(CH_3)_2$ | H | H | N | CH | N | CH |
| 1492. | 2 | O | H | $CH_2CH(CH_3)_2$ | H | $C_6H_{11}$ | H | H | N | CH | N | CH |
| 1493. | 2 | O | H | $CH_2CH(CH_3)_2$ | H | Ph | H | H | N | CH | N | CH |
| 1494. | 2 | O | H | $CH_2CH(CH_3)_2$ | H | 2,6-dimethylphenyl | H | H | N | CH | N | CH |
| 1495. | 2 | O | H | $CH_2CH(CH_3)_2$ | H | 2,6-diisopropylphenyl | H | H | N | CH | N | CH |
| 1496. | 2 | O | H | $C_6H_{11}$ | H | $CH_3$ | H | H | N | CH | N | CH |
| 1497. | 2 | O | H | $C_6H_{11}$ | H | $CH(CH_3)_2$ | H | H | N | CH | N | CH |
| 1498. | 2 | O | H | $C_6H_{11}$ | H | $CH_2CH(CH_3)_2$ | H | H | N | CH | N | CH |
| 1499. | 2 | O | H | $C_6H_{11}$ | H | $C_6H_{11}$ | H | H | N | CH | N | CH |
| 1500. | 2 | O | H | $C_6H_{11}$ | H | Ph | H | H | N | CH | N | CH |
| 1501. | 2 | O | H | $C_6H_{11}$ | H | 2,6-dimethylphenyl | H | H | N | CH | N | CH |
| 1502. | 2 | O | H | $C_6H_{11}$ | H | 2,6-diisopropylphenyl | H | H | N | CH | N | CH |
| 1503. | 2 | O | H | Ph | H | $CH_3$ | H | H | N | CH | N | CH |
| 1504. | 2 | O | H | Ph | H | $CH(CH_3)_2$ | H | H | N | CH | N | CH |
| 1505. | 2 | O | H | Ph | H | $CH_2CH(CH_3)_2$ | H | H | N | CH | N | CH |
| 1506. | 2 | O | H | Ph | H | $C_6H_{11}$ | H | H | N | CH | N | CH |
| 1507. | 2 | O | H | Ph | H | Ph | H | H | N | CH | N | CH |
| 1508. | 2 | O | H | Ph | H | 2,6-dimethylphenyl | H | H | N | CH | N | CH |
| 1509. | 2 | O | H | Ph | H | 2,6-diisopropylphenyl | H | H | N | CH | N | CH |
| 1510. | 2 | O | H | 2,6-dimethylphenyl | H | $CH_3$ | H | H | N | CH | N | CH |
| 1511. | 2 | O | H | 2,6-dimethylphenyl | H | $CH(CH_3)_2$ | H | H | N | CH | N | CH |
| 1512. | 2 | O | H | 2,6-dimethylphenyl | H | $CH_2CH(CH_3)_2$ | H | H | N | CH | N | CH |
| 1513. | 2 | O | H | 2,6-dimethylphenyl | H | $C_6H_{11}$ | H | H | N | CH | N | CH |
| 1514. | 2 | O | H | 2,6-dimethylphenyl | H | Ph | H | H | N | CH | N | CH |
| 1515. | 2 | O | H | 2,6-dimethylphenyl | H | 2,6-dimethylphenyl | H | H | N | CH | N | CH |

-continued

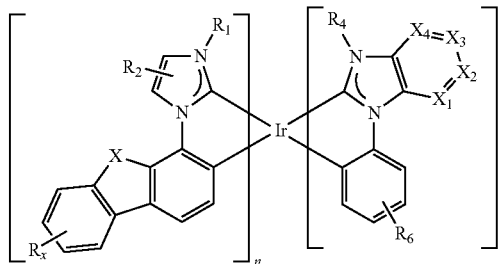

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1516. | 2 | O | H | 2,6-dimethylphenyl | H | 2,6-diisopropylphenyl | H | H | N | CH | N | CH |
| 1517. | 2 | O | H | 2,6-diisopropylphenyl | H | $CH_3$ | H | H | N | CH | N | CH |
| 1518. | 2 | O | H | 2,6-diisopropylphenyl | H | $CH(CH_3)_2$ | H | H | N | CH | N | CH |
| 1519. | 2 | O | H | 2,6-diisopropylphenyl | H | $CH_2CH(CH_3)_2$ | H | H | N | CH | N | CH |
| 1520. | 2 | O | H | 2,6-diisopropylphenyl | H | $C_6H_{11}$ | H | H | N | CH | N | CH |
| 1521. | 2 | O | H | 2,6-diisopropylphenyl | H | Ph | H | H | N | CH | N | CH |
| 1522. | 2 | O | H | 2,6-diisopropylphenyl | H | 2,6-dimethylphenyl | H | H | N | CH | N | CH |
| 1523. | 2 | O | H | 2,6-diisopropylphenyl | H | 2,6-diisopropylphenyl | H | H | N | CH | N | CH |
| 1524. | 2 | S | H | $CH_3$ | H | $CH_3$ | H | H | N | CH | N | CH |
| 1525. | 2 | S | H | $CH_3$ | H | $CH(CH_3)_2$ | H | H | N | CH | N | CH |
| 1526. | 2 | S | H | $CH_3$ | H | $CH_2CH(CH_3)_2$ | H | H | N | CH | N | CH |
| 1527. | 2 | S | H | $CH_3$ | H | $C_6H_{11}$ | H | H | N | CH | N | CH |
| 1528. | 2 | S | H | $CH_3$ | H | Ph | H | H | N | CH | N | CH |
| 1529. | 2 | S | H | $CH_3$ | H | 2,6-dimethylphenyl | H | H | N | CH | N | CH |
| 1530. | 2 | S | H | $CH_3$ | H | 2,6-diisopropylphenyl | H | H | N | CH | N | CH |
| 1531. | 2 | S | H | $CH(CH_3)_2$ | H | $CH_3$ | H | H | N | CH | N | CH |
| 1532. | 2 | S | H | $CH(CH_3)_2$ | H | $CH(CH_3)_2$ | H | H | N | CH | N | CH |
| 1533. | 2 | S | H | $CH(CH_3)_2$ | H | $CH_2CH(CH_3)_2$ | H | H | N | CH | N | CH |
| 1534. | 2 | S | H | $CH(CH_3)_2$ | H | $C_6H_{11}$ | H | H | N | CH | N | CH |
| 1535. | 2 | S | H | $CH(CH_3)_2$ | H | Ph | H | H | N | CH | N | CH |
| 1536. | 2 | S | H | $CH(CH_3)_2$ | H | 2,6-dimethylphenyl | H | H | N | CH | N | CH |
| 1537. | 2 | S | H | $CH(CH_3)_2$ | H | 2,6-diisopropylphenyl | H | H | N | CH | N | CH |
| 1538. | 2 | S | H | $CH_2CH(CH_3)_2$ | H | $CH_3$ | H | H | N | CH | N | CH |
| 1539. | 2 | S | H | $CH_2CH(CH_3)_2$ | H | $CH(CH_3)_2$ | H | H | N | CH | N | CH |
| 1540. | 2 | S | H | $CH_2CH(CH_3)_2$ | H | $CH_2CH(CH_3)_2$ | H | H | N | CH | N | CH |
| 1541. | 2 | S | H | $CH_2CH(CH_3)_2$ | H | $C_6H_{11}$ | H | H | N | CH | N | CH |
| 1542. | 2 | S | H | $CH_2CH(CH_3)_2$ | H | Ph | H | H | N | CH | N | CH |
| 1543. | 2 | S | H | $CH_2CH(CH_3)_2$ | H | 2,6-dimethylphenyl | H | H | N | CH | N | CH |
| 1544. | 2 | S | H | $CH_2CH(CH_3)_2$ | H | 2,6-diisopropylphenyl | H | H | N | CH | N | CH |
| 1545. | 2 | S | H | $C_6H_{11}$ | H | $CH_3$ | H | H | N | CH | N | CH |
| 1546. | 2 | S | H | $C_6H_{11}$ | H | $CH(CH_3)_2$ | H | H | N | CH | N | CH |
| 1547. | 2 | S | H | $C_6H_{11}$ | H | $CH_2CH(CH_3)_2$ | H | H | N | CH | N | CH |
| 1548. | 2 | S | H | $C_6H_{11}$ | H | $C_6H_{11}$ | H | H | N | CH | N | CH |
| 1549. | 2 | S | H | $C_6H_{11}$ | H | Ph | H | H | N | CH | N | CH |
| 1550. | 2 | S | H | $C_6H_{11}$ | H | 2,6-dimethylphenyl | H | H | N | CH | N | CH |
| 1551. | 2 | S | H | $C_6H_{11}$ | H | 2,6-diisopropylphenyl | H | H | N | CH | N | CH |
| 1552. | 2 | S | H | Ph | H | $CH_3$ | H | H | N | CH | N | CH |
| 1553. | 2 | S | H | Ph | H | $CH(CH_3)_2$ | H | H | N | CH | N | CH |
| 1554. | 2 | S | H | Ph | H | $CH_2CH(CH_3)_2$ | H | H | N | CH | N | CH |
| 1555. | 2 | S | H | Ph | H | $C_6H_{11}$ | H | H | N | CH | N | CH |
| 1556. | 2 | S | H | Ph | H | Ph | H | H | N | CH | N | CH |
| 1557. | 2 | S | H | Ph | H | 2,6-dimethylphenyl | H | H | N | CH | N | CH |
| 1558. | 2 | S | H | Ph | H | 2,6-diisopropylphenyl | H | H | N | CH | N | CH |

-continued

Formula VI

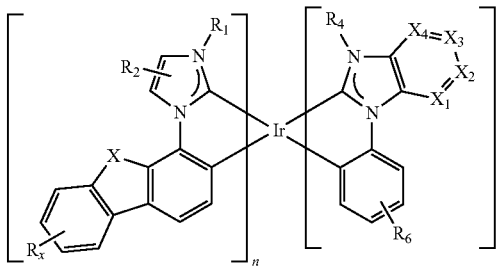

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1559. | 2 | S | H | 2,6-dimethylphenyl | H | $CH_3$ | H | H | N | CH | N | CH |
| 1560. | 2 | S | H | 2,6-dimethylphenyl | H | $CH(CH_3)_2$ | H | H | N | CH | N | CH |
| 1561. | 2 | S | H | 2,6-dimethylphenyl | H | $CH_2CH(CH_3)_2$ | H | H | N | CH | N | CH |
| 1562. | 2 | S | H | 2,6-dimethylphenyl | H | $C_6H_{11}$ | H | H | N | CH | N | CH |
| 1563. | 2 | S | H | 2,6-dimethylphenyl | H | Ph | H | H | N | CH | N | CH |
| 1564. | 2 | S | H | 2,6-dimethylphenyl | H | 2,6-dimethylphenyl | H | H | N | CH | N | CH |
| 1565. | 2 | S | H | 2,6-dimethylphenyl | H | 2,6-diisopropylphenyl | H | H | N | CH | N | CH |
| 1566. | 2 | S | H | 2,6-diisopropylphenyl | H | $CH_3$ | H | H | N | CH | N | CH |
| 1567. | 2 | S | H | 2,6-diisopropylphenyl | H | $CH(CH_3)_2$ | H | H | N | CH | N | CH |
| 1568. | 2 | S | H | 2,6-diisopropylphenyl | H | $CH_2CH(CH_3)_2$ | H | H | N | CH | N | CH |
| 1569. | 2 | S | H | 2,6-diisopropylphenyl | H | $C_6H_{11}$ | H | H | N | CH | N | CH |
| 1570. | 2 | S | H | 2,6-diisopropylphenyl | H | Ph | H | H | N | CH | N | CH |
| 1571. | 2 | S | H | 2,6-diisopropylphenyl | H | 2,6-dimethylphenyl | H | H | N | CH | N | CH |
| 1572. | 2 | S | H | 2,6-diisopropylphenyl | H | 2,6-diisopropylphenyl | H | H | N | CH | N | CH |
| 1573. | 1 | O | H | $CH_3$ | H | $CH_3$ | H | H | CH | N | CH | N |
| 1574. | 1 | O | H | $CH_3$ | H | $CH(CH_3)_2$ | H | H | CH | N | CH | N |
| 1575. | 1 | O | H | $CH_3$ | H | $CH_2CH(CH_3)_2$ | H | H | CH | N | CH | N |
| 1576. | 1 | O | H | $CH_3$ | H | $C_6H_{11}$ | H | H | CH | N | CH | N |
| 1577. | 1 | O | H | $CH_3$ | H | Ph | H | H | CH | N | CH | N |
| 1578. | 1 | O | H | $CH_3$ | H | 2,6-dimethylphenyl | H | H | CH | N | CH | N |
| 1579. | 1 | O | H | $CH_3$ | H | 2,6-diisopropylphenyl | H | H | CH | N | CH | N |
| 1580. | 1 | O | H | $CH(CH_3)_2$ | H | $CH_3$ | H | H | CH | N | CH | N |
| 1581. | 1 | O | H | $CH(CH_3)_2$ | H | $CH(CH_3)_2$ | H | H | CH | N | CH | N |
| 1582. | 1 | O | H | $CH(CH_3)_2$ | H | $CH_2CH(CH_3)_2$ | H | H | CH | N | CH | N |
| 1583. | 1 | O | H | $CH(CH_3)_2$ | H | $C_6H_{11}$ | H | H | CH | N | CH | N |
| 1584. | 1 | O | H | $CH(CH_3)_2$ | H | Ph | H | H | CH | N | CH | N |
| 1585. | 1 | O | H | $CH(CH_3)_2$ | H | 2,6-dimethylphenyl | H | H | CH | N | CH | N |
| 1586. | 1 | O | H | $CH(CH_3)_2$ | H | 2,6-diisopropylphenyl | H | H | CH | N | CH | N |
| 1587. | 1 | O | H | $CH_2CH(CH_3)_2$ | H | $CH_3$ | H | H | CH | N | CH | N |
| 1588. | 1 | O | H | $CH_2CH(CH_3)_2$ | H | $CH(CH_3)_2$ | H | H | CH | N | CH | N |
| 1589. | 1 | O | H | $CH_2CH(CH_3)_2$ | H | $CH_2CH(CH_3)_2$ | H | H | CH | N | CH | N |
| 1590. | 1 | O | H | $CH_2CH(CH_3)_2$ | H | $C_6H_{11}$ | H | H | CH | N | CH | N |
| 1591. | 1 | O | H | $CH_2CH(CH_3)_2$ | H | Ph | H | H | CH | N | CH | N |
| 1592. | 1 | O | H | $CH_2CH(CH_3)_2$ | H | 2,6-dimethylphenyl | H | H | CH | N | CH | N |
| 1593. | 1 | O | H | $CH_2CH(CH_3)_2$ | H | 2,6-diisopropylphenyl | H | H | CH | N | CH | N |
| 1594. | 1 | O | H | $C_6H_{11}$ | H | $CH_3$ | H | H | CH | N | CH | N |
| 1595. | 1 | O | H | $C_6H_{11}$ | H | $CH(CH_3)_2$ | H | H | CH | N | CH | N |
| 1596. | 1 | O | H | $C_6H_{11}$ | H | $CH_2CH(CH_3)_2$ | H | H | CH | N | CH | N |
| 1597. | 1 | O | H | $C_6H_{11}$ | H | $C_6H_{11}$ | H | H | CH | N | CH | N |
| 1598. | 1 | O | H | $C_6H_{11}$ | H | Ph | H | H | CH | N | CH | N |

-continued

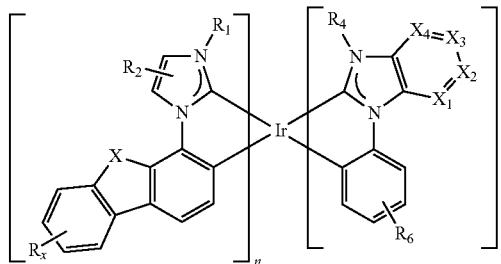

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1599. | 1 | O | H | $C_6H_{11}$ | H | 2,6-dimethylphenyl | H | H | CH | N | CH | N |
| 1600. | 1 | O | H | $C_6H_{11}$ | H | 2,6-diisopropylphenyl | H | H | CH | N | CH | N |
| 1601. | 1 | O | H | Ph | H | $CH_3$ | H | H | CH | N | CH | N |
| 1602. | 1 | O | H | Ph | H | $CH(CH_3)_2$ | H | H | CH | N | CH | N |
| 1603. | 1 | O | H | Ph | H | $CH_2CH(CH_3)_2$ | H | H | CH | N | CH | N |
| 1604. | 1 | O | H | Ph | H | $C_6H_{11}$ | H | H | CH | N | CH | N |
| 1605. | 1 | O | H | Ph | H | Ph | H | H | CH | N | CH | N |
| 1606. | 1 | O | H | Ph | H | 2,6-dimethylphenyl | H | H | CH | N | CH | N |
| 1607. | 1 | O | H | Ph | H | 2,6-diisopropylphenyl | H | H | CH | N | CH | N |
| 1608. | 1 | O | H | 2,6-dimethylphenyl | H | $CH_3$ | H | H | CH | N | CH | N |
| 1609. | 1 | O | H | 2,6-dimethylphenyl | H | $CH(CH_3)_2$ | H | H | CH | N | CH | N |
| 1610. | 1 | O | H | 2,6-dimethylphenyl | H | $CH_2CH(CH_3)_2$ | H | H | CH | N | CH | N |
| 1611. | 1 | O | H | 2,6-dimethylphenyl | H | $C_6H_{11}$ | H | H | CH | N | CH | N |
| 1612. | 1 | O | H | 2,6-dimethylphenyl | H | Ph | H | H | CH | N | CH | N |
| 1613. | 1 | O | H | 2,6-dimethylphenyl | H | 2,6-dimethylphenyl | H | H | CH | N | CH | N |
| 1614. | 1 | O | H | 2,6-dimethylphenyl | H | 2,6-diisopropylphenyl | H | H | CH | N | CH | N |
| 1615. | 1 | O | H | 2,6-diisopropylphenyl | H | $CH_3$ | H | H | CH | N | CH | N |
| 1616. | 1 | O | H | 2,6-diisopropylphenyl | H | $CH(CH_3)_2$ | H | H | CH | N | CH | N |
| 1617. | 1 | O | H | 2,6-diisopropylphenyl | H | $CH_2CH(CH_3)_2$ | H | H | CH | N | CH | N |
| 1618. | 1 | O | H | 2,6-diisopropylphenyl | H | $C_6H_{11}$ | H | H | CH | N | CH | N |
| 1619. | 1 | O | H | 2,6-diisopropylphenyl | H | Ph | H | H | CH | N | CH | N |
| 1620. | 1 | O | H | 2,6-diisopropylphenyl | H | 2,6-dimethylphenyl | H | H | CH | N | CH | N |
| 1621. | 1 | O | H | 2,6-diisopropylphenyl | H | 2,6-diisopropylphenyl | H | H | CH | N | CH | N |
| 1622. | 1 | S | H | $CH_3$ | H | $CH_3$ | H | H | CH | N | CH | N |
| 1623. | 1 | S | H | $CH_3$ | H | $CH(CH_3)_2$ | H | H | CH | N | CH | N |
| 1624. | 1 | S | H | $CH_3$ | H | $CH_2CH(CH_3)_2$ | H | H | CH | N | CH | N |
| 1625. | 1 | S | H | $CH_3$ | H | $C_6H_{11}$ | H | H | CH | N | CH | N |
| 1626. | 1 | S | H | $CH_3$ | H | Ph | H | H | CH | N | CH | N |
| 1627. | 1 | S | H | $CH_3$ | H | 2,6-dimethylphenyl | H | H | CH | N | CH | N |
| 1628. | 1 | S | H | $CH_3$ | H | 2,6-diisopropylphenyl | H | H | CH | N | CH | N |
| 1629. | 1 | S | H | $CH(CH_3)_2$ | H | $CH_3$ | H | H | CH | N | CH | N |
| 1630. | 1 | S | H | $CH(CH_3)_2$ | H | $CH(CH_3)_2$ | H | H | CH | N | CH | N |
| 1631. | 1 | S | H | $CH(CH_3)_2$ | H | $CH_2CH(CH_3)_2$ | H | H | CH | N | CH | N |
| 1632. | 1 | S | H | $CH(CH_3)_2$ | H | $C_6H_{11}$ | H | H | CH | N | CH | N |
| 1633. | 1 | S | H | $CH(CH_3)_2$ | H | Ph | H | H | CH | N | CH | N |
| 1634. | 1 | S | H | $CH(CH_3)_2$ | H | 2,6-dimethylphenyl | H | H | CH | N | CH | N |
| 1635. | 1 | S | H | $CH(CH_3)_2$ | H | 2,6-diisopropylphenyl | H | H | CH | N | CH | N |
| 1636. | 1 | S | H | $CH_2CH(CH_3)_2$ | H | $CH_3$ | H | H | CH | N | CH | N |
| 1637. | 1 | S | H | $CH_2CH(CH_3)_2$ | H | $CH(CH_3)_2$ | H | H | CH | N | CH | N |

-continued

Formula VI

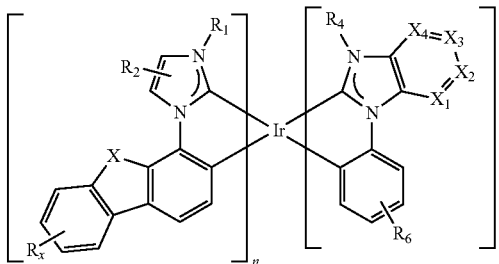

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1638. | 1 | S | H | $CH_2CH(CH_3)_2$ | H | $CH_2CH(CH_3)_2$ | H | H | CH | N | CH | N |
| 1639. | 1 | S | H | $CH_2CH(CH_3)_2$ | H | $C_6H_{11}$ | H | H | CH | N | CH | N |
| 1640. | 1 | S | H | $CH_2CH(CH_3)_2$ | H | Ph | H | H | CH | N | CH | N |
| 1641. | 1 | S | H | $CH_2CH(CH_3)_2$ | H | 2,6-dimethylphenyl | H | H | CH | N | CH | N |
| 1642. | 1 | S | H | $CH_2CH(CH_3)_2$ | H | 2,6-diisopropylphenyl | H | H | CH | N | CH | N |
| 1643. | 1 | S | H | $C_6H_{11}$ | H | $CH_3$ | H | H | CH | N | CH | N |
| 1644. | 1 | S | H | $C_6H_{11}$ | H | $CH(CH_3)_2$ | H | H | CH | N | CH | N |
| 1645. | 1 | S | H | $C_6H_{11}$ | H | $CH_2CH(CH_3)_2$ | H | H | CH | N | CH | N |
| 1646. | 1 | S | H | $C_6H_{11}$ | H | $C_6H_{11}$ | H | H | CH | N | CH | N |
| 1647. | 1 | S | H | $C_6H_{11}$ | H | Ph | H | H | CH | N | CH | N |
| 1648. | 1 | S | H | $C_6H_{11}$ | H | 2,6-dimethylphenyl | H | H | CH | N | CH | N |
| 1649. | 1 | S | H | $C_6H_{11}$ | H | 2,6-diisopropylphenyl | H | H | CH | N | CH | N |
| 1650. | 1 | S | H | Ph | H | $CH_3$ | H | H | CH | N | CH | N |
| 1651. | 1 | S | H | Ph | H | $CH(CH_3)_2$ | H | H | CH | N | CH | N |
| 1652. | 1 | S | H | Ph | H | $CH_2CH(CH_3)_2$ | H | H | CH | N | CH | N |
| 1653 | 1 | S | H | Ph | H | $C_6H_{11}$ | H | H | CH | N | CH | N |
| 1654. | 1 | S | H | Ph | H | Ph | H | H | CH | N | CH | N |
| 1655. | 1 | S | H | Ph | H | 2,6-dimethylphenyl | H | H | CH | N | CH | N |
| 1656. | 1 | S | H | Ph | H | 2,6-diisopropylphenyl | H | H | CH | N | CH | N |
| 1657. | 1 | S | H | 2,6-dimethylphenyl | H | $CH_3$ | H | H | CH | N | CH | N |
| 1658. | 1 | S | H | 2,6-dimethylphenyl | H | $CH(CH_3)_2$ | H | H | CH | N | CH | N |
| 1659. | 1 | S | H | 2,6-dimethylphenyl | H | $CH_2CH(CH_3)_2$ | H | H | CH | N | CH | N |
| 1660. | 1 | S | H | 2,6-dimethylphenyl | H | $C_6H_{11}$ | H | H | CH | N | CH | N |
| 1661. | 1 | S | H | 2,6-dimethylphenyl | H | Ph | H | H | CH | N | CH | N |
| 1662. | 1 | S | H | 2,6-dimethylphenyl | H | 2,6-dimethylphenyl | H | H | CH | N | CH | N |
| 1663. | 1 | S | H | 2,6-dimethylphenyl | H | 2,6-diisopropylphenyl | H | H | CH | N | CH | N |
| 1664. | 1 | S | H | 2,6-diisopropylphenyl | H | $CH_3$ | H | H | CH | N | CH | N |
| 1665. | 1 | S | H | 2,6-diisopropylphenyl | H | $CH(CH_3)_2$ | H | H | CH | N | CH | N |
| 1666. | 1 | S | H | 2,6-diisopropylphenyl | H | $CH_2CH(CH_3)_2$ | H | H | CH | N | CH | N |
| 1667. | 1 | S | H | 2,6-diisopropylphenyl | H | $C_6H_{11}$ | H | H | CH | N | CH | N |
| 1668. | 1 | S | H | 2,6-diisopropylphenyl | H | Ph | H | H | CH | N | CH | N |
| 1669. | 1 | S | H | 2,6-diisopropylphenyl | H | 2,6-dimethylphenyl | H | H | CH | N | CH | N |
| 1670. | 1 | S | H | 2,6-diisopropylphenyl | H | 2,6-diisopropylphenyl | H | H | CH | N | CH | N |
| 1671. | 2 | O | H | $CH_3$ | H | $CH_3$ | H | H | CH | N | CH | N |
| 1672. | 2 | O | H | $CH_3$ | H | $CH(CH_3)_2$ | H | H | CH | N | CH | N |
| 1673. | 2 | O | H | $CH_3$ | H | $CH_2CH(CH_3)_2$ | H | H | CH | N | CH | N |
| 1674. | 2 | O | H | $CH_3$ | H | $C_6H_{11}$ | H | H | CH | N | CH | N |
| 1675. | 2 | O | H | $CH_3$ | H | Ph | H | H | CH | N | CH | N |
| 1676. | 2 | O | H | $CH_3$ | H | 2,6-dimethylphenyl | H | H | CH | N | CH | N |

-continued

Formula VI

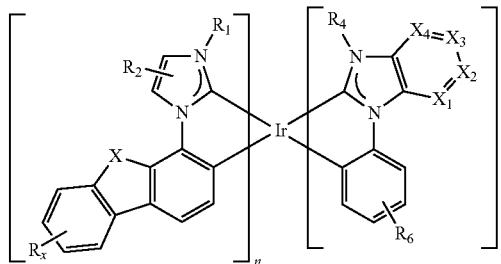

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1677. | 2 | O | H | $CH_3$ | H | 2,6-diisopropylphenyl | H | H | CH | N | CH | N |
| 1678. | 2 | O | H | $CH(CH_3)_2$ | H | $CH_3$ | H | H | CH | N | CH | N |
| 1679. | 2 | O | H | $CH(CH_3)_2$ | H | $CH(CH_3)_2$ | H | H | CH | N | CH | N |
| 1680. | 2 | O | H | $CH(CH_3)_2$ | H | $CH_2CH(CH_3)_2$ | H | H | CH | N | CH | N |
| 1681. | 2 | O | H | $CH(CH_3)_2$ | H | $C_6H_{11}$ | H | H | CH | N | CH | N |
| 1682. | 2 | O | H | $CH(CH_3)_2$ | H | Ph | H | H | CH | N | CH | N |
| 1683 | 2 | O | H | $CH(CH_3)_2$ | H | 2,6-dimethylphenyl | H | H | CH | N | CH | N |
| 1684. | 2 | O | H | $CH(CH_3)_2$ | H | 2,6-diisopropylphenyl | H | H | CH | N | CH | N |
| 1685. | 2 | O | H | $CH_2CH(CH_3)_2$ | H | $CH_3$ | H | H | CH | N | CH | N |
| 1686. | 2 | O | H | $CH_2CH(CH_3)_2$ | H | $CH(CH_3)_2$ | H | H | CH | N | CH | N |
| 1687. | 2 | O | H | $CH_2CH(CH_3)_2$ | H | $CH_2CH(CH_3)_2$ | H | H | CH | N | CH | N |
| 1688. | 2 | O | H | $CH_2CH(CH_3)_2$ | H | $C_6H_{11}$ | H | H | CH | N | CH | N |
| 1689. | 2 | O | H | $CH_2CH(CH_3)_2$ | H | Ph | H | H | CH | N | CH | N |
| 1690. | 2 | O | H | $CH_2CH(CH_3)_2$ | H | 2,6-dimethylphenyl | H | H | CH | N | CH | N |
| 1691. | 2 | O | H | $CH_2CH(CH_3)_2$ | H | 2,6-diisopropylphenyl | H | H | CH | N | CH | N |
| 1692. | 2 | O | H | $C_6H_{11}$ | H | $CH_3$ | H | H | CH | N | CH | N |
| 1693. | 2 | O | H | $C_6H_{11}$ | H | $CH(CH_3)_2$ | H | H | CH | N | CH | N |
| 1694. | 2 | O | H | $C_6H_{11}$ | H | $CH_2CH(CH_3)_2$ | H | H | CH | N | CH | N |
| 1695. | 2 | O | H | $C_6H_{11}$ | H | $C_6H_{11}$ | H | H | CH | N | CH | N |
| 1696. | 2 | O | H | $C_6H_{11}$ | H | Ph | H | H | CH | N | CH | N |
| 1697. | 2 | O | H | $C_6H_{11}$ | H | 2,6-dimethylphenyl | H | H | CH | N | CH | N |
| 1698. | 2 | O | H | $C_6H_{11}$ | H | 2,6-diisopropylphenyl | H | H | CH | N | CH | N |
| 1699. | 2 | O | H | Ph | H | $CH_3$ | H | H | CH | N | CH | N |
| 1700. | 2 | O | H | Ph | H | $CH(CH_3)_2$ | H | H | CH | N | CH | N |
| 1701. | 2 | O | H | Ph | H | $CH_2CH(CH_3)_2$ | H | H | CH | N | CH | N |
| 1702. | 2 | O | H | Ph | H | $C_6H_{11}$ | H | H | CH | N | CH | N |
| 1703. | 2 | O | H | Ph | H | Ph | H | H | CH | N | CH | N |
| 1704. | 2 | O | H | Ph | H | 2,6-dimethylphenyl | H | H | CH | N | CH | N |
| 1705. | 2 | O | H | Ph | H | 2,6-diisopropylphenyl | H | H | CH | N | CH | N |
| 1706. | 2 | O | H | 2,6-dimethylphenyl | H | $CH_3$ | H | H | CH | N | CH | N |
| 1707. | 2 | O | H | 2,6-dimethylphenyl | H | $CH(CH_3)_2$ | H | H | CH | N | CH | N |
| 1708. | 2 | O | H | 2,6-dimethylphenyl | H | $CH_2CH(CH_3)_2$ | H | H | CH | N | CH | N |
| 1709. | 2 | O | H | 2,6-dimethylphenyl | H | $C_6H_{11}$ | H | H | CH | N | CH | N |
| 1710. | 2 | O | H | 2,6-dimethylphenyl | H | Ph | H | H | CH | N | CH | N |
| 1711. | 2 | O | H | 2,6-dimethylphenyl | H | 2,6-dimethylphenyl | H | H | CH | N | CH | N |
| 1712. | 2 | O | H | 2,6-dimethylphenyl | H | 2,6-diisopropylphenyl | H | H | CH | N | CH | N |
| 1713. | 2 | O | H | 2,6-diisopropylphenyl | H | $CH_3$ | H | H | CH | N | CH | N |
| 1714. | 2 | O | H | 2,6-diisopropylphenyl | H | $CH(CH_3)_2$ | H | H | CH | N | CH | N |
| 1715. | 2 | O | H | 2,6-diisopropylphenyl | H | $CH_2CH(CH_3)_2$ | H | H | CH | N | CH | N |
| 1716. | 2 | O | H | 2,6-diisopropylphenyl | H | $C_6H_{11}$ | H | H | CH | N | CH | N |

-continued

Formula VI

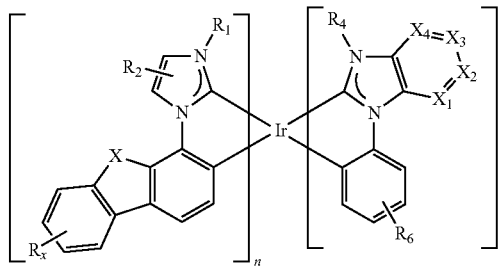

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1717. | 2 | O | H | 2,6-diisopropylphenyl | H | Ph | H | H | CH | N | CH | N |
| 1718. | 2 | O | H | 2,6-diisopropylphenyl | H | 2,6-dimethylphenyl | H | H | CH | N | CH | N |
| 1719. | 2 | O | H | 2,6-diisopropylphenyl | H | 2,6-diisopropylphenyl | H | H | CH | N | CH | N |
| 1720. | 2 | S | H | $CH_3$ | H | $CH_3$ | H | H | CH | N | CH | N |
| 1721. | 2 | S | H | $CH_3$ | H | $CH(CH_3)_2$ | H | H | CH | N | CH | N |
| 1722. | 2 | S | H | $CH_3$ | H | $CH_2CH(CH_3)_2$ | H | H | CH | N | CH | N |
| 1723. | 2 | S | H | $CH_3$ | H | $C_6H_{11}$ | H | H | CH | N | CH | N |
| 1724. | 2 | S | H | $CH_3$ | H | Ph | H | H | CH | N | CH | N |
| 1725. | 2 | S | H | $CH_3$ | H | 2,6-dimethylphenyl | H | H | CH | N | CH | N |
| 1726. | 2 | S | H | $CH_3$ | H | 2,6-diisopropylphenyl | H | H | CH | N | CH | N |
| 1727. | 2 | S | H | $CH(CH_3)_2$ | H | $CH_3$ | H | H | CH | N | CH | N |
| 1728. | 2 | S | H | $CH(CH_3)_2$ | H | $CH(CH_3)_2$ | H | H | CH | N | CH | N |
| 1729. | 2 | S | H | $CH(CH_3)_2$ | H | $CH_2CH(CH_3)_2$ | H | H | CH | N | CH | N |
| 1730. | 2 | S | H | $CH(CH_3)_2$ | H | $C_6H_{11}$ | H | H | CH | N | CH | N |
| 1731. | 2 | S | H | $CH(CH_3)_2$ | H | Ph | H | H | CH | N | CH | N |
| 1732. | 2 | S | H | $CH(CH_3)_2$ | H | 2,6-dimethylphenyl | H | H | CH | N | CH | N |
| 1733. | 2 | S | H | $CH(CH_3)_2$ | H | 2,6-diisopropylphenyl | H | H | CH | N | CH | N |
| 1734. | 2 | S | H | $CH_2CH(CH_3)_2$ | H | $CH_3$ | H | H | CH | N | CH | N |
| 1735. | 2 | S | H | $CH_2CH(CH_3)_2$ | H | $CH(CH_3)_2$ | H | H | CH | N | CH | N |
| 1736. | 2 | S | H | $CH_2CH(CH_3)_2$ | H | $CH_2CH(CH_3)_2$ | H | H | CH | N | CH | N |
| 1737. | 2 | S | H | $CH_2CH(CH_3)_2$ | H | $C_6H_{11}$ | H | H | CH | N | CH | N |
| 1738. | 2 | S | H | $CH_2CH(CH_3)_2$ | H | Ph | H | H | CH | N | CH | N |
| 1739. | 2 | S | H | $CH_2CH(CH_3)_2$ | H | 2,6-dimethylphenyl | H | H | CH | N | CH | N |
| 1740. | 2 | S | H | $CH_2CH(CH_3)_2$ | H | 2,6-diisopropylphenyl | H | H | CH | N | CH | N |
| 1741. | 2 | S | H | $C_6H_{11}$ | H | $CH_3$ | H | H | CH | N | CH | N |
| 1742. | 2 | S | H | $C_6H_{11}$ | H | $CH(CH_3)_2$ | H | H | CH | N | CH | N |
| 1743. | 2 | S | H | $C_6H_{11}$ | H | $CH_2CH(CH_3)_2$ | H | H | CH | N | CH | N |
| 1744. | 2 | S | H | $C_6H_{11}$ | H | $C_6H_{11}$ | H | H | CH | N | CH | N |
| 1745. | 2 | S | H | $C_6H_{11}$ | H | Ph | H | H | CH | N | CH | N |
| 1746. | 2 | S | H | $C_6H_{11}$ | H | 2,6-dimethylphenyl | H | H | CH | N | CH | N |
| 1747. | 2 | S | H | $C_6H_{11}$ | H | 2,6-diisopropylphenyl | H | H | CH | N | CH | N |
| 1748. | 2 | S | H | Ph | H | $CH_3$ | H | H | CH | N | CH | N |
| 1749. | 2 | S | H | Ph | H | $CH(CH_3)_2$ | H | H | CH | N | CH | N |
| 1750. | 2 | S | H | Ph | H | $CH_2CH(CH_3)_2$ | H | H | CH | N | CH | N |
| 1751. | 2 | S | H | Ph | H | $C_6H_{11}$ | H | H | CH | N | CH | N |
| 1752. | 2 | S | H | Ph | H | Ph | H | H | CH | N | CH | N |
| 1753. | 2 | S | H | Ph | H | 2,6-dimethylphenyl | H | H | CH | N | CH | N |
| 1754. | 2 | S | H | Ph | H | 2,6-diisopropylphenyl | H | H | CH | N | CH | N |
| 1755. | 2 | S | H | 2,6-dimethylphenyl | H | $CH_3$ | H | H | CH | N | CH | N |
| 1756. | 2 | S | H | 2,6-dimethylphenyl | H | $CH(CH_3)_2$ | H | H | CH | N | CH | N |
| 1757. | 2 | S | H | 2,6-dimethylphenyl | H | $CH_2CH(CH_3)_2$ | H | H | CH | N | CH | N |
| 1758. | 2 | S | H | 2,6-dimethylphenyl | H | $C_6H_{11}$ | H | H | CH | N | CH | N |
| 1759. | 2 | S | H | 2,6-dimethylphenyl | H | Ph | H | H | CH | N | CH | N |

-continued

Formula VI

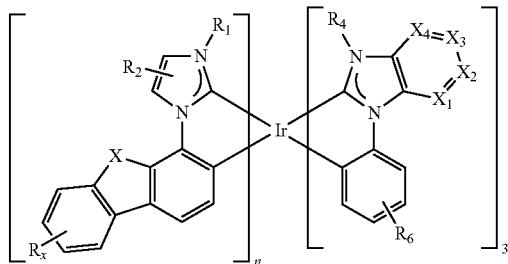

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1760. | 2 | S | H | 2,6-dimethylphenyl | H | 2,6-dimethylphenyl | H | H | CH | N | CH | N |
| 1761. | 2 | S | H | 2,6-dimethylphenyl | H | 2,6-diisopropylphenyl | H | H | CH | N | CH | N |
| 1762. | 2 | S | H | 2,6-diisopropylphenyl | H | $CH_3$ | H | H | CH | N | CH | N |
| 1763. | 2 | S | H | 2,6-diisopropylphenyl | H | $CH(CH_3)_2$ | H | H | CH | N | CH | N |
| 1764. | 2 | S | H | 2,6-diisopropylphenyl | H | $CH_2CH(CH_3)_2$ | H | H | CH | N | CH | N |
| 1765. | 2 | S | H | 2,6-diisopropylphenyl | H | $C_6H_{11}$ | H | H | CH | N | CH | N |
| 1766. | 2 | S | H | 2,6-diisopropylphenyl | H | Ph | H | H | CH | N | CH | N |
| 1767. | 2 | S | H | 2,6-diisopropylphenyl | H | 2,6-dimethylphenyl | H | H | CH | N | CH | N |
| 1768. | 2 | S | H | 2,6-diisopropylphenyl | H | 2,6-diisopropylphenyl | H | H | CH | N | CH | N |
| 1769. | 1 | O | H | $CH_3$ | H | $CH_3$ | H | H | N | CH | CH | N |
| 1770. | 1 | O | H | $CH_3$ | H | $CH(CH_3)_2$ | H | H | N | CH | CH | N |
| 1771. | 1 | O | H | $CH_3$ | H | $CH_2CH(CH_3)_2$ | H | H | N | CH | CH | N |
| 1772. | 1 | O | H | $CH_3$ | H | $C_6H_{11}$ | H | H | N | CH | CH | N |
| 1773. | 1 | O | H | $CH_3$ | H | Ph | H | H | N | CH | CH | N |
| 1774. | 1 | O | H | $CH_3$ | H | 2,6-dimethylphenyl | H | H | N | CH | CH | N |
| 1775. | 1 | O | H | $CH_3$ | H | 2,6-diisopropylphenyl | H | H | N | CH | CH | N |
| 1776. | 1 | O | H | $CH(CH_3)_2$ | H | $CH_3$ | H | H | N | CH | CH | N |
| 1777. | 1 | O | H | $CH(CH_3)_2$ | H | $CH(CH_3)_2$ | H | H | N | CH | CH | N |
| 1778. | 1 | O | H | $CH(CH_3)_2$ | H | $CH_2CH(CH_3)_2$ | H | H | N | CH | CH | N |
| 1779. | 1 | O | H | $CH(CH_3)_2$ | H | $C_6H_{11}$ | H | H | N | CH | CH | N |
| 1780. | 1 | O | H | $CH(CH_3)_2$ | H | Ph | H | H | N | CH | CH | N |
| 1781. | 1 | O | H | $CH(CH_3)_2$ | H | 2,6-dimethylphenyl | H | H | N | CH | CH | N |
| 1782. | 1 | O | H | $CH(CH_3)_2$ | H | 2,6-diisopropylphenyl | H | H | N | CH | CH | N |
| 1783. | 1 | O | H | $CH_2CH(CH_3)_2$ | H | $CH_3$ | H | H | N | CH | CH | N |
| 1784. | 1 | O | H | $CH_2CH(CH_3)_2$ | H | $CH(CH_3)_2$ | H | H | N | CH | CH | N |
| 1785. | 1 | O | H | $CH_2CH(CH_3)_2$ | H | $CH_2CH(CH_3)_2$ | H | H | N | CH | CH | N |
| 1786. | 1 | O | H | $CH_2CH(CH_3)_2$ | H | $C_6H_{11}$ | H | H | N | CH | CH | N |
| 1787. | 1 | O | H | $CH_2CH(CH_3)_2$ | H | Ph | H | H | N | CH | CH | N |
| 1788. | 1 | O | H | $CH_2CH(CH_3)_2$ | H | 2,6-dimethylphenyl | H | H | N | CH | CH | N |
| 1789. | 1 | O | H | $CH_2CH(CH_3)_2$ | H | 2,6-diisopropylphenyl | H | H | N | CH | CH | N |
| 1790. | 1 | O | H | $C_6H_{11}$ | H | $CH_3$ | H | H | N | CH | CH | N |
| 1791. | 1 | O | H | $C_6H_{11}$ | H | $CH(CH_3)_2$ | H | H | N | CH | CH | N |
| 1792. | 1 | O | H | $C_6H_{11}$ | H | $CH_2CH(CH_3)_2$ | H | H | N | CH | CH | N |
| 1793. | 1 | O | H | $C_6H_{11}$ | H | $C_6H_{11}$ | H | H | N | CH | CH | N |
| 1794. | 1 | O | H | $C_6H_{11}$ | H | Ph | H | H | N | CH | CH | N |
| 1795. | 1 | O | H | $C_6H_{11}$ | H | 2,6-dimethylphenyl | H | H | N | CH | CH | N |
| 1796. | 1 | O | H | $C_6H_{11}$ | H | 2,6-diisopropylphenyl | H | H | N | CH | CH | N |
| 1797. | 1 | O | H | Ph | H | $CH_3$ | H | H | N | CH | CH | N |
| 1798. | 1 | O | H | Ph | H | $CH(CH_3)_2$ | H | H | N | CH | CH | N |
| 1799. | 1 | O | H | Ph | H | $CH_2CH(CH_3)_2$ | H | H | N | CH | CH | N |
| 1800. | 1 | O | H | Ph | H | $C_6H_{11}$ | H | H | N | CH | CH | N |
| 1801. | 1 | O | H | Ph | H | Ph | H | H | N | CH | CH | N |
| 1802. | 1 | O | H | Ph | H | 2,6-dimethylphenyl | H | H | N | CH | CH | N |

-continued

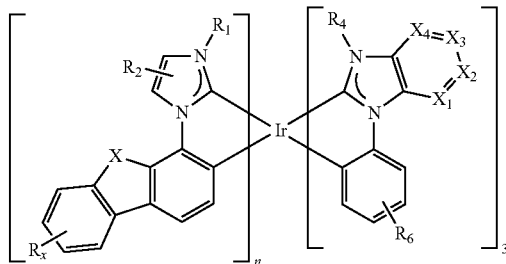

Formula VI

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1803. | 1 | O | H | Ph | H | 2,6-diisopropylphenyl | H | H | N | CH | CH | N |
| 1804. | 1 | O | H | 2,6-dimethylphenyl | H | $CH_3$ | H | H | N | CH | CH | N |
| 1805. | 1 | O | H | 2,6-dimethylphenyl | H | $CH(CH_3)_2$ | H | H | N | CH | CH | N |
| 1806. | 1 | O | H | 2,6-dimethylphenyl | H | $CH_2CH(CH_3)_2$ | H | H | N | CH | CH | N |
| 1807. | 1 | O | H | 2,6-dimethylphenyl | H | $C_6H_{11}$ | H | H | N | CH | CH | N |
| 1808. | 1 | O | H | 2,6-dimethylphenyl | H | Ph | H | H | N | CH | CH | N |
| 1809. | 1 | O | H | 2,6-dimethylphenyl | H | 2,6-dimethylphenyl | H | H | N | CH | CH | N |
| 1810. | 1 | O | H | 2,6-dimethylphenyl | H | 2,6-diisopropylphenyl | H | H | N | CH | CH | N |
| 1811. | 1 | O | H | 2,6-diisopropylphenyl | H | $CH_3$ | H | H | N | CH | CH | N |
| 1812. | 1 | O | H | 2,6-diisopropylphenyl | H | $CH(CH_3)_2$ | H | H | N | CH | CH | N |
| 1813. | 1 | O | H | 2,6-diisopropylphenyl | H | $CH_2CH(CH_3)_2$ | H | H | N | CH | CH | N |
| 1814. | 1 | O | H | 2,6-diisopropylphenyl | H | $C_6H_{11}$ | H | H | N | CH | CH | N |
| 1815. | 1 | O | H | 2,6-diisopropylphenyl | H | Ph | H | H | N | CH | CH | N |
| 1816. | 1 | O | H | 2,6-diisopropylphenyl | H | 2,6-dimethylphenyl | H | H | N | CH | CH | N |
| 1817. | 1 | O | H | 2,6-diisopropylphenyl | H | 2,6-diisopropylphenyl | H | H | N | CH | CH | N |
| 1818. | 1 | S | H | $CH_3$ | H | $CH_3$ | H | H | N | CH | CH | N |
| 1819. | 1 | S | H | $CH_3$ | H | $CH(CH_3)_2$ | H | H | N | CH | CH | N |
| 1820. | 1 | S | H | $CH_3$ | H | $CH_2CH(CH_3)_2$ | H | H | N | CH | CH | N |
| 1821. | 1 | S | H | $CH_3$ | H | $C_6H_{11}$ | H | H | N | CH | CH | N |
| 1822. | 1 | S | H | $CH_3$ | H | Ph | H | H | N | CH | CH | N |
| 1823. | 1 | S | H | $CH_3$ | H | 2,6-dimethylphenyl | H | H | N | CH | CH | N |
| 1824. | 1 | S | H | $CH_3$ | H | 2,6-diisopropylphenyl | H | H | N | CH | CH | N |
| 1825. | 1 | S | H | $CH(CH_3)_2$ | H | $CH_3$ | H | H | N | CH | CH | N |
| 1826. | 1 | S | H | $CH(CH_3)_2$ | H | $CH(CH_3)_2$ | H | H | N | CH | CH | N |
| 1827. | 1 | S | H | $CH(CH_3)_2$ | H | $CH_2CH(CH_3)_2$ | H | H | N | CH | CH | N |
| 1828. | 1 | S | H | $CH(CH_3)_2$ | H | $C_6H_{11}$ | H | H | N | CH | CH | N |
| 1829. | 1 | S | H | $CH(CH_3)_2$ | H | Ph | H | H | N | CH | CH | N |
| 1830. | 1 | S | H | $CH(CH_3)_2$ | H | 2,6-dimethylphenyl | H | H | N | CH | CH | N |
| 1831. | 1 | S | H | $CH(CH_3)_2$ | H | 2,6-diisopropylphenyl | H | H | N | CH | CH | N |
| 1832. | 1 | S | H | $CH_2CH(CH_3)_2$ | H | $CH_3$ | H | H | N | CH | CH | N |
| 1833. | 1 | S | H | $CH_2CH(CH_3)_2$ | H | $CH(CH_3)_2$ | H | H | N | CH | CH | N |
| 1834. | 1 | S | H | $CH_2CH(CH_3)_2$ | H | $CH_2CH(CH_3)_2$ | H | H | N | CH | CH | N |
| 1835. | 1 | S | H | $CH_2CH(CH_3)_2$ | H | $C_6H_{11}$ | H | H | N | CH | CH | N |
| 1836. | 1 | S | H | $CH_2CH(CH_3)_2$ | H | Ph | H | H | N | CH | CH | N |
| 1837. | 1 | S | H | $CH_2CH(CH_3)_2$ | H | 2,6-dimethylphenyl | H | H | N | CH | CH | N |
| 1838. | 1 | S | H | $CH_2CH(CH_3)_2$ | H | 2,6-diisopropylphenyl | H | H | N | CH | CH | N |
| 1839. | 1 | S | H | $C_6H_{11}$ | H | $CH_3$ | H | H | N | CH | CH | N |
| 1840. | 1 | S | H | $C_6H_{11}$ | H | $CH(CH_3)_2$ | H | H | N | CH | CH | N |
| 1841. | 1 | S | H | $C_6H_{11}$ | H | $CH_2CH(CH_3)_2$ | H | H | N | CH | CH | N |
| 1842. | 1 | S | H | $C_6H_{11}$ | H | $C_6H_{11}$ | H | H | N | CH | CH | N |

-continued

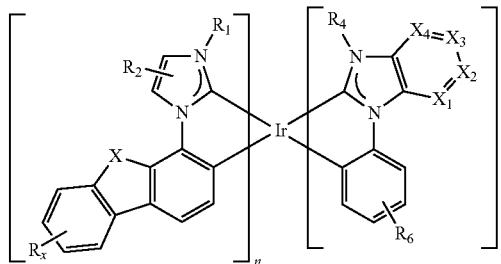

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1843. | 1 | S | H | $C_6H_{11}$ | H | Ph | H | H | N | CH | CH | N |
| 1844. | 1 | S | H | $C_6H_{11}$ | H | 2,6-dimethylphenyl | H | H | N | CH | CH | N |
| 1845. | 1 | S | H | $C_6H_{11}$ | H | 2,6-diisopropylphenyl | H | H | N | CH | CH | N |
| 1846. | 1 | S | H | Ph | H | $CH_3$ | H | H | N | CH | CH | N |
| 1847. | 1 | S | H | Ph | H | $CH(CH_3)_2$ | H | H | N | CH | CH | N |
| 1848. | 1 | S | H | Ph | H | $CH_2CH(CH_3)_2$ | H | H | N | CH | CH | N |
| 1849. | 1 | S | H | Ph | H | $C_6H_{11}$ | H | H | N | CH | CH | N |
| 1850. | 1 | S | H | Ph | H | Ph | H | H | N | CH | CH | N |
| 1851. | 1 | S | H | Ph | H | 2,6-dimethylphenyl | H | H | N | CH | CH | N |
| 1852. | 1 | S | H | Ph | H | 2,6-diisopropylphenyl | H | H | N | CH | CH | N |
| 1853. | 1 | S | H | 2,6-dimethylphenyl | H | $CH_3$ | H | H | N | CH | CH | N |
| 1854. | 1 | S | H | 2,6-dimethylphenyl | H | $CH(CH_3)_2$ | H | H | N | CH | CH | N |
| 1855. | 1 | S | H | 2,6-dimethylphenyl | H | $CH_2CH(CH_3)_2$ | H | H | N | CH | CH | N |
| 1856. | 1 | S | H | 2,6-dimethylphenyl | H | $C_6H_{11}$ | H | H | N | CH | CH | N |
| 1857. | 1 | S | H | 2,6-dimethylphenyl | H | Ph | H | H | N | CH | CH | N |
| 1858. | 1 | S | H | 2,6-dimethylphenyl | H | 2,6-dimethylphenyl | H | H | N | CH | CH | N |
| 1859. | 1 | S | H | 2,6-dimethylphenyl | H | 2,6-diisopropylphenyl | H | H | N | CH | CH | N |
| 1860. | 1 | S | H | 2,6-diisopropylphenyl | H | $CH_3$ | H | H | N | CH | CH | N |
| 1861. | 1 | S | H | 2,6-diisopropylphenyl | H | $CH(CH_3)_2$ | H | H | N | CH | CH | N |
| 1862. | 1 | S | H | 2,6-diisopropylphenyl | H | $CH_2CH(CH_3)_2$ | H | H | N | CH | CH | N |
| 1863. | 1 | S | H | 2,6-diisopropylphenyl | H | $C_6H_{11}$ | H | H | N | CH | CH | N |
| 1864. | 1 | S | H | 2,6-diisopropylphenyl | H | Ph | H | H | N | CH | CH | N |
| 1865. | 1 | S | H | 2,6-diisopropylphenyl | H | 2,6-dimethylphenyl | H | H | N | CH | CH | N |
| 1866. | 1 | S | H | 2,6-diisopropylphenyl | H | 2,6-diisopropylphenyl | H | H | N | CH | CH | N |
| 1867. | 2 | O | H | $CH_3$ | H | $CH_3$ | H | H | N | CH | CH | N |
| 1868. | 2 | O | H | $CH_3$ | H | $CH(CH_3)_2$ | H | H | N | CH | CH | N |
| 1869. | 2 | O | H | $CH_3$ | H | $CH_2CH(CH_3)_2$ | H | H | N | CH | CH | N |
| 1870. | 2 | O | H | $CH_3$ | H | $C_6H_{11}$ | H | H | N | CH | CH | N |
| 1871. | 2 | O | H | $CH_3$ | H | Ph | H | H | N | CH | CH | N |
| 1872. | 2 | O | H | $CH_3$ | H | 2,6-dimethylphenyl | H | H | N | CH | CH | N |
| 1873. | 2 | O | H | $CH_3$ | H | 2,6-diisopropylphenyl | H | H | N | CH | CH | N |
| 1874. | 2 | O | H | $CH(CH_3)_2$ | H | $CH_3$ | H | H | N | CH | CH | N |
| 1875. | 2 | O | H | $CH(CH_3)_2$ | H | $CH(CH_3)_2$ | H | H | N | CH | CH | N |
| 1876. | 2 | O | H | $CH(CH_3)_2$ | H | $CH_2CH(CH_3)_2$ | H | H | N | CH | CH | N |
| 1877. | 2 | O | H | $CH(CH_3)_2$ | H | $C_6H_{11}$ | H | H | N | CH | CH | N |
| 1878. | 2 | O | H | $CH(CH_3)_2$ | H | Ph | H | H | N | CH | CH | N |
| 1879. | 2 | O | H | $CH(CH_3)_2$ | H | 2,6-dimethylphenyl | H | H | N | CH | CH | N |
| 1880. | 2 | O | H | $CH(CH_3)_2$ | H | 2,6-diisopropylphenyl | H | H | N | CH | CH | N |
| 1881. | | | | | | | | | N | CH | CH | N |

-continued

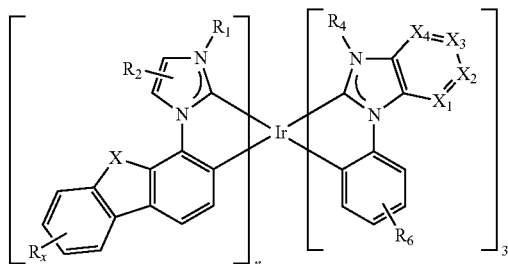

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1882. | 2 | O | H | $CH_2CH(CH_3)_2$ | H | $CH_3$ | H | H | N | CH | CH | N |
| 1883. | 2 | O | H | $CH_2CH(CH_3)_2$ | H | $CH(CH_3)_2$ | H | H | N | CH | CH | N |
| 1884. | 2 | O | H | $CH_2CH(CH_3)_2$ | H | $CH_2CH(CH_3)_2$ | H | H | N | CH | CH | N |
| 1885. | 2 | O | H | $CH_2CH(CH_3)_2$ | H | $C_6H_{11}$ | H | H | N | CH | CH | N |
| 1886. | 2 | O | H | $CH_2CH(CH_3)_2$ | H | Ph | H | H | N | CH | CH | N |
| 1887. | 2 | O | H | $CH_2CH(CH_3)_2$ | H | 2,6-dimethylphenyl | H | H | N | CH | CH | N |
| 1888. | 2 | O | H | $CH_2CH(CH_3)_2$ | H | 2,6-diisopropylphenyl | H | H | N | CH | CH | N |
| 1889. | 2 | O | H | $C_6H_{11}$ | H | $CH_3$ | H | H | N | CH | CH | N |
| 1890. | 2 | O | H | $C_6H_{11}$ | H | $CH(CH_3)_2$ | H | H | N | CH | CH | N |
| 1891. | 2 | O | H | $C_6H_{11}$ | H | $CH_2CH(CH_3)_2$ | H | H | N | CH | CH | N |
| 1892. | 2 | O | H | $C_6H_{11}$ | H | $C_6H_{11}$ | H | H | N | CH | CH | N |
| 1893. | 2 | O | H | $C_6H_{11}$ | H | Ph | H | H | N | CH | CH | N |
| 1894. | 2 | O | H | $C_6H_{11}$ | H | 2,6-dimethylphenyl | H | H | N | CH | CH | N |
| 1895. | 2 | O | H | $C_6H_{11}$ | H | 2,6-diisopropylphenyl | H | H | N | CH | CH | N |
| 1896. | 2 | O | H | Ph | H | $CH_3$ | H | H | N | CH | CH | N |
| 1897. | 2 | O | H | Ph | H | $CH(CH_3)_2$ | H | H | N | CH | CH | N |
| 1898. | 2 | O | H | Ph | H | $CH_2CH(CH_3)_2$ | H | H | N | CH | CH | N |
| 1899. | 2 | O | H | Ph | H | $C_6H_{11}$ | H | H | N | CH | CH | N |
| 1900. | 2 | O | H | Ph | H | Ph | H | H | N | CH | CH | N |
| 1901. | 2 | O | H | Ph | H | 2,6-dimethylphenyl | H | H | N | CH | CH | N |
| 1902. | 2 | O | H | Ph | H | 2,6-diisopropylphenyl | H | H | N | CH | CH | N |
| 1903. | 2 | O | H | 2,6-dimethylphenyl | H | $CH_3$ | H | H | N | CH | CH | N |
| 1904. | 2 | O | H | 2,6-dimethylphenyl | H | $CH(CH_3)_2$ | H | H | N | CH | CH | N |
| 1905. | 2 | O | H | 2,6-dimethylphenyl | H | $CH_2CH(CH_3)_2$ | H | H | N | CH | CH | N |
| 1906. | 2 | O | H | 2,6-dimethylphenyl | H | $C_6H_{11}$ | H | H | N | CH | CH | N |
| 1907. | 2 | O | H | 2,6-dimethylphenyl | H | Ph | H | H | N | CH | CH | N |
| 1908. | 2 | O | H | 2,6-dimethylphenyl | H | 2,6-dimethylphenyl | H | H | N | CH | CH | N |
| 1909. | 2 | O | H | 2,6-dimethylphenyl | H | 2,6-diisopropylphenyl | H | H | N | CH | CH | N |
| 1910. | 2 | O | H | 2,6-diisopropylphenyl | H | $CH_3$ | H | H | N | CH | CH | N |
| 1911. | 2 | O | H | 2,6-diisopropylphenyl | H | $CH(CH_3)_2$ | H | H | N | CH | CH | N |
| 1912. | 2 | O | H | 2,6-diisopropylphenyl | H | $CH_2CH(CH_3)_2$ | H | H | N | CH | CH | N |
| 1913. | 2 | O | H | 2,6-diisopropylphenyl | H | $C_6H_{11}$ | H | H | N | CH | CH | N |
| 1914. | 2 | O | H | 2,6-diisopropylphenyl | H | Ph | H | H | N | CH | CH | N |
| 1915. | 2 | O | H | 2,6-diisopropylphenyl | H | 2,6-dimethylphenyl | H | H | N | CH | CH | N |
| 1916. | 2 | O | H | 2,6-diisopropylphenyl | H | 2,6-diisopropylphenyl | H | H | N | CH | CH | N |
| 1917. | 2 | S | H | $CH_3$ | H | $CH_3$ | H | H | N | CH | CH | N |
| 1918. | 2 | S | H | $CH_3$ | H | $CH(CH_3)_2$ | H | H | N | CH | CH | N |
| 1919. | 2 | S | H | $CH_3$ | H | $CH_2CH(CH_3)_2$ | H | H | N | CH | CH | N |
| 1920. | 2 | S | H | $CH_3$ | H | $C_6H_{11}$ | H | H | N | CH | CH | N |
| 1921. | 2 | S | H | $CH_3$ | H | Ph | H | H | N | CH | CH | N |

-continued

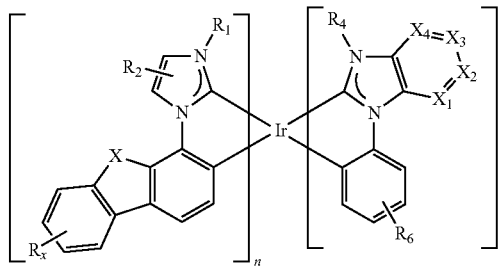

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1922. | 2 | S | H | $CH_3$ | H | 2,6-dimethylphenyl | H | H | N | CH | CH | N |
| 1923. | 2 | S | H | $CH_3$ | H | 2,6-diisopropylphenyl | H | H | N | CH | CH | N |
| 1924. | 2 | S | H | $CH(CH_3)_2$ | H | $CH_3$ | H | H | N | CH | CH | N |
| 1925. | 2 | S | H | $CH(CH_3)_2$ | H | $CH(CH_3)_2$ | H | H | N | CH | CH | N |
| 1926. | 2 | S | H | $CH(CH_3)_2$ | H | $CH_2CH(CH_3)_2$ | H | H | N | CH | CH | N |
| 1927. | 2 | S | H | $CH(CH_3)_2$ | H | $C_6H_{11}$ | H | H | N | CH | CH | N |
| 1928. | 2 | S | H | $CH(CH_3)_2$ | H | Ph | H | H | N | CH | CH | N |
| 1929. | 2 | S | H | $CH(CH_3)_2$ | H | 2,6-dimethylphenyl | H | H | N | CH | CH | N |
| 1930. | 2 | S | H | $CH(CH_3)_2$ | H | 2,6-diisopropylphenyl | H | H | N | CH | CH | N |
| 1931. | 2 | S | H | $CH_2CH(CH_3)_2$ | H | $CH_3$ | H | H | N | CH | CH | N |
| 1932. | 2 | S | H | $CH_2CH(CH_3)_2$ | H | $CH(CH_3)_2$ | H | H | N | CH | CH | N |
| 1933. | 2 | S | H | $CH_2CH(CH_3)_2$ | H | $CH_2CH(CH_3)_2$ | H | H | N | CH | CH | N |
| 1934. | 2 | S | H | $CH_2CH(CH_3)_2$ | H | $C_6H_{11}$ | H | H | N | CH | CH | N |
| 1935. | 2 | S | H | $CH_2CH(CH_3)_2$ | H | Ph | H | H | N | CH | CH | N |
| 1936. | 2 | S | H | $CH_2CH(CH_3)_2$ | H | 2,6-dimethylphenyl | H | H | N | CH | CH | N |
| 1937. | 2 | S | H | $CH_2CH(CH_3)_2$ | H | 2,6-diisopropylphenyl | H | H | N | CH | CH | N |
| 1938. | 2 | S | H | $C_6H_{11}$ | H | $CH_3$ | H | H | N | CH | CH | N |
| 1939. | 2 | S | H | $C_6H_{11}$ | H | $CH(CH_3)_2$ | H | H | N | CH | CH | N |
| 1940. | 2 | S | H | $C_6H_{11}$ | H | $CH_2CH(CH_3)_2$ | H | H | N | CH | CH | N |
| 1941. | 2 | S | H | $C_6H_{11}$ | H | $C_6H_{11}$ | H | H | N | CH | CH | N |
| 1942. | 2 | S | H | $C_6H_{11}$ | H | Ph | H | H | N | CH | CH | N |
| 1943. | 2 | S | H | $C_6H_{11}$ | H | 2,6-dimethylphenyl | H | H | N | CH | CH | N |
| 1944. | 2 | S | H | $C_6H_{11}$ | H | 2,6-diisopropylphenyl | H | H | N | CH | CH | N |
| 1945. | 2 | S | H | Ph | H | $CH_3$ | H | H | N | CH | CH | N |
| 1946. | 2 | S | H | Ph | H | $CH(CH_3)_2$ | H | H | N | CH | CH | N |
| 1947. | 2 | S | H | Ph | H | $CH_2CH(CH_3)_2$ | H | H | N | CH | CH | N |
| 1948. | 2 | S | H | Ph | H | $C_6H_{11}$ | H | H | N | CH | CH | N |
| 1949. | 2 | S | H | Ph | H | Ph | H | H | N | CH | CH | N |
| 1950. | 2 | S | H | Ph | H | 2,6-dimethylphenyl | H | H | N | CH | CH | N |
| 1951. | 2 | S | H | Ph | H | 2,6-diisopropylphenyl | H | H | N | CH | CH | N |
| 1952. | 2 | S | H | 2,6-dimethylphenyl | H | $CH_3$ | H | H | N | CH | CH | N |
| 1953. | 2 | S | H | 2,6-dimethylphenyl | H | $CH(CH_3)_2$ | H | H | N | CH | CH | N |
| 1954. | 2 | S | H | 2,6-dimethylphenyl | H | $CH_2CH(CH_3)_2$ | H | H | N | CH | CH | N |
| 1955. | 2 | S | H | 2,6-dimethylphenyl | H | $C_6H_{11}$ | H | H | N | CH | CH | N |
| 1956. | 2 | S | H | 2,6-dimethylphenyl | H | Ph | H | H | N | CH | CH | N |
| 1957. | 2 | S | H | 2,6-dimethylphenyl | H | 2,6-dimethylphenyl | H | H | N | CH | CH | N |
| 1958. | 2 | S | H | 2,6-dimethylphenyl | H | 2,6-diisopropylphenyl | H | H | N | CH | CH | N |
| 1959. | 2 | S | H | 2,6-diisopropylphenyl | H | $CH_3$ | H | H | N | CH | CH | N |
| 1960. | 2 | S | H | 2,6-diisopropylphenyl | H | $CH(CH_3)_2$ | H | H | N | CH | CH | N |
| 1961. | 2 | S | H | 2,6-diisopropylphenyl | H | $CH_2CH(CH_3)_2$ | H | H | N | CH | CH | N |

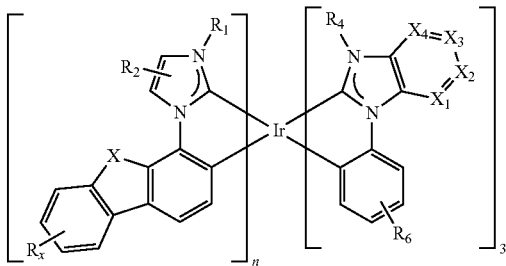

Formula VI

| Compd. | n | X | $R_x$ | $R_1$ | $R_2$ | $R_4$ | $R_5$ | $R_6$ | $X_1$ | $X_2$ | $X_3$ | $X_4$ |
|---|---|---|---|---|---|---|---|---|---|---|---|---|
| 1962. | 2 | S | H | 2,6-diisopropylphenyl | H | $C_6H_{11}$ | H | H | N | CH | CH | N |
| 1963. | 2 | S | H | 2,6-diisopropylphenyl | H | Ph | H | H | N | CH | CH | N |
| 1964. | 2 | S | H | 2,6-diisopropylphenyl | H | 2,6-dimethylphenyl | H | H | N | CH | CH | N |
| 1965. | 2 | S | H | 2,6-diisopropylphenyl | H | 2,6-diisopropylphenyl | H | H | N | CH | CH | N |

In one embodiment, the compound of Formula X has the following composition:

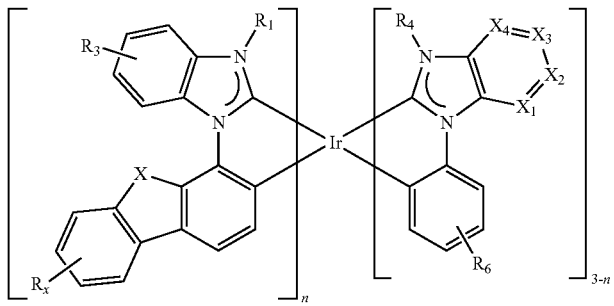

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 1966. | 1 | O | H | $CH_3$ | H | $CH_3$ | H | H | CH | CH | CH | CH |
| 1967. | 1 | O | H | $CH_3$ | H | $CH(CH_3)_2$ | H | H | CH | CH | CH | CH |
| 1968. | 1 | O | H | $CH_3$ | H | $CH_2CH(CH_3)_2$ | H | H | CH | CH | CH | CH |
| 1969. | 1 | O | H | $CH_3$ | H | $C_6H_{11}$ | H | H | CH | CH | CH | CH |
| 1970. | 1 | O | H | $CH_3$ | H | Ph | H | H | CH | CH | CH | CH |
| 1971. | 1 | O | H | $CH_3$ | H | 2,6-dimethylphenyl | H | H | CH | CH | CH | CH |
| 1972. | 1 | O | H | $CH_3$ | H | 2,6-diisopropylphenyl | H | H | CH | CH | CH | CH |
| 1973. | 1 | O | H | $CH(CH_3)_2$ | H | $CH_3$ | H | H | CH | CH | CH | CH |
| 1974. | 1 | O | H | $CH(CH_3)_2$ | H | $CH(CH_3)_2$ | H | H | CH | CH | CH | CH |
| 1975. | 1 | O | H | $CH(CH_3)_2$ | H | $CH_2CH(CH_3)_2$ | H | H | CH | CH | CH | CH |
| 1976. | 1 | O | H | $CH(CH_3)_2$ | H | $C_6H_{11}$ | H | H | CH | CH | CH | CH |
| 1977. | 1 | O | H | $CH(CH_3)_2$ | H | Ph | H | H | CH | CH | CH | CH |
| 1978. | 1 | O | H | $CH(CH_3)_2$ | H | 2,6-dimethylphenyl | H | H | CH | CH | CH | CH |
| 1979. | 1 | O | H | $CH(CH_3)_2$ | H | 2,6-diisopropylphenyl | H | H | CH | CH | CH | CH |
| 1980. | 1 | O | H | $CH_2CH(CH_3)_2$ | H | $CH_3$ | H | H | CH | CH | CH | CH |
| 1981. | 1 | O | H | $CH_2CH(CH_3)_2$ | H | $CH(CH_3)_2$ | H | H | CH | CH | CH | CH |
| 1982. | 1 | O | H | $CH_2CH(CH_3)_2$ | H | $CH_2CH(CH_3)_2$ | H | H | CH | CH | CH | CH |
| 1983. | 1 | O | H | $CH_2CH(CH_3)_2$ | H | $C_6H_{11}$ | H | H | CH | CH | CH | CH |
| 1984. | 1 | O | H | $CH_2CH(CH_3)_2$ | H | Ph | H | H | CH | CH | CH | CH |
| 1985. | 1 | O | H | $CH_2CH(CH_3)_2$ | H | 2,6-dimethylphenyl | H | H | CH | CH | CH | CH |
| 1986. | 1 | O | H | $CH_2CH(CH_3)_2$ | H | 2,6-diisopropylphenyl | H | H | CH | CH | CH | CH |
| 1987. | 1 | O | H | $C_6H_{11}$ | H | $CH_3$ | H | H | CH | CH | CH | CH |
| 1988. | 1 | O | H | $C_6H_{11}$ | H | $CH(CH_3)_2$ | H | H | CH | CH | CH | CH |
| 1989. | 1 | O | H | $C_6H_{11}$ | H | $CH_2CH(CH_3)_2$ | H | H | CH | CH | CH | CH |
| 1990. | 1 | O | H | $C_6H_{11}$ | H | $C_6H_{11}$ | H | H | CH | CH | CH | CH |

-continued

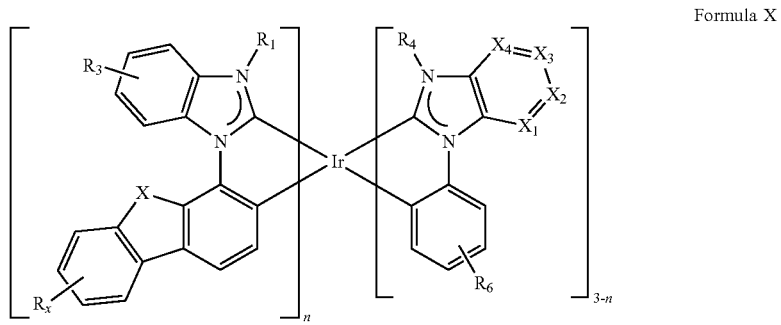

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 1991. | 1 | O | H | $C_6H_{11}$ | H | Ph | H | H | CH | CH | CH | CH |
| 1992. | 1 | O | H | $C_6H_{11}$ | H | 2,6-dimethylphenyl | H | H | CH | CH | CH | CH |
| 1993. | 1 | O | H | $C_6H_{11}$ | H | 2,6-diisopropylphenyl | H | H | CH | CH | CH | CH |
| 1994. | 1 | O | H | Ph | H | $CH_3$ | H | H | CH | CH | CH | CH |
| 1995. | 1 | O | H | Ph | H | $CH(CH_3)_2$ | H | H | CH | CH | CH | CH |
| 1996. | 1 | O | H | Ph | H | $CH_2CH(CH_3)_2$ | H | H | CH | CH | CH | CH |
| 1997. | 1 | O | H | Ph | H | $C_6H_{11}$ | H | H | CH | CH | CH | CH |
| 1998. | 1 | O | H | Ph | H | Ph | H | H | CH | CH | CH | CH |
| 1999. | 1 | O | H | Ph | H | 2,6-dimethylphenyl | H | H | CH | CH | CH | CH |
| 2000. | 1 | O | H | Ph | H | 2,6-diisopropylphenyl | H | H | CH | CH | CH | CH |
| 2001. | 1 | O | H | 2,6-dimethylphenyl | H | $CH_3$ | H | H | CH | CH | CH | CH |
| 2002. | 1 | O | H | 2,6-dimethylphenyl | H | $CH(CH_3)_2$ | H | H | CH | CH | CH | CH |
| 2003. | 1 | O | H | 2,6-dimethylphenyl | H | $CH_2CH(CH_3)_2$ | H | H | CH | CH | CH | CH |
| 2004. | 1 | O | H | 2,6-dimethylphenyl | H | $C_6H_{11}$ | H | H | CH | CH | CH | CH |
| 2005. | 1 | O | H | 2,6-dimethylphenyl | H | Ph | H | H | CH | CH | CH | CH |
| 2006. | 1 | O | H | 2,6-dimethylphenyl | H | 2,6-dimethylphenyl | H | H | CH | CH | CH | CH |
| 2007. | 1 | O | H | 2,6-dimethylphenyl | H | 2,6-diisopropylphenyl | H | H | CH | CH | CH | CH |
| 2008. | 1 | O | H | 2,6-diisopropylphenyl | H | $CH_3$ | H | H | CH | CH | CH | CH |
| 2009. | 1 | O | H | 2,6-diisopropylphenyl | H | $CH(CH_3)_2$ | H | H | CH | CH | CH | CH |
| 2010. | 1 | O | H | 2,6-diisopropylphenyl | H | $CH_2CH(CH_3)_2$ | H | H | CH | CH | CH | CH |
| 2011. | 1 | O | H | 2,6-diisopropylphenyl | H | $C_6H_{11}$ | H | H | CH | CH | CH | CH |
| 2012. | 1 | O | H | 2,6-diisopropylphenyl | H | Ph | H | H | CH | CH | CH | CH |
| 2013. | 1 | O | H | 2,6-diisopropylphenyl | H | 2,6-dimethylphenyl | H | H | CH | CH | CH | CH |
| 2014. | 1 | O | H | 2,6-diisopropylphenyl | H | 2,6-diisopropylphenyl | H | H | CH | CH | CH | CH |
| 2015. | 1 | S | H | $CH_3$ | H | $CH_3$ | H | H | CH | CH | CH | CH |
| 2016. | 1 | S | H | $CH_3$ | H | $CH(CH_3)_2$ | H | H | CH | CH | CH | CH |
| 2017. | 1 | S | H | $CH_3$ | H | $CH_2CH(CH_3)_2$ | H | H | CH | CH | CH | CH |
| 2018. | 1 | S | H | $CH_3$ | H | $C_6H_{11}$ | H | H | CH | CH | CH | CH |
| 2019. | 1 | S | H | $CH_3$ | H | Ph | H | H | CH | CH | CH | CH |
| 2020. | 1 | S | H | $CH_3$ | H | 2,6-dimethylphenyl | H | H | CH | CH | CH | CH |
| 2021. | 1 | S | H | $CH_3$ | H | 2,6-diisopropylphenyl | H | H | CH | CH | CH | CH |
| 2022. | 1 | S | H | $CH(CH_3)_2$ | H | $CH_3$ | H | H | CH | CH | CH | CH |
| 2023. | 1 | S | H | $CH(CH_3)_2$ | H | $CH(CH_3)_2$ | H | H | CH | CH | CH | CH |
| 2024. | 1 | S | H | $CH(CH_3)_2$ | H | $CH_2CH(CH_3)_2$ | H | H | CH | CH | CH | CH |
| 2025. | 1 | S | H | $CH(CH_3)_2$ | H | $C_6H_{11}$ | H | H | CH | CH | CH | CH |
| 2026. | 1 | S | H | $CH(CH_3)_2$ | H | Ph | H | H | CH | CH | CH | CH |
| 2027. | 1 | S | H | $CH(CH_3)_2$ | H | 2,6-dimethylphenyl | H | H | CH | CH | CH | CH |
| 2028. | 1 | S | H | $CH(CH_3)_2$ | H | 2,6-diisopropylphenyl | H | H | CH | CH | CH | CH |
| 2029. | 1 | S | H | $CH_2CH(CH_3)_2$ | H | $CH_3$ | H | H | CH | CH | CH | CH |
| 2030. | 1 | S | H | $CH_2CH(CH_3)_2$ | H | $CH(CH_3)_2$ | H | H | CH | CH | CH | CH |
| 2031. | 1 | S | H | $CH_2CH(CH_3)_2$ | H | $CH_2CH(CH_3)_2$ | H | H | CH | CH | CH | CH |
| 2032. | 1 | S | H | $CH_2CH(CH_3)_2$ | H | $C_6H_{11}$ | H | H | CH | CH | CH | CH |
| 2033. | 1 | S | H | $CH_2CH(CH_3)_2$ | H | Ph | H | H | CH | CH | CH | CH |
| 2034. | 1 | S | H | $CH_2CH(CH_3)_2$ | H | 2,6-dimethylphenyl | H | H | CH | CH | CH | CH |
| 2035. | 1 | S | H | $CH_2CH(CH_3)_2$ | H | 2,6-diisopropylphenyl | H | H | CH | CH | CH | CH |
| 2036. | 1 | S | H | $C_6H_{11}$ | H | $CH_3$ | H | H | CH | CH | CH | CH |
| 2037. | 1 | S | H | $C_6H_{11}$ | H | $CH(CH_3)_2$ | H | H | CH | CH | CH | CH |
| 2038. | 1 | S | H | $C_6H_{11}$ | H | $CH_2CH(CH_3)_2$ | H | H | CH | CH | CH | CH |
| 2039. | 1 | S | H | $C_6H_{11}$ | H | $C_6H_{11}$ | H | H | CH | CH | CH | CH |
| 2040. | 1 | S | H | $C_6H_{11}$ | H | Ph | H | H | CH | CH | CH | CH |
| 2041. | 1 | S | H | $C_6H_{11}$ | H | 2,6-dimethylphenyl | H | H | CH | CH | CH | CH |
| 2042. | 1 | S | H | $C_6H_{11}$ | H | 2,6-diisopropylphenyl | H | H | CH | CH | CH | CH |
| 2043. | 1 | S | H | Ph | H | $CH_3$ | H | H | CH | CH | CH | CH |
| 2044. | 1 | S | H | Ph | H | $CH(CH_3)_2$ | H | H | CH | CH | CH | CH |
| 2045. | 1 | S | H | Ph | H | $CH_2CH(CH_3)_2$ | H | H | CH | CH | CH | CH |
| 2046. | 1 | S | H | Ph | H | $C_6H_{11}$ | H | H | CH | CH | CH | CH |
| 2047. | 1 | S | H | Ph | H | Ph | H | H | CH | CH | CH | CH |
| 2048. | 1 | S | H | Ph | H | 2,6-dimethylphenyl | H | H | CH | CH | CH | CH |
| 2049. | 1 | S | H | Ph | H | 2,6-diisopropylphenyl | H | H | CH | CH | CH | CH |

-continued

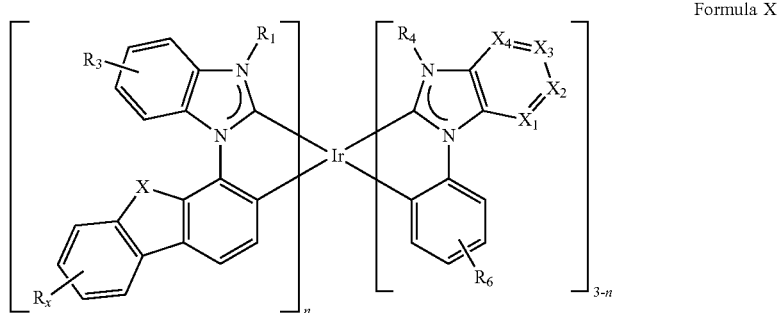

Formula X

Formula X

| Compd. | n | X | R$_x$ | R$_1$ | R$_3$ | R$_4$ | R$_5$ | R$_6$ | X$_1$ | X$_2$ | X$_3$ | X$_4$ |
|---|---|---|---|---|---|---|---|---|---|---|---|---|
| 2050. | 1 | S | H | 2,6-dimethylphenyl | H | CH$_3$ | H | H | CH | CH | CH | CH |
| 2051. | 1 | S | H | 2,6-dimethylphenyl | H | CH(CH$_3$)$_2$ | H | H | CH | CH | CH | CH |
| 2052. | 1 | S | H | 2,6-dimethylphenyl | H | CH$_2$CH(CH$_3$)$_2$ | H | H | CH | CH | CH | CH |
| 2053. | 1 | S | H | 2,6-dimethylphenyl | H | C$_6$H$_{11}$ | H | H | CH | CH | CH | CH |
| 2054. | 1 | S | H | 2,6-dimethylphenyl | H | Ph | H | H | CH | CH | CH | CH |
| 2055. | 1 | S | H | 2,6-dimethylphenyl | H | 2,6-dimethphenyl | H | H | CH | CH | CH | CH |
| 2056. | 1 | S | H | 2,6-dimethylphenyl | H | 2,6-diisopropylphenyl | H | H | CH | CH | CH | CH |
| 2057. | 1 | S | H | 2,6-diisopropylphenyl | H | CH$_3$ | H | H | CH | CH | CH | CH |
| 2058. | 1 | S | H | 2,6-diisopropylphenyl | H | CH(CH$_3$)$_2$ | H | H | CH | CH | CH | CH |
| 2059. | 1 | S | H | 2,6-diisopropylphenyl | H | CH$_2$CH(CH$_3$)$_2$ | H | H | CH | CH | CH | CH |
| 2060. | 1 | S | H | 2,6-diisopropylphenyl | H | C$_6$H$_{11}$ | H | H | CH | CH | CH | CH |
| 2061. | 1 | S | H | 2,6-diisopropylphenyl | H | Ph | H | H | CH | CH | CH | CH |
| 2062. | 1 | S | H | 2,6-diisopropylphenyl | H | 2,6-dimethylphenyl | H | H | CH | CH | CH | CH |
| 2063. | 1 | S | H | 2,6-diisopropylphenyl | H | 2,6-diisopropylphenyl | H | H | CH | CH | CH | CH |
| 2064. | 2 | O | H | CH$_3$ | H | CH$_3$ | H | H | CH | CH | CH | CH |
| 2065. | 2 | O | H | CH$_3$ | H | CH(CH$_3$)$_2$ | H | H | CH | CH | CH | CH |
| 2066. | 2 | O | H | CH$_3$ | H | CH$_2$CH(CH$_3$)$_2$ | H | H | CH | CH | CH | CH |
| 2067. | 2 | O | H | CH$_3$ | H | C$_6$H$_{11}$ | H | H | CH | CH | CH | CH |
| 2068. | 2 | O | H | CH$_3$ | H | Ph | H | H | CH | CH | CH | CH |
| 2069. | 2 | O | H | CH$_3$ | H | 2,6-dimethylphenyl | H | H | CH | CH | CH | CH |
| 2070. | 2 | O | H | CH$_3$ | H | 2,6-diisopropylphenyl | H | H | CH | CH | CH | CH |
| 2071. | 2 | O | H | CH(CH$_3$)$_2$ | H | CH$_3$ | H | H | CH | CH | CH | CH |
| 2072. | 2 | O | H | CH(CH$_3$)$_2$ | H | CH(CH$_3$)$_2$ | H | H | CH | CH | CH | CH |
| 2073. | 2 | O | H | CH(CH$_3$)$_2$ | H | CH$_2$CH(CH$_3$)$_2$ | H | H | CH | CH | CH | CH |
| 2074. | 2 | O | H | CH(CH$_3$)$_2$ | H | C$_6$H$_{11}$ | H | H | CH | CH | CH | CH |
| 2075. | 2 | O | H | CH(CH$_3$)$_2$ | H | Ph | H | H | CH | CH | CH | CH |
| 2076. | 2 | O | H | CH(CH$_3$)$_2$ | H | 2,6-dimethylphenyl | H | H | CH | CH | CH | CH |
| 2077. | 2 | O | H | CH(CH$_3$)$_2$ | H | 2,6-diisopropylphenyl | H | H | CH | CH | CH | CH |
| 2078. | | | | | | | | | CH | CH | CH | CH |
| 2079. | 2 | O | H | CH$_2$CH(CH$_3$)$_2$ | H | CH$_3$ | H | H | CH | CH | CH | CH |
| 2080. | 2 | O | H | CH$_2$CH(CH$_3$)$_2$ | H | CH(CH$_3$)$_2$ | H | H | CH | CH | CH | CH |
| 2081. | 2 | O | H | CH$_2$CH(CH$_3$)$_2$ | H | CH$_2$CH(CH$_3$)$_2$ | H | H | CH | CH | CH | CH |
| 2082. | 2 | O | H | CH$_2$CH(CH$_3$)$_2$ | H | C$_6$H$_{11}$ | H | H | CH | CH | CH | CH |
| 2083. | 2 | O | H | CH$_2$CH(CH$_3$)$_2$ | H | Ph | H | H | CH | CH | CH | CH |
| 2084. | 2 | O | H | CH$_2$CH(CH$_3$)$_2$ | H | 2,6-dimethylphenyl | H | H | CH | CH | CH | CH |
| 2085. | 2 | O | H | CH$_2$CH(CH$_3$)$_2$ | H | 2,6-diisopropylphenyl | H | H | CH | CH | CH | CH |
| 2086. | 2 | O | H | C$_6$H$_{11}$ | H | CH$_3$ | H | H | CH | CH | CH | CH |
| 2087. | 2 | O | H | C$_6$H$_{11}$ | H | CH(CH$_3$)$_2$ | H | H | CH | CH | CH | CH |
| 2088. | 2 | O | H | C$_6$H$_{11}$ | H | CH$_2$CH(CH$_3$)$_2$ | H | H | CH | CH | CH | CH |
| 2089. | 2 | O | H | C$_6$H$_{11}$ | H | C$_6$H$_{11}$ | H | H | CH | CH | CH | CH |
| 2090. | 2 | O | H | C$_6$H$_{11}$ | H | Ph | H | H | CH | CH | CH | CH |
| 2091. | 2 | O | H | C$_6$H$_{11}$ | H | 2,6-dimethylphenyl | H | H | CH | CH | CH | CH |
| 2092. | 2 | O | H | C$_6$H$_{11}$ | H | 2,6-diisopropylphenyl | H | H | CH | CH | CH | CH |
| 2093. | 2 | O | H | Ph | H | CH$_3$ | H | H | CH | CH | CH | CH |
| 2094. | 2 | O | H | Ph | H | CH(CH$_3$)$_2$ | H | H | CH | CH | CH | CH |
| 2095. | 2 | O | H | Ph | H | CH$_2$CH(CH$_3$)$_2$ | H | H | CH | CH | CH | CH |
| 2096. | 2 | O | H | Ph | H | C$_6$H$_{11}$ | H | H | CH | CH | CH | CH |
| 2097. | 2 | O | H | Ph | H | Ph | H | H | CH | CH | CH | CH |
| 2098. | 2 | O | H | Ph | H | 2,6-dimethylphenyl | H | H | CH | CH | CH | CH |
| 2099. | 2 | O | H | Ph | H | 2,6-diisopropylphenyl | H | H | CH | CH | CH | CH |
| 2100. | 2 | O | H | 2,6-dimethylphenyl | H | CH$_3$ | H | H | CH | CH | CH | CH |
| 2101. | 2 | O | H | 2,6-dimethylphenyl | H | CH(CH$_3$)$_2$ | H | H | CH | CH | CH | CH |
| 2102. | 2 | O | H | 2,6-dimethylphenyl | H | CH$_2$CH(CH$_3$)$_2$ | H | H | CH | CH | CH | CH |
| 2103. | 2 | O | H | 2,6-dimethylphenyl | H | C$_6$H$_{11}$ | H | H | CH | CH | CH | CH |
| 2104. | 2 | O | H | 2,6-dimethylphenyl | H | Ph | H | H | CH | CH | CH | CH |
| 2105. | 2 | O | H | 2,6-dimethylphenyl | H | 2,6-dimethylphenyl | H | H | CH | CH | CH | CH |
| 2106. | 2 | O | H | 2,6-dimethylphenyl | H | 2,6-diisopropylphenyl | H | H | CH | CH | CH | CH |
| 2107. | 2 | O | H | 2,6-diisopropylphenyl | H | CH$_3$ | H | H | CH | CH | CH | CH |
| 2108. | 2 | O | H | 2,6-diisopropylphenyl | H | CH(CH$_3$)$_2$ | H | H | CH | CH | CH | CH |

-continued

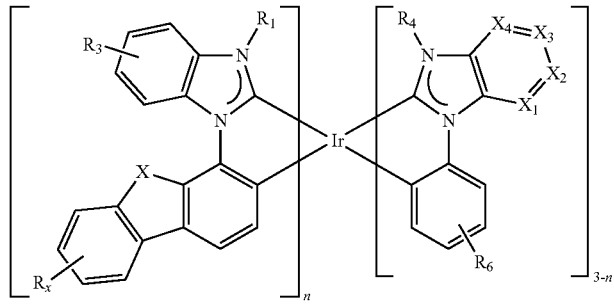

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2109. | 2 | O | H | 2,6-diisopropylphenyl | H | $CH_2CH(CH_3)_2$ | H | H | CH | CH | CH | CH |
| 2110. | 2 | O | H | 2,6-diisopropylphenyl | H | $C_6H_{11}$ | H | H | CH | CH | CH | CH |
| 2111. | 2 | O | H | 2,6-diisopropylphenyl | H | Ph | H | H | CH | CH | CH | CH |
| 2112. | 2 | O | H | 2,6-diisopropylphenyl | H | 2,6-dimethylphenyl | H | H | CH | CH | CH | CH |
| 2113. | 2 | O | H | 2,6-diisopropylphenyl | H | 2,6-diisopropylphenyl | H | H | CH | CH | CH | CH |
| 2114. | 2 | S | H | $CH_3$ | H | $CH_3$ | H | H | CH | CH | CH | CH |
| 2115. | 2 | S | H | $CH_3$ | H | $CH(CH_3)_2$ | H | H | CH | CH | CH | CH |
| 2116. | 2 | S | H | $CH_3$ | H | $CH_2CH(CH_3)_2$ | H | H | CH | CH | CH | CH |
| 2117. | 2 | S | H | $CH_3$ | H | $C_6H_{11}$ | H | H | CH | CH | CH | CH |
| 2118. | 2 | S | H | $CH_3$ | H | Ph | H | H | CH | CH | CH | CH |
| 2119. | 2 | S | H | $CH_3$ | H | 2,6-dimethylphenyl | H | H | CH | CH | CH | CH |
| 2120. | 2 | S | H | $CH_3$ | H | 2,6-diisopropylphenyl | H | H | CH | CH | CH | CH |
| 2121. | 2 | S | H | $CH(CH_3)_2$ | H | $CH_3$ | H | H | CH | CH | CH | CH |
| 2122. | 2 | S | H | $CH(CH_3)_2$ | H | $CH(CH_3)_2$ | H | H | CH | CH | CH | CH |
| 2123. | 2 | S | H | $CH(CH_3)_2$ | H | $CH_2CH(CH_3)_2$ | H | H | CH | CH | CH | CH |
| 2124. | 2 | S | H | $CH(CH_3)_2$ | H | $C_6H_{11}$ | H | H | CH | CH | CH | CH |
| 2125. | 2 | S | H | $CH(CH_3)_2$ | H | Ph | H | H | CH | CH | CH | CH |
| 2126. | 2 | S | H | $CH(CH_3)_2$ | H | 2,6-dimethylphenyl | H | H | CH | CH | CH | CH |
| 2127. | 2 | S | H | $CH(CH_3)_2$ | H | 2,6-diisopropylphenyl | H | H | CH | CH | CH | CH |
| 2128. | 2 | S | H | $CH_2CH(CH_3)_2$ | H | $CH_3$ | H | H | CH | CH | CH | CH |
| 2129. | 2 | S | H | $CH_2CH(CH_3)_2$ | H | $CH(CH_3)_2$ | H | H | CH | CH | CH | CH |
| 2130. | 2 | S | H | $CH_2CH(CH_3)_2$ | H | $CH_2CH(CH_3)_2$ | H | H | CH | CH | CH | CH |
| 2131. | 2 | S | H | $CH_2CH(CH_3)_2$ | H | $C_6H_{11}$ | H | H | CH | CH | CH | CH |
| 2132. | 2 | S | H | $CH_2CH(CH_3)_2$ | H | Ph | H | H | CH | CH | CH | CH |
| 2133. | 2 | S | H | $CH_2CH(CH_3)_2$ | H | 2,6-dimethylphenyl | H | H | CH | CH | CH | CH |
| 2134. | 2 | S | H | $CH_2CH(CH_3)_2$ | H | 2,6-diisopropylphenyl | H | H | CH | CH | CH | CH |
| 2135. | 2 | S | H | $C_6H_{11}$ | H | $CH_3$ | H | H | CH | CH | CH | CH |
| 2136. | 2 | S | H | $C_6H_{11}$ | H | $CH(CH_3)_2$ | H | H | CH | CH | CH | CH |
| 2137. | 2 | S | H | $C_6H_{11}$ | H | $CH_2CH(CH_3)_2$ | H | H | CH | CH | CH | CH |
| 2138. | 2 | S | H | $C_6H_{11}$ | H | $C_6H_{11}$ | H | H | CH | CH | CH | CH |
| 2139. | 2 | S | H | $C_6H_{11}$ | H | Ph | H | H | CH | CH | CH | CH |
| 2140. | 2 | S | H | $C_6H_{11}$ | H | 2,6-dimethylphenyl | H | H | CH | CH | CH | CH |
| 2141. | 2 | S | H | $C_6H_{11}$ | H | 2,6-diisopropylphenyl | H | H | CH | CH | CH | CH |
| 2142. | 2 | S | H | Ph | H | $CH_3$ | H | H | CH | CH | CH | CH |
| 2143. | 2 | S | H | Ph | H | $CH(CH_3)_2$ | H | H | CH | CH | CH | CH |
| 2144. | 2 | S | H | Ph | H | $CH_2CH(CH_3)_2$ | H | H | CH | CH | CH | CH |
| 2145. | 2 | S | H | Ph | H | $C_6H_{11}$ | H | H | CH | CH | CH | CH |
| 2146. | 2 | S | H | Ph | H | Ph | H | H | CH | CH | CH | CH |
| 2147. | 2 | S | H | Ph | H | 2,6-dimethylphenyl | H | H | CH | CH | CH | CH |
| 2148. | 2 | S | H | Ph | H | 2,6-diisopropylphenyl | H | H | CH | CH | CH | CH |
| 2149. | 2 | S | H | 2,6-dimethylphenyl | H | $CH_3$ | H | H | CH | CH | CH | CH |
| 2150. | 2 | S | H | 2,6-dimethylphenyl | H | $CH(CH_3)_2$ | H | H | CH | CH | CH | CH |
| 2151. | 2 | S | H | 2,6-dimethylphenyl | H | $CH_2CH(CH_3)_2$ | H | H | CH | CH | CH | CH |
| 2152. | 2 | S | H | 2,6-dimethylphenyl | H | $C_6H_{11}$ | H | H | CH | CH | CH | CH |
| 2153. | 2 | S | H | 2,6-dimethylphenyl | H | Ph | H | H | CH | CH | CH | CH |
| 2154. | 2 | S | H | 2,6-dimethylphenyl | H | 2,6-dimethylphenyl | H | H | CH | CH | CH | CH |
| 2155. | 2 | S | H | 2,6-dimethylphenyl | H | 2,6-diisopropylphenyl | H | H | CH | CH | CH | CH |
| 2156. | 2 | S | H | 2,6-diisopropylphenyl | H | $CH_3$ | H | H | CH | CH | CH | CH |
| 2157. | 2 | S | H | 2,6-diisopropylphenyl | H | $CH(CH_3)_2$ | H | H | CH | CH | CH | CH |
| 2158. | 2 | S | H | 2,6-diisopropylphenyl | H | $CH_2CH(CH_3)_2$ | H | H | CH | CH | CH | CH |
| 2159. | 2 | S | H | 2,6-diisopropylphenyl | H | $C_6H_{11}$ | H | H | CH | CH | CH | CH |
| 2160. | 2 | S | H | 2,6-diisopropylphenyl | H | Ph | H | H | CH | CH | CH | CH |
| 2161. | 2 | S | H | 2,6-diisopropylphenyl | H | 2,6-dimethylphenyl | H | H | CH | CH | CH | CH |
| 2162. | 2 | S | H | 2,6-diisopropylphenyl | H | 2,6-diisopropylphenyl | H | H | CH | CH | CH | CH |
| 2163. | 1 | O | H | $CH_3$ | H | $CH_3$ | H | H | N | CH | CH | CH |
| 2164. | 1 | O | H | $CH_3$ | H | $CH(CH_3)_2$ | H | H | N | CH | CH | CH |
| 2165. | 1 | O | H | $CH_3$ | H | $CH_2CH(CH_3)_2$ | H | H | N | CH | CH | CH |
| 2166. | 1 | O | H | $CH_3$ | H | $C_6H_{11}$ | H | H | N | CH | CH | CH |
| 2167. | 1 | O | H | $CH_3$ | H | Ph | H | H | N | CH | CH | CH |

-continued

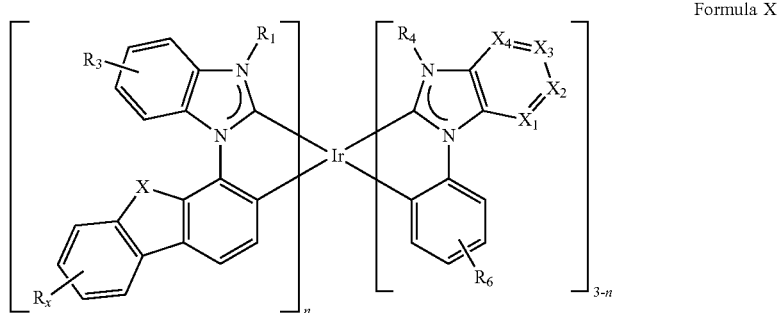

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2168. | 1 | O | H | $CH_3$ | H | 2,6-dimethylphenyl | H | H | N | CH | CH | CH |
| 2169. | 1 | O | H | $CH_3$ | H | 2,6-diisopropylphenyl | H | H | N | CH | CH | CH |
| 2170. | 1 | O | H | $CH(CH_3)_2$ | H | $CH_3$ | H | H | N | CH | CH | CH |
| 2171. | 1 | O | H | $CH(CH_3)_2$ | H | $CH(CH_3)_2$ | H | H | N | CH | CH | CH |
| 2172. | 1 | O | H | $CH(CH_3)_2$ | H | $CH_2CH(CH_3)_2$ | H | H | N | CH | CH | CH |
| 2173. | 1 | O | H | $CH(CH_3)_2$ | H | $C_6H_{11}$ | H | H | N | CH | CH | CH |
| 2174. | 1 | O | H | $CH(CH_3)_2$ | H | Ph | H | H | N | CH | CH | CH |
| 2175. | 1 | O | H | $CH(CH_3)_2$ | H | 2,6-dimethylphenyl | H | H | N | CH | CH | CH |
| 2176. | 1 | O | H | $CH(CH_3)_2$ | H | 2,6-diisopropylphenyl | H | H | N | CH | CH | CH |
| 2177. | 1 | O | H | $CH_2CH(CH_3)_2$ | H | $CH_3$ | H | H | N | CH | CH | CH |
| 2178. | 1 | O | H | $CH_2CH(CH_3)_2$ | H | $CH(CH_3)_2$ | H | H | N | CH | CH | CH |
| 2179. | 1 | O | H | $CH_2CH(CH_3)_2$ | H | $CH_2CH(CH_3)_2$ | H | H | N | CH | CH | CH |
| 2180. | 1 | O | H | $CH_2CH(CH_3)_2$ | H | $C_6H_{11}$ | H | H | N | CH | CH | CH |
| 2181. | 1 | O | H | $CH_2CH(CH_3)_2$ | H | Ph | H | H | N | CH | CH | CH |
| 2182. | 1 | O | H | $CH_2CH(CH_3)_2$ | H | 2,6-dimethylphenyl | H | H | N | CH | CH | CH |
| 2183. | 1 | O | H | $CH_2CH(CH_3)_2$ | H | 2,6-diisopropylphenyl | H | H | N | CH | CH | CH |
| 2184. | 1 | O | H | $C_6H_{11}$ | H | $CH_3$ | H | H | N | CH | CH | CH |
| 2185. | 1 | O | H | $C_6H_{11}$ | H | $CH(CH_3)_2$ | H | H | N | CH | CH | CH |
| 2186. | 1 | O | H | $C_6H_{11}$ | H | $CH_2CH(CH_3)_2$ | H | H | N | CH | CH | CH |
| 2187. | 1 | O | H | $C_6H_{11}$ | H | $C_6H_{11}$ | H | H | N | CH | CH | CH |
| 2188. | 1 | O | H | $C_6H_{11}$ | H | Ph | H | H | N | CH | CH | CH |
| 2189. | 1 | O | H | $C_6H_{11}$ | H | 2,6-dimethylphenyl | H | H | N | CH | CH | CH |
| 2190. | 1 | O | H | $C_6H_{11}$ | H | 2,6-diisopropylphenyl | H | H | N | CH | CH | CH |
| 2191. | 1 | O | H | Ph | H | $CH_3$ | H | H | N | CH | CH | CH |
| 2192. | 1 | O | H | Ph | H | $CH(CH_3)_2$ | H | H | N | CH | CH | CH |
| 2193. | 1 | O | H | Ph | H | $CH_2CH(CH_3)_2$ | H | H | N | CH | CH | CH |
| 2194. | 1 | O | H | Ph | H | $C_6H_{11}$ | H | H | N | CH | CH | CH |
| 2195. | 1 | O | H | Ph | H | Ph | H | H | N | CH | CH | CH |
| 2196. | 1 | O | H | Ph | H | 2,6-dimethylphenyl | H | H | N | CH | CH | CH |
| 2197. | 1 | O | H | Ph | H | 2,6-diisopropylphenyl | H | H | N | CH | CH | CH |
| 2198. | 1 | O | H | 2,6-dimethylphenyl | H | $CH_3$ | H | H | N | CH | CH | CH |
| 2199. | 1 | O | H | 2,6-dimethylphenyl | H | $CH(CH_3)_2$ | H | H | N | CH | CH | CH |
| 2200. | 1 | O | H | 2,6-dimethylphenyl | H | $CH_2CH(CH_3)_2$ | H | H | N | CH | CH | CH |
| 2201. | 1 | O | H | 2,6-dimethylphenyl | H | $C_6H_{11}$ | H | H | N | CH | CH | CH |
| 2202. | 1 | O | H | 2,6-dimethylphenyl | H | Ph | H | H | N | CH | CH | CH |
| 2203. | 1 | O | H | 2,6-dimethylphenyl | H | 2,6-dimethylphenyl | H | H | N | CH | CH | CH |
| 2204. | 1 | O | H | 2,6-dimethylphenyl | H | 2,6-diisopropylphenyl | H | H | N | CH | CH | CH |
| 2205. | 1 | O | H | 2,6-diisopropylphenyl | H | $CH_3$ | H | H | N | CH | CH | CH |
| 2206. | 1 | O | H | 2,6-diisopropylphenyl | H | $CH(CH_3)_2$ | H | H | N | CH | CH | CH |
| 2207. | 1 | O | H | 2,6-diisopropylphenyl | H | $CH_2CH(CH_3)_2$ | H | H | N | CH | CH | CH |
| 2208. | 1 | O | H | 2,6-diisopropylphenyl | H | $C_6H_{11}$ | H | H | N | CH | CH | CH |
| 2209. | 1 | O | H | 2,6-diisopropylphenyl | H | Ph | H | H | N | CH | CH | CH |
| 2210. | 1 | O | H | 2,6-diisopropylphenyl | H | 2,6-dimethylphenyl | H | H | N | CH | CH | CH |
| 2211. | 1 | O | H | 2,6-diisopropylphenyl | H | 2,6-diisopropylphenyl | H | H | N | CH | CH | CH |
| 2212. | 1 | S | H | $CH_3$ | H | $CH_3$ | H | H | N | CH | CH | CH |
| 2213. | 1 | S | H | $CH_3$ | H | $CH(CH_3)_2$ | H | H | N | CH | CH | CH |
| 2214. | 1 | S | H | $CH_3$ | H | $CH_2CH(CH_3)_2$ | H | H | N | CH | CH | CH |
| 2215. | 1 | S | H | $CH_3$ | H | $C_6H_{11}$ | H | H | N | CH | CH | CH |
| 2216. | 1 | S | H | $CH_3$ | H | Ph | H | H | N | CH | CH | CH |
| 2217. | 1 | S | H | $CH_3$ | H | 2,6-dimethylphenyl | H | H | N | CH | CH | CH |
| 2218. | 1 | S | H | $CH_3$ | H | 2,6-diisopropylphenyl | H | H | N | CH | CH | CH |
| 2219. | 1 | S | H | $CH(CH_3)_2$ | H | $CH_3$ | H | H | N | CH | CH | CH |
| 2220. | 1 | S | H | $CH(CH_3)_2$ | H | $CH(CH_3)_2$ | H | H | N | CH | CH | CH |
| 2221. | 1 | S | H | $CH(CH_3)_2$ | H | $CH_2CH(CH_3)_2$ | H | H | N | CH | CH | CH |
| 2222. | 1 | S | H | $CH(CH_3)_2$ | H | $C_6H_{11}$ | H | H | N | CH | CH | CH |
| 2223. | 1 | S | H | $CH(CH_3)_2$ | H | Ph | H | H | N | CH | CH | CH |
| 2224. | 1 | S | H | $CH(CH_3)_2$ | H | 2,6-dimethylphenyl | H | H | N | CH | CH | CH |
| 2225. | 1 | S | H | $CH(CH_3)_2$ | H | 2,6-diisopropylphenyl | H | H | N | CH | CH | CH |
| 2226. | 1 | S | H | $CH_2CH(CH_3)_2$ | H | $CH_3$ | H | H | N | CH | CH | CH |

-continued

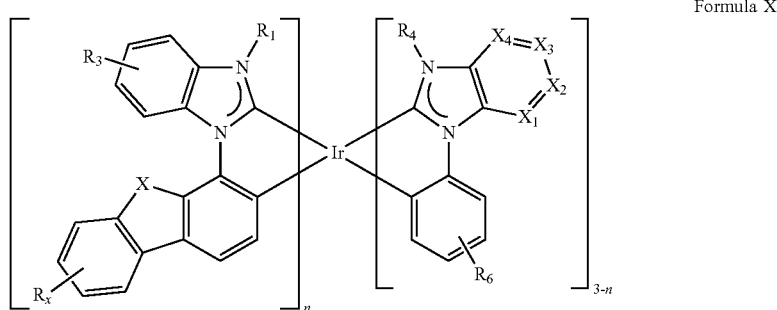

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2227. | 1 | S | H | $CH_2CH(CH_3)_2$ | H | $CH(CH_3)_2$ | H | H | N | CH | CH | CH |
| 2228. | 1 | S | H | $CH_2CH(CH_3)_2$ | H | $CH_2CH(CH_3)_2$ | H | H | N | CH | CH | CH |
| 2229. | 1 | S | H | $CH_2CH(CH_3)_2$ | H | $C_6H_{11}$ | H | H | N | CH | CH | CH |
| 2230. | 1 | S | H | $CH_2CH(CH_3)_2$ | H | Ph | H | H | N | CH | CH | CH |
| 2231. | 1 | S | H | $CH_2CH(CH_3)_2$ | H | 2,6-dimethylphenyl | H | H | N | CH | CH | CH |
| 2232. | 1 | S | H | $CH_2CH(CH_3)_2$ | H | 2,6-diisopropylphenyl | H | H | N | CH | CH | CH |
| 2233. | 1 | S | H | $C_6H_{11}$ | H | $CH_3$ | H | H | N | CH | CH | CH |
| 2234. | 1 | S | H | $C_6H_{11}$ | H | $CH(CH_3)_2$ | H | H | N | CH | CH | CH |
| 2235. | 1 | S | H | $C_6H_{11}$ | H | $CH_2CH(CH_3)_2$ | H | H | N | CH | CH | CH |
| 2236. | 1 | S | H | $C_6H_{11}$ | H | $C_6H_{11}$ | H | H | N | CH | CH | CH |
| 2237. | 1 | S | H | $C_6H_{11}$ | H | Ph | H | H | N | CH | CH | CH |
| 2238. | 1 | S | H | $C_6H_{11}$ | H | 2,6-dimethylphenyl | H | H | N | CH | CH | CH |
| 2239. | 1 | S | H | $C_6H_{11}$ | H | 2,6-diisopropylphenyl | H | H | N | CH | CH | CH |
| 2240. | 1 | S | H | Ph | H | $CH_3$ | H | H | N | CH | CH | CH |
| 2241. | 1 | S | H | Ph | H | $CH(CH_3)_2$ | H | H | N | CH | CH | CH |
| 2242. | 1 | S | H | Ph | H | $CH_2CH(CH_3)_2$ | H | H | N | CH | CH | CH |
| 2243. | 1 | S | H | Ph | H | $C_6H_{11}$ | H | H | N | CH | CH | CH |
| 2244. | 1 | S | H | Ph | H | Ph | H | H | N | CH | CH | CH |
| 2245. | 1 | S | H | Ph | H | 2,6-dimethylphenyl | H | H | N | CH | CH | CH |
| 2246. | 1 | S | H | Ph | H | 2,6-diisopropylphenyl | H | H | N | CH | CH | CH |
| 2247. | 1 | S | H | 2,6-dimethylphenyl | H | $CH_3$ | H | H | N | CH | CH | CH |
| 2248. | 1 | S | H | 2,6-dimethylphenyl | H | $CH(CH_3)_2$ | H | H | N | CH | CH | CH |
| 2249. | 1 | S | H | 2,6-dimethylphenyl | H | $CH_2CH(CH_3)_2$ | H | H | N | CH | CH | CH |
| 2250. | 1 | S | H | 2,6-dimethylphenyl | H | $C_6H_{11}$ | H | H | N | CH | CH | CH |
| 2251. | 1 | S | H | 2,6-dimethylphenyl | H | Ph | H | H | N | CH | CH | CH |
| 2252. | 1 | S | H | 2,6-dimethylphenyl | H | 2,6-dimethylphenyl | H | H | N | CH | CH | CH |
| 2253. | 1 | S | H | 2,6-dimethylphenyl | H | 2,6-diisopropylphenyl | H | H | N | CH | CH | CH |
| 2254. | 1 | S | H | 2,6-diisopropylphenyl | H | $CH_3$ | H | H | N | CH | CH | CH |
| 2255. | 1 | S | H | 2,6-diisopropylphenyl | H | $CH(CH_3)_2$ | H | H | N | CH | CH | CH |
| 2256. | 1 | S | H | 2,6-diisopropylphenyl | H | $CH_2CH(CH_3)_2$ | H | H | N | CH | CH | CH |
| 2257. | 1 | S | H | 2,6-diisopropylphenyl | H | $C_6H_{11}$ | H | H | N | CH | CH | CH |
| 2258. | 1 | S | H | 2,6-diisopropylphenyl | H | Ph | H | H | N | CH | CH | CH |
| 2259. | 1 | S | H | 2,6-diisopropylphenyl | H | 2,6-dimethylphenyl | H | H | N | CH | CH | CH |
| 2260. | 1 | S | H | 2,6-diisopropylphenyl | H | 2,6-diisopropylphenyl | H | H | N | CH | CH | CH |
| 2261. | 2 | O | H | $CH_3$ | H | $CH_3$ | H | H | N | CH | CH | CH |
| 2262. | 2 | O | H | $CH_3$ | H | $CH(CH_3)_2$ | H | H | N | CH | CH | CH |
| 2263. | 2 | O | H | $CH_3$ | H | $CH_2CH(CH_3)_2$ | H | H | N | CH | CH | CH |
| 2264. | 2 | O | H | $CH_3$ | H | $C_6H_{11}$ | H | H | N | CH | CH | CH |
| 2265. | 2 | O | H | $CH_3$ | H | Ph | H | H | N | CH | CH | CH |
| 2266. | 2 | O | H | $CH_3$ | H | 2,6-dimethylphenyl | H | H | N | CH | CH | CH |
| 2267. | 2 | O | H | $CH_3$ | H | 2,6-diisopropylphenyl | H | H | N | CH | CH | CH |
| 2268. | 2 | O | H | $CH(CH_3)_2$ | H | $CH_3$ | H | H | N | CH | CH | CH |
| 2269. | 2 | O | H | $CH(CH_3)_2$ | H | $CH(CH_3)_2$ | H | H | N | CH | CH | CH |
| 2270. | 2 | O | H | $CH(CH_3)_2$ | H | $CH_2CH(CH_3)_2$ | H | H | N | CH | CH | CH |
| 2271. | 2 | O | H | $CH(CH_3)_2$ | H | $C_6H_{11}$ | H | H | N | CH | CH | CH |
| 2272. | 2 | O | H | $CH(CH_3)_2$ | H | Ph | H | H | N | CH | CH | CH |
| 2273. | 2 | O | H | $CH(CH_3)_2$ | H | 2,6-methylphenyl | H | H | N | CH | CH | CH |
| 2274. | 2 | O | H | $CH(CH_3)_2$ | H | 2,6-diisopropylphenyl | H | H | N | CH | CH | CH |
| 2275. | 2 | O | H | $CH_2CH(CH_3)_2$ | H | $CH_3$ | H | H | N | CH | CH | CH |
| 2276. | 2 | O | H | $CH_2CH(CH_3)_2$ | H | $CH(CH_3)_2$ | H | H | N | CH | CH | CH |
| 2277. | 2 | O | H | $CH_2CH(CH_3)_2$ | H | $CH_2CH(CH_3)_2$ | H | H | N | CH | CH | CH |
| 2278. | 2 | O | H | $CH_2CH(CH_3)_2$ | H | $C_6H_{11}$ | H | H | N | CH | CH | CH |
| 2279. | 2 | O | H | $CH_2CH(CH_3)_2$ | H | Ph | H | H | N | CH | CH | CH |
| 2280. | 2 | O | H | $CH_2CH(CH_3)_2$ | H | 2,6-dimethylphenyl | H | H | N | CH | CH | CH |
| 2281. | 2 | O | H | $CH_2CH(CH_3)_2$ | H | 2,6-diisopropylphenyl | H | H | N | CH | CH | CH |
| 2282. | 2 | O | H | $C_6H_{11}$ | H | $CH_3$ | H | H | N | CH | CH | CH |
| 2283. | 2 | O | H | $C_6H_{11}$ | H | $CH(CH_3)_2$ | H | H | N | CH | CH | CH |
| 2284. | 2 | O | H | $C_6H_{11}$ | H | $CH_2CH(CH_3)_2$ | H | H | N | CH | CH | CH |
| 2285. | 2 | O | H | $C_6H_{11}$ | H | $C_6H_{11}$ | H | H | N | CH | CH | CH |

-continued

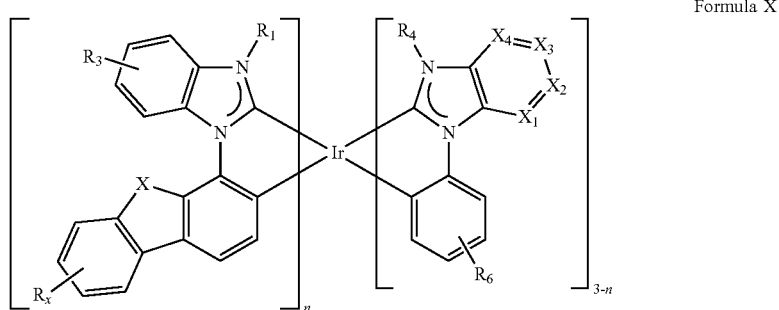

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2286. | 2 | O | H | $C_6H_{11}$ | H | Ph | H | H | N | CH | CH | CH |
| 2287. | 2 | O | H | $C_6H_{11}$ | H | 2,6-dimethylphenyl | H | H | N | CH | CH | CH |
| 2288. | 2 | O | H | $C_6H_{11}$ | H | 2,6-diisopropylphenyl | H | H | N | CH | CH | CH |
| 2289. | 2 | O | H | Ph | H | $CH_3$ | H | H | N | CH | CH | CH |
| 2290. | 2 | O | H | Ph | H | $CH(CH_3)_2$ | H | H | N | CH | CH | CH |
| 2291. | 2 | O | H | Ph | H | $CH_2CH(CH_3)_2$ | H | H | N | CH | CH | CH |
| 2292. | 2 | O | H | Ph | H | $C_6H_{11}$ | H | H | N | CH | CH | CH |
| 2293. | 2 | O | H | Ph | H | Ph | H | H | N | CH | CH | CH |
| 2294. | 2 | O | H | Ph | H | 2,6-dimethylphenyl | H | H | N | CH | CH | CH |
| 2295. | 2 | O | H | Ph | H | 2,6-diisopropylphenyl | H | H | N | CH | CH | CH |
| 2296. | 2 | O | H | 2,6-dimethylphenyl | H | $CH_3$ | H | H | N | CH | CH | CH |
| 2297. | 2 | O | H | 2,6-dimethylphenyl | H | $CH(CH_3)_2$ | H | H | N | CH | CH | CH |
| 2298. | 2 | O | H | 2,6-dimethylphenyl | H | $CH_2CH(CH_3)_2$ | H | H | N | CH | CH | CH |
| 2299. | 2 | O | H | 2,6-dimethylphenyl | H | $C_6H_{11}$ | H | H | N | CH | CH | CH |
| 2300. | 2 | O | H | 2,6-dimethylphenyl | H | Ph | H | H | N | CH | CH | CH |
| 2301. | 2 | O | H | 2,6-dimethylphenyl | H | 2,6-dimethylphenyl | H | H | N | CH | CH | CH |
| 2302. | 2 | O | H | 2,6-dimethylphenyl | H | 2,6-diisopropylphenyl | H | H | N | CH | CH | CH |
| 2303. | 2 | O | H | 2,6-diisopropylphenyl | H | $CH_3$ | H | H | N | CH | CH | CH |
| 2304. | 2 | O | H | 2,6-diisopropylphenyl | H | $CH(CH_3)_2$ | H | H | N | CH | CH | CH |
| 2305. | 2 | O | H | 2,6-diisopropylphenyl | H | $CH_2CH(CH_3)_2$ | H | H | N | CH | CH | CH |
| 2306. | 2 | O | H | 2,6-diisopropylphenyl | H | $C_6H_{11}$ | H | H | N | CH | CH | CH |
| 2307. | 2 | O | H | 2,6-diisopropylphenyl | H | Ph | H | H | N | CH | CH | CH |
| 2308. | 2 | O | H | 2,6-diisopropylphenyl | H | 2,6-dimethylphenyl | H | H | N | CH | CH | CH |
| 2309. | 2 | O | H | 2,6-diisopropylphenyl | H | 2,6-diisopropylphenyl | H | H | N | CH | CH | CH |
| 2310. | 2 | S | H | $CH_3$ | H | $CH_3$ | H | H | N | CH | CH | CH |
| 2311. | 2 | S | H | $CH_3$ | H | $CH(CH_3)_2$ | H | H | N | CH | CH | CH |
| 2312. | 2 | S | H | $CH_3$ | H | $CH_2CH(CH_3)_2$ | H | H | N | CH | CH | CH |
| 2313. | 2 | S | H | $CH_3$ | H | $C_6H_{11}$ | H | H | N | CH | CH | CH |
| 2314. | 2 | S | H | $CH_3$ | H | Ph | H | H | N | CH | CH | CH |
| 2315. | 2 | S | H | $CH_3$ | H | 2,6-dimethylphenyl | H | H | N | CH | CH | CH |
| 2316. | 2 | S | H | $CH_3$ | H | 2,6-diisopropylphenyl | H | H | N | CH | CH | CH |
| 2317. | 2 | S | H | $CH(CH_3)_2$ | H | $CH_3$ | H | H | N | CH | CH | CH |
| 2318. | 2 | S | H | $CH(CH_3)_2$ | H | $CH(CH_3)_2$ | H | H | N | CH | CH | CH |
| 2319. | 2 | S | H | $CH(CH_3)_2$ | H | $CH_2CH(CH_3)_2$ | H | H | N | CH | CH | CH |
| 2320. | 2 | S | H | $CH(CH_3)_2$ | H | $C_6H_{11}$ | H | H | N | CH | CH | CH |
| 2321. | 2 | S | H | $CH(CH_3)_2$ | H | Ph | H | H | N | CH | CH | CH |
| 2322. | 2 | S | H | $CH(CH_3)_2$ | H | 2,6-dimethylphenyl | H | H | N | CH | CH | CH |
| 2323. | 2 | S | H | $CH(CH_3)_2$ | H | 2,6-diisopropylphenyl | H | H | N | CH | CH | CH |
| 2324. | 2 | S | H | $CH_2CH(CH_3)_2$ | H | $CH_3$ | H | H | N | CH | CH | CH |
| 2325. | 2 | S | H | $CH_2CH(CH_3)_2$ | H | $CH(CH_3)_2$ | H | H | N | CH | CH | CH |
| 2326. | 2 | S | H | $CH_2CH(CH_3)_2$ | H | $CH_2CH(CH_3)_2$ | H | H | N | CH | CH | CH |
| 2327. | 2 | S | H | $CH_2CH(CH_3)_2$ | H | $C_6H_{11}$ | H | H | N | CH | CH | CH |
| 2328. | 2 | S | H | $CH_2CH(CH_3)_2$ | H | Ph | H | H | N | CH | CH | CH |
| 2329. | 2 | S | H | $CH_2CH(CH_3)_2$ | H | 2,6-dimethylphenyl | H | H | N | CH | CH | CH |
| 2330. | 2 | S | H | $CH_2CH(CH_3)_2$ | H | 2,6-diisopropylphenyl | H | H | N | CH | CH | CH |
| 2331. | 2 | S | H | $C_6H_{11}$ | H | $CH_3$ | H | H | N | CH | CH | CH |
| 2332. | 2 | S | H | $C_6H_{11}$ | H | $CH(CH_3)_2$ | H | H | N | CH | CH | CH |
| 2333. | 2 | S | H | $C_6H_{11}$ | H | $CH_2CH(CH_3)_2$ | H | H | N | CH | CH | CH |
| 2334. | 2 | S | H | $C_6H_{11}$ | H | $C_6H_{11}$ | H | H | N | CH | CH | CH |
| 2335. | 2 | S | H | $C_6H_{11}$ | H | Ph | H | H | N | CH | CH | CH |
| 2336. | 2 | S | H | $C_6H_{11}$ | H | 2,6-dimethylphenyl | H | H | N | CH | CH | CH |
| 2337. | 2 | S | H | $C_6H_{11}$ | H | 2,6-diisopropylphenyl | H | H | N | CH | CH | CH |
| 2338. | 2 | S | H | Ph | H | $CH_3$ | H | H | N | CH | CH | CH |
| 2339. | 2 | S | H | Ph | H | $CH(CH_3)_2$ | H | H | N | CH | CH | CH |
| 2340. | 2 | S | H | Ph | H | $CH_2CH(CH_3)_2$ | H | H | N | CH | CH | CH |
| 2341. | 2 | S | H | Ph | H | $C_6H_{11}$ | H | H | N | CH | CH | CH |
| 2342. | 2 | S | H | Ph | H | Ph | H | H | N | CH | CH | CH |
| 2343. | 2 | S | H | Ph | H | 2,6-dimethylphenyl | H | H | N | CH | CH | CH |
| 2344. | 2 | S | H | Ph | H | 2,6-diisopropylphenyl | H | H | N | CH | CH | CH |

-continued

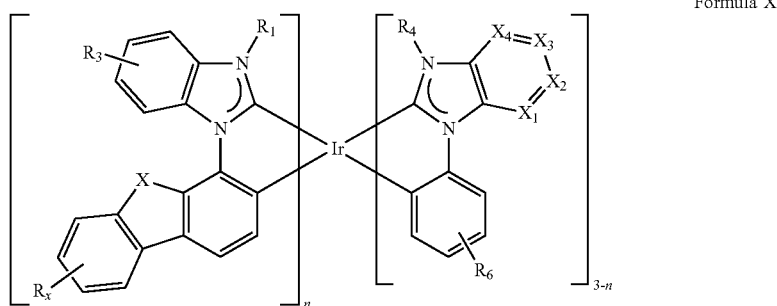

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2345. | 2 | S | H | 2,6-dimethylphenyl | H | $CH_3$ | H | H | N | CH | CH | CH |
| 2346. | 2 | S | H | 2,6-dimethylphenyl | H | $CH(CH_3)_2$ | H | H | N | CH | CH | CH |
| 2347. | 2 | S | H | 2,6-dimethylphenyl | H | $CH_2CH(CH_3)_2$ | H | H | N | CH | CH | CH |
| 2348. | 2 | S | H | 2,6-dimethylphenyl | H | $C_6H_{11}$ | H | H | N | CH | CH | CH |
| 2349. | 2 | S | H | 2,6-dimethylphenyl | H | Ph | H | H | N | CH | CH | CH |
| 2350. | 2 | S | H | 2,6-dimethylphenyl | H | 2,6-dimethylphenyl | H | H | N | CH | CH | CH |
| 2351. | 2 | S | H | 2,6-dimethylphenyl | H | 2,6-diisopropylphenyl | H | H | N | CH | CH | CH |
| 2352. | 2 | S | H | 2,6-diisopropylphenyl | H | $CH_3$ | H | H | N | CH | CH | CH |
| 2353. | 2 | S | H | 2,6-diisopropylphenyl | H | $CH(CH_3)_2$ | H | H | N | CH | CH | CH |
| 2354. | 2 | S | H | 2,6-diisopropylphenyl | H | $CH_2CH(CH_3)_2$ | H | H | N | CH | CH | CH |
| 2355. | 2 | S | H | 2,6-diisopropylphenyl | H | $C_6H_{11}$ | H | H | N | CH | CH | CH |
| 2356. | 2 | S | H | 2,6-diisopropylphenyl | H | Ph | H | H | N | CH | CH | CH |
| 2357. | 2 | S | H | 2,6-diisopropylphenyl | H | 2,6-dimethylphenyl | H | H | N | CH | CH | CH |
| 2358. | 2 | S | H | 2,6-diisopropylphenyl | H | 2,6-diisopropylphenyl | H | H | N | CH | CH | CH |
| 2359. | 1 | O | H | $CH_3$ | H | $CH_3$ | H | H | CH | N | CH | CH |
| 2360. | 1 | O | H | $CH_3$ | H | $CH(CH_3)_2$ | H | H | CH | N | CH | CH |
| 2361. | 1 | O | H | $CH_3$ | H | $CH_2CH(CH_3)_2$ | H | H | CH | N | CH | CH |
| 2362. | 1 | O | H | $CH_3$ | H | $C_6H_{11}$ | H | H | CH | N | CH | CH |
| 2363. | 1 | O | H | $CH_3$ | H | Ph | H | H | CH | N | CH | CH |
| 2364. | 1 | O | H | $CH_3$ | H | 2,6-dimethylphenyl | H | H | CH | N | CH | CH |
| 2365. | 1 | O | H | $CH_3$ | H | 2,6-diisopropylphenyl | H | H | CH | N | CH | CH |
| 2366. | 1 | O | H | $CH(CH_3)_2$ | H | $CH_3$ | H | H | CH | N | CH | CH |
| 2367. | 1 | O | H | $CH(CH_3)_2$ | H | $CH(CH_3)_2$ | H | H | CH | N | CH | CH |
| 2368. | 1 | O | H | $CH(CH_3)_2$ | H | $CH_2CH(CH_3)_2$ | H | H | CH | N | CH | CH |
| 2369. | 1 | O | H | $CH(CH_3)_2$ | H | $C_6H_{11}$ | H | H | CH | N | CH | CH |
| 2370. | 1 | O | H | $CH(CH_3)_2$ | H | Ph | H | H | CH | N | CH | CH |
| 2371. | 1 | O | H | $CH(CH_3)_2$ | H | 2,6-dimethylphenyl | H | H | CH | N | CH | CH |
| 2372. | 1 | O | H | $CH(CH_3)_2$ | H | 2,6-diisopropylphenyl | H | H | CH | N | CH | CH |
| 2373. | 1 | O | H | $CH_2CH(CH_3)_2$ | H | $CH_3$ | H | H | CH | N | CH | CH |
| 2374. | 1 | O | H | $CH_2CH(CH_3)_2$ | H | $CH(CH_3)_2$ | H | H | CH | N | CH | CH |
| 2375. | 1 | O | H | $CH_2CH(CH_3)_2$ | H | $CH_2CH(CH_3)_2$ | H | H | CH | N | CH | CH |
| 2376. | 1 | O | H | $CH_2CH(CH_3)_2$ | H | $C_6H_{11}$ | H | H | CH | N | CH | CH |
| 2377. | 1 | O | H | $CH_2CH(CH_3)_2$ | H | Ph | H | H | CH | N | CH | CH |
| 2378. | 1 | O | H | $CH_2CH(CH_3)_2$ | H | 2,6-dimethylphenyl | H | H | CH | N | CH | CH |
| 2379. | 1 | O | H | $CH_2CH(CH_3)_2$ | H | 2,6-diisopropylphenyl | H | H | CH | N | CH | CH |
| 2380. | 1 | O | H | $C_6H_{11}$ | H | $CH_3$ | H | H | CH | N | CH | CH |
| 2381. | 1 | O | H | $C_6H_{11}$ | H | $CH(CH_3)_2$ | H | H | CH | N | CH | CH |
| 2382. | 1 | O | H | $C_6H_{11}$ | H | $CH_2CH(CH_3)_2$ | H | H | CH | N | CH | CH |
| 2383. | 1 | O | H | $C_6H_{11}$ | H | $C_6H_{11}$ | H | H | CH | N | CH | CH |
| 2384. | 1 | O | H | $C_6H_{11}$ | H | Ph | H | H | CH | N | CH | CH |
| 2385. | 1 | O | H | $C_6H_{11}$ | H | 2,6-dimethylphenyl | H | H | CH | N | CH | CH |
| 2386. | 1 | O | H | $C_6H_{11}$ | H | 2,6-diisopropylphenyl | H | H | CH | N | CH | CH |
| 2387. | 1 | O | H | Ph | H | $CH_3$ | H | H | CH | N | CH | CH |
| 2388. | 1 | O | H | Ph | H | $CH(CH_3)_2$ | H | H | CH | N | CH | CH |
| 2389. | 1 | O | H | Ph | H | $CH_2CH(CH_3)_2$ | H | H | CH | N | CH | CH |
| 2390. | 1 | O | H | Ph | H | $C_6H_{11}$ | H | H | CH | N | CH | CH |
| 2391. | 1 | O | H | Ph | H | Ph | H | H | CH | N | CH | CH |
| 2392. | 1 | O | H | Ph | H | 2,6-dimethylphenyl | H | H | CH | N | CH | CH |
| 2393. | 1 | O | H | Ph | H | 2,6-diisopropylphenyl | H | H | CH | N | CH | CH |
| 2394. | 1 | O | H | 2,6-dimethylphenyl | H | $CH_3$ | H | H | CH | N | CH | CH |
| 2395. | 1 | O | H | 2,6-dimethylphenyl | H | $CH(CH_3)_2$ | H | H | CH | N | CH | CH |
| 2396. | 1 | O | H | 2,6-dimethylphenyl | H | $CH_2CH(CH_3)_2$ | H | H | CH | N | CH | CH |
| 2397. | 1 | O | H | 2,6-dimethylphenyl | H | $C_6H_{11}$ | H | H | CH | N | CH | CH |
| 2398. | 1 | O | H | 2,6-dimethylphenyl | H | Ph | H | H | CH | N | CH | CH |
| 2399. | 1 | O | H | 2,6-dimethylphenyl | H | 2,6-dimethylphenyl | H | H | CH | N | CH | CH |
| 2400. | 1 | O | H | 2,6-dimethylphenyl | H | 2,6-diisopropylphenyl | H | H | CH | N | CH | CH |
| 2401. | 1 | O | H | 2,6-diisopropylphenyl | H | $CH_3$ | H | H | CH | N | CH | CH |
| 2402. | 1 | O | H | 2,6-diisopropylphenyl | H | $CH(CH_3)_2$ | H | H | CH | N | CH | CH |
| 2403. | 1 | O | H | 2,6-diisopropylphenyl | H | $CH_2CH(CH_3)_2$ | H | H | CH | N | CH | CH |

-continued

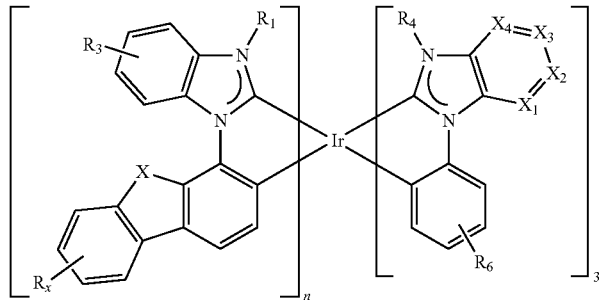

Formula X

| Compd. | n | X | R$_x$ | R$_1$ | R$_3$ | R$_4$ | R$_5$ | R$_6$ | X$_1$ | X$_2$ | X$_3$ | X$_4$ |
|---|---|---|---|---|---|---|---|---|---|---|---|---|
| 2404. | 1 | O | H | 2,6-diisopropylphenyl | H | C$_6$H$_{11}$ | H | H | CH | N | CH | CH |
| 2405. | 1 | O | H | 2,6-diisopropylphenyl | H | Ph | H | H | CH | N | CH | CH |
| 2406. | 1 | O | H | 2,6-diisopropylphenyl | H | 2,6-dimethylphenyl | H | H | CH | N | CH | CH |
| 2407. | 1 | O | H | 2,6-diisopropylphenyl | H | 2,6-diisopropylphenyl | H | H | CH | N | CH | CH |
| 2408. | 1 | S | H | CH$_3$ | H | CH$_3$ | H | H | CH | N | CH | CH |
| 2409. | 1 | S | H | CH$_3$ | H | CH(CH$_3$)$_2$ | H | H | CH | N | CH | CH |
| 2410. | 1 | S | H | CH$_3$ | H | CH$_2$CH(CH$_3$)$_2$ | H | H | CH | N | CH | CH |
| 2411. | 1 | S | H | CH$_3$ | H | C$_6$H$_{11}$ | H | H | CH | N | CH | CH |
| 2412. | 1 | S | H | CH$_3$ | H | Ph | H | H | CH | N | CH | CH |
| 2413. | 1 | S | H | CH$_3$ | H | 2,6-dimethylphenyl | H | H | CH | N | CH | CH |
| 2414. | 1 | S | H | CH$_3$ | H | 2,6-diisopropylphenyl | H | H | CH | N | CH | CH |
| 2415. | 1 | S | H | CH(CH$_3$)$_2$ | H | CH$_3$ | H | H | CH | N | CH | CH |
| 2416. | 1 | S | H | CH(CH$_3$)$_2$ | H | CH(CH$_3$)$_2$ | H | H | CH | N | CH | CH |
| 2417. | 1 | S | H | CH(CH$_3$)$_2$ | H | CH$_2$CH(CH$_3$)$_2$ | H | H | CH | N | CH | CH |
| 2418. | 1 | S | H | CH(CH$_3$)$_2$ | H | C$_6$H$_{11}$ | H | H | CH | N | CH | CH |
| 2419. | 1 | S | H | CH(CH$_3$)$_2$ | H | Ph | H | H | CH | N | CH | CH |
| 2420. | 1 | S | H | CH(CH$_3$)$_2$ | H | 2,6-dimethylphenyl | H | H | CH | N | CH | CH |
| 2421. | 1 | S | H | CH(CH$_3$)$_2$ | H | 2,6-diisopropylphenyl | H | H | CH | N | CH | CH |
| 2422. | 1 | S | H | CH$_2$CH(CH$_3$)$_2$ | H | CH$_3$ | H | H | CH | N | CH | CH |
| 2423. | 1 | S | H | CH$_2$CH(CH$_3$)$_2$ | H | CH(CH$_3$)$_2$ | H | H | CH | N | CH | CH |
| 2424. | 1 | S | H | CH$_2$CH(CH$_3$)$_2$ | H | CH$_2$CH(CH$_3$)$_2$ | H | H | CH | N | CH | CH |
| 2425. | 1 | S | H | CH$_2$CH(CH$_3$)$_2$ | H | C$_6$H$_{11}$ | H | H | CH | N | CH | CH |
| 2426. | 1 | S | H | CH$_2$CH(CH$_3$)$_2$ | H | Ph | H | H | CH | N | CH | CH |
| 2427. | 1 | S | H | CH$_2$CH(CH$_3$)$_2$ | H | 2,6-dimethylphenyl | H | H | CH | N | CH | CH |
| 2428. | 1 | S | H | CH$_2$CH(CH$_3$)$_2$ | H | 2,6-diisopropylphenyl | H | H | CH | N | CH | CH |
| 2429. | 1 | S | H | C$_6$H$_{11}$ | H | CH$_3$ | H | H | CH | N | CH | CH |
| 2430. | 1 | S | H | C$_6$H$_{11}$ | H | CH(CH$_3$)$_2$ | H | H | CH | N | CH | CH |
| 2431. | 1 | S | H | C$_6$H$_{11}$ | H | CH$_2$CH(CH$_3$)$_2$ | H | H | CH | N | CH | CH |
| 2432. | 1 | S | H | C$_6$H$_{11}$ | H | C$_6$H$_{11}$ | H | H | CH | N | CH | CH |
| 2433. | 1 | S | H | C$_6$H$_{11}$ | H | Ph | H | H | CH | N | CH | CH |
| 2434. | 1 | S | H | C$_6$H$_{11}$ | H | 2,6-dimethylphenyl | H | H | CH | N | CH | CH |
| 2435. | 1 | S | H | C$_6$H$_{11}$ | H | 2,6-diisopropylphenyl | H | H | CH | N | CH | CH |
| 2436. | 1 | S | H | Ph | H | CH$_3$ | H | H | CH | N | CH | CH |
| 2437. | 1 | S | H | Ph | H | CH(CH$_3$)$_2$ | H | H | CH | N | CH | CH |
| 2438. | 1 | S | H | Ph | H | CH$_2$CH(CH$_3$)$_2$ | H | H | CH | N | CH | CH |
| 2439. | 1 | S | H | Ph | H | C$_6$H$_{11}$ | H | H | CH | N | CH | CH |
| 2440. | 1 | S | H | Ph | H | Ph | H | H | CH | N | CH | CH |
| 2441. | 1 | S | H | Ph | H | 2,6-dimethylphenyl | H | H | CH | N | CH | CH |
| 2442. | 1 | S | H | Ph | H | 2,6-diisopropylphenyl | H | H | CH | N | CH | CH |
| 2443. | 1 | S | H | 2,6-dimethylphenyl | H | CH$_3$ | H | H | CH | N | CH | CH |
| 2444. | 1 | S | H | 2,6-dimethylphenyl | H | CH(CH$_3$)$_2$ | H | H | CH | N | CH | CH |
| 2445. | 1 | S | H | 2,6-dimethylphenyl | H | CH$_2$CH(CH$_3$)$_2$ | H | H | CH | N | CH | CH |
| 2446. | 1 | S | H | 2,6-dimethylphenyl | H | C$_6$H$_{11}$ | H | H | CH | N | CH | CH |
| 2447. | 1 | S | H | 2,6-dimethylphenyl | H | Ph | H | H | CH | N | CH | CH |
| 2448. | 1 | S | H | 2,6-dimethylphenyl | H | 2,6-dimethylphenyl | H | H | CH | N | CH | CH |
| 2449. | 1 | S | H | 2,6-dimethylphenyl | H | 2,6-diisopropylphenyl | H | H | CH | N | CH | CH |
| 2450. | 1 | S | H | 2,6-diisopropylphenyl | H | CH$_3$ | H | H | CH | N | CH | CH |
| 2451. | 1 | S | H | 2,6-diisopropylphenyl | H | CH(CH$_3$)$_2$ | H | H | CH | N | CH | CH |
| 2452. | 1 | S | H | 2,6-diisopropylphenyl | H | CH$_2$CH(CH$_3$)$_2$ | H | H | CH | N | CH | CH |
| 2453. | 1 | S | H | 2,6-diisopropylphenyl | H | C$_6$H$_{11}$ | H | H | CH | N | CH | CH |
| 2454. | 1 | S | H | 2,6-diisopropylphenyl | H | Ph | H | H | CH | N | CH | CH |
| 2455. | 1 | S | H | 2,6-diisopropylphenyl | H | 2,6-dimethylphenyl | H | H | CH | N | CH | CH |
| 2456. | 1 | S | H | 2,6-diisopropylphenyl | H | 2,6-diisopropylphenyl | H | H | CH | N | CH | CH |
| 2457. | 2 | O | H | CH$_3$ | H | CH$_3$ | H | H | CH | N | CH | CH |
| 2458. | 2 | O | H | CH$_3$ | H | CH(CH$_3$)$_2$ | H | H | CH | N | CH | CH |
| 2459. | 2 | O | H | CH$_3$ | H | CH$_2$CH(CH$_3$)$_2$ | H | H | CH | N | CH | CH |
| 2460. | 2 | O | H | CH$_3$ | H | C$_6$H$_{11}$ | H | H | CH | N | CH | CH |
| 2461. | 2 | O | H | CH$_3$ | H | Ph | H | H | CH | N | CH | CH |
| 2462. | 2 | O | H | CH$_3$ | H | 2,6-dimethylphenyl | H | H | CH | N | CH | CH |

-continued

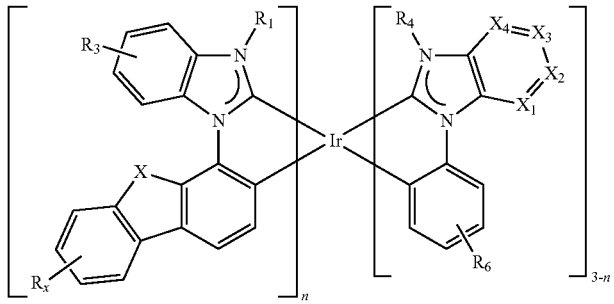

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2463. | 2 | O | H | $CH_3$ | H | 2,6-diisopropylphenyl | H | H | CH | N | CH | CH |
| 2464. | 2 | O | H | $CH(CH_3)_2$ | H | $CH_3$ | H | H | CH | N | CH | CH |
| 2465. | 2 | O | H | $CH(CH_3)_2$ | H | $CH(CH_3)_2$ | H | H | CH | N | CH | CH |
| 2466. | 2 | O | H | $CH(CH_3)_2$ | H | $CH_2CH(CH_3)_2$ | H | H | CH | N | CH | CH |
| 2467. | 2 | O | H | $CH(CH_3)_2$ | H | $C_6H_{11}$ | H | H | CH | N | CH | CH |
| 2468. | 2 | O | H | $CH(CH_3)_2$ | H | Ph | H | H | CH | N | CH | CH |
| 2469. | 2 | O | H | $CH(CH_3)_2$ | H | 2,6-dimethylphenyl | H | H | CH | N | CH | CH |
| 2470. | 2 | O | H | $CH(CH_3)_2$ | H | 2,6-diisopropylphenyl | H | H | CH | N | CH | CH |
| 2471. | 2 | O | H | $CH_2CH(CH_3)_2$ | H | $CH_3$ | H | H | CH | N | CH | CH |
| 2472. | 2 | O | H | $CH_2CH(CH_3)_2$ | H | $CH(CH_3)_2$ | H | H | CH | N | CH | CH |
| 2473. | 2 | O | H | $CH_2CH(CH_3)_2$ | H | $CH_2CH(CH_3)_2$ | H | H | CH | N | CH | CH |
| 2474. | 2 | O | H | $CH_2CH(CH_3)_2$ | H | $C_6H_{11}$ | H | H | CH | N | CH | CH |
| 2475. | 2 | O | H | $CH_2CH(CH_3)_2$ | H | Ph | H | H | CH | N | CH | CH |
| 2476. | 2 | O | H | $CH_2CH(CH_3)_2$ | H | 2,6-dimethylphenyl | H | H | CH | N | CH | CH |
| 2477. | 2 | O | H | $CH_2CH(CH_3)_2$ | H | 2,6-diisopropylphenyl | H | H | CH | N | CH | CH |
| 2478. | 2 | O | H | $C_6H_{11}$ | H | $CH_3$ | H | H | CH | N | CH | CH |
| 2479. | 2 | O | H | $C_6H_{11}$ | H | $CH(CH_3)_2$ | H | H | CH | N | CH | CH |
| 2480. | 2 | O | H | $C_6H_{11}$ | H | $CH_2CH(CH_3)_2$ | H | H | CH | N | CH | CH |
| 2481. | 2 | O | H | $C_6H_{11}$ | H | $C_6H_{11}$ | H | H | CH | N | CH | CH |
| 2482. | 2 | O | H | $C_6H_{11}$ | H | Ph | H | H | CH | N | CH | CH |
| 2483. | 2 | O | H | $C_6H_{11}$ | H | 2,6-dimethylphenyl | H | H | CH | N | CH | CH |
| 2484. | 2 | O | H | $C_6H_{11}$ | H | 2,6-diisopropylphenyl | H | H | CH | N | CH | CH |
| 2485. | 2 | O | H | Ph | H | $CH_3$ | H | H | CH | N | CH | CH |
| 2486. | 2 | O | H | Ph | H | $CH(CH_3)_2$ | H | H | CH | N | CH | CH |
| 2487. | 2 | O | H | Ph | H | $CH_2CH(CH_3)_2$ | H | H | CH | N | CH | CH |
| 2488. | 2 | O | H | Ph | H | $C_6H_{11}$ | H | H | CH | N | CH | CH |
| 2489. | 2 | O | H | Ph | H | Ph | H | H | CH | N | CH | CH |
| 2490. | 2 | O | H | Ph | H | 2,6-dimethylphenyl | H | H | CH | N | CH | CH |
| 2491. | 2 | O | H | Ph | H | 2,6-diisopropylphenyl | H | H | CH | N | CH | CH |
| 2492. | 2 | O | H | 2,6-dimethylphenyl | H | $CH_3$ | H | H | CH | N | CH | CH |
| 2493. | 2 | O | H | 2,6-dimethylphenyl | H | $CH(CH_3)_2$ | H | H | CH | N | CH | CH |
| 2494. | 2 | O | H | 2,6-dimethylphenyl | H | $CH_2CH(CH_3)_2$ | H | H | CH | N | CH | CH |
| 2495. | 2 | O | H | 2,6-dimethylphenyl | H | $C_6H_{11}$ | H | H | CH | N | CH | CH |
| 2496. | 2 | O | H | 2,6-dimethylphenyl | H | Ph | H | H | CH | N | CH | CH |
| 2497. | 2 | O | H | 2,6-dimethylphenyl | H | 2,6-dimethylphenyl | H | H | CH | N | CH | CH |
| 2498. | 2 | O | H | 2,6-dimethylphenyl | H | 2,6-diisopropylphenyl | H | H | CH | N | CH | CH |
| 2499. | 2 | O | H | 2,6-diisopropylphenyl | H | $CH_3$ | H | H | CH | N | CH | CH |
| 2500. | 2 | O | H | 2,6-diisopropylphenyl | H | $CH(CH_3)_2$ | H | H | CH | N | CH | CH |
| 2501. | 2 | O | H | 2,6-diisopropylphenyl | H | $CH_2CH(CH_3)_2$ | H | H | CH | N | CH | CH |
| 2502. | 2 | O | H | 2,6-diisopropylphenyl | H | $C_6H_{11}$ | H | H | CH | N | CH | CH |
| 2503. | 2 | O | H | 2,6-diisopropylphenyl | H | Ph | H | H | CH | N | CH | CH |
| 2504. | 2 | O | H | 2,6-diisopropylphenyl | H | 2,6-dimethylphenyl | H | H | CH | N | CH | CH |
| 2505. | 2 | O | H | 2,6-diisopropylphenyl | H | 2,6-diisopropylphenyl | H | H | CH | N | CH | CH |
| 2506. | 2 | S | H | $CH_3$ | H | $CH_3$ | H | H | CH | N | CH | CH |
| 2507. | 2 | S | H | $CH_3$ | H | $CH(CH_3)_2$ | H | H | CH | N | CH | CH |
| 2508. | 2 | S | H | $CH_3$ | H | $CH_2CH(CH_3)_2$ | H | H | CH | N | CH | CH |
| 2509. | 2 | S | H | $CH_3$ | H | $C_6H_{11}$ | H | H | CH | N | CH | CH |
| 2510. | 2 | S | H | $CH_3$ | H | Ph | H | H | CH | N | CH | CH |
| 2511. | 2 | S | H | $CH_3$ | H | 2,6-dimethylphenyl | H | H | CH | N | CH | CH |
| 2512. | 2 | S | H | $CH_3$ | H | 2,6-diisopropylphenyl | H | H | CH | N | CH | CH |
| 2513. | 2 | S | H | $CH(CH_3)_2$ | H | $CH_3$ | H | H | CH | N | CH | CH |
| 2514. | 2 | S | H | $CH(CH_3)_2$ | H | $CH(CH_3)_2$ | H | H | CH | N | CH | CH |
| 2515. | 2 | S | H | $CH(CH_3)_2$ | H | $CH_2CH(CH_3)_2$ | H | H | CH | N | CH | CH |
| 2516. | 2 | S | H | $CH(CH_3)_2$ | H | $C_6H_{11}$ | H | H | CH | N | CH | CH |
| 2517. | 2 | S | H | $CH(CH_3)_2$ | H | Ph | H | H | CH | N | CH | CH |
| 2518. | 2 | S | H | $CH(CH_3)_2$ | H | 2,6-dimethylphenyl | H | H | CH | N | CH | CH |
| 2519. | 2 | S | H | $CH(CH_3)_2$ | H | 2,6-diisopropylphenyl | H | H | CH | N | CH | CH |
| 2520. | 2 | S | H | $CH_2CH(CH_3)_2$ | H | $CH_3$ | H | H | CH | N | CH | CH |
| 2521. | 2 | S | H | $CH_2CH(CH_3)_2$ | H | $CH(CH_3)_2$ | H | H | CH | N | CH | CH |

-continued

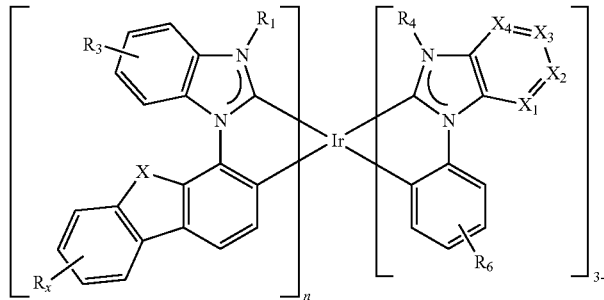

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2522. | 2 | S | H | $CH_2CH(CH_3)_2$ | H | $CH_2CH(CH_3)_2$ | H | H | CH | N | CH | CH |
| 2523. | 2 | S | H | $CH_2CH(CH_3)_2$ | H | $C_6H_{11}$ | H | H | CH | N | CH | CH |
| 2524. | 2 | S | H | $CH_2CH(CH_3)_2$ | H | Ph | H | H | CH | N | CH | CH |
| 2525. | 2 | S | H | $CH_2CH(CH_3)_2$ | H | 2,6-dimethylphenyl | H | H | CH | N | CH | CH |
| 2526. | 2 | S | H | $CH_2CH(CH_3)_2$ | H | 2,6-diisopropylphenyl | H | H | CH | N | CH | CH |
| 2527. | 2 | S | H | $C_6H_{11}$ | H | $CH_3$ | H | H | CH | N | CH | CH |
| 2528. | 2 | S | H | $C_6H_{11}$ | H | $CH(CH_3)_2$ | H | H | CH | N | CH | CH |
| 2529. | 2 | S | H | $C_6H_{11}$ | H | $CH_2CH(CH_3)_2$ | H | H | CH | N | CH | CH |
| 2530. | 2 | S | H | $C_6H_{11}$ | H | $C_6H_{11}$ | H | H | CH | N | CH | CH |
| 2531. | 2 | S | H | $C_6H_{11}$ | H | Ph | H | H | CH | N | CH | CH |
| 2532. | 2 | S | H | $C_6H_{11}$ | H | 2,6-dimethylphenyl | H | H | CH | N | CH | CH |
| 2533. | 2 | S | H | $C_6H_{11}$ | H | 2,6-diisopropylphenyl | H | H | CH | N | CH | CH |
| 2534. | 2 | S | H | Ph | H | $CH_3$ | H | H | CH | N | CH | CH |
| 2535. | 2 | S | H | Ph | H | $CH(CH_3)_2$ | H | H | CH | N | CH | CH |
| 2536. | 2 | S | H | Ph | H | $CH_2CH(CH_3)_2$ | H | H | CH | N | CH | CH |
| 2537. | 2 | S | H | Ph | H | $C_6H_{11}$ | H | H | CH | N | CH | CH |
| 2538. | 2 | S | H | Ph | H | Ph | H | H | CH | N | CH | CH |
| 2539. | 2 | S | H | Ph | H | 2,6-dimethylphenyl | H | H | CH | N | CH | CH |
| 2540. | 2 | S | H | Ph | H | 2,6-diisopropylphenyl | H | H | CH | N | CH | CH |
| 2541. | 2 | S | H | 2,6-dimethylphenyl | H | $CH_3$ | H | H | CH | N | CH | CH |
| 2542. | 2 | S | H | 2,6-dimethylphenyl | H | $CH(CH_3)_2$ | H | H | CH | N | CH | CH |
| 2543. | 2 | S | H | 2,6-dimethylphenyl | H | $CH_2CH(CH_3)_2$ | H | H | CH | N | CH | CH |
| 2544. | 2 | S | H | 2,6-dimethylphenyl | H | $C_6H_{11}$ | H | H | CH | N | CH | CH |
| 2545. | 2 | S | H | 2,6-dimethylphenyl | H | Ph | H | H | CH | N | CH | CH |
| 2546. | 2 | S | H | 2,6-dimethylphenyl | H | 2,6-dimethylphenyl | H | H | CH | N | CH | CH |
| 2547. | 2 | S | H | 2,6-dimethylphenyl | H | 2,6-diisopropylphenyl | H | H | CH | N | CH | CH |
| 2548. | 2 | S | H | 2,6-diisopropylphenyl | H | $CH_3$ | H | H | CH | N | CH | CH |
| 2549. | 2 | S | H | 2,6-diisopropylphenyl | H | $CH(CH_3)_2$ | H | H | CH | N | CH | CH |
| 2550. | 2 | S | H | 2,6-diisopropylphenyl | H | $CH_2CH(CH_3)_2$ | H | H | CH | N | CH | CH |
| 2551. | 2 | S | H | 2,6-diisopropylphenyl | H | $C_6H_{11}$ | H | H | CH | N | CH | CH |
| 2552. | 2 | S | H | 2,6-diisopropylphenyl | H | Ph | H | H | CH | N | CH | CH |
| 2553. | 2 | S | H | 2,6-diisopropylphenyl | H | 2,6-dimethylphenyl | H | H | CH | N | CH | CH |
| 2554. | 2 | S | H | 2,6-diisopropylphenyl | H | 2,6-diisopropylphenyl | H | H | CH | N | CH | CH |
| 2555. | 1 | O | H | $CH_3$ | H | $CH_3$ | H | H | CH | CH | N | CH |
| 2556. | 1 | O | H | $CH_3$ | H | $CH(CH_3)_2$ | H | H | CH | CH | N | CH |
| 2557. | 1 | O | H | $CH_3$ | H | $CH_2CH(CH_3)_2$ | H | H | CH | CH | N | CH |
| 2558. | 1 | O | H | $CH_3$ | H | $C_6H_{11}$ | H | H | CH | CH | N | CH |
| 2559. | 1 | O | H | $CH_3$ | H | Ph | H | H | CH | CH | N | CH |
| 2560. | 1 | O | H | $CH_3$ | H | 2,6-dimethylphenyl | H | H | CH | CH | N | CH |
| 2561. | 1 | O | H | $CH_3$ | H | 2,6-diisopropylphenyl | H | H | CH | CH | N | CH |
| 2562. | 1 | O | H | $CH(CH_3)_2$ | H | $CH_3$ | H | H | CH | CH | N | CH |
| 2563. | 1 | O | H | $CH(CH_3)_2$ | H | $CH(CH_3)_2$ | H | H | CH | CH | N | CH |
| 2564. | 1 | O | H | $CH(CH_3)_2$ | H | $CH_2CH(CH_3)_2$ | H | H | CH | CH | N | CH |
| 2565. | 1 | O | H | $CH(CH_3)_2$ | H | $C_6H_{11}$ | H | H | CH | CH | N | CH |
| 2566. | 1 | O | H | $CH(CH_3)_2$ | H | Ph | H | H | CH | CH | N | CH |
| 2567. | 1 | O | H | $CH(CH_3)_2$ | H | 2,6-dimethylphenyl | H | H | CH | CH | N | CH |
| 2568. | 1 | O | H | $CH(CH_3)_2$ | H | 2,6-diisopropylphenyl | H | H | CH | CH | N | CH |
| 2569. | 1 | O | H | $CH_2CH(CH_3)_2$ | H | $CH_3$ | H | H | CH | CH | N | CH |
| 2570. | 1 | O | H | $CH_2CH(CH_3)_2$ | H | $CH(CH_3)_2$ | H | H | CH | CH | N | CH |
| 2571. | 1 | O | H | $CH_2CH(CH_3)_2$ | H | $CH_2CH(CH_3)_2$ | H | H | CH | CH | N | CH |
| 2572. | 1 | O | H | $CH_2CH(CH_3)_2$ | H | $C_6H_{11}$ | H | H | CH | CH | N | CH |
| 2573. | 1 | O | H | $CH_2CH(CH_3)_2$ | H | Ph | H | H | CH | CH | N | CH |
| 2574. | 1 | O | H | $CH_2CH(CH_3)_2$ | H | 2,6-dimethylphenyl | H | H | CH | CH | N | CH |
| 2575. | 1 | O | H | $CH_2CH(CH_3)_2$ | H | 2,6-diisopropylphenyl | H | H | CH | CH | N | CH |
| 2576. | 1 | O | H | $C_6H_{11}$ | H | $CH_3$ | H | H | CH | CH | N | CH |
| 2577. | 1 | O | H | $C_6H_{11}$ | H | $CH(CH_3)_2$ | H | H | CH | CH | N | CH |
| 2578. | 1 | O | H | $C_6H_{11}$ | H | $CH_2CH(CH_3)_2$ | H | H | CH | CH | N | CH |
| 2579. | 1 | O | H | $C_6H_{11}$ | H | $C_6H_{11}$ | H | H | CH | CH | N | CH |
| 2580. | 1 | O | H | $C_6H_{11}$ | H | Ph | H | H | CH | CH | N | CH |

-continued

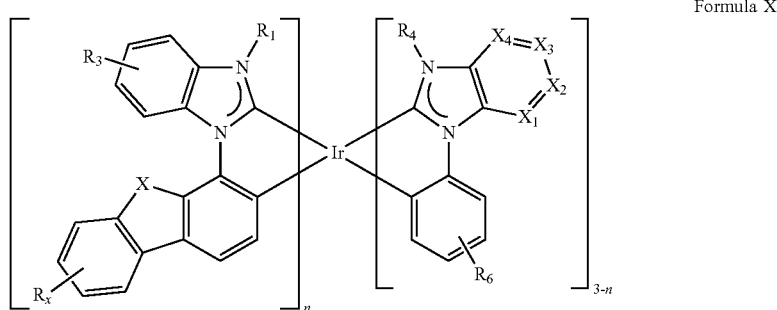

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2581. | 1 | O | H | $C_6H_{11}$ | H | 2,6-dimethylphenyl | H | H | CH | CH | N | CH |
| 2582. | 1 | O | H | $C_6H_{11}$ | H | 2,6-diisopropylphenyl | H | H | CH | CH | N | CH |
| 2583. | 1 | O | H | Ph | H | $CH_3$ | H | H | CH | CH | N | CH |
| 2584. | 1 | O | H | Ph | H | $CH(CH_3)_2$ | H | H | CH | CH | N | CH |
| 2585. | 1 | O | H | Ph | H | $CH_2CH(CH_3)_2$ | H | H | CH | CH | N | CH |
| 2586. | 1 | O | H | Ph | H | $C_6H_{11}$ | H | H | CH | CH | N | CH |
| 2587. | 1 | O | H | Ph | H | Ph | H | H | CH | CH | N | CH |
| 2588. | 1 | O | H | Ph | H | 2,6-dimethylphenyl | H | H | CH | CH | N | CH |
| 2589. | 1 | O | H | Ph | H | 2,6-diisopropylphenyl | H | H | CH | CH | N | CH |
| 2590. | 1 | O | H | 2,6-dimethylphenyl | H | $CH_3$ | H | H | CH | CH | N | CH |
| 2591. | 1 | O | H | 2,6-dimethylphenyl | H | $CH(CH_3)_2$ | H | H | CH | CH | N | CH |
| 2592. | 1 | O | H | 2,6-dimethylphenyl | H | $CH_2CH(CH_3)_2$ | H | H | CH | CH | N | CH |
| 2593. | 1 | O | H | 2,6-dimethylphenyl | H | $C_6H_{11}$ | H | H | CH | CH | N | CH |
| 2594. | 1 | O | H | 2,6-dimethylphenyl | H | Ph | H | H | CH | CH | N | CH |
| 2595. | 1 | O | H | 2,6-dimethylphenyl | H | 2,6-dimethylphenyl | H | H | CH | CH | N | CH |
| 2596. | 1 | O | H | 2,6-dimethylphenyl | H | 2,6-diisopropylphenyl | H | H | CH | CH | N | CH |
| 2597. | 1 | O | H | 2,6-diisopropylphenyl | H | $CH_3$ | H | H | CH | CH | N | CH |
| 2598. | 1 | O | H | 2,6-diisopropylphenyl | H | $CH(CH_3)_2$ | H | H | CH | CH | N | CH |
| 2599. | 1 | O | H | 2,6-diisopropylphenyl | H | $CH_2CH(CH_3)_2$ | H | H | CH | CH | N | CH |
| 2600. | 1 | O | H | 2,6-diisopropylphenyl | H | $C_6H_{11}$ | H | H | CH | CH | N | CH |
| 2601. | 1 | O | H | 2,6-diisopropylphenyl | H | Ph | H | H | CH | CH | N | CH |
| 2602. | 1 | O | H | 2,6-diisopropylphenyl | H | 2,6-dimethylphenyl | H | H | CH | CH | N | CH |
| 2603. | 1 | O | H | 2,6-diisopropylphenyl | H | 2,6-diisopropylphenyl | H | H | CH | CH | N | CH |
| 2604. | 1 | S | H | $CH_3$ | H | $CH_3$ | H | H | CH | CH | N | CH |
| 2605. | 1 | S | H | $CH_3$ | H | $CH(CH_3)_2$ | H | H | CH | CH | N | CH |
| 2606. | 1 | S | H | $CH_3$ | H | $CH_2CH(CH_3)_2$ | H | H | CH | CH | N | CH |
| 2607. | 1 | S | H | $CH_3$ | H | $C_6H_{11}$ | H | H | CH | CH | N | CH |
| 2608. | 1 | S | H | $CH_3$ | H | Ph | H | H | CH | CH | N | CH |
| 2609. | 1 | S | H | $CH_3$ | H | 2,6-dimethylphenyl | H | H | CH | CH | N | CH |
| 2610. | 1 | S | H | $CH_3$ | H | 2,6-diisopropylphenyl | H | H | CH | CH | N | CH |
| 2611. | 1 | S | H | $CH(CH_3)_2$ | H | $CH_3$ | H | H | CH | CH | N | CH |
| 2612. | 1 | S | H | $CH(CH_3)_2$ | H | $CH(CH_3)_2$ | H | H | CH | CH | N | CH |
| 2613. | 1 | S | H | $CH(CH_3)_2$ | H | $CH_2CH(CH_3)_2$ | H | H | CH | CH | N | CH |
| 2614. | 1 | S | H | $CH(CH_3)_2$ | H | $C_6H_{11}$ | H | H | CH | CH | N | CH |
| 2615. | 1 | S | H | $CH(CH_3)_2$ | H | Ph | H | H | CH | CH | N | CH |
| 2616. | 1 | S | H | $CH(CH_3)_2$ | H | 2,6-dimethylphenyl | H | H | CH | CH | N | CH |
| 2617. | 1 | S | H | $CH(CH_3)_2$ | H | 2,6-diisopropylphenyl | H | H | CH | CH | N | CH |
| 2618. | 1 | S | H | $CH_2CH(CH_3)_2$ | H | $CH_3$ | H | H | CH | CH | N | CH |
| 2619. | 1 | S | H | $CH_2CH(CH_3)_2$ | H | $CH(CH_3)_2$ | H | H | CH | CH | N | CH |
| 2620. | 1 | S | H | $CH_2CH(CH_3)_2$ | H | $CH_2CH(CH_3)_2$ | H | H | CH | CH | N | CH |
| 2621. | 1 | S | H | $CH_2CH(CH_3)_2$ | H | $C_6H_{11}$ | H | H | CH | CH | N | CH |
| 2622. | 1 | S | H | $CH_2CH(CH_3)_2$ | H | Ph | H | H | CH | CH | N | CH |
| 2623. | 1 | S | H | $CH_2CH(CH_3)_2$ | H | 2,6-dimethylphenyl | H | H | CH | CH | N | CH |
| 2624. | 1 | S | H | $CH_2CH(CH_3)_2$ | H | 2,6-diisopropylphenyl | H | H | CH | CH | N | CH |
| 2625. | 1 | S | H | $C_6H_{11}$ | H | $CH_3$ | H | H | CH | CH | N | CH |
| 2626. | 1 | S | H | $C_6H_{11}$ | H | $CH(CH_3)_2$ | H | H | CH | CH | N | CH |
| 2627. | 1 | S | H | $C_6H_{11}$ | H | $CH_2CH(CH_3)_2$ | H | H | CH | CH | N | CH |
| 2628. | 1 | S | H | $C_6H_{11}$ | H | $C_6H_{11}$ | H | H | CH | CH | N | CH |
| 2629. | 1 | S | H | $C_6H_{11}$ | H | Ph | H | H | CH | CH | N | CH |
| 2630. | 1 | S | H | $C_6H_{11}$ | H | 2,6-dimethylphenyl | H | H | CH | CH | N | CH |
| 2631. | 1 | S | H | $C_6H_{11}$ | H | 2,6-diisopropylphenyl | H | H | CH | CH | N | CH |
| 2632. | 1 | S | H | Ph | H | $CH_3$ | H | H | CH | CH | N | CH |
| 2633. | 1 | S | H | Ph | H | $CH(CH_3)_2$ | H | H | CH | CH | N | CH |
| 2634. | 1 | S | H | Ph | H | $CH_2CH(CH_3)_2$ | H | H | CH | CH | N | CH |
| 2635. | 1 | S | H | Ph | H | $C_6H_{11}$ | H | H | CH | CH | N | CH |
| 2636. | 1 | S | H | Ph | H | Ph | H | H | CH | CH | N | CH |
| 2637. | 1 | S | H | Ph | H | 2,6-dimethylphenyl | H | H | CH | CH | N | CH |
| 2638. | 1 | S | H | Ph | H | 2,6-diisopropylphenyl | H | H | CH | CH | N | CH |
| 2639. | 1 | S | H | 2,6-dimethylphenyl | H | $CH_3$ | H | H | CH | CH | N | CH |

-continued

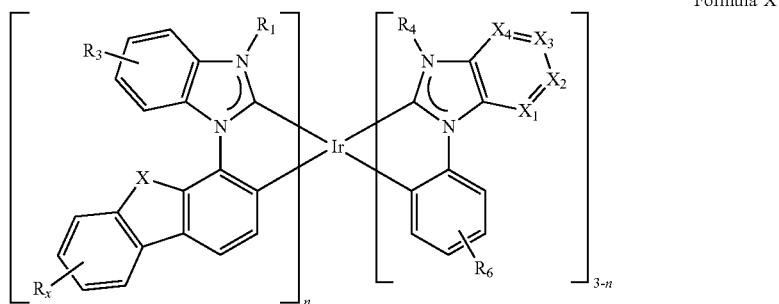

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2640. | 1 | S | H | 2,6-dimethylphenyl | H | $CH(CH_3)_2$ | H | H | CH | CH | N | CH |
| 2641. | 1 | S | H | 2,6-dimethylphenyl | H | $CH_2CH(CH_3)_2$ | H | H | CH | CH | N | CH |
| 2642. | 1 | S | H | 2,6-dimethylphenyl | H | $C_6H_{11}$ | H | H | CH | CH | N | CH |
| 2643. | 1 | S | H | 2,6-dimethylphenyl | H | Ph | H | H | CH | CH | N | CH |
| 2644. | 1 | S | H | 2,6-dimethylphenyl | H | 2,6-dimethylphenyl | H | H | CH | CH | N | CH |
| 2645. | 1 | S | H | 2,6-dimethylphenyl | H | 2,6-diisopropylphenyl | H | H | CH | CH | N | CH |
| 2646. | 1 | S | H | 2,6-diisopropylphenyl | H | $CH_3$ | H | H | CH | CH | N | CH |
| 2647. | 1 | S | H | 2,6-diisopropylphenyl | H | $CH(CH_3)_2$ | H | H | CH | CH | N | CH |
| 2648. | 1 | S | H | 2,6-diisopropylphenyl | H | $CH_2CH(CH_3)_2$ | H | H | CH | CH | N | CH |
| 2649. | 1 | S | H | 2,6-diisopropylphenyl | H | $C_6H_{11}$ | H | H | CH | CH | N | CH |
| 2650. | 1 | S | H | 2,6-diisopropylphenyl | H | Ph | H | H | CH | CH | N | CH |
| 2651. | 1 | S | H | 2,6-diisopropylphenyl | H | 2,6-dimethylphenyl | H | H | CH | CH | N | CH |
| 2652. | 1 | S | H | 2,6-diisopropylphenyl | H | 2,6-diisopropylphenyl | H | H | CH | CH | N | CH |
| 2653. | 2 | O | H | $CH_3$ | H | $CH_3$ | H | H | CH | CH | N | CH |
| 2654. | 2 | O | H | $CH_3$ | H | $CH(CH_3)_2$ | H | H | CH | CH | N | CH |
| 2655. | 2 | O | H | $CH_3$ | H | $CH_2CH(CH_3)_2$ | H | H | CH | CH | N | CH |
| 2656. | 2 | O | H | $CH_3$ | H | $C_6H_{11}$ | H | H | CH | CH | N | CH |
| 2657. | 2 | O | H | $CH_3$ | H | Ph | H | H | CH | CH | N | CH |
| 2658. | 2 | O | H | $CH_3$ | H | 2,6-dimethylphenyl | H | H | CH | CH | N | CH |
| 2659. | 2 | O | H | $CH_3$ | H | 2,6-diisopropylphenyl | H | H | CH | CH | N | CH |
| 2660. | 2 | O | H | $CH(CH_3)_2$ | H | $CH_3$ | H | H | CH | CH | N | CH |
| 2661. | 2 | O | H | $CH(CH_3)_2$ | H | $CH(CH_3)_2$ | H | H | CH | CH | N | CH |
| 2662. | 2 | O | H | $CH(CH_3)_2$ | H | $CH_2CH(CH_3)_2$ | H | H | CH | CH | N | CH |
| 2663. | 2 | O | H | $CH(CH_3)_2$ | H | $C_6H_{11}$ | H | H | CH | CH | N | CH |
| 2664. | 2 | O | H | $CH(CH_3)_2$ | H | Ph | H | H | CH | CH | N | CH |
| 2665. | 2 | O | H | $CH(CH_3)_2$ | H | 2,6-dimethylphenyl | H | H | CH | CH | N | CH |
| 2666. | 2 | O | H | $CH(CH_3)_2$ | H | 2,6-diisopropylphenyl | H | H | CH | CH | N | CH |
| 2667. | | | | | | | | | CH | CH | N | CH |
| 2668. | 2 | O | H | $CH_2CH(CH_3)_2$ | H | $CH_3$ | H | H | CH | CH | N | CH |
| 2669. | 2 | O | H | $CH_2CH(CH_3)_2$ | H | $CH(CH_3)_2$ | H | H | CH | CH | N | CH |
| 2670. | 2 | O | H | $CH_2CH(CH_3)_2$ | H | $CH_2CH(CH_3)_2$ | H | H | CH | CH | N | CH |
| 2671. | 2 | O | H | $CH_2CH(CH_3)_2$ | H | $C_6H_{11}$ | H | H | CH | CH | N | CH |
| 2672. | 2 | O | H | $CH_2CH(CH_3)_2$ | H | Ph | H | H | CH | CH | N | CH |
| 2673. | 2 | O | H | $CH_2CH(CH_3)_2$ | H | 2,6-dimethylphenyl | H | H | CH | CH | N | CH |
| 2674. | 2 | O | H | $CH_2CH(CH_3)_2$ | H | 2,6-diisopropylphenyl | H | H | CH | CH | N | CH |
| 2675. | 2 | O | H | $C_6H_{11}$ | H | $CH_3$ | H | H | CH | CH | N | CH |
| 2676. | 2 | O | H | $C_6H_{11}$ | H | $CH(CH_3)_2$ | H | H | CH | CH | N | CH |
| 2677. | 2 | O | H | $C_6H_{11}$ | H | $CH_2CH(CH_3)_2$ | H | H | CH | CH | N | CH |
| 2678. | 2 | O | H | $C_6H_{11}$ | H | $C_6H_{11}$ | H | H | CH | CH | N | CH |
| 2679. | 2 | O | H | $C_6H_{11}$ | H | Ph | H | H | CH | CH | N | CH |
| 2680. | 2 | O | H | $C_6H_{11}$ | H | 2,6-dimethylphenyl | H | H | CH | CH | N | CH |
| 2681. | 2 | O | H | $C_6H_{11}$ | H | 2,6-diisopropylphenyl | H | H | CH | CH | N | CH |
| 2682. | 2 | O | H | Ph | H | $CH_3$ | H | H | CH | CH | N | CH |
| 2683. | 2 | O | H | Ph | H | $CH(CH_3)_2$ | H | H | CH | CH | N | CH |
| 2684. | 2 | O | H | Ph | H | $CH_2CH(CH_3)_2$ | H | H | CH | CH | N | CH |
| 2685. | 2 | O | H | Ph | H | $C_6H_{11}$ | H | H | CH | CH | N | CH |
| 2686. | 2 | O | H | Ph | H | Ph | H | H | CH | CH | N | CH |
| 2687. | 2 | O | H | Ph | H | 2,6-dimethylphenyl | H | H | CH | CH | N | CH |
| 2688. | 2 | O | H | Ph | H | 2,6-diisopropylphenyl | H | H | CH | CH | N | CH |
| 2689. | 2 | O | H | 2,6-dimethylphenyl | H | $CH_3$ | H | H | CH | CH | N | CH |
| 2690. | 2 | O | H | 2,6-dimethylphenyl | H | $CH(CH_3)_2$ | H | H | CH | CH | N | CH |
| 2691. | 2 | O | H | 2,6-dimethylphenyl | H | $CH_2CH(CH_3)_2$ | H | H | CH | CH | N | CH |
| 2692. | 2 | O | H | 2,6-dimethylphenyl | H | $C_6H_{11}$ | H | H | CH | CH | N | CH |
| 2693. | 2 | O | H | 2,6-dimethylphenyl | H | Ph | H | H | CH | CH | N | CH |
| 2694. | 2 | O | H | 2,6-dimethylphenyl | H | 2,6-dimethyhenyl | H | H | CH | CH | N | CH |
| 2695. | 2 | O | H | 2,6-dimethylphenyl | H | 2,6-diisopropylphenyl | H | H | CH | CH | N | CH |
| 2696. | 2 | O | H | 2,6-diisopropylphenyl | H | $CH_3$ | H | H | CH | CH | N | CH |
| 2697. | 2 | O | H | 2,6-diisopropylphenyl | H | $CH(CH_3)_2$ | H | H | CH | CH | N | CH |
| 2698. | 2 | O | H | 2,6-diisopropylphenyl | H | $CH_2CH(CH_3)_2$ | H | H | CH | CH | N | CH |

-continued

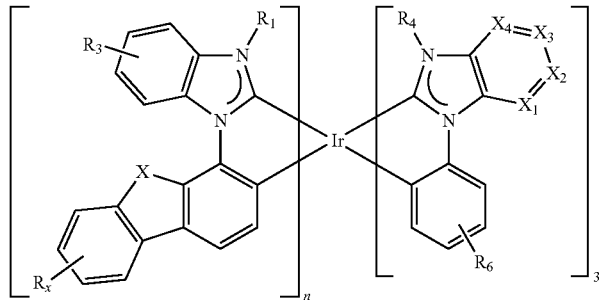

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2699. | 2 | O | H | 2,6-diisopropylphenyl | H | $C_6H_{11}$ | H | H | CH | CH | N | CH |
| 2700. | 2 | O | H | 2,6-diisopropylphenyl | H | Ph | H | H | CH | CH | N | CH |
| 2701. | 2 | O | H | 2,6-diisopropylphenyl | H | 2,6-dimethylphenyl | H | H | CH | CH | N | CH |
| 2702. | 2 | O | H | 2,6-diisopropylphenyl | H | 2,6-diisopropylphenyl | H | H | CH | CH | N | CH |
| 2703. | 2 | S | H | $CH_3$ | H | $CH_3$ | H | H | CH | CH | N | CH |
| 2704. | 2 | S | H | $CH_3$ | H | $CH(CH_3)_2$ | H | H | CH | CH | N | CH |
| 2705. | 2 | S | H | $CH_3$ | H | $CH_2CH(CH_3)_2$ | H | H | CH | CH | N | CH |
| 2706. | 2 | S | H | $CH_3$ | H | $C_6H_{11}$ | H | H | CH | CH | N | CH |
| 2707. | 2 | S | H | $CH_3$ | H | Ph | H | H | CH | CH | N | CH |
| 2708. | 2 | S | H | $CH_3$ | H | 2,6-dimethylphenyl | H | H | CH | CH | N | CH |
| 2709. | 2 | S | H | $CH_3$ | H | 2,6-diisopropylphenyl | H | H | CH | CH | N | CH |
| 2710. | 2 | S | H | $CH(CH_3)_2$ | H | $CH_3$ | H | H | CH | CH | N | CH |
| 2711. | 2 | S | H | $CH(CH_3)_2$ | H | $CH(CH_3)_2$ | H | H | CH | CH | N | CH |
| 2712. | 2 | S | H | $CH(CH_3)_2$ | H | $CH_2CH(CH_3)_2$ | H | H | CH | CH | N | CH |
| 2713. | 2 | S | H | $CH(CH_3)_2$ | H | $C_6H_{11}$ | H | H | CH | CH | N | CH |
| 2714. | 2 | S | H | $CH(CH_3)_2$ | H | Ph | H | H | CH | CH | N | CH |
| 2715. | 2 | S | H | $CH(CH_3)_2$ | H | 2,6-dimethylphenyl | H | H | CH | CH | N | CH |
| 2716. | 2 | S | H | $CH(CH_3)_2$ | H | 2,6-diisopropylphenyl | H | H | CH | CH | N | CH |
| 2717. | 2 | S | H | $CH_2CH(CH_3)_2$ | H | $CH_3$ | H | H | CH | CH | N | CH |
| 2718. | 2 | S | H | $CH_2CH(CH_3)_2$ | H | $CH(CH_3)_2$ | H | H | CH | CH | N | CH |
| 2719. | 2 | S | H | $CH_2CH(CH_3)_2$ | H | $CH_2CH(CH_3)_2$ | H | H | CH | CH | N | CH |
| 2720. | 2 | S | H | $CH_2CH(CH_3)_2$ | H | $C_6H_{11}$ | H | H | CH | CH | N | CH |
| 2721. | 2 | S | H | $CH_2CH(CH_3)_2$ | H | Ph | H | H | CH | CH | N | CH |
| 2722. | 2 | S | H | $CH_2CH(CH_3)_2$ | H | 2,6-dimethylphenyl | H | H | CH | CH | N | CH |
| 2723. | 2 | S | H | $CH_2CH(CH_3)_2$ | H | 2,6-diisopropylphenyl | H | H | CH | CH | N | CH |
| 2724. | 2 | S | H | $C_6H_{11}$ | H | $CH_3$ | H | H | CH | CH | N | CH |
| 2725. | 2 | S | H | $C_6H_{11}$ | H | $CH(CH_3)_2$ | H | H | CH | CH | N | CH |
| 2726. | 2 | S | H | $C_6H_{11}$ | H | $CH_2CH(CH_3)_2$ | H | H | CH | CH | N | CH |
| 2727. | 2 | S | H | $C_6H_{11}$ | H | $C_6H_{11}$ | H | H | CH | CH | N | CH |
| 2728. | 2 | S | H | $C_6H_{11}$ | H | Ph | H | H | CH | CH | N | CH |
| 2729. | 2 | S | H | $C_6H_{11}$ | H | 2,6-dimethylphenyl | H | H | CH | CH | N | CH |
| 2730. | 2 | S | H | $C_6H_{11}$ | H | 2,6-diisopropylphenyl | H | H | CH | CH | N | CH |
| 2731. | 2 | S | H | Ph | H | $CH_3$ | H | H | CH | CH | N | CH |
| 2732. | 2 | S | H | Ph | H | $CH(CH_3)_2$ | H | H | CH | CH | N | CH |
| 2733. | 2 | S | H | Ph | H | $CH_2CH(CH_3)_2$ | H | H | CH | CH | N | CH |
| 2734. | 2 | S | H | Ph | H | $C_6H_{11}$ | H | H | CH | CH | N | CH |
| 2735. | 2 | S | H | Ph | H | Ph | H | H | CH | CH | N | CH |
| 2736. | 2 | S | H | Ph | H | 2,6-dimethylphenyl | H | H | CH | CH | N | CH |
| 2737. | 2 | S | H | Ph | H | 2,6-diisopropylphenyl | H | H | CH | CH | N | CH |
| 2738. | 2 | S | H | 2,6-dimethylphenyl | H | $CH_3$ | H | H | CH | CH | N | CH |
| 2739. | 2 | S | H | 2,6-dimethylphenyl | H | $CH(CH_3)_2$ | H | H | CH | CH | N | CH |
| 2740. | 2 | S | H | 2,6-dimethylphenyl | H | $CH_2CH(CH_3)_2$ | H | H | CH | CH | N | CH |
| 2741. | 2 | S | H | 2,6-dimethylphenyl | H | $C_6H_{11}$ | H | H | CH | CH | N | CH |
| 2742. | 2 | S | H | 2,6-dimethylphenyl | H | Ph | H | H | CH | CH | N | CH |
| 2743. | 2 | S | H | 2,6-dimethylphenyl | H | 2,6-dimethylphenyl | H | H | CH | CH | N | CH |
| 2744. | 2 | S | H | 2,6-dimethylphenyl | H | 2,6-diisopropylphenyl | H | H | CH | CH | N | CH |
| 2745. | 2 | S | H | 2,6-diisopropylphenyl | H | $CH_3$ | H | H | CH | CH | N | CH |
| 2746. | 2 | S | H | 2,6-diisopropylphenyl | H | $CH(CH_3)_2$ | H | H | CH | CH | N | CH |
| 2747. | 2 | S | H | 2,6-diisopropylphenyl | H | $CH_2CH(CH_3)_2$ | H | H | CH | CH | N | CH |
| 2748. | 2 | S | H | 2,6-diisopropylphenyl | H | $C_6H_{11}$ | H | H | CH | CH | N | CH |
| 2749. | 2 | S | H | 2,6-diisopropylphenyl | H | Ph | H | H | CH | CH | N | CH |
| 2750. | 2 | S | H | 2,6-diisopropylphenyl | H | 2,6-dimethylphenyl | H | H | CH | CH | N | CH |
| 2751. | 2 | S | H | 2,6-diisopropylphenyl | H | 2,6-diisopropylphenyl | H | H | CH | CH | N | CH |
| 2752. | 1 | O | H | $CH_3$ | H | $CH_3$ | H | H | CH | CH | CH | N |
| 2753. | 1 | O | H | $CH_3$ | H | $CH(CH_3)_2$ | H | H | CH | CH | CH | N |
| 2754. | 1 | O | H | $CH_3$ | H | $CH_2CH(CH_3)_2$ | H | H | CH | CH | CH | N |
| 2755. | 1 | O | H | $CH_3$ | H | $C_6H_{11}$ | H | H | CH | CH | CH | N |
| 2756. | 1 | O | H | $CH_3$ | H | Ph | H | H | CH | CH | CH | N |
| 2757. | 1 | O | H | $CH_3$ | H | 2,6-dimethylphenyl | H | H | CH | CH | CH | N |

-continued

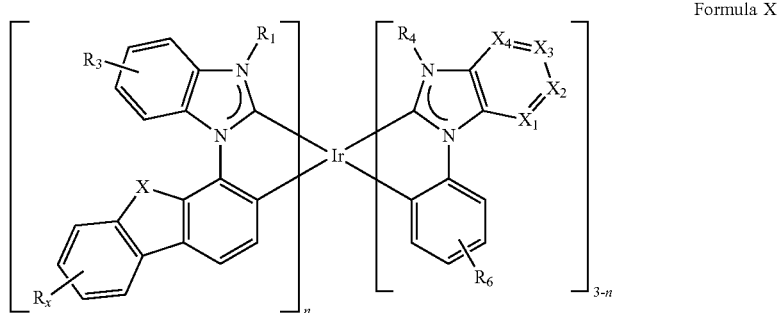

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2758. | 1 | O | H | $CH_3$ | H | 2,6-diisopropylphenyl | H | H | CH | CH | CH | N |
| 2759. | 1 | O | H | $CH(CH_3)_2$ | H | $CH_3$ | H | H | CH | CH | CH | N |
| 2760. | 1 | O | H | $CH(CH_3)_2$ | H | $CH(CH_3)_2$ | H | H | CH | CH | CH | N |
| 2761. | 1 | O | H | $CH(CH_3)_2$ | H | $CH_2CH(CH_3)_2$ | H | H | CH | CH | CH | N |
| 2762. | 1 | O | H | $CH(CH_3)_2$ | H | $C_6H_{11}$ | H | H | CH | CH | CH | N |
| 2763. | 1 | O | H | $CH(CH_3)_2$ | H | Ph | H | H | CH | CH | CH | N |
| 2764. | 1 | O | H | $CH(CH_3)_2$ | H | 2,6-dimethylphenyl | H | H | CH | CH | CH | N |
| 2765. | 1 | O | H | $CH(CH_3)_2$ | H | 2,6-diisopropylphenyl | H | H | CH | CH | CH | N |
| 2766. | 1 | O | H | $CH_2CH(CH_3)_2$ | H | $CH_3$ | H | H | CH | CH | CH | N |
| 2767. | 1 | O | H | $CH_2CH(CH_3)_2$ | H | $CH(CH_3)_2$ | H | H | CH | CH | CH | N |
| 2768. | 1 | O | H | $CH_2CH(CH_3)_2$ | H | $CH_2CH(CH_3)_2$ | H | H | CH | CH | CH | N |
| 2769. | 1 | O | H | $CH_2CH(CH_3)_2$ | H | $C_6H_{11}$ | H | H | CH | CH | CH | N |
| 2770. | 1 | O | H | $CH_2CH(CH_3)_2$ | H | Ph | H | H | CH | CH | CH | N |
| 2771. | 1 | O | H | $CH_2CH(CH_3)_2$ | H | 2,6-dimethylphenyl | H | H | CH | CH | CH | N |
| 2772. | 1 | O | H | $CH_2CH(CH_3)_2$ | H | 2,6-diisopropylphenyl | H | H | CH | CH | CH | N |
| 2773. | 1 | O | H | $C_6H_{11}$ | H | $CH_3$ | H | H | CH | CH | CH | N |
| 2774. | 1 | O | H | $C_6H_{11}$ | H | $CH(CH_3)_2$ | H | H | CH | CH | CH | N |
| 2775. | 1 | O | H | $C_6H_{11}$ | H | $CH_2CH(CH_3)_2$ | H | H | CH | CH | CH | N |
| 2776. | 1 | O | H | $C_6H_{11}$ | H | $C_6H_{11}$ | H | H | CH | CH | CH | N |
| 2777. | 1 | O | H | $C_6H_{11}$ | H | Ph | H | H | CH | CH | CH | N |
| 2778. | 1 | O | H | $C_6H_{11}$ | H | 2,6-dimethylphenyl | H | H | CH | CH | CH | N |
| 2779. | 1 | O | H | $C_6H_{11}$ | H | 2,6-diisopropylphenyl | H | H | CH | CH | CH | N |
| 2780. | 1 | O | H | Ph | H | $CH_3$ | H | H | CH | CH | CH | N |
| 2781. | 1 | O | H | Ph | H | $CH(CH_3)_2$ | H | H | CH | CH | CH | N |
| 2782. | 1 | O | H | Ph | H | $CH_2CH(CH_3)_2$ | H | H | CH | CH | CH | N |
| 2783. | 1 | O | H | Ph | H | $C_6H_{11}$ | H | H | CH | CH | CH | N |
| 2784. | 1 | O | H | Ph | H | Ph | H | H | CH | CH | CH | N |
| 2785. | 1 | O | H | Ph | H | 2,6-dimethylphenyl | H | H | CH | CH | CH | N |
| 2786. | 1 | O | H | Ph | H | 2,6-diisopropylphenyl | H | H | CH | CH | CH | N |
| 2787. | 1 | O | H | 2,6-dimethylphenyl | H | $CH_3$ | H | H | CH | CH | CH | N |
| 2788. | 1 | O | H | 2,6-dimethylphenyl | H | $CH(CH_3)_2$ | H | H | CH | CH | CH | N |
| 2789. | 1 | O | H | 2,6-dimethylphenyl | H | $CH_2CH(CH_3)_2$ | H | H | CH | CH | CH | N |
| 2790. | 1 | O | H | 2,6-dimethylphenyl | H | $C_6H_{11}$ | H | H | CH | CH | CH | N |
| 2791. | 1 | O | H | 2,6-dimethylphenyl | H | Ph | H | H | CH | CH | CH | N |
| 2792. | 1 | O | H | 2,6-dimethylphenyl | H | 2,6-dimethylphenyl | H | H | CH | CH | CH | N |
| 2793. | 1 | O | H | 2,6-dimethylphenyl | H | 2,6-diisopropylphenyl | H | H | CH | CH | CH | N |
| 2794. | 1 | O | H | 2,6-diisopropylphenyl | H | $CH_3$ | H | H | CH | CH | CH | N |
| 2795. | 1 | O | H | 2,6-diisopropylphenyl | H | $CH(CH_3)_2$ | H | H | CH | CH | CH | N |
| 2796. | 1 | O | H | 2,6-diisopropylphenyl | H | $CH_2CH(CH_3)_2$ | H | H | CH | CH | CH | N |
| 2797. | 1 | O | H | 2,6-diisopropylphenyl | H | $C_6H_{11}$ | H | H | CH | CH | CH | N |
| 2798. | 1 | O | H | 2,6-diisopropylphenyl | H | Ph | H | H | CH | CH | CH | N |
| 2799. | 1 | O | H | 2,6-diisopropylphenyl | H | 2,6-dimethylphenyl | H | H | CH | CH | CH | N |
| 2800. | 1 | O | H | 2,6-diisopropylphenyl | H | 2,6-diisopropylphenyl | H | H | CH | CH | CH | N |
| 2801. | 1 | S | H | $CH_3$ | H | $CH_3$ | H | H | CH | CH | CH | N |
| 2802. | 1 | S | H | $CH_3$ | H | $CH(CH_3)_2$ | H | H | CH | CH | CH | N |
| 2803. | 1 | S | H | $CH_3$ | H | $CH_2CH(CH_3)_2$ | H | H | CH | CH | CH | N |
| 2804. | 1 | S | H | $CH_3$ | H | $C_6H_{11}$ | H | H | CH | CH | CH | N |
| 2805. | 1 | S | H | $CH_3$ | H | Ph | H | H | CH | CH | CH | N |
| 2806. | 1 | S | H | $CH_3$ | H | 2,6-dimethylphenyl | H | H | CH | CH | CH | N |
| 2807. | 1 | S | H | $CH_3$ | H | 2,6-diisopropylphenyl | H | H | CH | CH | CH | N |
| 2808. | 1 | S | H | $CH(CH_3)_2$ | H | $CH_3$ | H | H | CH | CH | CH | N |
| 2809. | 1 | S | H | $CH(CH_3)_2$ | H | $CH(CH_3)_2$ | H | H | CH | CH | CH | N |
| 2810. | 1 | S | H | $CH(CH_3)_2$ | H | $CH_2CH(CH_3)_2$ | H | H | CH | CH | CH | N |
| 2811. | 1 | S | H | $CH(CH_3)_2$ | H | $C_6H_{11}$ | H | H | CH | CH | CH | N |
| 2812. | 1 | S | H | $CH(CH_3)_2$ | H | Ph | H | H | CH | CH | CH | N |
| 2813. | 1 | S | H | $CH(CH_3)_2$ | H | 2,6-dimethylphenyl | H | H | CH | CH | CH | N |
| 2814. | 1 | S | H | $CH(CH_3)_2$ | H | 2,6-diisopropylphenyl | H | H | CH | CH | CH | N |
| 2815. | 1 | S | H | $CH_2CH(CH_3)_2$ | H | $CH_3$ | H | H | CH | CH | CH | N |
| 2816. | 1 | S | H | $CH_2CH(CH_3)_2$ | H | $CH(CH_3)_2$ | H | H | CH | CH | CH | N |

-continued

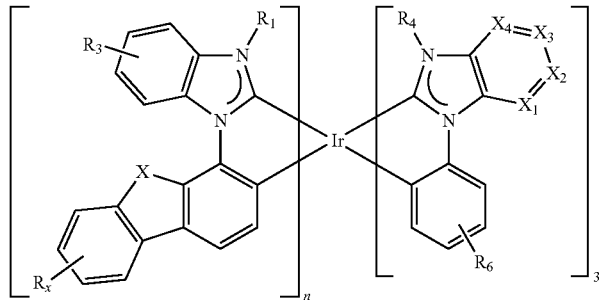

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2817. | 1 | S | H | $CH_2CH(CH_3)_2$ | H | $CH_2CH(CH_3)_2$ | H | H | CH | CH | CH | N |
| 2818. | 1 | S | H | $CH_2CH(CH_3)_2$ | H | $C_6H_{11}$ | H | H | CH | CH | CH | N |
| 2819. | 1 | S | H | $CH_2CH(CH_3)_2$ | H | Ph | H | H | CH | CH | CH | N |
| 2820. | 1 | S | H | $CH_2CH(CH_3)_2$ | H | 2,6-dimethylphenyl | H | H | CH | CH | CH | N |
| 2821. | 1 | S | H | $CH_2CH(CH_3)_2$ | H | 2,6-diisopropylphenyl | H | H | CH | CH | CH | N |
| 2822. | 1 | S | H | $C_6H_{11}$ | H | $CH_3$ | H | H | CH | CH | CH | N |
| 2823. | 1 | S | H | $C_6H_{11}$ | H | $CH(CH_3)_2$ | H | H | CH | CH | CH | N |
| 2824. | 1 | S | H | $C_6H_{11}$ | H | $CH_2CH(CH_3)_2$ | H | H | CH | CH | CH | N |
| 2825. | 1 | S | H | $C_6H_{11}$ | H | $C_6H_{11}$ | H | H | CH | CH | CH | N |
| 2826. | 1 | S | H | $C_6H_{11}$ | H | Ph | H | H | CH | CH | CH | N |
| 2827. | 1 | S | H | $C_6H_{11}$ | H | 2,6-dimethylphenyl | H | H | CH | CH | CH | N |
| 2828. | 1 | S | H | $C_6H_{11}$ | H | 2,6-diisopropylphenyl | H | H | CH | CH | CH | N |
| 2829. | 1 | S | H | Ph | H | $CH_3$ | H | H | CH | CH | CH | N |
| 2830. | 1 | S | H | Ph | H | $CH(CH_3)_2$ | H | H | CH | CH | CH | N |
| 2831. | 1 | S | H | Ph | H | $CH_2CH(CH_3)_2$ | H | H | CH | CH | CH | N |
| 2832. | 1 | S | H | Ph | H | $C_6H_{11}$ | H | H | CH | CH | CH | N |
| 2833. | 1 | S | H | Ph | H | Ph | H | H | CH | CH | CH | N |
| 2834. | 1 | S | H | Ph | H | 2,6-dimethylphenyl | H | H | CH | CH | CH | N |
| 2835. | 1 | S | H | Ph | H | 2,6-diisopropylphenyl | H | H | CH | CH | CH | N |
| 2836. | 1 | S | H | 2,6-dimethylphenyl | H | $CH_3$ | H | H | CH | CH | CH | N |
| 2837. | 1 | S | H | 2,6-dimethylphenyl | H | $CH(CH_3)_2$ | H | H | CH | CH | CH | N |
| 2838. | 1 | S | H | 2,6-dimethylphenyl | H | $CH_2CH(CH_3)_2$ | H | H | CH | CH | CH | N |
| 2839. | 1 | S | H | 2,6-dimethylphenyl | H | $C_6H_{11}$ | H | H | CH | CH | CH | N |
| 2840. | 1 | S | H | 2,6-dimethylphenyl | H | Ph | H | H | CH | CH | CH | N |
| 2841. | 1 | S | H | 2,6-dimethylphenyl | H | 2,6-dimethylphenyl | H | H | CH | CH | CH | N |
| 2842. | 1 | S | H | 2,6-dimethylphenyl | H | 2,6-diisopropylphenyl | H | H | CH | CH | CH | N |
| 2843. | 1 | S | H | 2,6-diisopropylphenyl | H | $CH_3$ | H | H | CH | CH | CH | N |
| 2844. | 1 | S | H | 2,6-diisopropylphenyl | H | $CH(CH_3)_2$ | H | H | CH | CH | CH | N |
| 2845. | 1 | S | H | 2,6-diisopropylphenyl | H | $CH_2CH(CH_3)_2$ | H | H | CH | CH | CH | N |
| 2846. | 1 | S | H | 2,6-diisopropylphenyl | H | $C_6H_{11}$ | H | H | CH | CH | CH | N |
| 2847. | 1 | S | H | 2,6-diisopropylphenyl | H | Ph | H | H | CH | CH | CH | N |
| 2848. | 1 | S | H | 2,6-diisopropylphenyl | H | 2,6-dimethylphenyl | H | H | CH | CH | CH | N |
| 2849. | 1 | S | H | 2,6-diisopropylphenyl | H | 2,6-diisopropylphenyl | H | H | CH | CH | CH | N |
| 2850. | 2 | O | H | $CH_3$ | H | $CH_3$ | H | H | CH | CH | CH | N |
| 2851. | 2 | O | H | $CH_3$ | H | $CH(CH_3)_2$ | H | H | CH | CH | CH | N |
| 2852. | 2 | O | H | $CH_3$ | H | $CH_2CH(CH_3)_2$ | H | H | CH | CH | CH | N |
| 2853. | 2 | O | H | $CH_3$ | H | $C_6H_{11}$ | H | H | CH | CH | CH | N |
| 2854. | 2 | O | H | $CH_3$ | H | Ph | H | H | CH | CH | CH | N |
| 2855. | 2 | O | H | $CH_3$ | H | 2,6-dimethylphenyl | H | H | CH | CH | CH | N |
| 2856. | 2 | O | H | $CH_3$ | H | 2,6-diisopropylphenyl | H | H | CH | CH | CH | N |
| 2857. | 2 | O | H | $CH(CH_3)_2$ | H | $CH_3$ | H | H | CH | CH | CH | N |
| 2858. | 2 | O | H | $CH(CH_3)_2$ | H | $CH(CH_3)_2$ | H | H | CH | CH | CH | N |
| 2859. | 2 | O | H | $CH(CH_3)_2$ | H | $CH_2CH(CH_3)_2$ | H | H | CH | CH | CH | N |
| 2860. | 2 | O | H | $CH(CH_3)_2$ | H | $C_6H_{11}$ | H | H | CH | CH | CH | N |
| 2861. | 2 | O | H | $CH(CH_3)_2$ | H | Ph | H | H | CH | CH | CH | N |
| 2862. | 2 | O | H | $CH(CH_3)_2$ | H | 2,6-dimethylphenyl | H | H | CH | CH | CH | N |
| 2863. | 2 | O | H | $CH(CH_3)_2$ | H | 2,6-diisopropylphenyl | H | H | CH | CH | CH | N |
| 2864. | 2 | O | H | $CH_2CH(CH_3)_2$ | H | $CH_3$ | H | H | CH | CH | CH | N |
| 2865. | 2 | O | H | $CH_2CH(CH_3)_2$ | H | $CH(CH_3)_2$ | H | H | CH | CH | CH | N |
| 2866. | 2 | O | H | $CH_2CH(CH_3)_2$ | H | $CH_2CH(CH_3)_2$ | H | H | CH | CH | CH | N |
| 2867. | 2 | O | H | $CH_2CH(CH_3)_2$ | H | $C_6H_{11}$ | H | H | CH | CH | CH | N |
| 2868. | 2 | O | H | $CH_2CH(CH_3)_2$ | H | Ph | H | H | CH | CH | CH | N |
| 2869. | 2 | O | H | $CH_2CH(CH_3)_2$ | H | 2,6-dimethylphenyl | H | H | CH | CH | CH | N |
| 2870. | 2 | O | H | $CH_2CH(CH_3)_2$ | H | 2,6-diisopropylphenyl | H | H | CH | CH | CH | N |
| 2871. | 2 | O | H | $C_6H_{11}$ | H | $CH_3$ | H | H | CH | CH | CH | N |
| 2872. | 2 | O | H | $C_6H_{11}$ | H | $CH(CH_3)_2$ | H | H | CH | CH | CH | N |
| 2873. | 2 | O | H | $C_6H_{11}$ | H | $CH_2CH(CH_3)_2$ | H | H | CH | CH | CH | N |
| 2874. | 2 | O | H | $C_6H_{11}$ | H | $C_6H_{11}$ | H | H | CH | CH | CH | N |
| 2875. | 2 | O | H | $C_6H_{11}$ | H | Ph | H | H | CH | CH | CH | N |

-continued

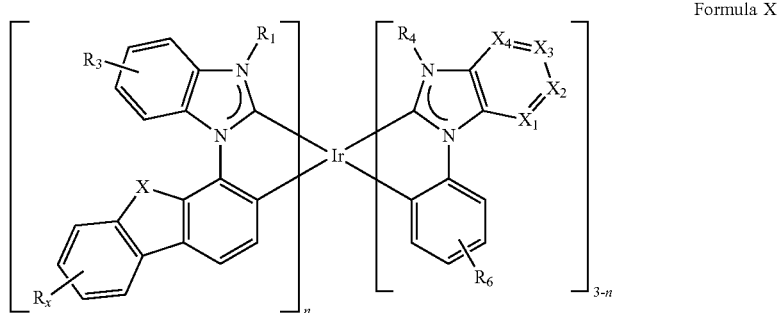

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2876. | 2 | O | H | $C_6H_{11}$ | H | 2,6-dimethylphenyl | H | H | CH | CH | CH | N |
| 2877. | 2 | O | H | $C_6H_{11}$ | H | 2,6-diisopropylphenyl | H | H | CH | CH | CH | N |
| 2878. | 2 | O | H | Ph | H | $CH_3$ | H | H | CH | CH | CH | N |
| 2879. | 2 | O | H | Ph | H | $CH(CH_3)_2$ | H | H | CH | CH | CH | N |
| 2880. | 2 | O | H | Ph | H | $CH_2CH(CH_3)_2$ | H | H | CH | CH | CH | N |
| 2881. | 2 | O | H | Ph | H | $C_6H_{11}$ | H | H | CH | CH | CH | N |
| 2882. | 2 | O | H | Ph | H | Ph | H | H | CH | CH | CH | N |
| 2883. | 2 | O | H | Ph | H | 2,6-dimethylphenyl | H | H | CH | CH | CH | N |
| 2884. | 2 | O | H | Ph | H | 2,6-diisopropylphenyl | H | H | CH | CH | CH | N |
| 2885. | 2 | O | H | 2,6-dimethylphenyl | H | $CH_3$ | H | H | CH | CH | CH | N |
| 2886. | 2 | O | H | 2,6-dimethylphenyl | H | $CH(CH_3)_2$ | H | H | CH | CH | CH | N |
| 2887. | 2 | O | H | 2,6-dimethylphenyl | H | $CH_2CH(CH_3)_2$ | H | H | CH | CH | CH | N |
| 2888. | 2 | O | H | 2,6-dimethylphenyl | H | $C_6H_{11}$ | H | H | CH | CH | CH | N |
| 2889. | 2 | O | H | 2,6-dimethylphenyl | H | Ph | H | H | CH | CH | CH | N |
| 2890. | 2 | O | H | 2,6-dimethylphenyl | H | 2,6-dimethylphenyl | H | H | CH | CH | CH | N |
| 2891. | 2 | O | H | 2,6-dimethylphenyl | H | 2,6-diisopropylphenyl | H | H | CH | CH | CH | N |
| 2892. | 2 | O | H | 2,6-diisopropylphenyl | H | $CH_3$ | H | H | CH | CH | CH | N |
| 2893. | 2 | O | H | 2,6-diisopropylphenyl | H | $CH(CH_3)_2$ | H | H | CH | CH | CH | N |
| 2894. | 2 | O | H | 2,6-diisopropylphenyl | H | $CH_2CH(CH_3)_2$ | H | H | CH | CH | CH | N |
| 2895. | 2 | O | H | 2,6-diisopropylphenyl | H | $C_6H_{11}$ | H | H | CH | CH | CH | N |
| 2896. | 2 | O | H | 2,6-diisopropylphenyl | H | Ph | H | H | CH | CH | CH | N |
| 2897. | 2 | O | H | 2,6-diisopropylphenyl | H | 2,6-dimethylphenyl | H | H | CH | CH | CH | N |
| 2898. | 2 | O | H | 2,6-diisopropylphenyl | H | 2,6-diisopropylphenyl | H | H | CH | CH | CH | N |
| 2899. | 2 | S | H | $CH_3$ | H | $CH_3$ | H | H | CH | CH | CH | N |
| 2900. | 2 | S | H | $CH_3$ | H | $CH(CH_3)_2$ | H | H | CH | CH | CH | N |
| 2901. | 2 | S | H | $CH_3$ | H | $CH_2CH(CH_3)_2$ | H | H | CH | CH | CH | N |
| 2902. | 2 | S | H | $CH_3$ | H | $C_6H_{11}$ | H | H | CH | CH | CH | N |
| 2903. | 2 | S | H | $CH_3$ | H | Ph | H | H | CH | CH | CH | N |
| 2904. | 2 | S | H | $CH_3$ | H | 2,6-dimethylphenyl | H | H | CH | CH | CH | N |
| 2905. | 2 | S | H | $CH_3$ | H | 2,6-diisopropylphenyl | H | H | CH | CH | CH | N |
| 2906. | 2 | S | H | $CH(CH_3)_2$ | H | $CH_3$ | H | H | CH | CH | CH | N |
| 2907. | 2 | S | H | $CH(CH_3)_2$ | H | $CH(CH_3)_2$ | H | H | CH | CH | CH | N |
| 2908. | 2 | S | H | $CH(CH_3)_2$ | H | $CH_2CH(CH_3)_2$ | H | H | CH | CH | CH | N |
| 2909. | 2 | S | H | $CH(CH_3)_2$ | H | $C_6H_{11}$ | H | H | CH | CH | CH | N |
| 2910. | 2 | S | H | $CH(CH_3)_2$ | H | Ph | H | H | CH | CH | CH | N |
| 2911. | 2 | S | H | $CH(CH_3)_2$ | H | 2,6-dimethylphenyl | H | H | CH | CH | CH | N |
| 2912. | 2 | S | H | $CH(CH_3)_2$ | H | 2,6-diisopropylphenyl | H | H | CH | CH | CH | N |
| 2913. | 2 | S | H | $CH_2CH(CH_3)_2$ | H | $CH_3$ | H | H | CH | CH | CH | N |
| 2914. | 2 | S | H | $CH_2CH(CH_3)_2$ | H | $CH(CH_3)_2$ | H | H | CH | CH | CH | N |
| 2915. | 2 | S | H | $CH_2CH(CH_3)_2$ | H | $CH_2CH(CH_3)_2$ | H | H | CH | CH | CH | N |
| 2916. | 2 | S | H | $CH_2CH(CH_3)_2$ | H | $C_6H_{11}$ | H | H | CH | CH | CH | N |
| 2917. | 2 | S | H | $CH_2CH(CH_3)_2$ | H | Ph | H | H | CH | CH | CH | N |
| 2918. | 2 | S | H | $CH_2CH(CH_3)_2$ | H | 2,6-dimethylphenyl | H | H | CH | CH | CH | N |
| 2919. | 2 | S | H | $CH_2CH(CH_3)_2$ | H | 2,6-diisopropylphenyl | H | H | CH | CH | CH | N |
| 2920. | 2 | S | H | $C_6H_{11}$ | H | $CH_3$ | H | H | CH | CH | CH | N |
| 2921. | 2 | S | H | $C_6H_{11}$ | H | $CH(CH_3)_2$ | H | H | CH | CH | CH | N |
| 2922. | 2 | S | H | $C_6H_{11}$ | H | $CH_2CH(CH_3)_2$ | H | H | CH | CH | CH | N |
| 2923. | 2 | S | H | $C_6H_{11}$ | H | $C_6H_{11}$ | H | H | CH | CH | CH | N |
| 2924. | 2 | S | H | $C_6H_{11}$ | H | Ph | H | H | CH | CH | CH | N |
| 2925. | 2 | S | H | $C_6H_{11}$ | H | 2,6-dimethylphenyl | H | H | CH | CH | CH | N |
| 2926. | 2 | S | H | $C_6H_{11}$ | H | 2,6-diisopropylphenyl | H | H | CH | CH | CH | N |
| 2927. | 2 | S | H | Ph | H | $CH_3$ | H | H | CH | CH | CH | N |
| 2928. | 2 | S | H | Ph | H | $CH(CH_3)_2$ | H | H | CH | CH | CH | N |
| 2929. | 2 | S | H | Ph | H | $CH_2CH(CH_3)_2$ | H | H | CH | CH | CH | N |
| 2930. | 2 | S | H | Ph | H | $C_6H_{11}$ | H | H | CH | CH | CH | N |
| 2931. | 2 | S | H | Ph | H | Ph | H | H | CH | CH | CH | N |
| 2932. | 2 | S | H | Ph | H | 2,6-dimethylphenyl | H | H | CH | CH | CH | N |
| 2933. | 2 | S | H | Ph | H | 2,6-diisopropylphenyl | H | H | CH | CH | CH | N |
| 2934. | 2 | S | H | 2,6-dimethylphenyl | H | $CH_3$ | H | H | CH | CH | CH | N |

-continued

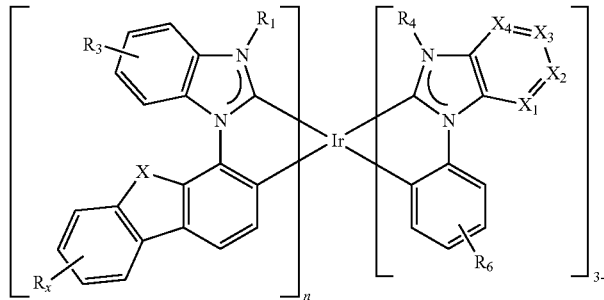

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2935. | 2 | S | H | 2,6-dimethylphenyl | H | $CH(CH_3)_2$ | H | H | CH | CH | CH | N |
| 2936. | 2 | S | H | 2,6-dimethylphenyl | H | $CH_2CH(CH_3)_2$ | H | H | CH | CH | CH | N |
| 2937. | 2 | S | H | 2,6-dimethylphenyl | H | $C_6H_{11}$ | H | H | CH | CH | CH | N |
| 2938. | 2 | S | H | 2,6-dimethylphenyl | H | Ph | H | H | CH | CH | CH | N |
| 2939. | 2 | S | H | 2,6-dimethylphenyl | H | 2,6-dimethylphenyl | H | H | CH | CH | CH | N |
| 2940. | 2 | S | H | 2,6-dimethylphenyl | H | 2,6-diisopropylphenyl | H | H | CH | CH | CH | N |
| 2941. | 2 | S | H | 2,6-diisopropylphenyl | H | $CH_3$ | H | H | CH | CH | CH | N |
| 2942. | 2 | S | H | 2,6-diisopropylphenyl | H | $CH(CH_3)_2$ | H | H | CH | CH | CH | N |
| 2943. | 2 | S | H | 2,6-diisopropylphenyl | H | $CH_2CH(CH_3)_2$ | H | H | CH | CH | CH | N |
| 2944. | 2 | S | H | 2,6-diisopropylphenyl | H | $C_6H_{11}$ | H | H | CH | CH | CH | N |
| 2945. | 2 | S | H | 2,6-diisopropylphenyl | H | Ph | H | H | CH | CH | CH | N |
| 2946. | 2 | S | H | 2,6-diisopropylphenyl | H | 2,6-dimethylphenyl | H | H | CH | CH | CH | N |
| 2947. | 2 | S | H | 2,6-diisopropylphenyl | H | 2,6-diisopropylphenyl | H | H | CH | CH | CH | N |
| 2948. | 1 | O | H | $CH_3$ | H | $CH_3$ | H | H | N | CH | N | CH |
| 2949. | 1 | O | H | $CH_3$ | H | $CH(CH_3)_2$ | H | H | N | CH | N | CH |
| 2950. | 1 | O | H | $CH_3$ | H | $CH_2CH(CH_3)_2$ | H | H | N | CH | N | CH |
| 2951. | 1 | O | H | $CH_3$ | H | $C_6H_{11}$ | H | H | N | CH | N | CH |
| 2952. | 1 | O | H | $CH_3$ | H | Ph | H | H | N | CH | N | CH |
| 2953. | 1 | O | H | $CH_3$ | H | 2,6-dimethylphenyl | H | H | N | CH | N | CH |
| 2954. | 1 | O | H | $CH_3$ | H | 2,6-diisopropylphenyl | H | H | N | CH | N | CH |
| 2955. | 1 | O | H | $CH(CH_3)_2$ | H | $CH_3$ | H | H | N | CH | N | CH |
| 2956. | 1 | O | H | $CH(CH_3)_2$ | H | $CH(CH_3)_2$ | H | H | N | CH | N | CH |
| 2957. | 1 | O | H | $CH(CH_3)_2$ | H | $CH_2CH(CH_3)_2$ | H | H | N | CH | N | CH |
| 2958. | 1 | O | H | $CH(CH_3)_2$ | H | $C_6H_{11}$ | H | H | N | CH | N | CH |
| 2959. | 1 | O | H | $CH(CH_3)_2$ | H | Ph | H | H | N | CH | N | CH |
| 2960. | 1 | O | H | $CH(CH_3)_2$ | H | 2,6-dimethylphenyl | H | H | N | CH | N | CH |
| 2961. | 1 | O | H | $CH(CH_3)_2$ | H | 2,6-diisopropylphenyl | H | H | N | CH | N | CH |
| 2962. | 1 | O | H | $CH_2CH(CH_3)_2$ | H | $CH_3$ | H | H | N | CH | N | CH |
| 2963. | 1 | O | H | $CH_2CH(CH_3)_2$ | H | $CH(CH_3)_2$ | H | H | N | CH | N | CH |
| 2964. | 1 | O | H | $CH_2CH(CH_3)_2$ | H | $CH_2CH(CH_3)_2$ | H | H | N | CH | N | CH |
| 2965. | 1 | O | H | $CH_2CH(CH_3)_2$ | H | $C_6H_{11}$ | H | H | N | CH | N | CH |
| 2966. | 1 | O | H | $CH_2CH(CH_3)_2$ | H | Ph | H | H | N | CH | N | CH |
| 2967. | 1 | O | H | $CH_2CH(CH_3)_2$ | H | 2,6-dimethylphenyl | H | H | N | CH | N | CH |
| 2968. | 1 | O | H | $CH_2CH(CH_3)_2$ | H | 2,6-diisopropylphenyl | H | H | N | CH | N | CH |
| 2969. | 1 | O | H | $C_6H_{11}$ | H | $CH_3$ | H | H | N | CH | N | CH |
| 2970. | 1 | O | H | $C_6H_{11}$ | H | $CH(CH_3)_2$ | H | H | N | CH | N | CH |
| 2971. | 1 | O | H | $C_6H_{11}$ | H | $CH_2CH(CH_3)_2$ | H | H | N | CH | N | CH |
| 2972. | 1 | O | H | $C_6H_{11}$ | H | $C_6H_{11}$ | H | H | N | CH | N | CH |
| 2973. | 1 | O | H | $C_6H_{11}$ | H | Ph | H | H | N | CH | N | CH |
| 2974. | 1 | O | H | $C_6H_{11}$ | H | 2,6-dimethylphenyl | H | H | N | CH | N | CH |
| 2975. | 1 | O | H | $C_6H_{11}$ | H | 2,6-diisopropylphenyl | H | H | N | CH | N | CH |
| 2976. | 1 | O | H | Ph | H | $CH_3$ | H | H | N | CH | N | CH |
| 2977. | 1 | O | H | Ph | H | $CH(CH_3)_2$ | H | H | N | CH | N | CH |
| 2978. | 1 | O | H | Ph | H | $CH_2CH(CH_3)_2$ | H | H | N | CH | N | CH |
| 2979. | 1 | O | H | Ph | H | $C_6H_{11}$ | H | H | N | CH | N | CH |
| 2980. | 1 | O | H | Ph | H | Ph | H | H | N | CH | N | CH |
| 2981. | 1 | O | H | Ph | H | 2,6-dimethylphenyl | H | H | N | CH | N | CH |
| 2982. | 1 | O | H | Ph | H | 2,6-diisopropylphenyl | H | H | N | CH | N | CH |
| 2983. | 1 | O | H | 2,6-dimethylphenyl | H | $CH_3$ | H | H | N | CH | N | CH |
| 2984. | 1 | O | H | 2,6-dimethylphenyl | H | $CH(CH_3)_2$ | H | H | N | CH | N | CH |
| 2985. | 1 | O | H | 2,6-dimethylphenyl | H | $CH_2CH(CH_3)_2$ | H | H | N | CH | N | CH |
| 2986. | 1 | O | H | 2,6-dimethylphenyl | H | $C_6H_{11}$ | H | H | N | CH | N | CH |
| 2987. | 1 | O | H | 2,6-dimethylphenyl | H | Ph | H | H | N | CH | N | CH |
| 2988. | 1 | O | H | 2,6-dimethylphenyl | H | 2,6-dimethylphenyl | H | H | N | CH | N | CH |
| 2989. | 1 | O | H | 2,6-dimethylphenyl | H | 2,6-diisopropylphenyl | H | H | N | CH | N | CH |
| 2990. | 1 | O | H | 2,6-diisopropylphenyl | H | $CH_3$ | H | H | N | CH | N | CH |
| 2991. | 1 | O | H | 2,6-diisopropylphenyl | H | $CH(CH_3)_2$ | H | H | N | CH | N | CH |
| 2992. | 1 | O | H | 2,6-diisopropylphenyl | H | $CH_2CH(CH_3)_2$ | H | H | N | CH | N | CH |
| 2993. | 1 | O | H | 2,6-diisopropylphenyl | H | $C_6H_{11}$ | H | H | N | CH | N | CH |

-continued

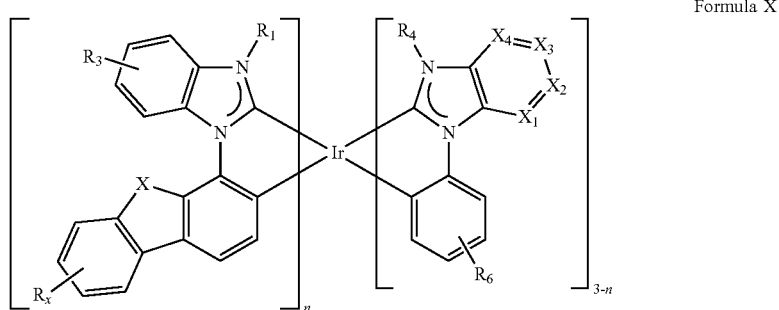

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 2994. | 1 | O | H | 2,6-diisopropylphenyl | H | Ph | H | H | N | CH | N | CH |
| 2995. | 1 | O | H | 2,6-diisopropylphenyl | H | 2,6-dimethylphenyl | H | H | N | CH | N | CH |
| 2996. | 1 | O | H | 2,6-diisopropylphenyl | H | 2,6-diisopropylphenyl | H | H | N | CH | N | CH |
| 2997. | 1 | S | H | $CH_3$ | H | $CH_3$ | H | H | N | CH | N | CH |
| 2998. | 1 | S | H | $CH_3$ | H | $CH(CH_3)_2$ | H | H | N | CH | N | CH |
| 2999. | 1 | S | H | $CH_3$ | H | $CH_2CH(CH_3)_2$ | H | H | N | CH | N | CH |
| 3000. | 1 | S | H | $CH_3$ | H | $C_6H_{11}$ | H | H | N | CH | N | CH |
| 3001. | 1 | S | H | $CH_3$ | H | Ph | H | H | N | CH | N | CH |
| 3002. | 1 | S | H | $CH_3$ | H | 2,6-dimethylphenyl | H | H | N | CH | N | CH |
| 3003. | 1 | S | H | $CH_3$ | H | 2,6-diisopropylphenyl | H | H | N | CH | N | CH |
| 3004. | 1 | S | H | $CH(CH_3)_2$ | H | $CH_3$ | H | H | N | CH | N | CH |
| 3005. | 1 | S | H | $CH(CH_3)_2$ | H | $CH(CH_3)_2$ | H | H | N | CH | N | CH |
| 3006. | 1 | S | H | $CH(CH_3)_2$ | H | $CH_2CH(CH_3)_2$ | H | H | N | CH | N | CH |
| 3007. | 1 | S | H | $CH(CH_3)_2$ | H | $C_6H_{11}$ | H | H | N | CH | N | CH |
| 3008. | 1 | S | H | $CH(CH_3)_2$ | H | Ph | H | H | N | CH | N | CH |
| 3009. | 1 | S | H | $CH(CH_3)_2$ | H | 2,6-dimethylphenyl | H | H | N | CH | N | CH |
| 3010. | 1 | S | H | $CH(CH_3)_2$ | H | 2,6-diisopropylphenyl | H | H | N | CH | N | CH |
| 3011. | 1 | S | H | $CH_2CH(CH_3)_2$ | H | $CH_3$ | H | H | N | CH | N | CH |
| 3012. | 1 | S | H | $CH_2CH(CH_3)_2$ | H | $CH(CH_3)_2$ | H | H | N | CH | N | CH |
| 3013. | 1 | S | H | $CH_2CH(CH_3)_2$ | H | $CH_2CH(CH_3)_2$ | H | H | N | CH | N | CH |
| 3014. | 1 | S | H | $CH_2CH(CH_3)_2$ | H | $C_6H_{11}$ | H | H | N | CH | N | CH |
| 3015. | 1 | S | H | $CH_2CH(CH_3)_2$ | H | Ph | H | H | N | CH | N | CH |
| 3016. | 1 | S | H | $CH_2CH(CH_3)_2$ | H | 2,6-dimethylphenyl | H | H | N | CH | N | CH |
| 3017. | 1 | S | H | $CH_2CH(CH_3)_2$ | H | 2,6-diisopropylphenyl | H | H | N | CH | N | CH |
| 3018. | 1 | S | H | $C_6H_{11}$ | H | $CH_3$ | H | H | N | CH | N | CH |
| 3019. | 1 | S | H | $C_6H_{11}$ | H | $CH(CH_3)_2$ | H | H | N | CH | N | CH |
| 3020. | 1 | S | H | $C_6H_{11}$ | H | $CH_2CH(CH_3)_2$ | H | H | N | CH | N | CH |
| 3021. | 1 | S | H | $C_6H_{11}$ | H | $C_6H_{11}$ | H | H | N | CH | N | CH |
| 3022. | 1 | S | H | $C_6H_{11}$ | H | Ph | H | H | N | CH | N | CH |
| 3023. | 1 | S | H | $C_6H_{11}$ | H | 2,6-dimethylphenyl | H | H | N | CH | N | CH |
| 3024. | 1 | S | H | $C_6H_{11}$ | H | 2,6-diisopropylphenyl | H | H | N | CH | N | CH |
| 3025. | 1 | S | H | Ph | H | $CH_3$ | H | H | N | CH | N | CH |
| 3026. | 1 | S | H | Ph | H | $CH(CH_3)_2$ | H | H | N | CH | N | CH |
| 3027. | 1 | S | H | Ph | H | $CH_2CH(CH_3)_2$ | H | H | N | CH | N | CH |
| 3028. | 1 | S | H | Ph | H | $C_6H_{11}$ | H | H | N | CH | N | CH |
| 3029. | 1 | S | H | Ph | H | Ph | H | H | N | CH | N | CH |
| 3030. | 1 | S | H | Ph | H | 2,6-dimethylphenyl | H | H | N | CH | N | CH |
| 3031. | 1 | S | H | Ph | H | 2,6-diisopropylphenyl | H | H | N | CH | N | CH |
| 3032. | 1 | S | H | 2,6-dimethylphenyl | H | $CH_3$ | H | H | N | CH | N | CH |
| 3033. | 1 | S | H | 2,6-dimethylphenyl | H | $CH(CH_3)_2$ | H | H | N | CH | N | CH |
| 3034. | 1 | S | H | 2,6-dimethylphenyl | H | $CH_2CH(CH_3)_2$ | H | H | N | CH | N | CH |
| 3035. | 1 | S | H | 2,6-dimethylphenyl | H | $C_6H_{11}$ | H | H | N | CH | N | CH |
| 3036. | 1 | S | H | 2,6-dimethylphenyl | H | Ph | H | H | N | CH | N | CH |
| 3037. | 1 | S | H | 2,6-dimethylphenyl | H | 2,6-dimethylphenyl | H | H | N | CH | N | CH |
| 3038. | 1 | S | H | 2,6-dimethylphenyl | H | 2,6-diisopropylphenyl | H | H | N | CH | N | CH |
| 3039. | 1 | S | H | 2,6-diisopropylphenyl | H | $CH_3$ | H | H | N | CH | N | CH |
| 3040. | 1 | S | H | 2,6-diisopropylphenyl | H | $CH(CH_3)_2$ | H | H | N | CH | N | CH |
| 3041. | 1 | S | H | 2,6-diisopropylphenyl | H | $CH_2CH(CH_3)_2$ | H | H | N | CH | N | CH |
| 3042. | 1 | S | H | 2,6-diisopropylphenyl | H | $C_6H_{11}$ | H | H | N | CH | N | CH |
| 3043. | 1 | S | H | 2,6-diisopropylphenyl | H | Ph | H | H | N | CH | N | CH |
| 3044. | 1 | S | H | 2,6-diisopropylphenyl | H | 2,6-dimethylphenyl | H | H | N | CH | N | CH |
| 3045. | 1 | S | H | 2,6-diisopropylphenyl | H | 2,6-diisopropylphenyl | H | H | N | CH | N | CH |
| 3046. | 2 | O | H | $CH_3$ | H | $CH_3$ | H | H | N | CH | N | CH |
| 3047. | 2 | O | H | $CH_3$ | H | $CH(CH_3)_2$ | H | H | N | CH | N | CH |
| 3048. | 2 | O | H | $CH_3$ | H | $CH_2CH(CH_3)_2$ | H | H | N | CH | N | CH |
| 3049. | 2 | O | H | $CH_3$ | H | $C_6H_{11}$ | H | H | N | CH | N | CH |
| 3050. | 2 | O | H | $CH_3$ | H | Ph | H | H | N | CH | N | CH |
| 3051. | 2 | O | H | $CH_3$ | H | 2,6-dimethylphenyl | H | H | N | CH | N | CH |
| 3052. | 2 | O | H | $CH_3$ | H | 2,6-diisopropylphenyl | H | H | N | CH | N | CH |

-continued

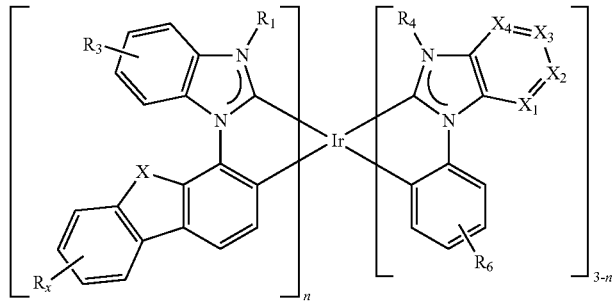

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3053. | 2 | O | H | $CH(CH_3)_2$ | H | $CH_3$ | H | H | N | CH | N | CH |
| 3054. | 2 | O | H | $CH(CH_3)_2$ | H | $CH(CH_3)_2$ | H | H | N | CH | N | CH |
| 3055. | 2 | O | H | $CH(CH_3)_2$ | H | $CH_2CH(CH_3)_2$ | H | H | N | CH | N | CH |
| 3056. | 2 | O | H | $CH(CH_3)_2$ | H | $C_6H_{11}$ | H | H | N | CH | N | CH |
| 3057. | 2 | O | H | $CH(CH_3)_2$ | H | Ph | H | H | N | CH | N | CH |
| 3058. | 2 | O | H | $CH(CH_3)_2$ | H | 2,6-dimethylphenyl | H | H | N | CH | N | CH |
| 3059. | 2 | O | H | $CH(CH_3)_2$ | H | 2,6-diisopropylphenyl | H | H | N | CH | N | CH |
| 3060. | 2 | O | H | $CH_2CH(CH_3)_2$ | H | $CH_3$ | H | H | N | CH | N | CH |
| 3061. | 2 | O | H | $CH_2CH(CH_3)_2$ | H | $CH(CH_3)_2$ | H | H | N | CH | N | CH |
| 3062. | 2 | O | H | $CH_2CH(CH_3)_2$ | H | $CH_2CH(CH_3)_2$ | H | H | N | CH | N | CH |
| 3063. | 2 | O | H | $CH_2CH(CH_3)_2$ | H | $C_6H_{11}$ | H | H | N | CH | N | CH |
| 3064. | 2 | O | H | $CH_2CH(CH_3)_2$ | H | Ph | H | H | N | CH | N | CH |
| 3065. | 2 | O | H | $CH_2CH(CH_3)_2$ | H | 2,6-dimethylphenyl | H | H | N | CH | N | CH |
| 3066. | 2 | O | H | $CH_2CH(CH_3)_2$ | H | 2,6-diisopropylphenyl | H | H | N | CH | N | CH |
| 3067. | 2 | O | H | $C_6H_{11}$ | H | $CH_3$ | H | H | N | CH | N | CH |
| 3068. | 2 | O | H | $C_6H_{11}$ | H | $CH(CH_3)_2$ | H | H | N | CH | N | CH |
| 3069. | 2 | O | H | $C_6H_{11}$ | H | $CH_2CH(CH_3)_2$ | H | H | N | CH | N | CH |
| 3070. | 2 | O | H | $C_6H_{11}$ | H | $C_6H_{11}$ | H | H | N | CH | N | CH |
| 3071. | 2 | O | H | $C_6H_{11}$ | H | Ph | H | H | N | CH | N | CH |
| 3072. | 2 | O | H | $C_6H_{11}$ | H | 2,6-dimethylphenyl | H | H | N | CH | N | CH |
| 3073. | 2 | O | H | $C_6H_{11}$ | H | 2,6-diisopropylphenyl | H | H | N | CH | N | CH |
| 3074. | 2 | O | H | Ph | H | $CH_3$ | H | H | N | CH | N | CH |
| 3075. | 2 | O | H | Ph | H | $CH(CH_3)_2$ | H | H | N | CH | N | CH |
| 3076. | 2 | O | H | Ph | H | $CH_2CH(CH_3)_2$ | H | H | N | CH | N | CH |
| 3077. | 2 | O | H | Ph | H | $C_6H_{11}$ | H | H | N | CH | N | CH |
| 3078. | 2 | O | H | Ph | H | Ph | H | H | N | CH | N | CH |
| 3079. | 2 | O | H | Ph | H | 2,6-dimethylphenyl | H | H | N | CH | N | CH |
| 3080. | 2 | O | H | Ph | H | 2,6-diisopropylphenyl | H | H | N | CH | N | CH |
| 3081. | 2 | O | H | 2,6-dimethylphenyl | H | $CH_3$ | H | H | N | CH | N | CH |
| 3082. | 2 | O | H | 2,6-dimethylphenyl | H | $CH(CH_3)_2$ | H | H | N | CH | N | CH |
| 3083. | 2 | O | H | 2,6-dimethylphenyl | H | $CH_2CH(CH_3)_2$ | H | H | N | CH | N | CH |
| 3084. | 2 | O | H | 2,6-dimethylphenyl | H | $C_6H_{11}$ | H | H | N | CH | N | CH |
| 3085. | 2 | O | H | 2,6-dimethylphenyl | H | Ph | H | H | N | CH | N | CH |
| 3086. | 2 | O | H | 2,6-dimethylphenyl | H | 2,6-dimethylphenyl | H | H | N | CH | N | CH |
| 3087. | 2 | O | H | 2,6-dimethylphenyl | H | 2,6-diisopropylphenyl | H | H | N | CH | N | CH |
| 3088. | 2 | O | H | 2,6-diisopropylphenyl | H | $CH_3$ | H | H | N | CH | N | CH |
| 3089. | 2 | O | H | 2,6-diisopropylphenyl | H | $CH(CH_3)_2$ | H | H | N | CH | N | CH |
| 3090. | 2 | O | H | 2,6-diisopropylphenyl | H | $CH_2CH(CH_3)_2$ | H | H | N | CH | N | CH |
| 3091. | 2 | O | H | 2,6-diisopropylphenyl | H | $C_6H_{11}$ | H | H | N | CH | N | CH |
| 3092. | 2 | O | H | 2,6-diisopropylphenyl | H | Ph | H | H | N | CH | N | CH |
| 3093. | 2 | O | H | 2,6-diisopropylphenyl | H | 2,6-dimethylphenyl | H | H | N | CH | N | CH |
| 3094. | 2 | O | H | 2,6-diisopropylphenyl | H | 2,6-diisopropylphenyl | H | H | N | CH | N | CH |
| 3095. | 2 | S | H | $CH_3$ | H | $CH_3$ | H | H | N | CH | N | CH |
| 3096. | 2 | S | H | $CH_3$ | H | $CH(CH_3)_2$ | H | H | N | CH | N | CH |
| 3097. | 2 | S | H | $CH_3$ | H | $CH_2CH(CH_3)_2$ | H | H | N | CH | N | CH |
| 3098. | 2 | S | H | $CH_3$ | H | $C_6H_{11}$ | H | H | N | CH | N | CH |
| 3099. | 2 | S | H | $CH_3$ | H | Ph | H | H | N | CH | N | CH |
| 3100. | 2 | S | H | $CH_3$ | H | 2,6-dimethylphenyl | H | H | N | CH | N | CH |
| 3101. | 2 | S | H | $CH_3$ | H | 2,6-diisopropylphenyl | H | H | N | CH | N | CH |
| 3102. | 2 | S | H | $CH(CH_3)_2$ | H | $CH_3$ | H | H | N | CH | N | CH |
| 3103. | 2 | S | H | $CH(CH_3)_2$ | H | $CH(CH_3)_2$ | H | H | N | CH | N | CH |
| 3104. | 2 | S | H | $CH(CH_3)_2$ | H | $CH_2CH(CH_3)_2$ | H | H | N | CH | N | CH |
| 3105. | 2 | S | H | $CH(CH_3)_2$ | H | $C_6H_{11}$ | H | H | N | CH | N | CH |
| 3106. | 2 | S | H | $CH(CH_3)_2$ | H | Ph | H | H | N | CH | N | CH |
| 3107. | 2 | S | H | $CH(CH_3)_2$ | H | 2,6-dimethylphenyl | H | H | N | CH | N | CH |
| 3108. | 2 | S | H | $CH(CH_3)_2$ | H | 2,6-diisopropylphenyl | H | H | N | CH | N | CH |
| 3109. | 2 | S | H | $CH_2CH(CH_3)_2$ | H | $CH_3$ | H | H | N | CH | N | CH |
| 3110. | 2 | S | H | $CH_2CH(CH_3)_2$ | H | $CH(CH_3)_2$ | H | H | N | CH | N | CH |
| 3111. | 2 | S | H | $CH_2CH(CH_3)_2$ | H | $CH_2CH(CH_3)_2$ | H | H | N | CH | N | CH |

-continued

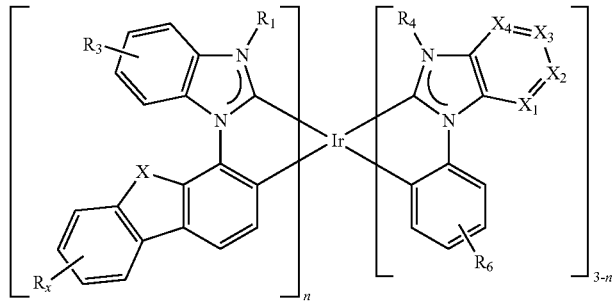

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3112. | 2 | S | H | $CH_2CH(CH_3)_2$ | H | $C_6H_{11}$ | H | H | N | CH | N | CH |
| 3113. | 2 | S | H | $CH_2CH(CH_3)_2$ | H | Ph | H | H | N | CH | N | CH |
| 3114. | 2 | S | H | $CH_2CH(CH_3)_2$ | H | 2,6-dimethylphenyl | H | H | N | CH | N | CH |
| 3115. | 2 | S | H | $CH_2CH(CH_3)_2$ | H | 2,6-diisopropylphenyl | H | H | N | CH | N | CH |
| 3116. | 2 | S | H | $C_6H_{11}$ | H | $CH_3$ | H | H | N | CH | N | CH |
| 3117. | 2 | S | H | $C_6H_{11}$ | H | $CH(CH_3)_2$ | H | H | N | CH | N | CH |
| 3118. | 2 | S | H | $C_6H_{11}$ | H | $CH_2CH(CH_3)_2$ | H | H | N | CH | N | CH |
| 3119. | 2 | S | H | $C_6H_{11}$ | H | $C_6H_{11}$ | H | H | N | CH | N | CH |
| 3120. | 2 | S | H | $C_6H_{11}$ | H | Ph | H | H | N | CH | N | CH |
| 3121. | 2 | S | H | $C_6H_{11}$ | H | 2,6-dimethylphenyl | H | H | N | CH | N | CH |
| 3122. | 2 | S | H | $C_6H_{11}$ | H | 2,6-diisopropylphenyl | H | H | N | CH | N | CH |
| 3123. | 2 | S | H | Ph | H | $CH_3$ | H | H | N | CH | N | CH |
| 3124. | 2 | S | H | Ph | H | $CH(CH_3)_2$ | H | H | N | CH | N | CH |
| 3125. | 2 | S | H | Ph | H | $CH_2CH(CH_3)_2$ | H | H | N | CH | N | CH |
| 3126. | 2 | S | H | Ph | H | $C_6H_{11}$ | H | H | N | CH | N | CH |
| 3127. | 2 | S | H | Ph | H | Ph | H | H | N | CH | N | CH |
| 3128. | 2 | S | H | Ph | H | 2,6-dimethylphenyl | H | H | N | CH | N | CH |
| 3129. | 2 | S | H | Ph | H | 2,6-diisopropylphenyl | H | H | N | CH | N | CH |
| 3130. | 2 | S | H | 2,6-dimethylphenyl | H | $CH_3$ | H | H | N | CH | N | CH |
| 3131. | 2 | S | H | 2,6-dimethylphenyl | H | $CH(CH_3)_2$ | H | H | N | CH | N | CH |
| 3132. | 2 | S | H | 2,6-dimethylphenyl | H | $CH_2CH(CH_3)_2$ | H | H | N | CH | N | CH |
| 3133. | 2 | S | H | 2,6-dimethylphenyl | H | $C_6H_{11}$ | H | H | N | CH | N | CH |
| 3134. | 2 | S | H | 2,6-dimethylphenyl | H | Ph | H | H | N | CH | N | CH |
| 3135. | 2 | S | H | 2,6-dimethylphenyl | H | 2,6-dimethylphenyl | H | H | N | CH | N | CH |
| 3136. | 2 | S | H | 2,6-dimethylphenyl | H | 2,6-diisopropylphenyl | H | H | N | CH | N | CH |
| 3137. | 2 | S | H | 2,6-diisopropylphenyl | H | $CH_3$ | H | H | N | CH | N | CH |
| 3138. | 2 | S | H | 2,6-diisopropylphenyl | H | $CH(CH_3)_2$ | H | H | N | CH | N | CH |
| 3139. | 2 | S | H | 2,6-diisopropylphenyl | H | $CH_2CH(CH_3)_2$ | H | H | N | CH | N | CH |
| 3140. | 2 | S | H | 2,6-diisopropylphenyl | H | $C_6H_{11}$ | H | H | N | CH | N | CH |
| 3141. | 2 | S | H | 2,6-diisopropylphenyl | H | Ph | H | H | N | CH | N | CH |
| 3142. | 2 | S | H | 2,6-diisopropylphenyl | H | 2,6-dimethylphenyl | H | H | N | CH | N | CH |
| 3143. | 2 | S | H | 2,6-diisopropylphenyl | H | 2,6-diisopropylphenyl | H | H | N | CH | N | CH |
| 3144. | | | | | | | | | | | | |
| 3145. | 1 | O | H | $CH_3$ | H | $CH_3$ | H | H | CH | N | CH | N |
| 3146. | 1 | O | H | $CH_3$ | H | $CH(CH_3)_2$ | H | H | CH | N | CH | N |
| 3147. | 1 | O | H | $CH_3$ | H | $CH_2CH(CH_3)_2$ | H | H | CH | N | CH | N |
| 3148. | 1 | O | H | $CH_3$ | H | $C_6H_{11}$ | H | H | CH | N | CH | N |
| 3149. | 1 | O | H | $CH_3$ | H | Ph | H | H | CH | N | CH | N |
| 3150. | 1 | O | H | $CH_3$ | H | 2,6-dimethylphenyl | H | H | CH | N | CH | N |
| 3151. | 1 | O | H | $CH_3$ | H | 2,6-diisopropylphenyl | H | H | CH | N | CH | N |
| 3152. | 1 | O | H | $CH(CH_3)_2$ | H | $CH_3$ | H | H | CH | N | CH | N |
| 3153. | 1 | O | H | $CH(CH_3)_2$ | H | $CH(CH_3)_2$ | H | H | CH | N | CH | N |
| 3154. | 1 | O | H | $CH(CH_3)_2$ | H | $CH_2CH(CH_3)_2$ | H | H | CH | N | CH | N |
| 3155. | 1 | O | H | $CH(CH_3)_2$ | H | $C_6H_{11}$ | H | H | CH | N | CH | N |
| 3156. | 1 | O | H | $CH(CH_3)_2$ | H | Ph | H | H | CH | N | CH | N |
| 3157. | 1 | O | H | $CH(CH_3)_2$ | H | 2,6-dimethylphenyl | H | H | CH | N | CH | N |
| 3158. | 1 | O | H | $CH(CH_3)_2$ | H | 2,6-diisopropylphenyl | H | H | CH | N | CH | N |
| 3159. | 1 | O | H | $CH_2CH(CH_3)_2$ | H | $CH_3$ | H | H | CH | N | CH | N |
| 3160. | 1 | O | H | $CH_2CH(CH_3)_2$ | H | $CH(CH_3)_2$ | H | H | CH | N | CH | N |
| 3161. | 1 | O | H | $CH_2CH(CH_3)_2$ | H | $CH_2CH(GH_3)_2$ | H | H | CH | N | CH | N |
| 3162. | 1 | O | H | $CH_2CH(CH_3)_2$ | H | $C_6H_{11}$ | H | H | CH | N | CH | N |
| 3163. | 1 | O | H | $CH_2CH(CH_3)_2$ | H | Ph | H | H | CH | N | CH | N |
| 3164. | 1 | O | H | $CH_2CH(CH_3)_2$ | H | 2,6-dimethylphenyl | H | H | CH | N | CH | N |
| 3165. | 1 | O | H | $CH_2CH(CH_3)_2$ | H | 2,6-diisopropylphenyl | H | H | CH | N | CH | N |
| 3166. | 1 | O | H | $C_6H_{11}$ | H | $CH_3$ | H | H | CH | N | CH | N |
| 3167. | 1 | O | H | $C_6H_{11}$ | H | $CH(CH_3)_2$ | H | H | CH | N | CH | N |
| 3168. | 1 | O | H | $C_6H_{11}$ | H | $CH_2CH(CH_3)_2$ | H | H | CH | N | CH | N |
| 3169. | 1 | O | H | $C_6H_{11}$ | H | $C_6H_{11}$ | H | H | CH | N | CH | N |
| 3170. | 1 | O | H | $C_6H_{11}$ | H | Ph | H | H | CH | N | CH | N |

-continued

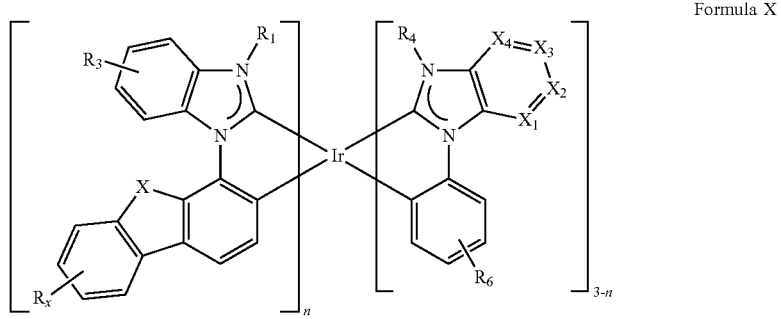

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3171. | 1 | O | H | $C_6H_{11}$ | H | 2,6-dimethylphenyl | H | H | CH | N | CH | N |
| 3172. | 1 | O | H | $C_6H_{11}$ | H | 2,6-diisopropylphenyl | H | H | CH | N | CH | N |
| 3173. | 1 | O | H | Ph | H | $CH_3$ | H | H | CH | N | CH | N |
| 3174. | 1 | O | H | Ph | H | $CH(CH_3)_2$ | H | H | CH | N | CH | N |
| 3175. | 1 | O | H | Ph | H | $CH_2CH(CH_3)_2$ | H | H | CH | N | CH | N |
| 3176. | 1 | O | H | Ph | H | $C_6H_{11}$ | H | H | CH | N | CH | N |
| 3177. | 1 | O | H | Ph | H | Ph | H | H | CH | N | CH | N |
| 3178. | 1 | O | H | Ph | H | 2,6-dimethylphenyl | H | H | CH | N | CH | N |
| 3179. | 1 | O | H | Ph | H | 2,6-diisopropylphenyl | H | H | CH | N | CH | N |
| 3180. | 1 | O | H | 2,6-dimethylphenyl | H | $CH_3$ | H | H | CH | N | CH | N |
| 3181. | 1 | O | H | 2,6-dimethylphenyl | H | $CH(CH_3)_2$ | H | H | CH | N | CH | N |
| 3182. | 1 | O | H | 2,6-dimethylphenyl | H | $CH_2CH(CH_3)_2$ | H | H | CH | N | CH | N |
| 3183. | 1 | O | H | 2,6-dimethylphenyl | H | $C_6H_{11}$ | H | H | CH | N | CH | N |
| 3184. | 1 | O | H | 2,6-dimethylphenyl | H | Ph | H | H | CH | N | CH | N |
| 3185. | 1 | O | H | 2,6-dimethylphenyl | H | 2,6-dimethylphenyl | H | H | CH | N | CH | N |
| 3186. | 1 | O | H | 2,6-dimethylphenyl | H | 2,6-diisopropylphenyl | H | H | CH | N | CH | N |
| 3187. | 1 | O | H | 2,6-diisopropylphenyl | H | $CH_3$ | H | H | CH | N | CH | N |
| 3188. | 1 | O | H | 2,6-diisopropylphenyl | H | $CH(CH_3)_2$ | H | H | CH | N | CH | N |
| 3189. | 1 | O | H | 2,6-diisopropylphenyl | H | $CH_2CH(CH_3)_2$ | H | H | CH | N | CH | N |
| 3190. | 1 | O | H | 2,6-diisopropylphenyl | H | $C_6H_{11}$ | H | H | CH | N | CH | N |
| 3191. | 1 | O | H | 2,6-diisopropylphenyl | H | Ph | H | H | CH | N | CH | N |
| 3192. | 1 | O | H | 2,6-diisopropylphenyl | H | 2,6-dimethylphenyl | H | H | CH | N | CH | N |
| 3193. | 1 | O | H | 2,6-diisopropylphenyl | H | 2,6-diisopropylphenyl | H | H | CH | N | CH | N |
| 3194. | 1 | S | H | $CH_3$ | H | $CH_3$ | H | H | CH | N | CH | N |
| 3195. | 1 | S | H | $CH_3$ | H | $CH(CH_3)_2$ | H | H | CH | N | CH | N |
| 3196. | 1 | S | H | $CH_3$ | H | $CH_2CH(CH_3)_2$ | H | H | CH | N | CH | N |
| 3197. | 1 | S | H | $CH_3$ | H | $C_6H_{11}$ | H | H | CH | N | CH | N |
| 3198. | 1 | S | H | $CH_3$ | H | Ph | H | H | CH | N | CH | N |
| 3199. | 1 | S | H | $CH_3$ | H | 2,6-dimethylphenyl | H | H | CH | N | CH | N |
| 3200. | 1 | S | H | $CH_3$ | H | 2,6-diisopropylphenyl | H | H | CH | N | CH | N |
| 3201. | 1 | S | H | $CH(CH_3)_2$ | H | $CH_3$ | H | H | CH | N | CH | N |
| 3202. | 1 | S | H | $CH(CH_3)_2$ | H | $CH(CH_3)_2$ | H | H | CH | N | CH | N |
| 3203. | 1 | S | H | $CH(CH_3)_2$ | H | $CH_2CH(CH_3)_2$ | H | H | CH | N | CH | N |
| 3204. | 1 | S | H | $CH(CH_3)_2$ | H | $C_6H_{11}$ | H | H | CH | N | CH | N |
| 3205. | 1 | S | H | $CH(CH_3)_2$ | H | Ph | H | H | CH | N | CH | N |
| 3206. | 1 | S | H | $CH(CH_3)_2$ | H | 2,6-dimethylphenyl | H | H | CH | N | CH | N |
| 3207. | 1 | S | H | $CH(CH_3)_2$ | H | 2,6-diisopropylphenyl | H | H | CH | N | CH | N |
| 3208. | 1 | S | H | $CH_2CH(CH_3)_2$ | H | $CH_3$ | H | H | CH | N | CH | N |
| 3209. | 1 | S | H | $CH_2CH(CH_3)_2$ | H | $CH(CH_3)_2$ | H | H | CH | N | CH | N |
| 3210. | 1 | S | H | $CH_2CH(CH_3)_2$ | H | $CH_2CH(CH_3)_2$ | H | H | CH | N | CH | N |
| 3211. | 1 | S | H | $CH_2CH(CH_3)_2$ | H | $C_6H_{11}$ | H | H | CH | N | CH | N |
| 3212. | 1 | S | H | $CH_2CH(CH_3)_2$ | H | Ph | H | H | CH | N | CH | N |
| 3213. | 1 | S | H | $CH_2CH(CH_3)_2$ | H | 2,6-dimethylphenyl | H | H | CH | N | CH | N |
| 3214. | 1 | S | H | $CH_2CH(CH_3)_2$ | H | 2,6-diisopropylphenyl | H | H | CH | N | CH | N |
| 3215. | 1 | S | H | $C_6H_{11}$ | H | $CH_3$ | H | H | CH | N | CH | N |
| 3216. | 1 | S | H | $C_6H_{11}$ | H | $CH(CH_3)_2$ | H | H | CH | N | CH | N |
| 3217. | 1 | S | H | $C_6H_{11}$ | H | $CH_2CH(CH_3)_2$ | H | H | CH | N | CH | N |
| 3218. | 1 | S | H | $C_6H_{11}$ | H | $C_6H_{11}$ | H | H | CH | N | CH | N |
| 3219. | 1 | S | H | $C_6H_{11}$ | H | Ph | H | H | CH | N | CH | N |
| 3220. | 1 | S | H | $C_6H_{11}$ | H | 2,6-dimethylphenyl | H | H | CH | N | CH | N |
| 3221. | 1 | S | H | $C_6H_{11}$ | H | 2,6-diisopropylphenyl | H | H | CH | N | CH | N |
| 3222. | 1 | S | H | Ph | H | $CH_3$ | H | H | CH | N | CH | N |
| 3223. | 1 | S | H | Ph | H | $CH(CH_3)_2$ | H | H | CH | N | CH | N |
| 3224. | 1 | S | H | Ph | H | $CH_2CH(CH_3)_2$ | H | H | CH | N | CH | N |
| 3225. | 1 | S | H | Ph | H | $C_6H_{11}$ | H | H | CH | N | CH | N |
| 3226. | 1 | S | H | Ph | H | Ph | H | H | CH | N | CH | N |
| 3227. | 1 | S | H | Ph | H | 2,6-dimethylphenyl | H | H | CH | N | CH | N |
| 3228. | 1 | S | H | Ph | H | 2,6-diisopropylphenyl | H | H | CH | N | CH | N |
| 3229. | 1 | S | H | 2,6-dimethylphenyl | H | $CH_3$ | H | H | CH | N | CH | N |

-continued

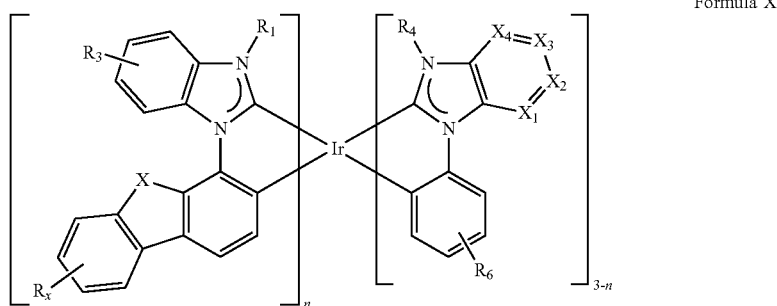

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3230. | 1 | S | H | 2,6-dimethylphenyl | H | $CH(CH_3)_2$ | H | H | CH | N | CH | N |
| 3231. | 1 | S | H | 2,6-dimethylphenyl | H | $CH_2CH(CH_3)_2$ | H | H | CH | N | CH | N |
| 3232. | 1 | S | H | 2,6-dimethylphenyl | H | $C_6H_{11}$ | H | H | CH | N | CH | N |
| 3233. | 1 | S | H | 2,6-dimethylphenyl | H | Ph | H | H | CH | N | CH | N |
| 3234. | 1 | S | H | 2,6-dimethylphenyl | H | 2,6-dimethylphenyl | H | H | CH | N | CH | N |
| 3235. | 1 | S | H | 2,6-dimethylphenyl | H | 2,6-diisopropylphenyl | H | H | CH | N | CH | N |
| 3236. | 1 | S | H | 2,6-diisopropylphenyl | H | $CH_3$ | H | H | CH | N | CH | N |
| 3237. | 1 | S | H | 2,6-diisopropylphenyl | H | $CH(CH_3)_2$ | H | H | CH | N | CH | N |
| 3238. | 1 | S | H | 2,6-diisopropylphenyl | H | $CH_2CH(CH_3)_2$ | H | H | CH | N | CH | N |
| 3239. | 1 | S | H | 2,6-diisopropylphenyl | H | $C_6H_{11}$ | H | H | CH | N | CH | N |
| 3240. | 1 | S | H | 2,6-diisopropylphenyl | H | Ph | H | H | CH | N | CH | N |
| 3241. | 1 | S | H | 2,6-diisopropylphenyl | H | 2,6-dimethylphenyl | H | H | CH | N | CH | N |
| 3242. | 1 | S | H | 2,6-diisopropylphenyl | H | 2,6-diisopropylphenyl | H | H | CH | N | CH | N |
| 3243. | 2 | O | H | $CH_3$ | H | $CH_3$ | H | H | CH | N | CH | N |
| 3244. | 2 | O | H | $CH_3$ | H | $CH(CH_3)_2$ | H | H | CH | N | CH | N |
| 3245. | 2 | O | H | $CH_3$ | H | $CH_2CH(CH_3)_2$ | H | H | CH | N | CH | N |
| 3246. | 2 | O | H | $CH_3$ | H | $C_6H_{11}$ | H | H | CH | N | CH | N |
| 3247. | 2 | O | H | $CH_3$ | H | Ph | H | H | CH | N | CH | N |
| 3248. | 2 | O | H | $CH_3$ | H | 2,6-dimethylphenyl | H | H | CH | N | CH | N |
| 3249. | 2 | O | H | $CH_3$ | H | 2,6-diisopropylphenyl | H | H | CH | N | CH | N |
| 3250. | 2 | O | H | $CH(CH_3)_2$ | H | $CH_3$ | H | H | CH | N | CH | N |
| 3251. | 2 | O | H | $CH(CH_3)_2$ | H | $CH(CH_3)_2$ | H | H | CH | N | CH | N |
| 3252. | 2 | O | H | $CH(CH_3)_2$ | H | $CH_2CH(CH_3)_2$ | H | H | CH | N | CH | N |
| 3253. | 2 | O | H | $CH(CH_3)_2$ | H | $C_6H_{11}$ | H | H | CH | N | CH | N |
| 3254. | 2 | O | H | $CH(CH_3)_2$ | H | Ph | H | H | CH | N | CH | N |
| 3255. | 2 | O | H | $CH(CH_3)_2$ | H | 2,6-dimethylphenyl | H | H | CH | N | CH | N |
| 3256. | 2 | O | H | $CH(CH_3)_2$ | H | 2,6-diisopropylphenyl | H | H | CH | N | CH | N |
| 3257. | | | | | | | | | CH | N | CH | N |
| 3258. | 2 | O | H | $CH_2CH(CH_3)_2$ | H | $CH_3$ | H | H | CH | N | CH | N |
| 3259. | 2 | O | H | $CH_2CH(CH_3)_2$ | H | $CH(CH_3)_2$ | H | H | CH | N | CH | N |
| 3260. | 2 | O | H | $CH_2CH(CH_3)_2$ | H | $CH_2CH(CH_3)_2$ | H | H | CH | N | CH | N |
| 3261. | 2 | O | H | $CH_2CH(CH_3)_2$ | H | $C_6H_{11}$ | H | H | CH | N | CH | N |
| 3262. | 2 | O | H | $CH_2CH(CH_3)_2$ | H | Ph | H | H | CH | N | CH | N |
| 3263. | 2 | O | H | $CH_2CH(CH_3)_2$ | H | 2,6-dimethylphenyl | H | H | CH | N | CH | N |
| 3264. | 2 | O | H | $CH_2CH(CH_3)_2$ | H | 2,6-diisopropylphenyl | H | H | CH | N | CH | N |
| 3265. | 2 | O | H | $C_6H_{11}$ | H | $CH_3$ | H | H | CH | N | CH | N |
| 3266. | 2 | O | H | $C_6H_{11}$ | H | $CH(CH_3)_2$ | H | H | CH | N | CH | N |
| 3267. | 2 | O | H | $C_6H_{11}$ | H | $CH_2CH(CH_3)_2$ | H | H | CH | N | CH | N |
| 3268. | 2 | O | H | $C_6H_{11}$ | H | $C_6H_{11}$ | H | H | CH | N | CH | N |
| 3269. | 2 | O | H | $C_6H_{11}$ | H | Ph | H | H | CH | N | CH | N |
| 3270. | 2 | O | H | $C_6H_{11}$ | H | 2,6-dimethylphenyl | H | H | CH | N | CH | N |
| 3271. | 2 | O | H | $C_6H_{11}$ | H | 2,6-diisopropylphenyl | H | H | CH | N | CH | N |
| 3272. | 2 | O | H | Ph | H | $CH_3$ | H | H | CH | N | CH | N |
| 3273. | 2 | O | H | Ph | H | $CH(CH_3)_2$ | H | H | CH | N | CH | N |
| 3274. | 2 | O | H | Ph | H | $CH_2CH(CH_3)_2$ | H | H | CH | N | CH | N |
| 3275. | 2 | O | H | Ph | H | $C_6H_{11}$ | H | H | CH | N | CH | N |
| 3276. | 2 | O | H | Ph | H | Ph | H | H | CH | N | CH | N |
| 3277. | 2 | O | H | Ph | H | 2,6-dimethylphenyl | H | H | CH | N | CH | N |
| 3278. | 2 | O | H | Ph | H | 2,6-diisopropylphenyl | H | H | CH | N | CH | N |
| 3279. | 2 | O | H | 2,6-dimethylphenyl | H | $CH_3$ | H | H | CH | N | CH | N |
| 3280. | 2 | O | H | 2,6-dimethylphenyl | H | $CH(CH_3)_2$ | H | H | CH | N | CH | N |
| 3281. | 2 | O | H | 2,6-dimethylphenyl | H | $CH_2CH(CH_3)_2$ | H | H | CH | N | CH | N |
| 3282. | 2 | O | H | 2,6-dimethylphenyl | H | $C_6H_{11}$ | H | H | CH | N | CH | N |
| 3283. | 2 | O | H | 2,6-dimethylphenyl | H | Ph | H | H | CH | N | CH | N |
| 3284. | 2 | O | H | 2,6-dimethylphenyl | H | 2,6-dimethylphenyl | H | H | CH | N | CH | N |
| 3285. | 2 | O | H | 2,6-dimethylphenyl | H | 2,6-diisopropylphenyl | H | H | CH | N | CH | N |
| 3286. | 2 | O | H | 2,6-diisopropylphenyl | H | $CH_3$ | H | H | CH | N | CH | N |
| 3287. | 2 | O | H | 2,6-diisopropylphenyl | H | $CH(CH_3)_2$ | H | H | CH | N | CH | N |
| 3288. | 2 | O | H | 2,6-diisopropylphenyl | H | $CH_2CH(CH_3)_2$ | H | H | CH | N | CH | N |

-continued

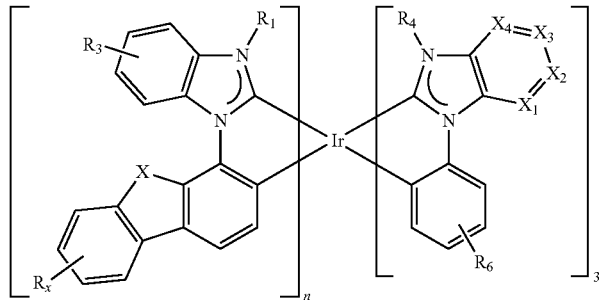

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3289. | 2 | O | H | 2,6-diisopropylphenyl | H | $C_6H_{11}$ | H | H | CH | N | CH | N |
| 3290. | 2 | O | H | 2,6-diisopropylphenyl | H | Ph | H | H | CH | N | CH | N |
| 3291. | 2 | O | H | 2,6-diisopropylphenyl | H | 2,6-dimethylphenyl | H | H | CH | N | CH | N |
| 3292. | 2 | O | H | 2,6-diisopropylphenyl | H | 2,6-diisopropylphenyl | H | H | CH | N | CH | N |
| 3293. | 2 | S | H | $CH_3$ | H | $CH_3$ | H | H | CH | N | CH | N |
| 3294. | 2 | S | H | $CH_3$ | H | $CH(CH_3)_2$ | H | H | CH | N | CH | N |
| 3295. | 2 | S | H | $CH_3$ | H | $CH_2CH(CH_3)_2$ | H | H | CH | N | CH | N |
| 3296. | 2 | S | H | $CH_3$ | H | $C_6H_{11}$ | H | H | CH | N | CH | N |
| 3297. | 2 | S | H | $CH_3$ | H | Ph | H | H | CH | N | CH | N |
| 3298. | 2 | S | H | $CH_3$ | H | 2,6-dimethylphenyl | H | H | CH | N | CH | N |
| 3299. | 2 | S | H | $CH_3$ | H | 2,6-diisopropylphenyl | H | H | CH | N | CH | N |
| 3300. | 2 | S | H | $CH(CH_3)_2$ | H | $CH_3$ | H | H | CH | N | CH | N |
| 3301. | 2 | S | H | $CH(CH_3)_2$ | H | $CH(CH_3)_2$ | H | H | CH | N | CH | N |
| 3302. | 2 | S | H | $CH(CH_3)_2$ | H | $CH_2CH(CH_3)_2$ | H | H | CH | N | CH | N |
| 3303. | 2 | S | H | $CH(CH_3)_2$ | H | $C_6H_{11}$ | H | H | CH | N | CH | N |
| 3304. | 2 | S | H | $CH(CH_3)_2$ | H | Ph | H | H | CH | N | CH | N |
| 3305. | 2 | S | H | $CH(CH_3)_2$ | H | 2,6-dimethylphenyl | H | H | CH | N | CH | N |
| 3306. | 2 | S | H | $CH(CH_3)_2$ | H | 2,6-diisopropylphenyl | H | H | CH | N | CH | N |
| 3307. | 2 | S | H | $CH_2CH(CH_3)_2$ | H | $CH_3$ | H | H | CH | N | CH | N |
| 3308. | 2 | S | H | $CH_2CH(CH_3)_2$ | H | $CH(CH_3)_2$ | H | H | CH | N | CH | N |
| 3309. | 2 | S | H | $CH_2CH(CH_3)_2$ | H | $CH_2CH(CH_3)_2$ | H | H | CH | N | CH | N |
| 3310. | 2 | S | H | $CH_2CH(CH_3)_2$ | H | $C_6H_{11}$ | H | H | CH | N | CH | N |
| 3311. | 2 | S | H | $CH_2CH(CH_3)_2$ | H | Ph | H | H | CH | N | CH | N |
| 3312. | 2 | S | H | $CH_2CH(CH_3)_2$ | H | 2,6-dimethylphenyl | H | H | CH | N | CH | N |
| 3313. | 2 | S | H | $CH_2CH(CH_3)_2$ | H | 2,6-diisopropylphenyl | H | H | CH | N | CH | N |
| 3314. | 2 | S | H | $C_6H_{11}$ | H | $CH_3$ | H | H | CH | N | CH | N |
| 3315. | 2 | S | H | $C_6H_{11}$ | H | $CH(CH_3)_2$ | H | H | CH | N | CH | N |
| 3316. | 2 | S | H | $C_6H_{11}$ | H | $CH_2CH(CH_3)_2$ | H | H | CH | N | CH | N |
| 3317. | 2 | S | H | $C_6H_{11}$ | H | $C_6H_{11}$ | H | H | CH | N | CH | N |
| 3318. | 2 | S | H | $C_6H_{11}$ | H | Ph | H | H | CH | N | CH | N |
| 3319. | 2 | S | H | $C_6H_{11}$ | H | 2,6-dimethylphenyl | H | H | CH | N | CH | N |
| 3320. | 2 | S | H | $C_6H_{11}$ | H | 2,6-diisopropylphenyl | H | H | CH | N | CH | N |
| 3321. | 2 | S | H | Ph | H | $CH_3$ | H | H | CH | N | CH | N |
| 3322. | 2 | S | H | Ph | H | $CH(CH_3)_2$ | H | H | CH | N | CH | N |
| 3323. | 2 | S | H | Ph | H | $CH_2CH(CH_3)_2$ | H | H | CH | N | CH | N |
| 3324. | 2 | S | H | Ph | H | $C_6H_{11}$ | H | H | CH | N | CH | N |
| 3325. | 2 | S | H | Ph | H | Ph | H | H | CH | N | CH | N |
| 3326. | 2 | S | H | Ph | H | 2,6-dimethylphenyl | H | H | CH | N | CH | N |
| 3327. | 2 | S | H | Ph | H | 2,6-diisopropylphenyl | H | H | CH | N | CH | N |
| 3328. | 2 | S | H | 2,6-dimethylphenyl | H | $CH_3$ | H | H | CH | N | CH | N |
| 3329. | 2 | S | H | 2,6-dimethylphenyl | H | $CH(CH_3)_2$ | H | H | CH | N | CH | N |
| 3330. | 2 | S | H | 2,6-dimethylphenyl | H | $CH_2CH(CH_3)_2$ | H | H | CH | N | CH | N |
| 3331. | 2 | S | H | 2,6-dimethylphenyl | H | $C_6H_{11}$ | H | H | CH | N | CH | N |
| 3332. | 2 | S | H | 2,6-dimethylphenyl | H | Ph | H | H | CH | N | CH | N |
| 3333. | 2 | S | H | 2,6-dimethylphenyl | H | 2,6-dimethylphenyl | H | H | CH | N | CH | N |
| 3334. | 2 | S | H | 2,6-dimethylphenyl | H | 2,6-diisopropylphenyl | H | H | CH | N | CH | N |
| 3335. | 2 | S | H | 2,6-diisopropylphenyl | H | $CH_3$ | H | H | CH | N | CH | N |
| 3336. | 2 | S | H | 2,6-diisopropylphenyl | H | $CH(CH_3)_2$ | H | H | CH | N | CH | N |
| 3337. | 2 | S | H | 2,6-diisopropylphenyl | H | $CH_2CH(CH_3)_2$ | H | H | CH | N | CH | N |
| 3338. | 2 | S | H | 2,6-diisopropylphenyl | H | $C_6H_{11}$ | H | H | CH | N | CH | N |
| 3339. | 2 | S | H | 2,6-diisopropylphenyl | H | Ph | H | H | CH | N | CH | N |
| 3340. | 2 | S | H | 2,6-diisopropylphenyl | H | 2,6-dimethylphenyl | H | H | CH | N | CH | N |
| 3341. | 2 | S | H | 2,6-diisopropylphenyl | H | 2,6-diisopropylphenyl | H | H | CH | N | CH | N |
| 3342. | 1 | O | H | $CH_3$ | H | $CH_3$ | H | H | N | CH | CH | N |
| 3343. | 1 | O | H | $CH_3$ | H | $CH(CH_3)_2$ | H | H | N | CH | CH | N |
| 3344. | 1 | O | H | $CH_3$ | H | $CH_2CH(CH_3)_2$ | H | H | N | CH | CH | N |
| 3345. | 1 | O | H | $CH_3$ | H | $C_6H_{11}$ | H | H | N | CH | CH | N |
| 3346. | 1 | O | H | $CH_3$ | H | Ph | H | H | N | CH | CH | N |
| 3347. | 1 | O | H | $CH_3$ | H | 2,6-dimethylphenyl | H | H | N | CH | CH | N |

-continued

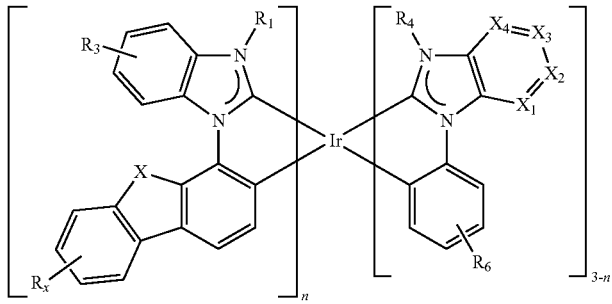

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3348. | 1 | O | H | $CH_3$ | H | 2,6-diisopropylphenyl | H | H | N | CH | CH | N |
| 3349. | 1 | O | H | $CH(CH_3)_2$ | H | $CH_3$ | H | H | N | CH | CH | N |
| 3350. | 1 | O | H | $CH(CH_3)_2$ | H | $CH(CH_3)_2$ | H | H | N | CH | CH | N |
| 3351. | 1 | O | H | $CH(CH_3)_2$ | H | $CH_2CH(CH_3)_2$ | H | H | N | CH | CH | N |
| 3352. | 1 | O | H | $CH(CH_3)_2$ | H | $C_6H_{11}$ | H | H | N | CH | CH | N |
| 3353. | 1 | O | H | $CH(CH_3)_2$ | H | Ph | H | H | N | CH | CH | N |
| 3354. | 1 | O | H | $CH(CH_3)_2$ | H | 2,6-dimethylphenyl | H | H | N | CH | CH | N |
| 3355. | 1 | O | H | $CH(CH_3)_2$ | H | 2,6-diisopropylphenyl | H | H | N | CH | CH | N |
| 3356. | 1 | O | H | $CH_2CH(CH_3)_2$ | H | $CH_3$ | H | H | N | CH | CH | N |
| 3357. | 1 | O | H | $CH_2CH(CH_3)_2$ | H | $CH(CH_3)_2$ | H | H | N | CH | CH | N |
| 3358. | 1 | O | H | $CH_2CH(CH_3)_2$ | H | $CH_2CH(CH_3)_2$ | H | H | N | CH | CH | N |
| 3359. | 1 | O | H | $CH_2CH(CH_3)_2$ | H | $C_6H_{11}$ | H | H | N | CH | CH | N |
| 3360. | 1 | O | H | $CH_2CH(CH_3)_2$ | H | Ph | H | H | N | CH | CH | N |
| 3361. | 1 | O | H | $CH_2CH(CH_3)_2$ | H | 2,6-dimethylphenyl | H | H | N | CH | CH | N |
| 3362. | 1 | O | H | $CH_2CH(CH_3)_2$ | H | 2,6-diisopropylphenyl | H | H | N | CH | CH | N |
| 3363. | 1 | O | H | $C_6H_{11}$ | H | $CH_3$ | H | H | N | CH | CH | N |
| 3364. | 1 | O | H | $C_6H_{11}$ | H | $CH(CH_3)_2$ | H | H | N | CH | CH | N |
| 3365. | 1 | O | H | $C_6H_{11}$ | H | $CH_2CH(CH_3)_2$ | H | H | N | CH | CH | N |
| 3366. | 1 | O | H | $C_6H_{11}$ | H | $C_6H_{11}$ | H | H | N | CH | CH | N |
| 3367. | 1 | O | H | $C_6H_{11}$ | H | Ph | H | H | N | CH | CH | N |
| 3368. | 1 | O | H | $C_6H_{11}$ | H | 2,6-dimethylphenyl | H | H | N | CH | CH | N |
| 3369. | 1 | O | H | $C_6H_{11}$ | H | 2,6-diisopropylphenyl | H | H | N | CH | CH | N |
| 3370. | 1 | O | H | Ph | H | $CH_3$ | H | H | N | CH | CH | N |
| 3371. | 1 | O | H | Ph | H | $CH(CH_3)_2$ | H | H | N | CH | CH | N |
| 3372. | 1 | O | H | Ph | H | $CH_2CH(CH_3)_2$ | H | H | N | CH | CH | N |
| 3373. | 1 | O | H | Ph | H | $C_6H_{11}$ | H | H | N | CH | CH | N |
| 3374. | 1 | O | H | Ph | H | Ph | H | H | N | CH | CH | N |
| 3375. | 1 | O | H | Ph | H | 2,6-dimethylphenyl | H | H | N | CH | CH | N |
| 3376. | 1 | O | H | Ph | H | 2,6-diisopropylphenyl | H | H | N | CH | CH | N |
| 3377. | 1 | O | H | 2,6-dimethylphenyl | H | $CH_3$ | H | H | N | CH | CH | N |
| 3378. | 1 | O | H | 2,6-dimethylphenyl | H | $CH(CH_3)_2$ | H | H | N | CH | CH | N |
| 3379. | 1 | O | H | 2,6-dimethylphenyl | H | $CH_2CH(CH_3)_2$ | H | H | N | CH | CH | N |
| 3380. | 1 | O | H | 2,6-dimethylphenyl | H | $C_6H_{11}$ | H | H | N | CH | CH | N |
| 3381. | 1 | O | H | 2,6-dimethylphenyl | H | Ph | H | H | N | CH | CH | N |
| 3382. | 1 | O | H | 2,6-dimethylphenyl | H | 2,6-dimethylphenyl | H | H | N | CH | CH | N |
| 3383. | 1 | O | H | 2,6-dimethylphenyl | H | 2,6-diisopropylphenyl | H | H | N | CH | CH | N |
| 3384. | 1 | O | H | 2,6-diisopropylphenyl | H | $CH_3$ | H | H | N | CH | CH | N |
| 3385. | 1 | O | H | 2,6-diisopropylphenyl | H | $CH(CH_3)_2$ | H | H | N | CH | CH | N |
| 3386. | 1 | O | H | 2,6-diisopropylphenyl | H | $CH_2CH(CH_3)_2$ | H | H | N | CH | CH | N |
| 3387. | 1 | O | H | 2,6-diisopropylphenyl | H | $C_6H_{11}$ | H | H | N | CH | CH | N |
| 3388. | 1 | O | H | 2,6-diisopropylphenyl | H | Ph | H | H | N | CH | CH | N |
| 3389. | 1 | O | H | 2,6-diisopropylphenyl | H | 2,6-dimethylphenyl | H | H | N | CH | CH | N |
| 3390. | 1 | O | H | 2,6-diisopropylphenyl | H | 2,6-diisopropylphenyl | H | H | N | CH | CH | N |
| 3391. | 1 | S | H | $CH_3$ | H | $CH_3$ | H | H | N | CH | CH | N |
| 3392. | 1 | S | H | $CH_3$ | H | $CH(CH_3)_2$ | H | H | N | CH | CH | N |
| 3393. | 1 | S | H | $CH_3$ | H | $CH_2CH(CH_3)_2$ | H | H | N | CH | CH | N |
| 3394. | 1 | S | H | $CH_3$ | H | $C_6H_{11}$ | H | H | N | CH | CH | N |
| 3395. | 1 | S | H | $CH_3$ | H | Ph | H | H | N | CH | CH | N |
| 3396. | 1 | S | H | $CH_3$ | H | 2,6-dimethylphenyl | H | H | N | CH | CH | N |
| 3397. | 1 | S | H | $CH_3$ | H | 2,6-diisopropylphenyl | H | H | N | CH | CH | N |
| 3398. | 1 | S | H | $CH(CH_3)_2$ | H | $CH_3$ | H | H | N | CH | CH | N |
| 3399. | 1 | S | H | $CH(CH_3)_2$ | H | $CH(CH_3)_2$ | H | H | N | CH | CH | N |
| 3400. | 1 | S | H | $CH(CH_3)_2$ | H | $CH_2CH(CH_3)_2$ | H | H | N | CH | CH | N |
| 3401. | 1 | S | H | $CH(CH_3)_2$ | H | $C_6H_{11}$ | H | H | N | CH | CH | N |
| 3402. | 1 | S | H | $CH(CH_3)_2$ | H | Ph | H | H | N | CH | CH | N |
| 3403. | 1 | S | H | $CH(CH_3)_2$ | H | 2,6-dimethylphenyl | H | H | N | CH | CH | N |
| 3404. | 1 | S | H | $CH(CH_3)_2$ | H | 2,6-diisopropylphenyl | H | H | N | CH | CH | N |
| 3405. | 1 | S | H | $CH_2CH(CH_3)_2$ | H | $CH_3$ | H | H | N | CH | CH | N |
| 3406. | 1 | S | H | $CH_2CH(CH_3)_2$ | H | $CH(CH_3)_2$ | H | H | N | CH | CH | N |

-continued

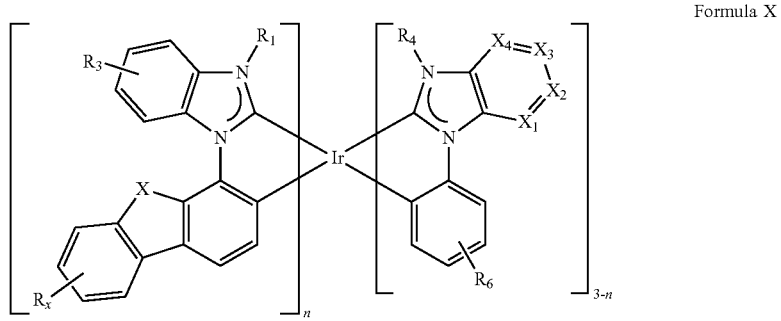

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3407. | 1 | S | H | $CH_2CH(CH_3)_2$ | H | $CH_2CH(CH_3)_2$ | H | H | N | CH | CH | N |
| 3408. | 1 | S | H | $CH_2CH(CH_3)_2$ | H | $C_6H_{11}$ | H | H | N | CH | CH | N |
| 3409. | 1 | S | H | $CH_2CH(CH_3)_2$ | H | Ph | H | H | N | CH | CH | N |
| 3410. | 1 | S | H | $CH_2CH(CH_3)_2$ | H | 2,6-dimethylphenyl | H | H | N | CH | CH | N |
| 3411. | 1 | S | H | $CH_2CH(CH_3)_2$ | H | 2,6-diisopropylphenyl | H | H | N | CH | CH | N |
| 3412. | 1 | S | H | $C_6H_{11}$ | H | $CH_3$ | H | H | N | CH | CH | N |
| 3413. | 1 | S | H | $C_6H_{11}$ | H | $CH(CH_3)_2$ | H | H | N | CH | CH | N |
| 3414. | 1 | S | H | $C_6H_{11}$ | H | $CH_2CH(CH_3)_2$ | H | H | N | CH | CH | N |
| 3415. | 1 | S | H | $C_6H_{11}$ | H | $C_6H_{11}$ | H | H | N | CH | CH | N |
| 3416. | 1 | S | H | $C_6H_{11}$ | H | Ph | H | H | N | CH | CH | N |
| 3417. | 1 | S | H | $C_6H_{11}$ | H | 2,6-dimethylphenyl | H | H | N | CH | CH | N |
| 3418. | 1 | S | H | $C_6H_{11}$ | H | 2,6-diisopropylphenyl | H | H | N | CH | CH | N |
| 3419. | 1 | S | H | Ph | H | $CH_3$ | H | H | N | CH | CH | N |
| 3420. | 1 | S | H | Ph | H | $CH(CH_3)_2$ | H | H | N | CH | CH | N |
| 3421. | 1 | S | H | Ph | H | $CH_2CH(CH_3)_2$ | H | H | N | CH | CH | N |
| 3422. | 1 | S | H | Ph | H | $C_6H_{11}$ | H | H | N | CH | CH | N |
| 3423. | 1 | S | H | Ph | H | Ph | H | H | N | CH | CH | N |
| 3424. | 1 | S | H | Ph | H | 2,6-dimethylphenyl | H | H | N | CH | CH | N |
| 3425. | 1 | S | H | Ph | H | 2,6-diisopropylphenyl | H | H | N | CH | CH | N |
| 3426. | 1 | S | H | 2,6-dimethylphenyl | H | $CH_3$ | H | H | N | CH | CH | N |
| 3427. | 1 | S | H | 2,6-dimethylphenyl | H | $CH(CH_3)_2$ | H | H | N | CH | CH | N |
| 3428. | 1 | S | H | 2,6-dimethylphenyl | H | $CH_2CH(CH_3)_2$ | H | H | N | CH | CH | N |
| 3429. | 1 | S | H | 2,6-dimethylphenyl | H | $C_6H_{11}$ | H | H | N | CH | CH | N |
| 3430. | 1 | S | H | 2,6-dimethylphenyl | H | Ph | H | H | N | CH | CH | N |
| 3431. | 1 | S | H | 2,6-dimethylphenyl | H | 2,6-dimethylphenyl | H | H | N | CH | CH | N |
| 3432. | 1 | S | H | 2,6-dimethylphenyl | H | 2,6-diisopropylphenyl | H | H | N | CH | CH | N |
| 3433. | 1 | S | H | 2,6-diisopropylphenyl | H | $CH_3$ | H | H | N | CH | CH | N |
| 3434. | 1 | S | H | 2,6-diisopropylphenyl | H | $CH(CH_3)_2$ | H | H | N | CH | CH | N |
| 3435. | 1 | S | H | 2,6-diisopropylphenyl | H | $CH_2CH(CH_3)_2$ | H | H | N | CH | CH | N |
| 3436. | 1 | S | H | 2,6-diisopropylphenyl | H | $C_6H_{11}$ | H | H | N | CH | CH | N |
| 3437. | 1 | S | H | 2,6-diisopropylphenyl | H | Ph | H | H | N | CH | CH | N |
| 3438. | 1 | S | H | 2,6-diisopropylphenyl | H | 2,6-dimethylphenyl | H | H | N | CH | CH | N |
| 3439. | 1 | S | H | 2,6-diisopropylphenyl | H | 2,6-diisopropylphenyl | H | H | N | CH | CH | N |
| 3440. | 2 | O | H | $CH_3$ | H | $CH_3$ | H | H | N | CH | CH | N |
| 3441. | 2 | O | H | $CH_3$ | H | $CH(CH_3)_2$ | H | H | N | CH | CH | N |
| 3442. | 2 | O | H | $CH_3$ | H | $CH_2CH(CH_3)_2$ | H | H | N | CH | CH | N |
| 3443. | 2 | O | H | $CH_3$ | H | $C_6H_{11}$ | H | H | N | CH | CH | N |
| 3444. | 2 | O | H | $CH_3$ | H | Ph | H | H | N | CH | CH | N |
| 3445. | 2 | O | H | $CH_3$ | H | 2,6-dimethylphenyl | H | H | N | CH | CH | N |
| 3446. | 2 | O | H | $CH_3$ | H | 2,6-diisopropylphenyl | H | H | N | CH | CH | N |
| 3447. | 2 | O | H | $CH(CH_3)_2$ | H | $CH_3$ | H | H | N | CH | CH | N |
| 3448. | 2 | O | H | $CH(CH_3)_2$ | H | $CH(CH_3)_2$ | H | H | N | CH | CH | N |
| 3449. | 2 | O | H | $CH(CH_3)_2$ | H | $CH_2CH(CH_3)_2$ | H | H | N | CH | CH | N |
| 3450. | 2 | O | H | $CH(CH_3)_2$ | H | $C_6H_{11}$ | H | H | N | CH | CH | N |
| 3451. | 2 | O | H | $CH(CH_3)_2$ | H | Ph | H | H | N | CH | CH | N |
| 3452. | 2 | O | H | $CH(CH_3)_2$ | H | 2,6-dimethylphenyl | H | H | N | CH | CH | N |
| 3453. | 2 | O | H | $CH(CH_3)_2$ | H | 2,6-diisopropylphenyl | H | H | N | CH | CH | N |
| 3454. | | | | | | | | | N | CH | CH | N |
| 3455. | 2 | O | H | $CH_2CH(CH_3)_2$ | H | $CH_3$ | H | H | N | CH | CH | N |
| 3456. | 2 | O | H | $CH_2CH(CH_3)_2$ | H | $CH(CH_3)_2$ | H | H | N | CH | CH | N |
| 3457. | 2 | O | H | $CH_2CH(CH_3)_2$ | H | $CH_2CH(CH_3)_2$ | H | H | N | CH | CH | N |
| 3458. | 2 | O | H | $CH_2CH(CH_3)_2$ | H | $C_6H_{11}$ | H | H | N | CH | CH | N |
| 3459. | 2 | O | H | $CH_2CH(CH_3)_2$ | H | Ph | H | H | N | CH | CH | N |
| 3460. | 2 | O | H | $CH_2CH(CH_3)_2$ | H | 2,6-dimethylphenyl | H | H | N | CH | CH | N |
| 3461. | 2 | O | H | $CH_2CH(CH_3)_2$ | H | 2,6-diisopropylphenyl | H | H | N | CH | CH | N |
| 3462. | 2 | O | H | $C_6H_{11}$ | H | $CH_3$ | H | H | N | CH | CH | N |
| 3463. | 2 | O | H | $C_6H_{11}$ | H | $CH(CH_3)_2$ | H | H | N | CH | CH | N |
| 3464. | 2 | O | H | $C_6H_{11}$ | H | $CH_2CH(CH_3)_2$ | H | H | N | CH | CH | N |
| 3465. | 2 | O | H | $C_6H_{11}$ | H | $C_6H_{11}$ | H | H | N | CH | CH | N |

-continued

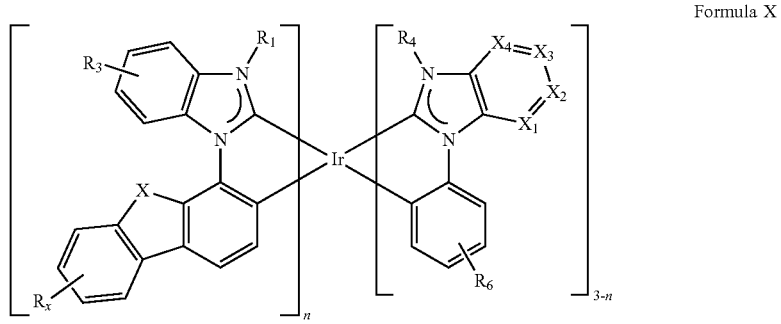

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3466. | 2 | O | H | $C_6H_{11}$ | H | Ph | H | H | N | CH | CH | N |
| 3467. | 2 | O | H | $C_6H_{11}$ | H | 2,6-dimethylphenyl | H | H | N | CH | CH | N |
| 3468. | 2 | O | H | $C_6H_{11}$ | H | 2,6-diisopropylphenyl | H | H | N | CH | CH | N |
| 3469. | 2 | O | H | Ph | H | $CH_3$ | H | H | N | CH | CH | N |
| 3470. | 2 | O | H | Ph | H | $CH(CH_3)_2$ | H | H | N | CH | CH | N |
| 3471. | 2 | O | H | Ph | H | $CH_2CH(CH_3)_2$ | H | H | N | CH | CH | N |
| 3472. | 2 | O | H | Ph | H | $C_6H_{11}$ | H | H | N | CH | CH | N |
| 3473. | 2 | O | H | Ph | H | Ph | H | H | N | CH | CH | N |
| 3474. | 2 | O | H | Ph | H | 2,6-dimethylphenyl | H | H | N | CH | CH | N |
| 3475. | 2 | O | H | Ph | H | 2,6-diisopropylphenyl | H | H | N | CH | CH | N |
| 3476. | 2 | O | H | 2,6-dimethylphenyl | H | $CH_3$ | H | H | N | CH | CH | N |
| 3477. | 2 | O | H | 2,6-dimethylphenyl | H | $CH(CH_3)_2$ | H | H | N | CH | CH | N |
| 3478. | 2 | O | H | 2,6-dimethylphenyl | H | $CH_2CH(CH_3)_2$ | H | H | N | CH | CH | N |
| 3479. | 2 | O | H | 2,6-dimethylphenyl | H | $C_6H_{11}$ | H | H | N | CH | CH | N |
| 3480. | 2 | O | H | 2,6-dimethylphenyl | H | Ph | H | H | N | CH | CH | N |
| 3481. | 2 | O | H | 2,6-dimethylphenyl | H | 2,6-dimethylphenyl | H | H | N | CH | CH | N |
| 3482. | 2 | O | H | 2,6-dimethylphenyl | H | 2,6-diisopropylphenyl | H | H | N | CH | CH | N |
| 3483. | 2 | O | H | 2,6-diisopropylphenyl | H | $CH_3$ | H | H | N | CH | CH | N |
| 3484. | 2 | O | H | 2,6-diisopropylphenyl | H | $CH(CH_3)_2$ | H | H | N | CH | CH | N |
| 3485. | 2 | O | H | 2,6-diisopropylphenyl | H | $CH_2CH(CH_3)_2$ | H | H | N | CH | CH | N |
| 3486. | 2 | O | H | 2,6-diisopropylphenyl | H | $C_6H_{11}$ | H | H | N | CH | CH | N |
| 3487. | 2 | O | H | 2,6-diisopropylphenyl | H | Ph | H | H | N | CH | CH | N |
| 3488. | 2 | O | H | 2,6-diisopropylphenyl | H | 2,6-dimethylphenyl | H | H | N | CH | CH | N |
| 3489. | 2 | O | H | 2,6-diisopropylphenyl | H | 2,6-diisopropylphenyl | H | H | N | CH | CH | N |
| 3490. | 2 | S | H | $CH_3$ | H | $CH_3$ | H | H | N | CH | CH | N |
| 3491. | 2 | S | H | $CH_3$ | H | $CH(CH_3)_2$ | H | H | N | CH | CH | N |
| 3492. | 2 | S | H | $CH_3$ | H | $CH_2CH(CH_3)_2$ | H | H | N | CH | CH | N |
| 3493. | 2 | S | H | $CH_3$ | H | $C_6H_{11}$ | H | H | N | CH | CH | N |
| 3494. | 2 | S | H | $CH_3$ | H | Ph | H | H | N | CH | CH | N |
| 3495. | 2 | S | H | $CH_3$ | H | 2,6-dimethylphenyl | H | H | N | CH | CH | N |
| 3496. | 2 | S | H | $CH_3$ | H | 2,6-diisopropylphenyl | H | H | N | CH | CH | N |
| 3497. | 2 | S | H | $CH(CH_3)_2$ | H | $CH_3$ | H | H | N | CH | CH | N |
| 3498. | 2 | S | H | $CH(CH_3)_2$ | H | $CH(CH_3)_2$ | H | H | N | CH | CH | N |
| 3499. | 2 | S | H | $CH(CH_3)_2$ | H | $CH_2CH(CH_3)_2$ | H | H | N | CH | CH | N |
| 3500. | 2 | S | H | $CH(CH_3)_2$ | H | $C_6H_{11}$ | H | H | N | CH | CH | N |
| 3501. | 2 | S | H | $CH(CH_3)_2$ | H | Ph | H | H | N | CH | CH | N |
| 3502. | 2 | S | H | $CH(CH_3)_2$ | H | 2,6-dimethylphenyl | H | H | N | CH | CH | N |
| 3503. | 2 | S | H | $CH(CH_3)_2$ | H | 2,6-diisopropylphenyl | H | H | N | CH | CH | N |
| 3504. | 2 | S | H | $CH_2CH(CH_3)_2$ | H | $CH_3$ | H | H | N | CH | CH | N |
| 3505 | 2 | S | H | $CH_2CH(CH_3)_2$ | H | $CH(CH_3)_2$ | H | H | N | CH | CH | N |
| 3506. | 2 | S | H | $CH_2CH(CH_3)_2$ | H | $CH_2CH(CH_3)_2$ | H | H | N | CH | CH | N |
| 3507. | 2 | S | H | $CH_2CH(CH_3)_2$ | H | $C_6H_{11}$ | H | H | N | CH | CH | N |
| 3508. | 2 | S | H | $CH_2CH(CH_3)_2$ | H | Ph | H | H | N | CH | CH | N |
| 3509. | 2 | S | H | $CH_2CH(CH_3)_2$ | H | 2,6-dimethylphenyl | H | H | N | CH | CH | N |
| 3510. | 2 | S | H | $CH_2CH(CH_3)_2$ | H | 2,6-diisopropylphenyl | H | H | N | CH | CH | N |
| 3511. | 2 | S | H | $C_6H_{11}$ | H | $CH_3$ | H | H | N | CH | CH | N |
| 3512. | 2 | S | H | $C_6H_{11}$ | H | $CH(CH_3)_2$ | H | H | N | CH | CH | N |
| 3513. | 2 | S | H | $C_6H_{11}$ | H | $CH_2CH(CH_3)_2$ | H | H | N | CH | CH | N |
| 3514. | 2 | S | H | $C_6H_{11}$ | H | $C_6H_{11}$ | H | H | N | CH | CH | N |
| 3515. | 2 | S | H | $C_6H_{11}$ | H | Ph | H | H | N | CH | CH | N |
| 3516. | 2 | S | H | $C_6H_{11}$ | H | 2,6-dimethylphenyl | H | H | N | CH | CH | N |
| 3517. | 2 | S | H | $C_6H_{11}$ | H | 2,6-diisopropylphenyl | H | H | N | CH | CH | N |
| 3518. | 2 | S | H | Ph | H | $CH_3$ | H | H | N | CH | CH | N |
| 3519. | 2 | S | H | Ph | H | $CH(CH_3)_2$ | H | H | N | CH | CH | N |
| 3520. | 2 | S | H | Ph | H | $CH_2CH(CH_3)_2$ | H | H | N | CH | CH | N |

-continued

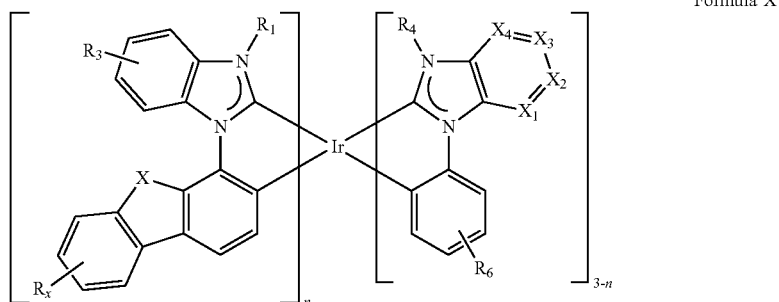

Formula X

Formula X

| Compd. | n | X | $R_x$ | $R_1$ | $R_3$ | $R_4$ | $R_5$ | $R_6$ | $X_1$ | $X_2$ | $X_3$ | $X_4$ |
|---|---|---|---|---|---|---|---|---|---|---|---|---|
| 3521. | 2 | S | H | Ph | H | $C_6H_{11}$ | H | H | N | CH | CH | N |
| 3522. | 2 | S | H | Ph | H | Ph | H | H | N | CH | CH | N |
| 3523. | 2 | S | H | Ph | H | 2,6-dimethylphenyl | H | H | N | CH | CH | N |
| 3524. | 2 | S | H | Ph | H | 2,6-diisopropylphenyl | H | H | N | CH | CH | N |
| 3525. | 2 | S | H | 2,6-dimethylphenyl | H | $CH_3$ | H | H | N | CH | CH | N |
| 3526. | 2 | S | H | 2,6-dimethylphenyl | H | $CH(CH_3)_2$ | H | H | N | CH | CH | N |
| 3527. | 2 | S | H | 2,6-dimethylphenyl | H | $CH_2CH(CH_3)_2$ | H | H | N | CH | CH | N |
| 3528. | 2 | S | H | 2,6-dimethylphenyl | H | $C_6H_{11}$ | H | H | N | CH | CH | N |
| 3529. | 2 | S | H | 2,6-dimethylphenyl | H | Ph | H | H | N | CH | CH | N |
| 3530. | 2 | S | H | 2,6-dimethylphenyl | H | 2,6-dimethylphenyl | H | H | N | CH | CH | N |
| 3531. | 2 | S | H | 2,6-dimethylphenyl | H | 2,6-diisopropylphenyl | H | H | N | CH | CH | N |
| 3532. | 2 | S | H | 2,6-diisopropylphenyl | H | $CH_3$ | H | H | N | CH | CH | N |
| 3533. | 2 | S | H | 2,6-diisopropylphenyl | H | $CH(CH_3)_2$ | H | H | N | CH | CH | N |
| 3534. | 2 | S | H | 2,6-diisopropylphenyl | H | $CH_2CH(CH_3)_2$ | H | H | N | CH | CH | N |
| 3535. | 2 | S | H | 2,6-diisopropylphenyl | H | $C_6H_{11}$ | H | H | N | CH | CH | N |
| 3536. | 2 | S | H | 2,6-diisopropylphenyl | H | Ph | H | H | N | CH | CH | N |
| 3537. | 2 | S | H | 2,6-diisopropylphenyl | H | 2,6-dimethylphenyl | H | H | N | CH | CH | N |
| 3538. | 2 | S | H | 2,6-diisopropylphenyl | H | 2,6-diisopropylphenyl | H | H | N | CH | CH | N |

Many known metal carbene complexes have poor OLED device performance. There are many possible factors can contribute to this poor performance, such as high sublimation temperature of the emitter, long triplet transient lifetime of the emitter, low triplet of the host, unbalanced charges in the device, etc. In the presently disclosed compounds, two different carbene ligands are used to tune the color and photophysical properties in deep blue emitters, making the compounds heteroleptic. Through this approach, different physical properties can be tuned by different set of ligands within a single molecule.

DFT calculations were used to predict the properties of disclosed compounds and comparative compounds. The HOMO, LUMO, the HOMO-LUMO energy gap and triplet energies for each structure were calculated using DFT calculations with the Gaussian software package at the B3LYP/cep-31g functional and basis set. The DFT calculations are summarized in Table 1. Ex. is an abbreviation for Example, Compd. is an abbreviation for Compound, CC is an abbreviation for Comparative Compound.

TABLE 1

DFT results

| Ex. | Compd. No. | Structure | HOMO (eV) | LUMO (eV) | Gap (eV) | $T_1$ (nm) |
|---|---|---|---|---|---|---|
| 1 | 197 | 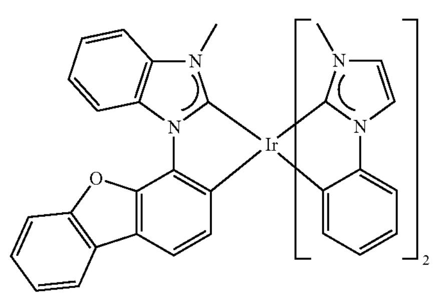 | −4.86 | −0.65 | −4.21 | 453 |

TABLE 1-continued

| | | | DFT results | | | |
|---|---|---|---|---|---|---|
| Ex. | Compd. No. | Structure | HOMO (eV) | LUMO (eV) | Gap (eV) | T$_1$ (nm) |
| 2 | CC1 | | −5.07 | −0.85 | −4.22 | 451 |
| 3 | 4001 | | −4.86 | −1.13 | −3.73 | 451 |
| 4 | CC2 | | −5.15 | −1.38 | −3.76 | 450 |
| 5 | 4002 | | −5.04 | −1.49 | −3.55 | 450 |
| 6 | CC3 | | −5.56 | −1.95 | −3.62 | 448 |

TABLE 1-continued

DFT results

| Ex. | Compd. No. | Structure | HOMO (eV) | LUMO (eV) | Gap (eV) | T₁ (nm) |
|---|---|---|---|---|---|---|
| 7 | 1 | 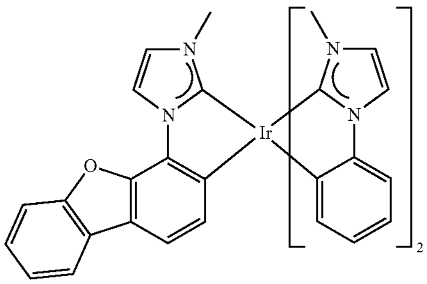 | −4.80 | −0.59 | −4.21 | 451 |
| 8 | 99 | 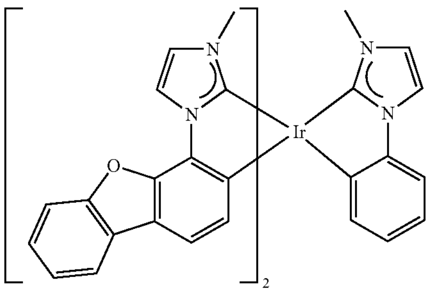 | −4.86 | −0.67 | −4.19 | 451 |
| 9 | CC4 | 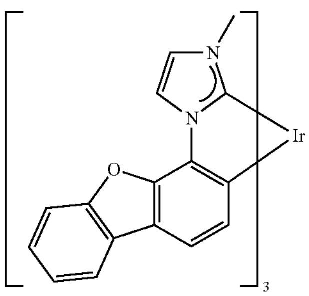 | −4.91 | −0.73 | −4.18 | 451 |
| 10 | 590 | 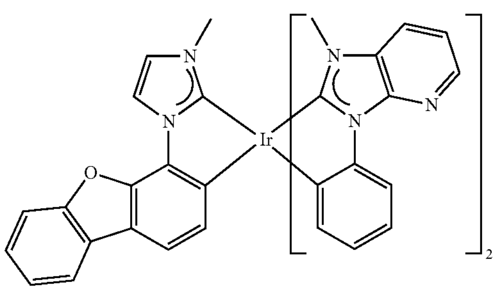 | −5.03 | −1.41 | −3.61 | 448 |
| 11 | 1180 | 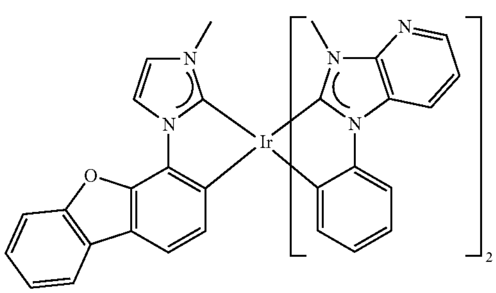 | −5.11 | −1.40 | −3.72 | 448 |

TABLE 1-continued

DFT results

| Ex. | Compd. No. | Structure | HOMO (eV) | LUMO (eV) | Gap (eV) | T₁ (nm) |
|---|---|---|---|---|---|---|
| 12 | 688 | 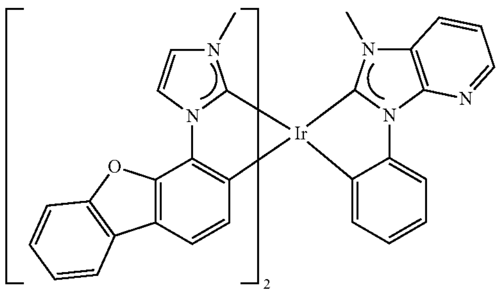 | −4.97 | −1.38 | −3.59 | 449 |
| 13 | 1278 | 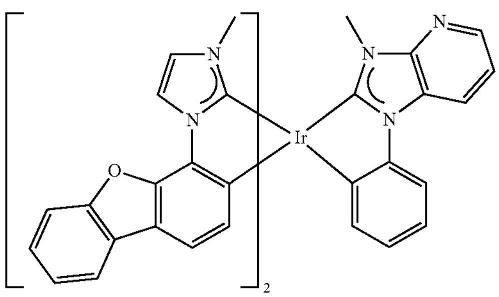 | −5.01 | −1.35 | −3.66 | 449 |

Table 1 shows HOMO, LUMO energy levels, the HOMO-LUMO energy gap and triplet energies for a series of dibenzofuran (DBF) containing heteroleptic carbene complexes, in comparison to homoleptic tris complexes, i.e., CC1 to CC4. It can be seen in this table from Ex. 1 to 9 that when one or two DBF containing carbene ligands in a tris complex is replaced by another carbene complex, for example,

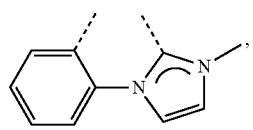

its HOMO energy is raised up in each case while maintaining its T₁ energy. The biggest difference of 0.52 eV can be seen in Ex. 5 vs. Ex. 6. The HOMO of heteroleptic complex 4002 is −5.04 eV, while its tris CC3 is −5.56 eV. Without being bound by theory, it is believed that a higher HOMO energy of an emitter will facilitate the emitter to trap the hole, which can result in better device efficiency and lifetime.

Ex. 10 to 13 are for DBF containing heteroleptic carbene complex with one or two carbene ligands having fused pyridine on imidazole ring. It has been unexpectedly shown that the singlet gaps of these compounds (−3.59 to −3.72 eV.) are much narrower than that of tris compound (−4.18 eV for CC4), and their T₁ energies (448, 449 nm) actually become higher than that of tris compound (451 nm). This is opposite to the usual case that the change of singlet gap of a compound will shift at the same direction as the change of its triplet energy. Without being bound by theory, with a certain triplet emission energy, the emitter having a smaller singlet energy is highly desired. Lowering the singlet energy is expected to reduce the likelihood of singlet excited state decomposition, thereby resulting in improved device lifetimes.

Physical Characterization

Photo physical characterization has been done with inventive complex 4003 vs. comparative complex CC1. PMMA and Ir complex (5 wt %) are weighed out and dissolved in toluene. The solution is filtered through a 2 micron filter and drop cast onto a precleaned quartz substrate. PL quantum efficiency ($\Phi_T$) measurements were carried out on a Hamamatsu C9920 system equipped with a xenon lamp, integrating sphere and a model C10027 photonic multi-channel analyzer. PL transient lifetime ($\tau_T$) measurements were carried out by time correlated single photon counting method using a Horiba Jobin Yvon Fluorolog-3 integrated with an IBH datastation hub using a 335 nm nanoLED as the excitation source. All measurement was conducted at room temperature, and the results are summarized in Table 2.

TABLE 2

Physical Characterization

| Ex. | Compd. No. | Structure | T1 (nm) | $\Phi_T$ (%) | $\tau_T$ (μs) |
|---|---|---|---|---|---|
| 21 | 4003 | 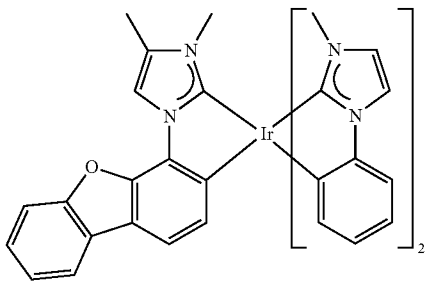 | 450 | 87 | 15 |
| 22 | CC1 | 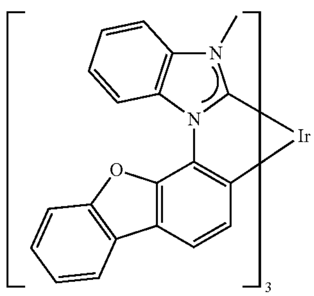 | 442 | 71 | 28 |

Based on the photo physical characterization, it is unexpectedly observed that the heteroleptic carbene complex 4003 has much higher PL quantum efficiency, and smaller PL transient lifetime. Without being bound by theory, a smaller transient lifetime will reduce the chance of decomposition and excited state quenching of triplet exciton of the emitter, which will in turn enhance device performance. A higher PL quantum efficiency value of an emitter is desired for a high efficiency device performance.

Device Examples

Representative device examples are fabricated by high vacuum (<10$^{-7}$ Torr) thermal evaporation (VTE). The anode electrode is 800 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of H$_2$O and O$_2$) immediately after fabrication, and a moisture getter is incorporated inside the package.

The organic stack in representative device examples consists of sequentially, from the ITO surface, 100 Å of LG101 (purchased from LG Chem) as the hole injection layer (HIL), 300 Å of hole transporting layer (HTL), 300 Å of 15 wt % of a compound of Formula I doped in Compound H or other materials as the emissive layer (EML), 50 Å blocking layer (BL), 350 Å Alq as the electron transport layer (ETL). Some representative device structures are shown in Table 3.

Compound A

-continued

Compound B

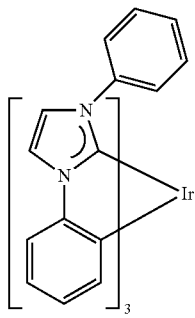

Compound H

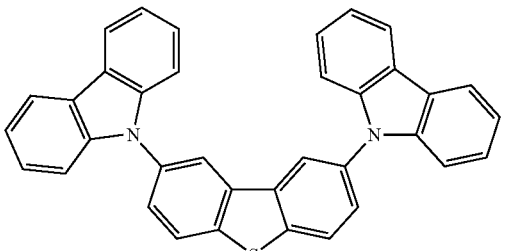

NPD

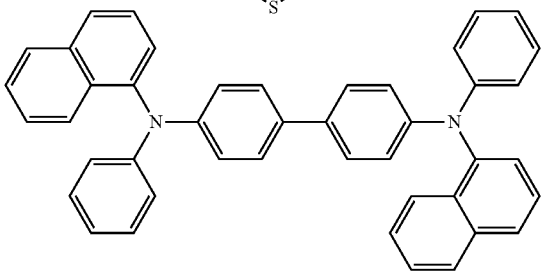

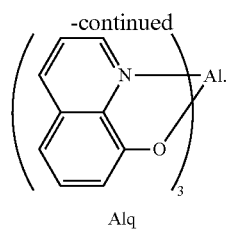

Alq

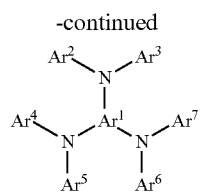

TABLE 3

| | | | VTE Phosphorescent OLEDs | | | |
|---|---|---|---|---|---|---|
| Example | HIL (100 Å) | HTL (300 Å) | EML (300 Å, 15%) | | BL (50 Å) | ETL (350 Å) |
| 31 | LG101 | NPD | Compound H | Compound 4003 | Compound H | Alq |
| 32 | LG101 | NPD | Compound H2 | Compound 4003 | Compound H | Alq |
| 33 | LG101 | Compound B | Compound H2 | Compound 4003 | Compound H | Alq |
| 34 | LG101 | Compound B | Compound H2 | Compound 4003 | Compound H2 | Alq |
| 35 | LG101 | NPD | Compound 590 | Compound A | Compound 590 | Alq |
| 36 | LG101 | Compound 1 | Compound H2 | Compound 4003 | Compound H2 | Alq |
| 37 | LG101 | NPD | Compound H | Compound 1 | Compound H | Alq |
| 38 | LG101 | NPD | Compound H2 | Compound 1 | Compound H | Alq |
| 39 | LG101 | Compound B | Compound H2 | Compound 1 | Compound H | Alq |
| 40 | LG101 | Compound B | Compound H2 | Compound 1 | Compound H2 | Alq |
| 41 | LG101 | Compound 1 | Compound H2 | Compound 1 | Compound H2 | Alq |

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

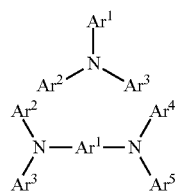

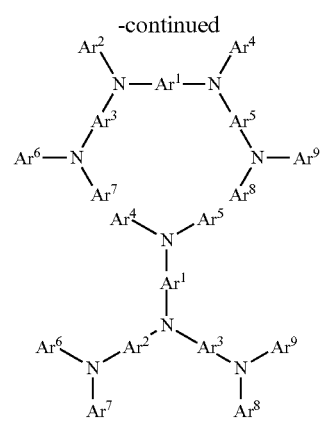

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

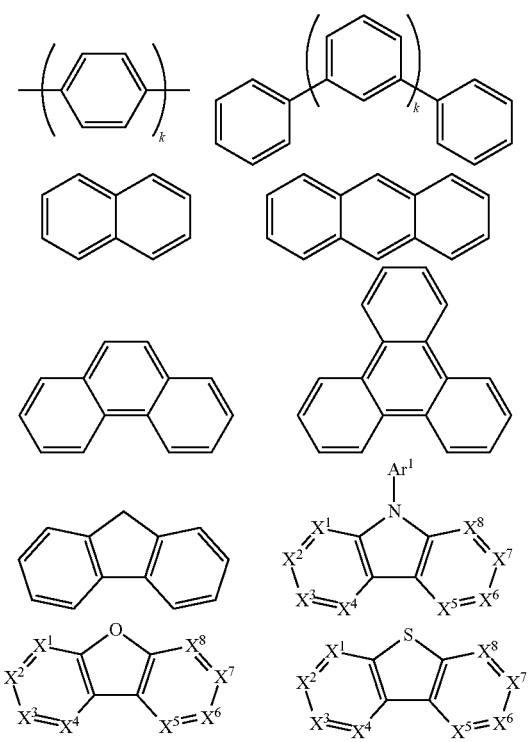

k is an integer from 1 to 20; $X^1$ to $X^8$ is C (including CH) or N; $Ar^1$ has the same group defined above.

Examples of metal complexes used in HIL or HTL include, but not limit to the following general formula:

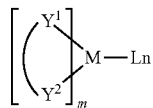

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.
In another aspect, $(Y^1-Y^2)$ is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

Host:
The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

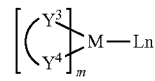

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

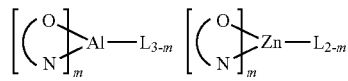

(O—N) is a bidentate ligand, having metal coordinated to atoms O and N.

In another aspect, M is selected from Ir and Pt.
In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom; nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

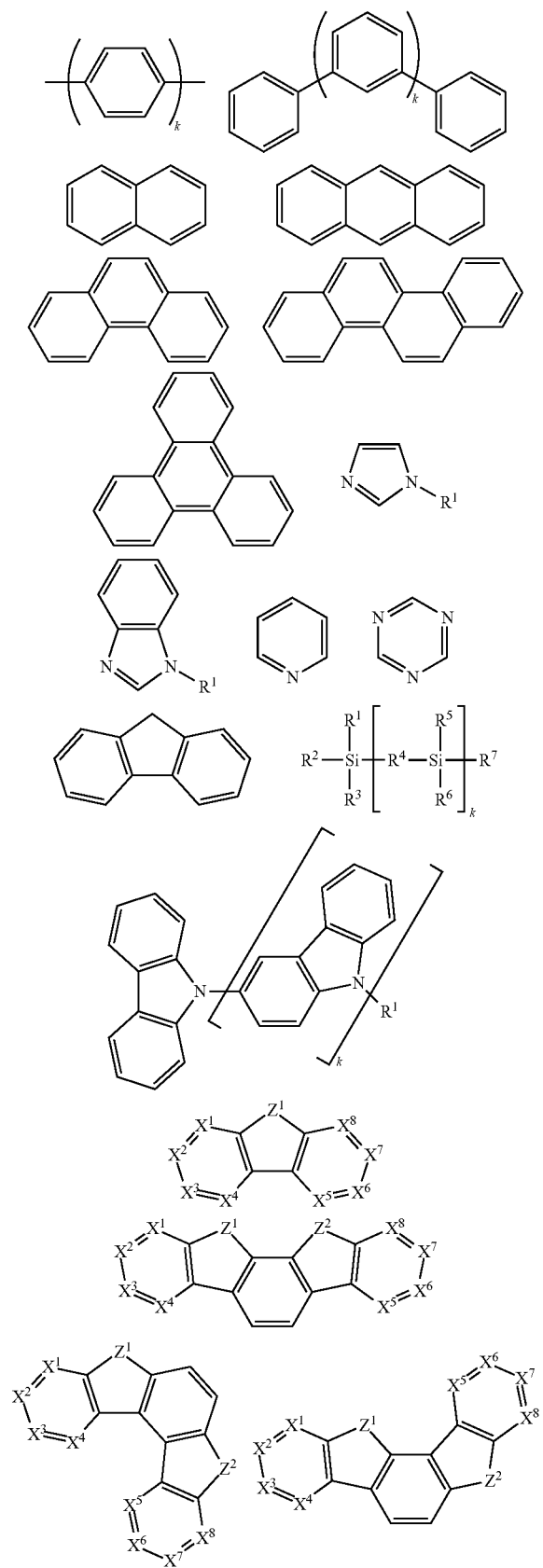

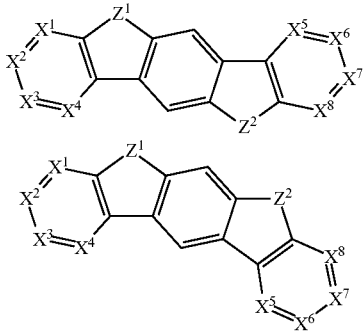

R¹ to R⁷ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X¹ to X⁸ is selected from C (including CH) or N.

Z¹ and Z² is selected from NR¹, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

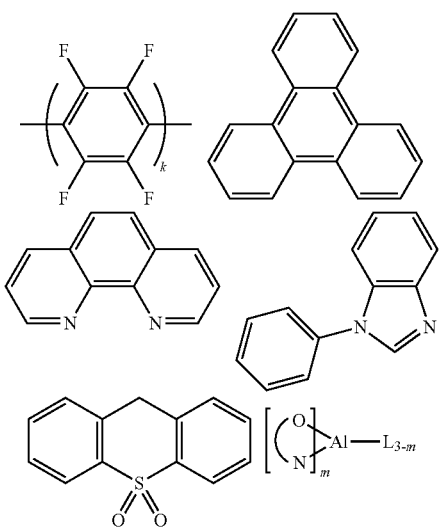

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

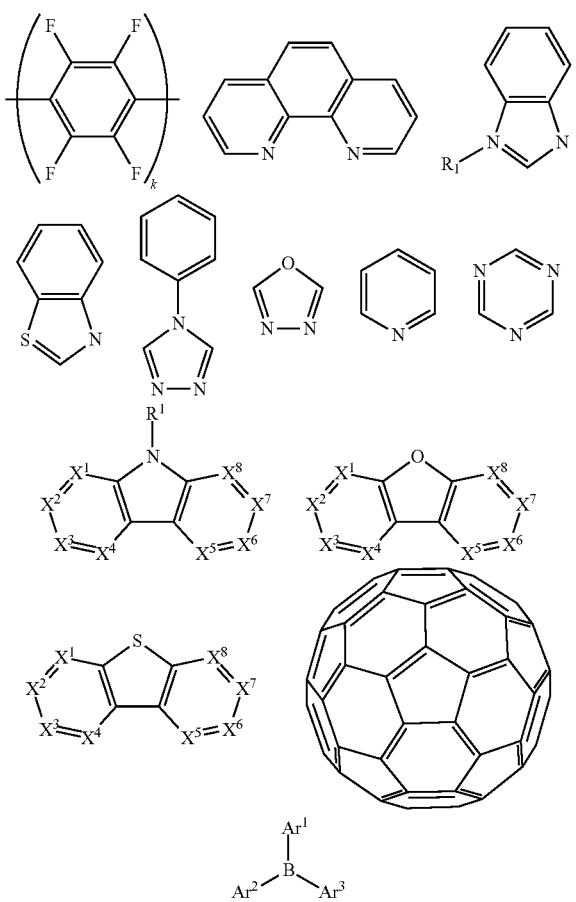

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^a$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

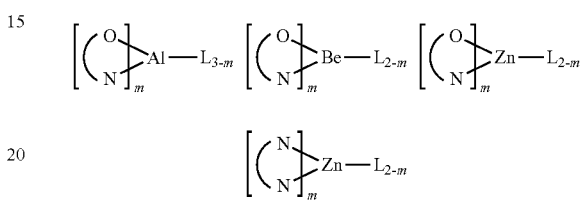

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 4-continued

| MATERIAL | EXAMPLES OF MATERIAL | PUBLICATIONS |
| --- | --- | --- |
| Starburst triarylamines | | J. Lumin. 72-74, 985 (1997) |
| CF$_x$ Fluorohydrocarbon polymer | $-\!\!+\!\text{CH}_x\text{F}_y\!+\!\!-_n$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | and | EP1725079A1 |

TABLE 4-continued
| MATERIAL | EXAMPLES OF MATERIAL | PUBLICATIONS |
|---|---|---|
| | 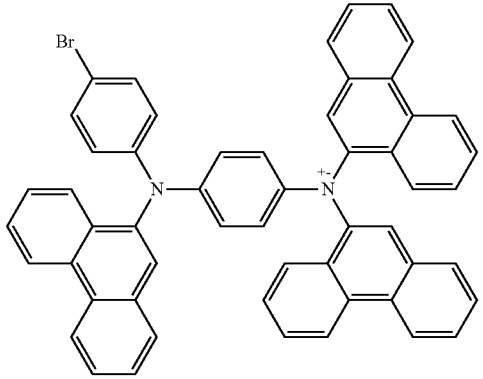 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 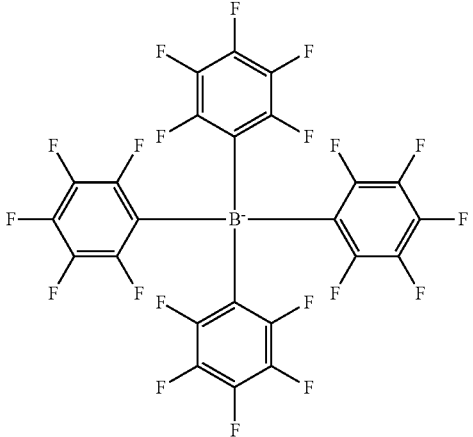 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 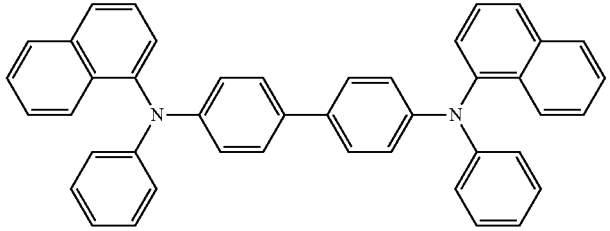 + MoO$_x$ | US20050123751<br>SID Symposium Digest, 37, 923 (2006)<br>WO2009018009 |
| n-type semiconducting organic complexes | 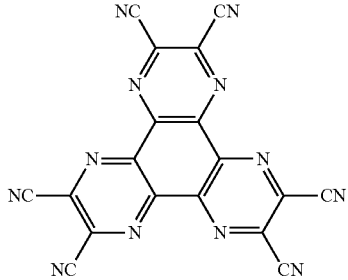 [SMILES: N#Cc1nc2c3nc(C#N)c(C#N)nc3c3nc(C#N)c(C#N)nc3c2nc1C#N] | US20020158242 |
| Metal organometallic complexes | 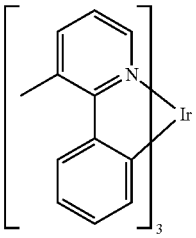 | US20060240279 |

TABLE 4-continued
| MATERIAL | EXAMPLES OF MATERIAL | PUBLICATIONS |
|---|---|---|
| Cross-linkable compounds | 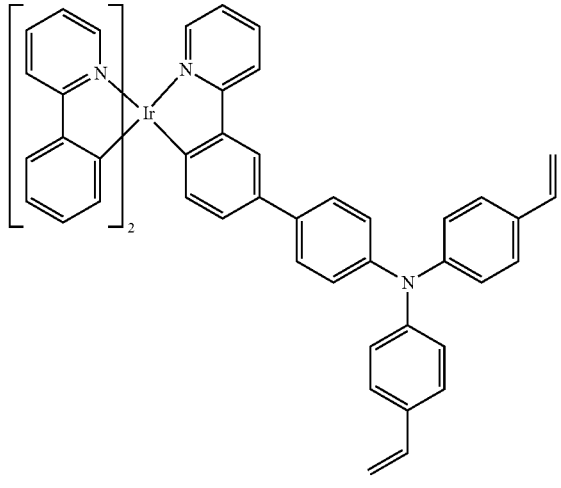 | US20080220265 |
| Polythiophene based polymers and copolymers | 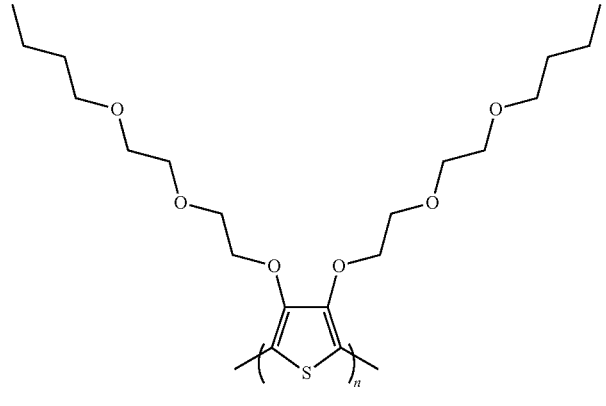 | WO2011075644<br>EP2350216 |
| Hole transporting materials | | |
| Triarylamines (e.g., TPD, α-NPD) | 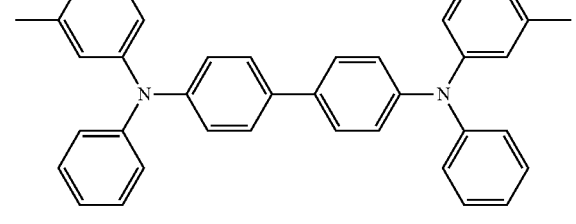 | Appl. Phys. Lett. 51, 913 (1987) |
| | 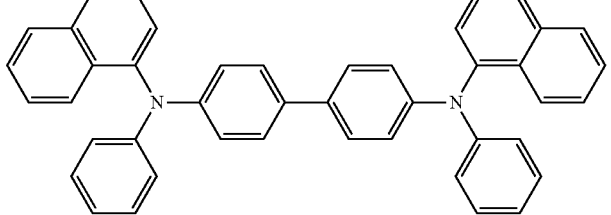 | U.S. Pat. No. 5,061,569 |

TABLE 4-continued
| MATERIAL | EXAMPLES OF MATERIAL | PUBLICATIONS |
|---|---|---|
| | 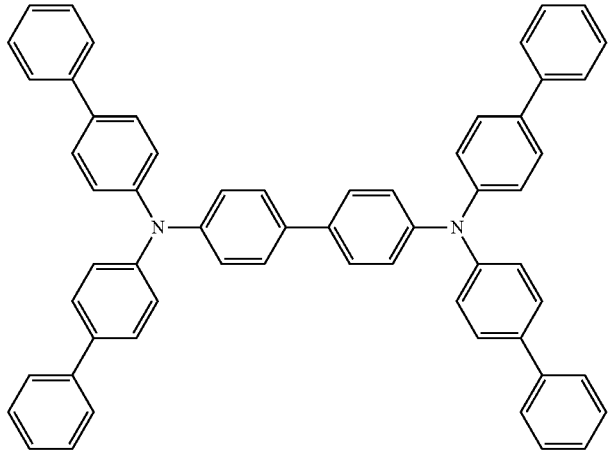 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 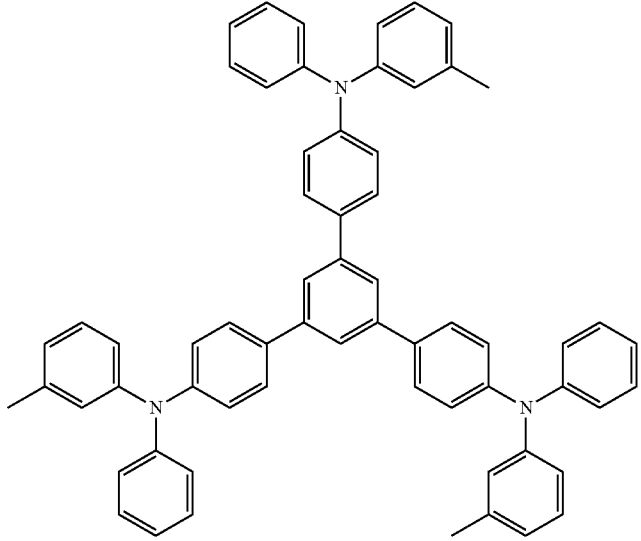 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 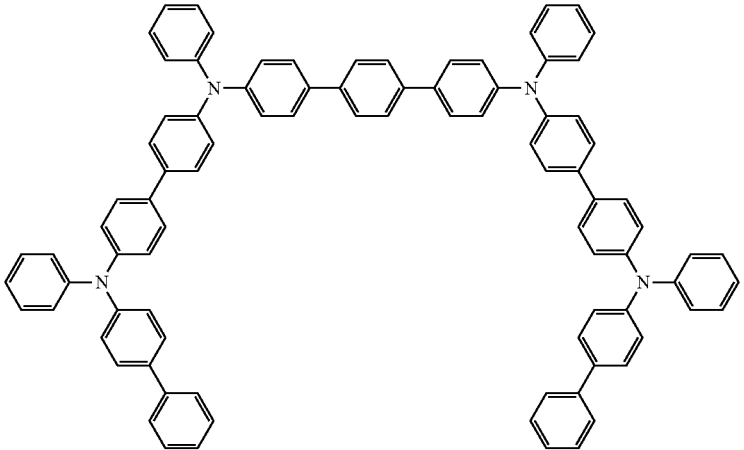 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

| MATERIAL | EXAMPLES OF MATERIAL | PUBLICATIONS |
|---|---|---|
| | 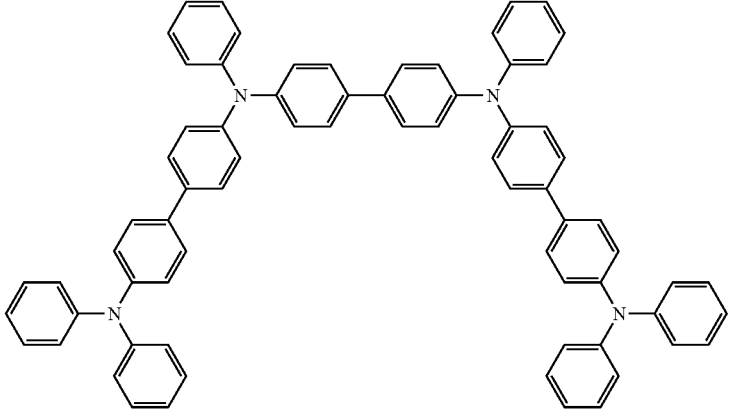 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 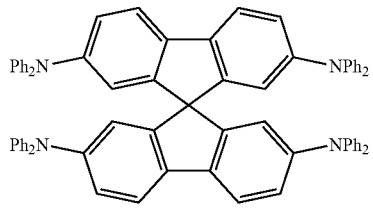 | Synth. Met. 91, 209 (1997) |
| Arylamine carbazole compounds | 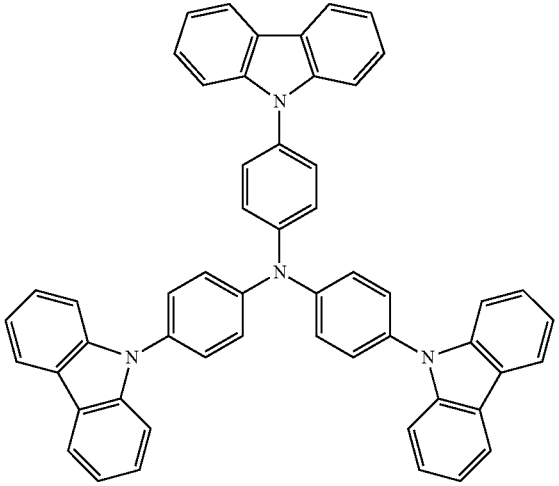 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/ (di)benzofuran | 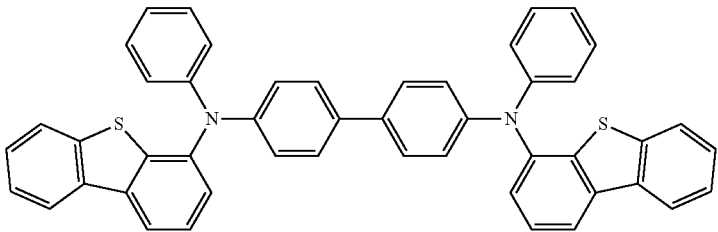 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |

TABLE 4-continued
| MATERIAL | EXAMPLES OF MATERIAL | PUBLICATIONS |
|---|---|---|
| Indolocarbazoles | 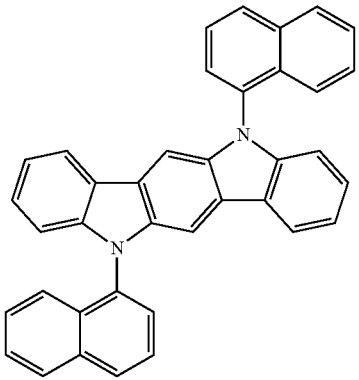 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 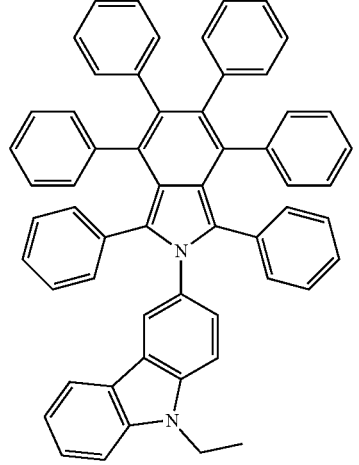 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 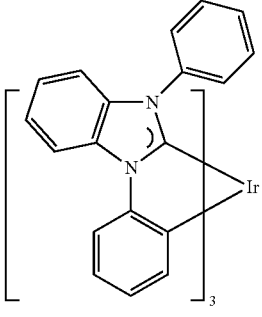 | US20080018221 |
Phosphorescent OLED host materials
Red hosts
| Arylcarbazoles | 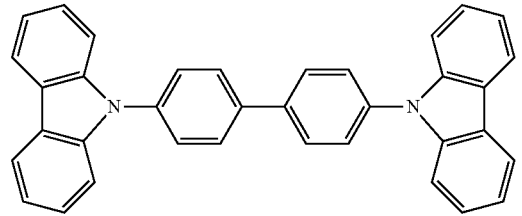 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 4-continued

| MATERIAL | EXAMPLES OF MATERIAL | PUBLICATIONS |
|---|---|---|
| Metal 8-hydroxyquinolates (e.g., Alq3, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 4-continued

| MATERIAL | EXAMPLES OF MATERIAL | PUBLICATIONS |
|---|---|---|
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 4-continued
| MATERIAL | EXAMPLES OF MATERIAL | PUBLICATIONS |
|---|---|---|
| | 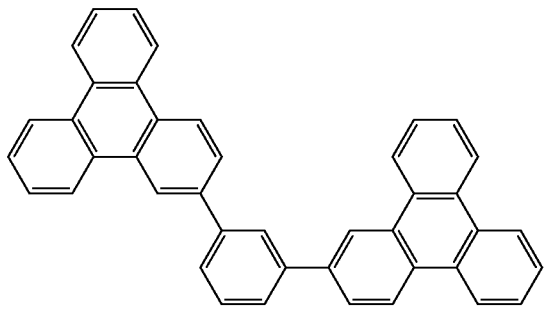 [SMILES: c1cc(-c2ccc3c4ccccc4c4ccccc4c3c2)cc(-c2ccc3c4ccccc4c4ccccc4c3c2)c1] | US20060280965 |
| | 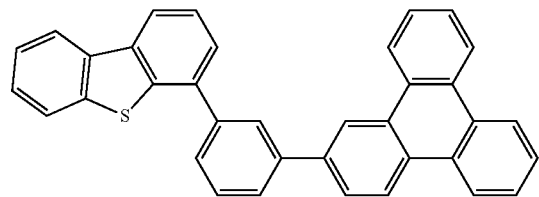 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 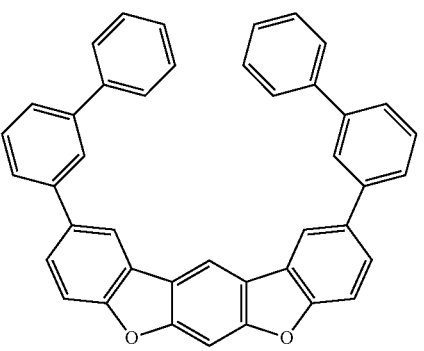 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 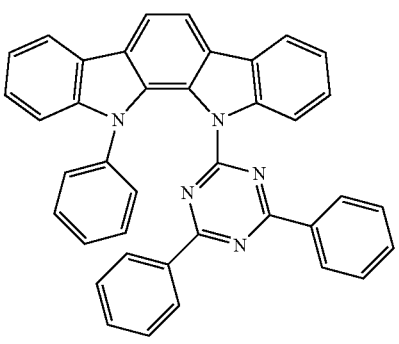 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 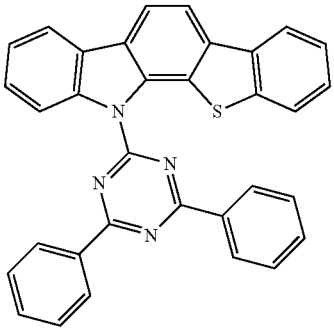 [SMILES: c1ccc(-c2nc(-c3ccccc3)nc(-n3c4ccccc4c4ccc5c6ccccc6sc5c43)n2)cc1] | WO2010107244 |

TABLE 4-continued

| MATERIAL | EXAMPLES OF MATERIAL | PUBLICATIONS |
|---|---|---|
| Aza-carbazole/ DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 4-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocabazoles | | WO2007063796 |

TABLE 4-continued

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE 4-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| MATERIAL | EXAMPLES OF MATERIAL | PUBLICATIONS |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 4-continued
| MATERIAL | EXAMPLES OF MATERIAL | PUBLICATIONS |
|---|---|---|
| | 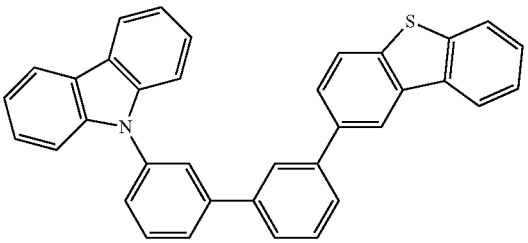 [SMILES: c1cc(-c2cccc(-n3c4ccccc4c4ccccc43)c2)cc(-c2ccc3sc4ccccc4c3c2)c1] | US20090030202, US20090017330 |
| | 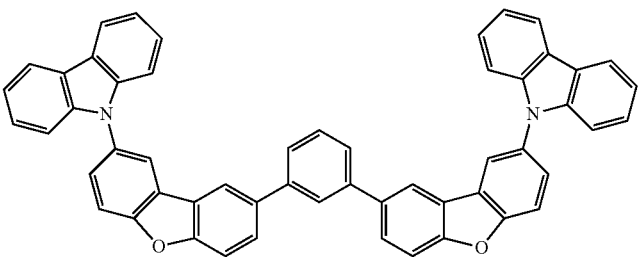 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 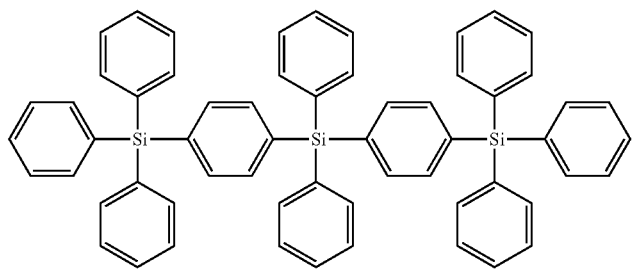 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 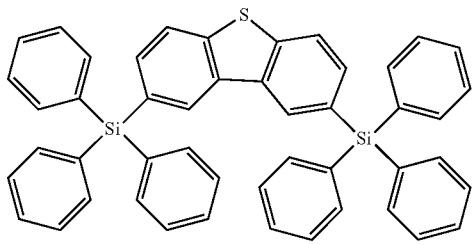 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 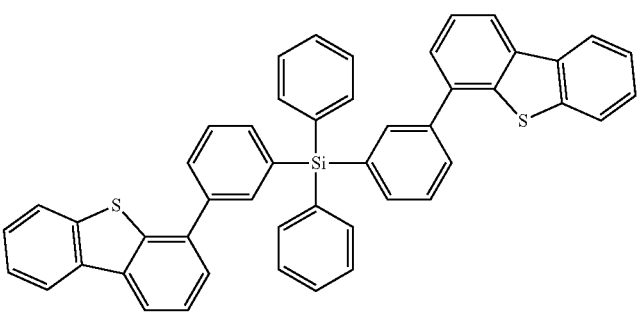 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 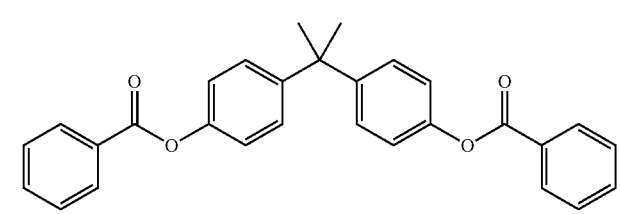 [SMILES: CC(C)(c1ccc(OC(=O)c2ccccc2)cc1)c1ccc(OC(=O)c2ccccc2)cc1] | WO2006100298 |

TABLE 4-continued
| MATERIAL | EXAMPLES OF MATERIAL | PUBLICATIONS |
|---|---|---|
| Carbazole linked by non-conjugated groups | 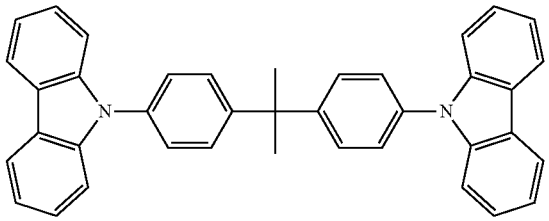 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 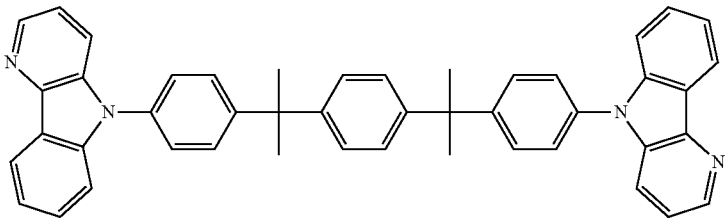 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 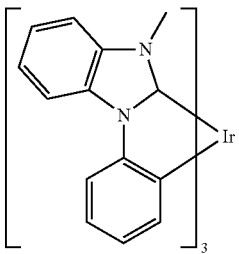 | U.S. Pat. No. 7,154,114 |
Phosphorescent dopants
Red dopants
| Heavy metal porphyrins (e.g., PtOEP) | 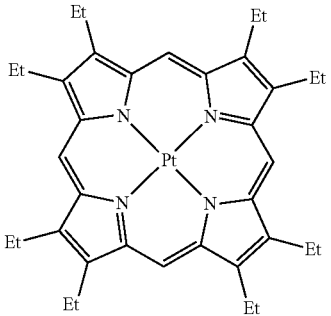 | Nature 395, 151 (1998) |
|---|---|---|
| Iridium(III) organometallic complexes | 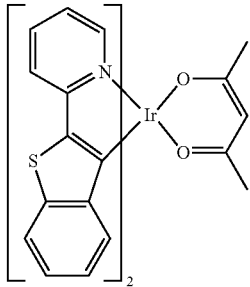 | Appl. Phys. Lett. 78, 1622 (2001) |

TABLE 4-continued

| MATERIAL | EXAMPLES OF MATERIAL | PUBLICATIONS |
| --- | --- | --- |
| | | US2006835469 |
| | | US2006835469 |
| | | US20060202194 |
| | | US20060202194 |
| | | US20070087321 |

TABLE 4-continued

| MATERIAL | EXAMPLES OF MATERIAL | PUBLICATIONS |
|---|---|---|
| | | US20080261076<br>US20100090591 |
| | | US20070087321 |
| | | Adv. Mater.<br>19, 739 (2007) |
| | | WO2009100991 |
| | | WO2008101842 |

TABLE 4-continued

| MATERIAL | EXAMPLES OF MATERIAL | PUBLICATIONS |
| --- | --- | --- |
|  |  | U.S. Pat. No. 7,232,618 |
| Platinum(II) organometallic complexes |  | WO2003040257 |
|  |  | US20070103060 |
| Osminum(III) complexes |  | Chem. Mater. 17, 3532 (2005) |
| Ruthenium(II) complexes |  | Adv. Mater. 17, 1059 (2005) |
| Rhenium (I), (II), and (III) complexes |  | US20050244673 |

TABLE 4-continued
| MATERIAL | EXAMPLES OF MATERIAL | PUBLICATIONS |
|---|---|---|
| | Green dopants | |
| Iridium(III) organometallic complexes | 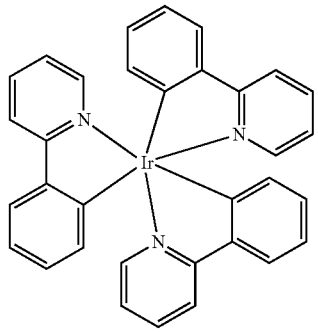<br>and its derivatives | Inorg. Chem. 40, 1704 (2001) |
| | 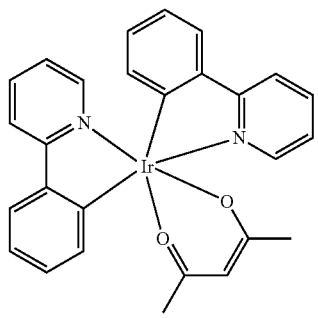 | US20020034656 |
| | 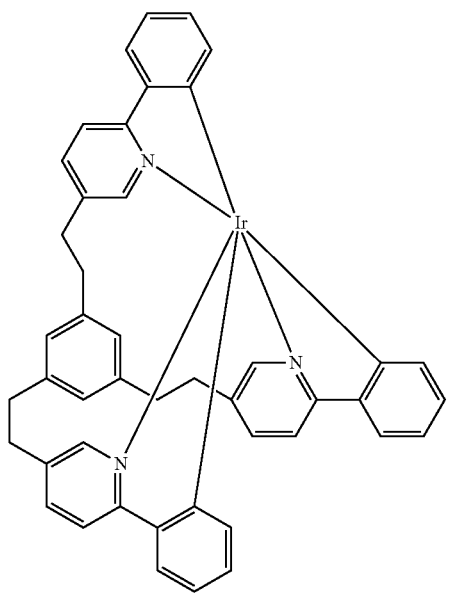 | U.S. Pat. No. 7,332,232 |

TABLE 4-continued
| MATERIAL | EXAMPLES OF MATERIAL | PUBLICATIONS |
|---|---|---|
| | 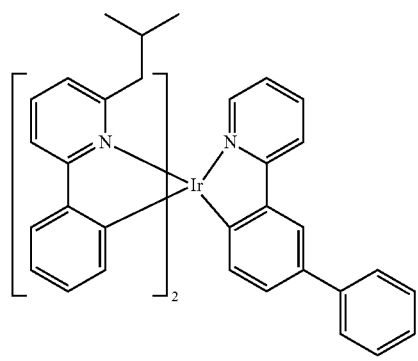 | US20090108737 |
| | 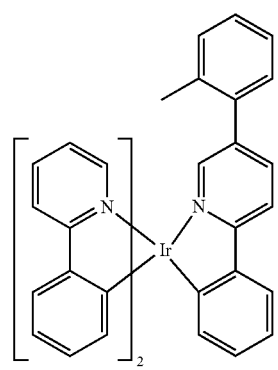 | WO2010028151 |
| | 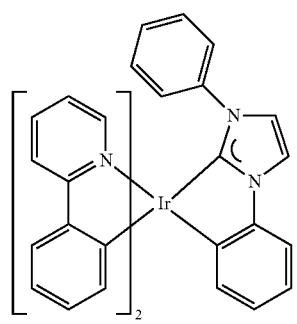 | EP1841834B |
| | 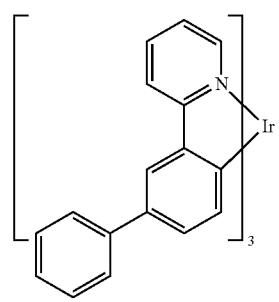 | US20060127696 |
| | 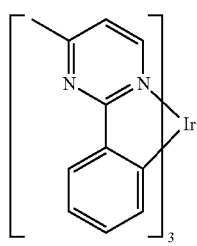 | US20090039776 |

TABLE 4-continued

| MATERIAL | EXAMPLES OF MATERIAL | PUBLICATIONS |
|---|---|---|
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

TABLE 4-continued

| MATERIAL | EXAMPLES OF MATERIAL | PUBLICATIONS |
|---|---|---|
| | | US20060008670 JP2007123392 |
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |

| MATERIAL | EXAMPLES OF MATERIAL | PUBLICATIONS |
|---|---|---|
| | 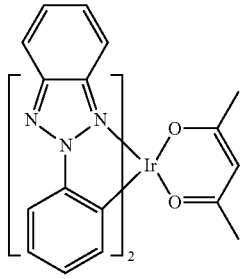 | US20080015355 |
| | 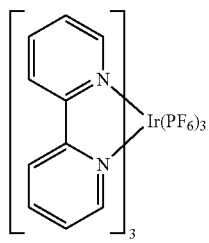 | US20010015432 |
| | 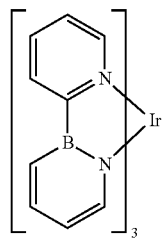 | US20100295032 |
| Monomer for polymeric metal organometallic compounds | 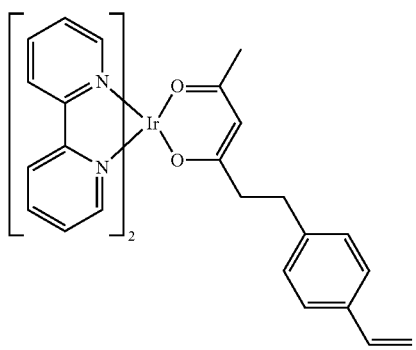 | U.S. Pat. No. 7,250,226, U.S. Pat. No. 7,396,598 |
| Pt(II) organometallic complexes, including polydentated ligands | 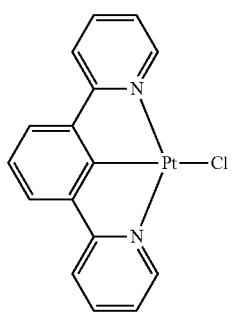 | Appl. Phys. Lett. 86, 153505 (2005) |

TABLE 4-continued
| MATERIAL | EXAMPLES OF MATERIAL | PUBLICATIONS |
|---|---|---|
| | 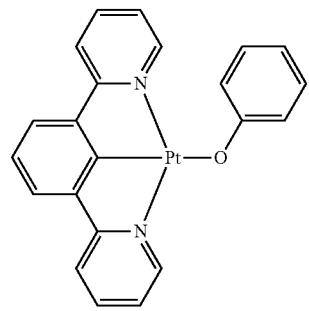 | Appl. Phys. Lett. 86, 153505 (2005) |
| | 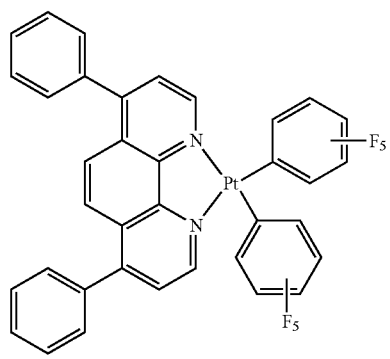 | Chem. Lett. 34, 592 (2005) |
| | 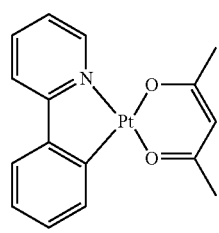 | WO2002015645 |
| | 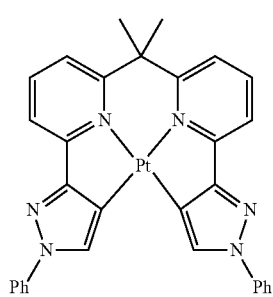 | US20060263635 |
| | 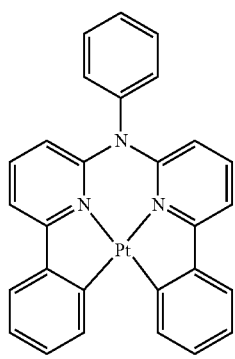 | US20060182992 US20070103060 |

| MATERIAL | EXAMPLES OF MATERIAL | PUBLICATIONS |
|---|---|---|
| Cu complexes | 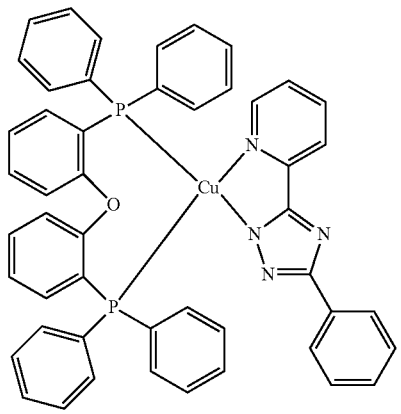 | WO2009000673 |
| | 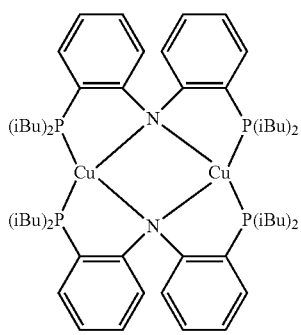 | US20070111026 |
| Gold complexes | 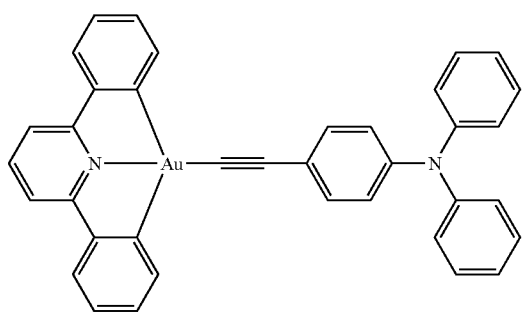 | Chem. Commun. 2906 (2005) |
| Rhenium(III) complexes | 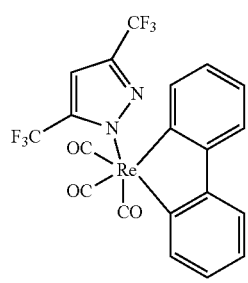 | Inorg. Chem. 42, 1248 (2003) |

TABLE 4-continued

| MATERIAL | EXAMPLES OF MATERIAL | PUBLICATIONS |
|---|---|---|
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 4-continued

| MATERIAL | EXAMPLES OF MATERIAL | PUBLICATIONS |
|---|---|---|
| Blue dopants | | |
| Iridium(III) organometallic complexes | | WO2002002714 |
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |
| | | WO2011051404 |

TABLE 4-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

| MATERIAL | EXAMPLES OF MATERIAL | PUBLICATIONS |
|---|---|---|
| | 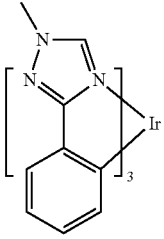 | Chem. Mater. 18, 5119 (2006) |
| | 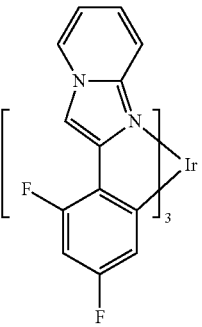 | Inorg. Chem. 46, 4308 (2007) |
| | 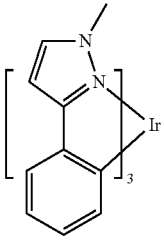 | WO2005123873 |
| | 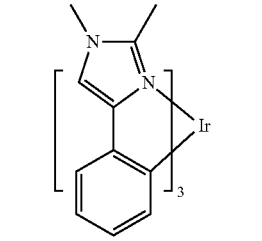 | WO2005123873 |
| | 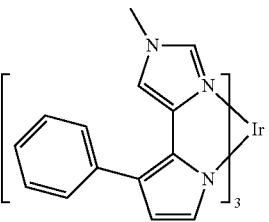 | WO2007004380 |

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 4-continued

| MATERIAL | EXAMPLES OF MATERIAL | PUBLICATIONS |
|---|---|---|
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 4-continued
| MATERIAL | EXAMPLES OF MATERIAL | PUBLICATIONS |
|---|---|---|
| Triphenylene compounds | 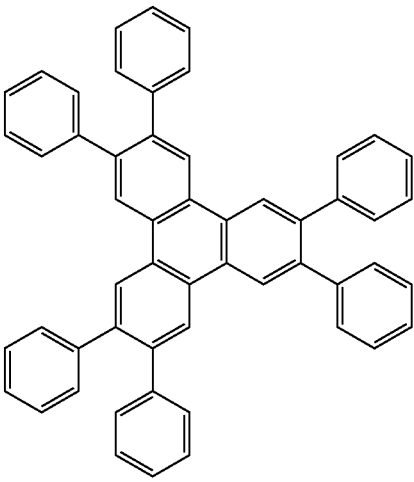 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 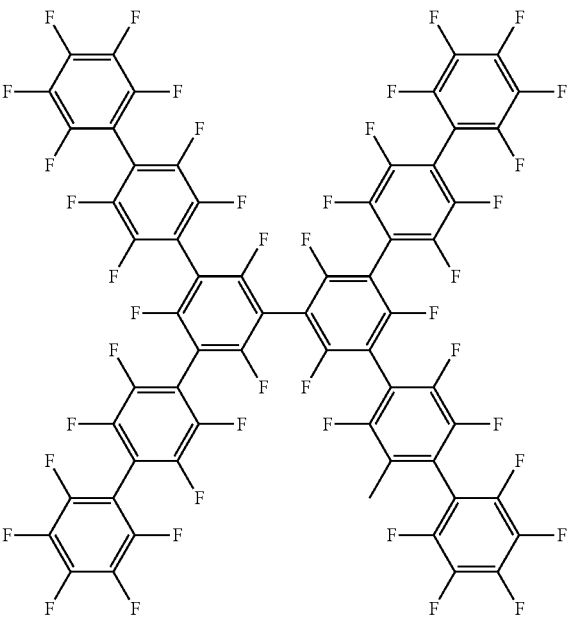 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 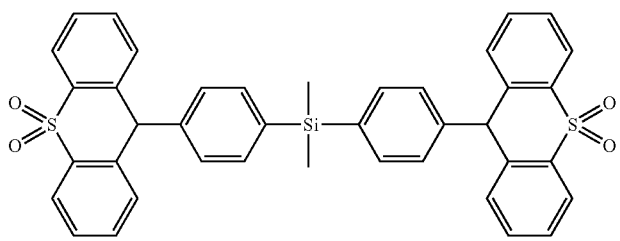 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 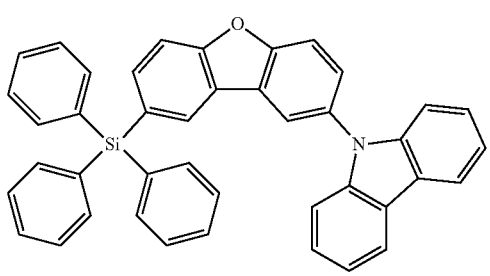 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 4-continued
| MATERIAL | EXAMPLES OF MATERIAL | PUBLICATIONS |
|---|---|---|
| Aza-carbazoles | 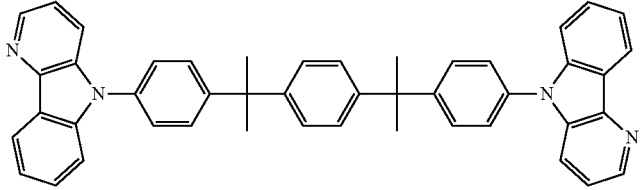 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| | | |
|---|---|---|
| Anthracene-benzoimidazole compounds | 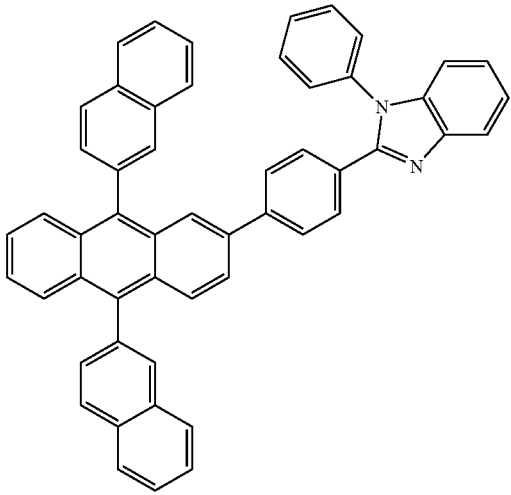 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 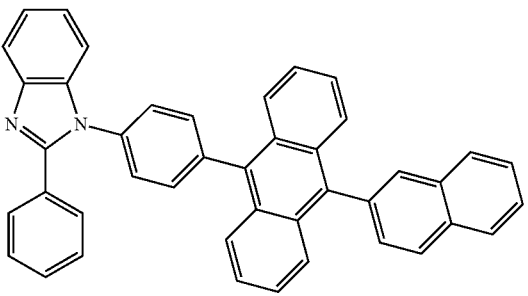 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 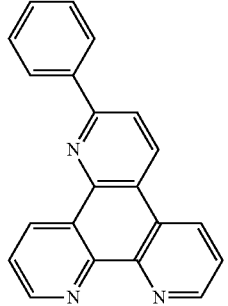 [SMILES: c1ccc(-c2ccc3c4cccnc4c4ncccc4c3n2)cc1] | US20090115316 |
| Anthracene-benzothiazole compounds | 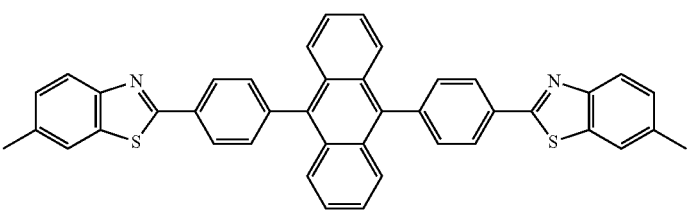 | Appl. Phys. Lett. 89, 063504 (2006) |

TABLE 4-continued

| MATERIAL | EXAMPLES OF MATERIAL | PUBLICATIONS |
| --- | --- | --- |
| Metal 8-hydroxyquinolates (e.g., Alq$_3$, Zrq$_4$) | | Appl. Phys. Lett. 51, 913 (1987) U.S. Pat. No. 7,230,107 |
| Metal hydroxy- benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g.,triazole, oxadiazole, imidazole, benzoimidazole) | | Appl. Phys. Lett. 74, 865 (1999) |
| | | Appl. Phys. Lett. 55, 1489 (1989) |

TABLE 4-continued
| MATERIAL | EXAMPLES OF MATERIAL | PUBLICATIONS |
|---|---|---|
| | 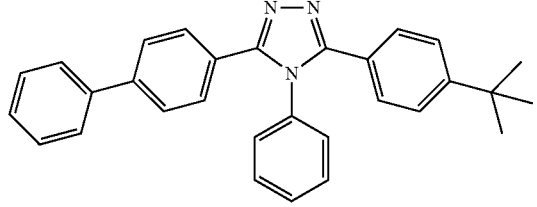 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 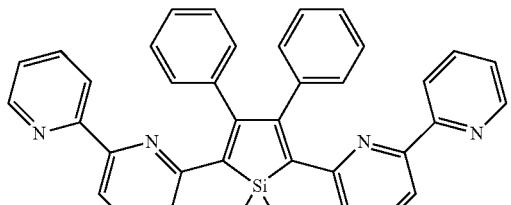 | Org. Electron. 4, 113 (2003) |
| Arylborane compounds | 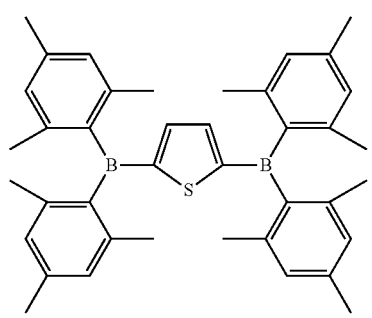 | J. Am. Chem. Soc. 120, 9714 (1998) |
| Fluorinated aromatic compounds | 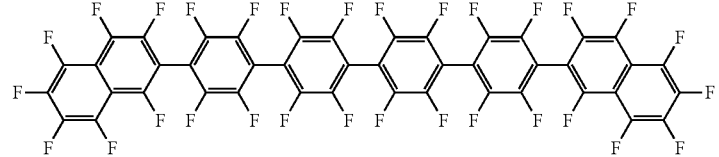 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 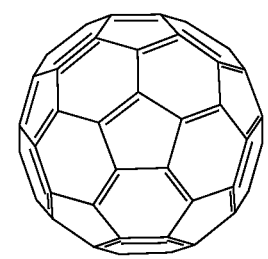 | US20090101870 |
| Triazine complexes | 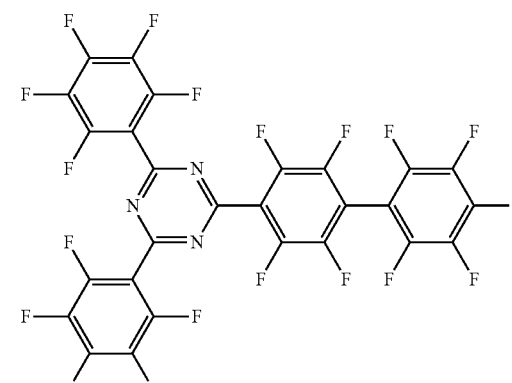 | US20040036077 |

| MATERIAL | EXAMPLES OF MATERIAL | PUBLICATIONS |
|---|---|---|
| Zn (N^N) complexes |  | U.S. Pat. No. 6,528,187 |

EXPERIMENTAL

Experimental Procedures:

Chemical abbreviations used throughout this document are as follows: dba is dibenzylideneacetone, EtOAc is ethyl acetate, PPh$_3$ is triphenylphosphine, dppf is 1,1'-bis(diphenylphosphino)ferrocene, DCM is dichloromethane, SPhos is dicyclohexyl(2',6'-dimethoxy-[1,1'-biphenyl]-3-yl)phosphine, THF is tetrahydrofuran.

A process for preparing the claimed iridium heteroleptic complexes is exemplified below:

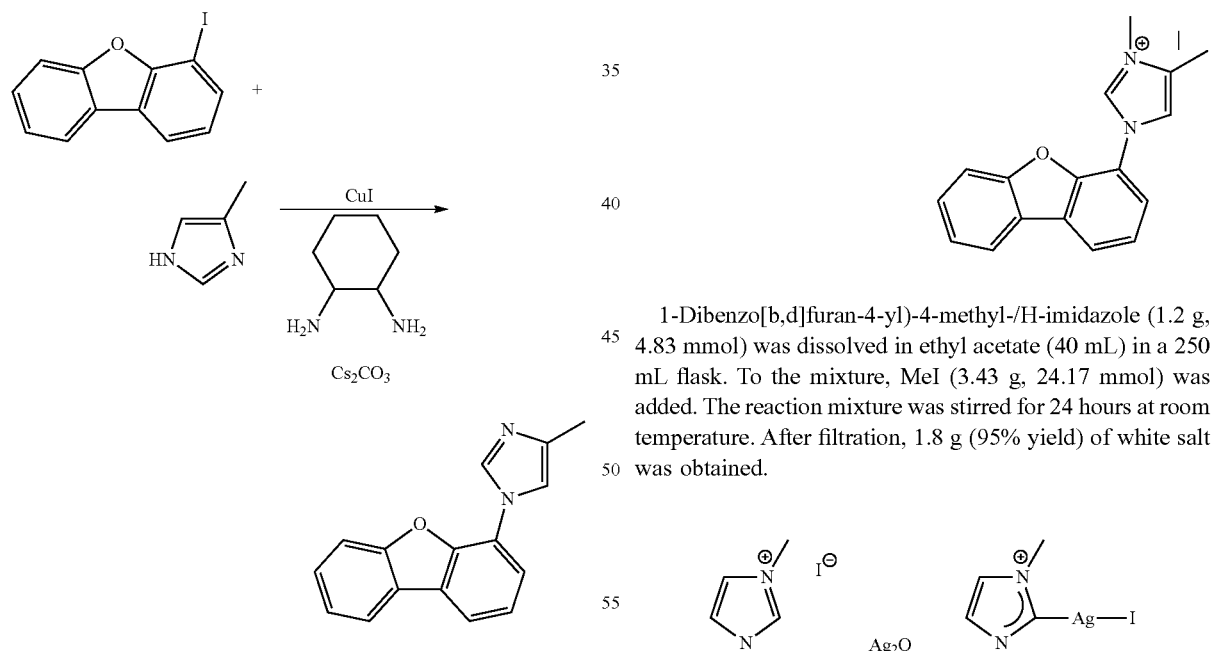

A 250 mL flask was charged with 4-iododibenzo[b,d]furan (2.8 g, 9.52 mmol), 4-methyl 1H-imidazole (1.56 g, 19.04 mmol), CuI (0.182 g, 0.95 mmol), Cs$_2$CO$_3$ (6.51 g, 20 mmol), cyclohexane-1,2-diamine (0.435 g, 3.81 mmol) and DMF (100 mL). The reaction mixture was bubbled with N$_2$ for 30 minutes and then heated up to 150° C. for 20 hours. The mixture was cooled down and added into water/ethyl acetate. The organic phase was washed with brine and run through a silica gel plug with ethyl acetate. After removal of solvent, the organic residue was recrystallized from ethyl acetate/hexane to get about 1.8 g (76% yield) white solid for next step.

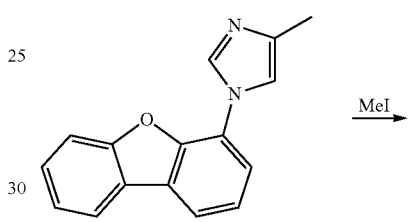

1-Dibenzo[b,d]furan-4-yl)-4-methyl-/H-imidazole (1.2 g, 4.83 mmol) was dissolved in ethyl acetate (40 mL) in a 250 mL flask. To the mixture, MeI (3.43 g, 24.17 mmol) was added. The reaction mixture was stirred for 24 hours at room temperature. After filtration, 1.8 g (95% yield) of white salt was obtained.

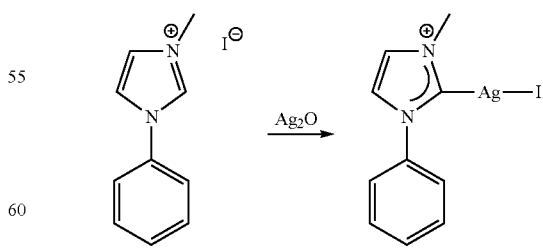

A 100 mL round bottom flask was charged with 3-methyl-1-phenyl-1H-imidazol-3-ium iodide (16.98 g, 59.3 mmol), silver oxide (6.88 g, 29.7 mmol) and acetonitrile (180 mL) to give a tan suspension. The reaction mixture was stirred at room temperature overnight. Solvent was removed by vacuum distillation and the residue was used for next step without purification.

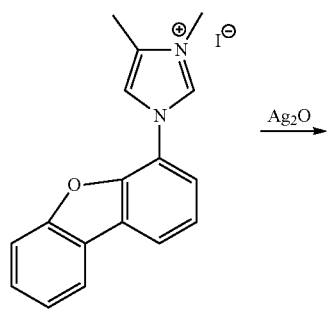

A 100 mL round-bottomed flask was charged with iodide salt (309 mg, 0.794 mmol), silver oxide (92 mg, 0.397 mmol), and acetonitrile (100 mL) to give a tan suspension. Reaction mixture was stirred in room temperature for overnight. Solvent was removed by vacuum distillation and residue was used for next step without purification.

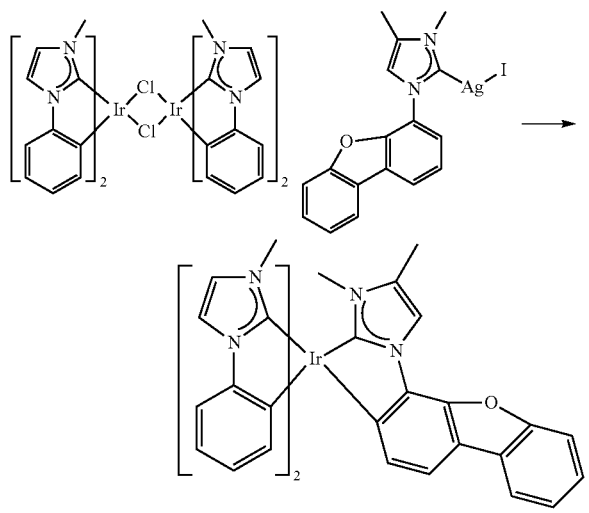

A 100 mL round-bottomed flask was charged with carbene dimer (287 mg, 0.265 mmol, prepared as described in US20050258742) and silver carbene complexes (395 mg, 0.795 mmol) in o-xylene (50 mL) to give a tan suspension. US20050258742 is herein incorporated in its entirety. The solution was heated to reflux for 3.5 hours. The solution was evaporated to dryness and the residue was subjected to column chromatography (SiO$_2$, pretreated with 20% Et$_3$N in hexanes, 50% EtOAc in hexanes) to yield the desired compound (46 mg, 11% yield, m/z (ESP+)=769)

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound comprising a heteroleptic iridium complex having the formula:

Formula II

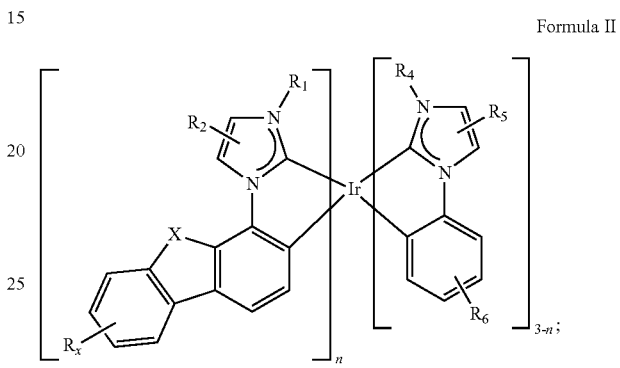

wherein X is selected from the group consisting of CRR', SiRR', C=O, N—R, B—R, O, S, SO, SO$_2$, and Se;

wherein R$_2$, R$_x$, R$_5$, and R$_6$ represent mono, di, tri, tetra substitutions or no substitution;

wherein R, R', R$_1$, R$_2$, R$_x$, R$_4$, R$_5$, and R$_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any two adjacent substituents are optionally joined together to form a ring, which may be further substituted; and wherein n is 1 or 2.

2. The compound of claim 1, wherein n is 2.
3. The compound of claim 1, wherein n is 1.
4. The compound of claim 1, wherein X is O.
5. The compound of claim 1, wherein X is S.
6. The compound of claim 1, wherein the compound has the formula:

Formula IV

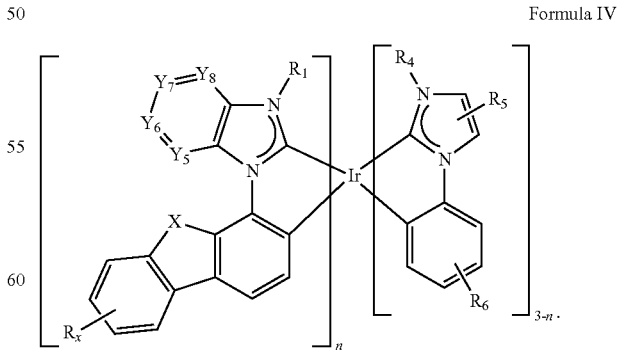

7. The compound of claim 1, wherein R$_1$ is alkyl or cycloalkyl.
8. The compound of claim 1, wherein R$_1$ is aryl or substituted aryl.

9. The compound of claim 8, wherein R₁ is a 2,6-disubstituted aryl.

10. The compound of claim 1, wherein the compound has the formula:

Formula VI

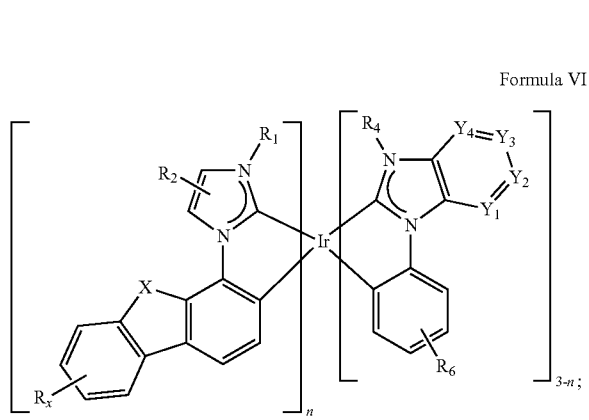

wherein Y₁ to Y₄ is CR₇ or N; and wherein each R₇ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

11. The compound of claim 10, wherein at least one of Y₁ to Y₄ is N.

12. The compound of claim 1, wherein the compound has the formula:

Formula VIII

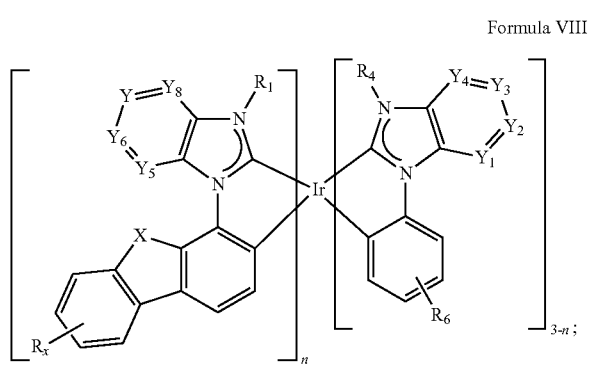

wherein Y₅ to Y₈ is CR₃ or N; and wherein each R₃ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of R₃ are optionally joined together to form a ring, which may be further substituted.

13. The compound of claim 12, wherein at least one of Y₁ to Y₄ is N.

14. The compound of claim 1, wherein the compound is selected from the group consisting of:

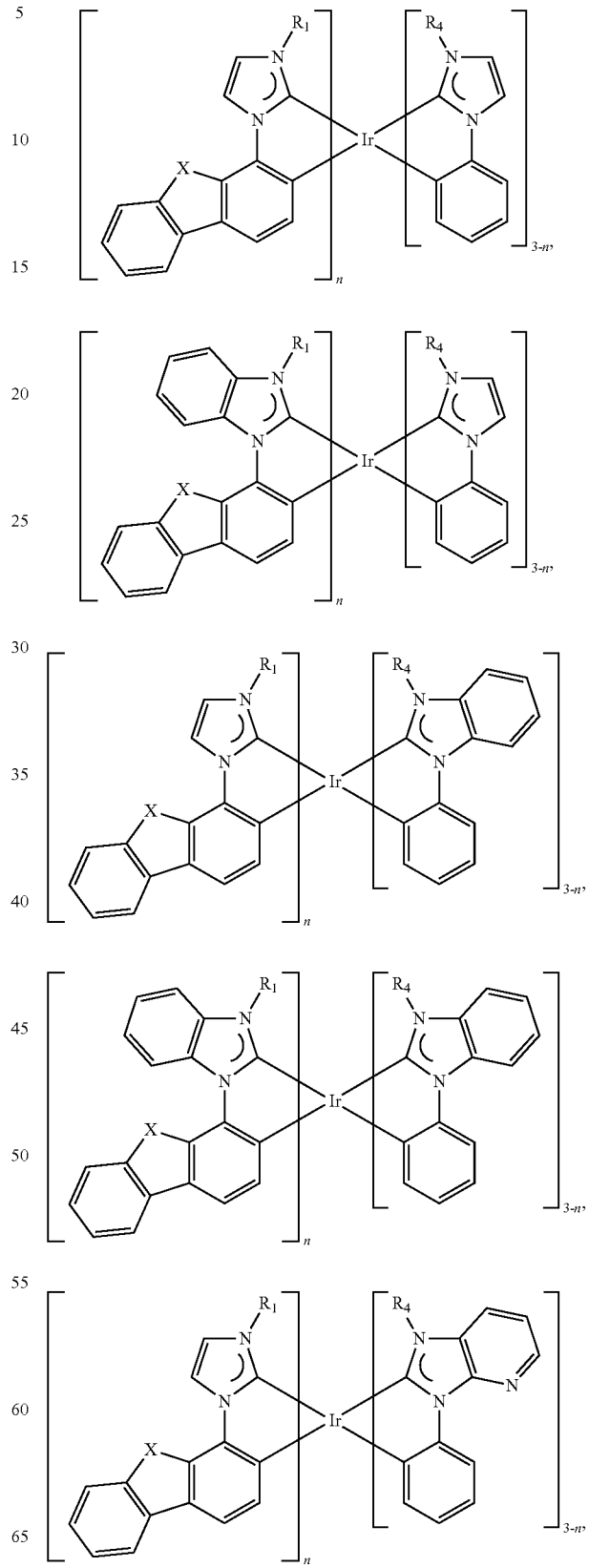

-continued
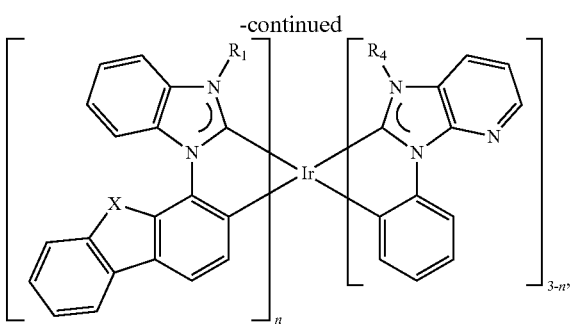 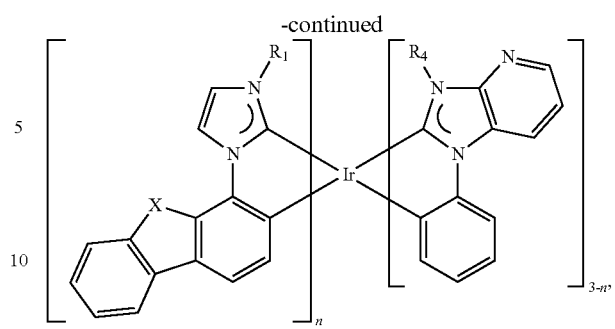
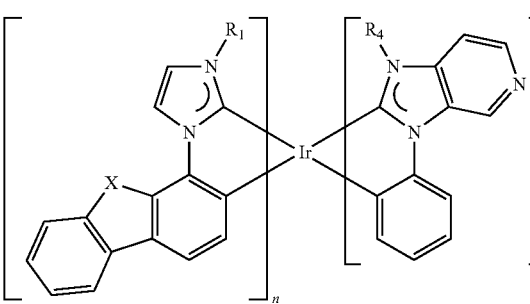 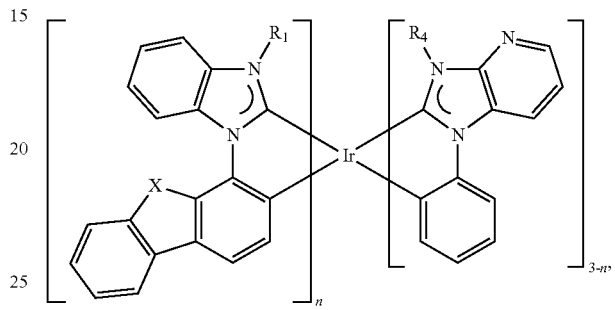
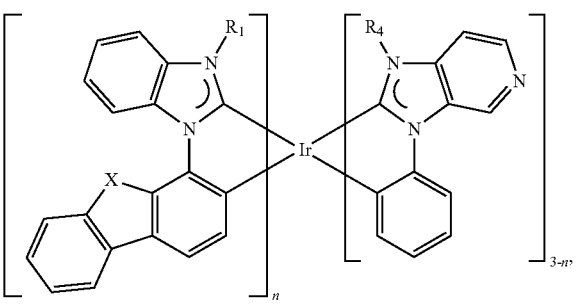 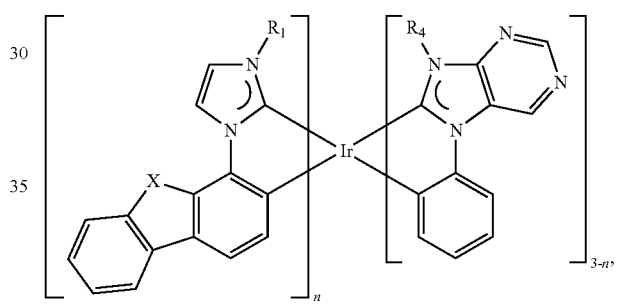
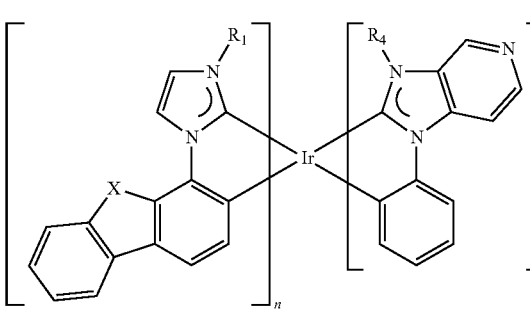 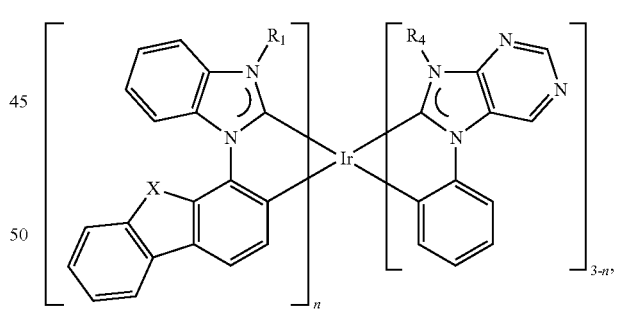
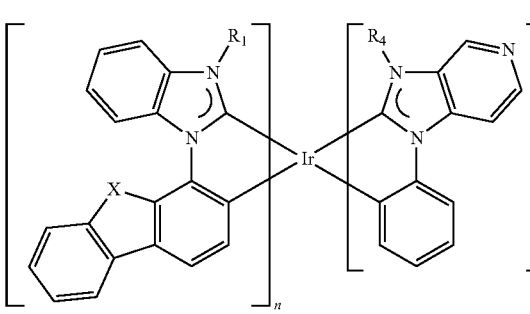 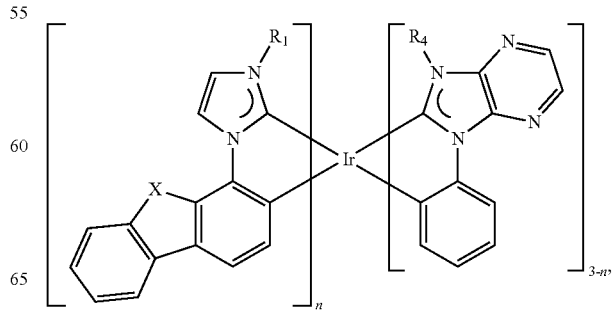

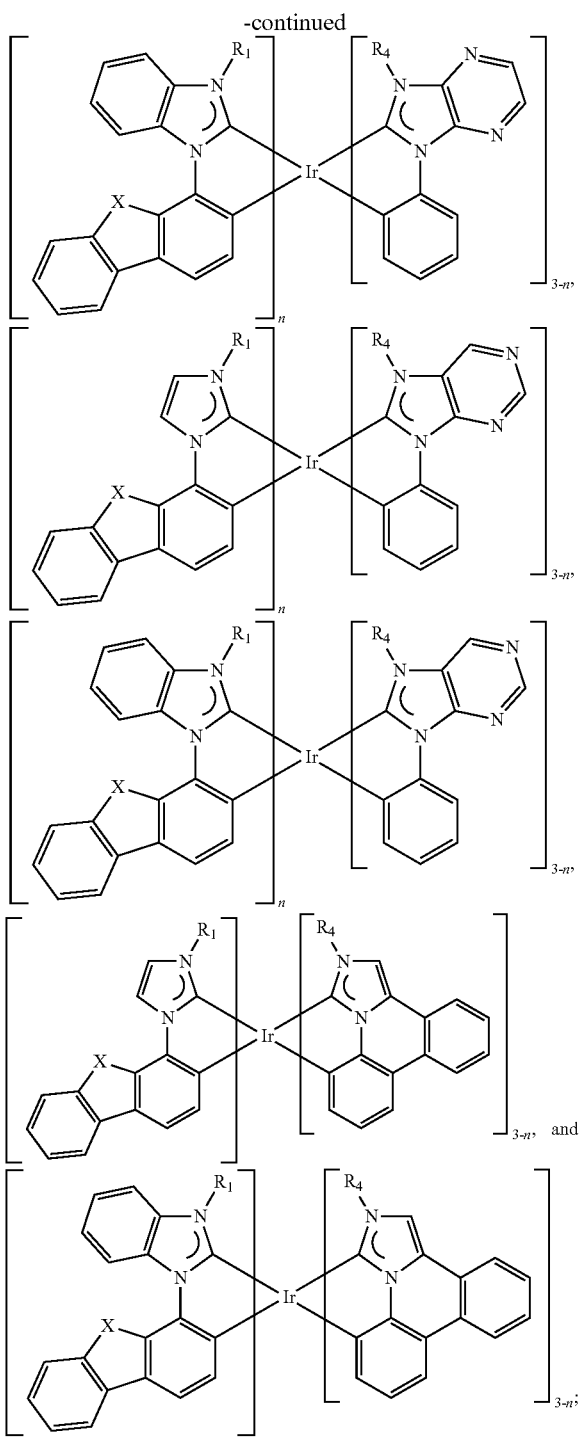

wherein X is O or S; and
wherein R₁ and R₄ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof, wherein any of the groups are optionally partially or fully deuterated.

15. The compound of claim 1, wherein the compound has the formula:

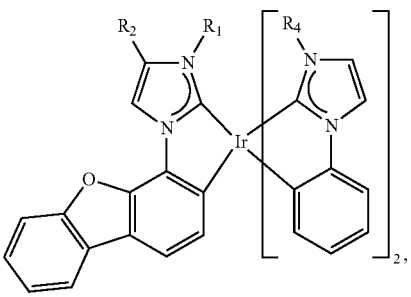

wherein $R_1$, $R_2$, and $R_4$ are alkyl.

16. The compound of claim 15, wherein $R_1$, $R_2$, and $R_4$ are methyl.

17. A first device comprising an organic light emitting device, further comprising:
an anode;
a cathode; and an organic layer, disposed between the anode and the cathode, comprising a compound having the formula:

Formula II

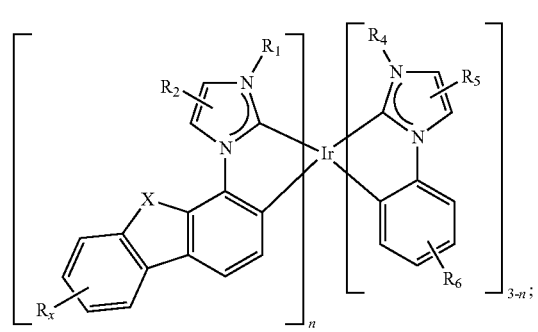

wherein X is selected from the group consisting of CRR', SiRR', C=O, N—R, B—R, O, S, SO, SO₂, and Se;
wherein $R_2$, $R_x$, $R_5$, and $R_6$ may represent mono, di, tri, tetra substitutions or no substitution;
wherein R, R', $R_1$, $R_2$, $R_x$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any two adjacent substituents are optionally joined together to form a ring, which may be further substituted; and wherein n is 1 or 2.

* * * * *